(12) United States Patent
Mainolfi

(10) Patent No.: US 11,014,882 B2
(45) Date of Patent: May 25, 2021

(54) 3-PHOSPHOGLYCERATE DEHYDROGENASE INHIBITORS AND USES THEREOF

(71) Applicant: Raze Therapeutics, Inc., Cambridge, MA (US)

(72) Inventor: Nello Mainolfi, Belmont, MA (US)

(73) Assignee: RAZE THERAPEUTICS, INC., Cambridge, MA (US)

(*) Notice: Subject to any disclaimer, the term of this patent is extended or adjusted under 35 U.S.C. 154(b) by 0 days.

(21) Appl. No.: 16/082,665

(22) PCT Filed: Mar. 8, 2017

(86) PCT No.: PCT/US2017/021436
§ 371 (c)(1),
(2) Date: Sep. 6, 2018

(87) PCT Pub. No.: WO2017/156179
PCT Pub. Date: Sep. 14, 2017

(65) Prior Publication Data
US 2019/0071400 A1 Mar. 7, 2019

Related U.S. Application Data

(60) Provisional application No. 62/305,940, filed on Mar. 9, 2016.

(51) Int. Cl.
| | | |
|---|---|---|
| C07D 209/42 | (2006.01) | |
| C07D 413/12 | (2006.01) | |
| C07D 405/12 | (2006.01) | |
| A61P 35/00 | (2006.01) | |

(52) U.S. Cl.
CPC ............ C07D 209/42 (2013.01); A61P 35/00 (2018.01); C07D 405/12 (2013.01); C07D 413/12 (2013.01)

(58) Field of Classification Search
CPC .................................................. C07D 209/42
See application file for complete search history.

(56) References Cited

U.S. PATENT DOCUMENTS

| | | | |
|---|---|---|---|
| 5,639,600 | A | 6/1997 | McGrath et al. |
| 6,552,065 | B2 | 4/2003 | Remiszewski et al. |
| 7,071,189 | B2 | 7/2006 | Kawashima et al. |
| 7,087,648 | B1 | 8/2006 | McGrath et al. |
| 7,390,799 | B2 | 6/2008 | Bruncko et al. |
| 8,138,347 | B2 | 3/2012 | Adams et al. |
| 2008/0293737 | A1 | 11/2008 | Martinborough et al. |
| 2011/0207767 | A1 | 8/2011 | Beusker et al. |
| 2013/0281430 | A1 | 10/2013 | Dahmann et al. |
| 2019/0071431 | A1 | 3/2019 | Mainolfi |

FOREIGN PATENT DOCUMENTS

| | | |
|---|---|---|
| WO | WO2000042213 | 7/2000 |
| WO | WO2001042246 | 6/2001 |
| WO | WO2003013484 | 2/2003 |
| WO | WO2003035621 | 5/2003 |
| WO | WO2003063794 | 8/2003 |
| WO | WO2004019973 | 3/2004 |
| WO | WO2004089925 | 10/2004 |
| WO | WO2004106328 | 12/2004 |
| WO | WO2005007623 | 1/2005 |
| WO | WO2005113554 | 12/2005 |
| WO | WO2006067445 | 6/2006 |
| WO | WO2006067446 | 6/2006 |
| WO | WO2006078846 | 7/2006 |
| WO | WO2006122806 | 11/2006 |
| WO | WO2007016176 | 2/2007 |
| WO | WO2007019344 | 2/2007 |
| WO | WO2007044729 | 4/2007 |
| WO | WO2007053452 | 5/2007 |
| WO | WO2007070514 | 6/2007 |
| WO | WO2007084786 | 7/2007 |
| WO | WO2007129161 | 11/2007 |
| WO | WO2008039218 | 4/2008 |
| WO | WO2008058037 | 5/2008 |
| WO | WO2008109943 | 9/2008 |
| WO | WO2008118802 | 10/2008 |
| WO | WO2009114512 | 9/2009 |
| WO | WO2011090760 | 7/2011 |
| WO | WO2015150097 | 10/2015 |

OTHER PUBLICATIONS

Caubre, et al. Document No. 122:81117, entered in STN on Jan. 12, 1995; retreived from STN.*
Hangauer, et al. Document No. 153:643306, retrieved from CAPLUS; Nov. 23, 2010.*
Sechi, et al. Document No. 157:372334, retrieved from CAPLUS; 2012.*
Berge, S. M. et al. Pharmaceutical Salts. J. Pharmaceutical Sciences, vol. 66, No. 1, Jan. 1977, pp. 1-19.
Cancer [online], [retrieved on Jul. 6, 2007]. Retrieved from the internet, URL http://www.nlm.nih.gov/medlineplus/cancer.html.
Daniell et al., "Design, synthesis, and biological evaluation of achiral analogs of duocarmycin SA," Bioorganic & Medicinal Chemistry Letters, 2005, 15(1):177-180.
Golub et al., "Molecular Classification of Cancer: Class Discovery and Class Predication by Gene Expression Monitoring," Science, 1999, 286:531-537.
Jun et al., "Requirement of the expression of 3-phosphoglycerate dehydrogenase for traversing S phase in murine T lymphocytes following polyclonal activation," Cell Immunology, vol. 287, No. 2, Feb. 2014 (pp. 78-85).
Lala et al., "Role of Nitric Oxide in Tumor Progression: Lessons from Experimental Tumors," Cancer and Metastasis Reviews, 1998, 17(1):91-106.

(Continued)

*Primary Examiner* — Shawquia Jackson
(74) *Attorney, Agent, or Firm* — Andrea L. C. Reid; Todd K. Macklin; Dechert LLP

(57) ABSTRACT

The present invention provides compounds, compositions thereof, and methods of using the same.

12 Claims, No Drawings

(56) References Cited

OTHER PUBLICATIONS

Mullarky et al., "Identification of a small molecule inhibitor of 3-phosphoglycerate dehydrogenase to target serine biosynthesis in cancers," Proceedings of the National Academy of Sciences of the United States of America, 2016, 113(7):1778-1783.
PCT International Preliminary Report on Patentability from PCT/US2017/021420 dated Sep. 11, 2018.
PCT International Search Report and Written Opinion from PCT/2017/021420 dated Jul. 3, 2017.
PCT International Preliminary Report on Patentability from PCT/US2017/021436 dated Sep. 11, 2018.
PCT International Search Report and Written Opinion from PCT/2017/021436 dated Jul. 3, 2017.
Supplementary European Search Report issued by the European Patent Office for European Patent App. 17764026.5, dated Jun. 5, 2019.
Supplementary European Search Report issued by the European Patent Office for European Patent App. 17764038.0, dated Oct. 10, 2019.
Zogg C., "Phosphoglycerate Dehydrogenase: Potential Therapeutic Target and Putative Metabolic Oncogene," Journal of Oncology, 2014, 4(12): 2502-2513.

* cited by examiner

3-PHOSPHOGLYCERATE DEHYDROGENASE INHIBITORS AND USES THEREOF

TECHNICAL FIELD OF THE INVENTION

The present invention relates to compounds and methods useful for inhibiting 3-phosphoglycerate dehydrogenase. The invention also provides pharmaceutically acceptable compositions comprising compounds of the present invention and methods of using said compositions in the treatment of various disorders.

BACKGROUND OF THE INVENTION

Phosphoglycerate dehydrogenase (PHGDH) catalyzes the first step in the biosynthesis of L-serine, which is the conversion of 3-phosphoglycerate into 3-phosphohydroxypyruvate with a reduction of nicotinamide adenine dinucleotide ($NAD^+$) to NADH.

Certain cancers, including human melanomas and breast cancers, can have high levels of PHGDH. These cancer cells are dependent on PHGDH for their growth and survival as PHGDH catalyzes serine production and may also be a significant source of NADPH in cancer cells. Targeting PHGDH by small molecule inhibitors could be a therapeutic strategy to reduce cancer cell growth and survival. Accordingly, there remains a need to find PHGDH inhibitors useful as therapeutic agents.

SUMMARY OF THE INVENTION

It has now been found that compounds of this invention, and pharmaceutically acceptable compositions thereof, are effective as PHGDH inhibitors. Such compounds have the general formula I:

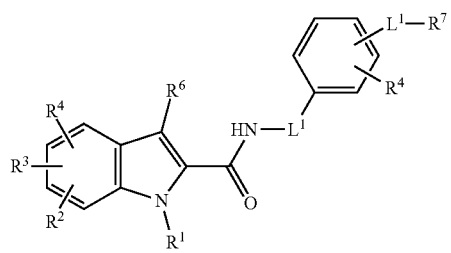

or a pharmaceutically acceptable salt thereof, wherein each of $R^1$, $R^2$, $R^3$, $R^4$, $R^5$, $R^6$, $R^7$, and $L^1$ is as defined and described herein.

Compounds of the present invention, and pharmaceutically acceptable compositions thereof, are useful for treating a variety of diseases, disorders or conditions, associated with PHGDH. Such diseases, disorders, or conditions include cellular proliferative disorders (e.g., cancer) such as those described herein.

DETAILED DESCRIPTION OF THE INVENTION

1. General Description of Certain Aspects of the Invention

Compounds of the present invention, and compositions thereof, are useful as inhibitors of PHGDH. Without wishing to be bound by any particular theory, it is believed that compounds of the present invention, and compositions thereof, may inhibit the activity of PHGDH and/or inhibit the production of NADPH, and thus reduce the growth of cells in proliferative disorders such as cancer.

In certain embodiments, the present invention provides a compound of formula I:

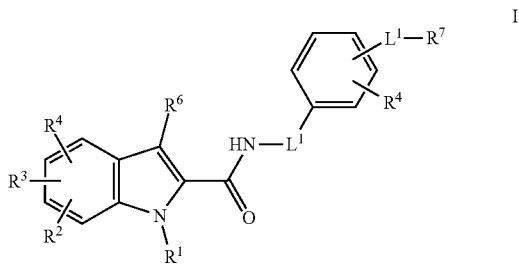

or a pharmaceutically acceptable salt thereof, wherein:

$R^1$ is hydrogen or $C_{1-4}$ alkyl;

each of $R^2$ and $R^3$ is independently halogen, —OR, —CN, $C_{1-6}$ aliphatic optionally substituted with 1, 2, or 3 halogens, or -L-R'; or $R^2$ and $R^3$ are optionally taken together with the carbon atoms to which they are attached and any intervening atoms to form a 5-8 membered partially unsaturated ring having 0-2 heteroatoms independently selected from nitrogen, oxygen, or sulfur;

$R^4$ is hydrogen, halogen, —$OR^5$, —CN, $C_{1-6}$ aliphatic optionally substituted with 1, 2, or 3 halogens, or -L-R';

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

$R^5$ is hydrogen, —$(CH_2)_n$-phenyl, or $C_{1-6}$ alkyl optionally substituted with 1, 2, or 3 halogens;

each L is independently a $C_{1-6}$ bivalent straight or branched hydrocarbon chain wherein 1-4 methylene units of the chain are independently and optionally replaced with —O—, —C(O)—, —C(O)O—, —OC(O)—, —OC(O)N(R)—, —(R)NC(O)O—, —C(O)N(R)—, —(R)NC(O)—, —N(R)—, —N(R)C(O)N(R)—, —S—, —SO—, or —$SO_2$—;

each R' is independently hydrogen, $C_{1-6}$ aliphatic, or an optionally substituted 4-8 membered saturated or partially unsaturated monocyclic heterocyclic ring having 1-2 heteroatoms independently selected from nitrogen, oxygen, or sulfur;

$R^6$ is hydrogen or $C_{1-4}$ alkyl;

$R^7$ is hydrogen, —$CO_2R$, $C_{1-6}$ optionally substituted aliphatic group, or a bivalent 3-7 membered ring;

$L^1$ is a covalent bond or a $C_{1-8}$ bivalent straight or branched hydrocarbon chain wherein 1-5 methylene units of the chain are independently and optionally replaced with —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)— —S—, —SO—, —SO$_2$—, —SO$_2$N(R)—, —(R)NSO$_2$—, —C(S)—, —C(S)O—, —OC(S)—, —C(S)N(R)—, —(R)NC(S)—, —(R)NC(S)N(R)—, or -Cy-;

each -Cy- is independently a bivalent 6-membered arylene ring containing 0-2 nitrogen atoms, or a bivalent 5-membered heteroarylene ring with 1-4 heteroatoms independently selected from nitrogen, oxygen, or sulfur, or a bivalent partially unsaturated 8-10 membered bicyclic heterocyclene ring with 1-4 heteroatoms independently selected from nitrogen, oxygen, or sulfur, wherein -Cy- is optionally substituted with 1 or 2 substituents independently selected from C$_{1-4}$ alkyl or —OR;

R$^8$ is hydrogen, —CO$_2$R, or C$_{1-6}$ optionally substituted aliphatic;

R$^9$ is hydrogen, halogen, C$_{1-4}$ alkyl, —CN, —OR, —(CH$_2$)$_n$-(optionally substituted phenyl), or L$^2$-R$^8$;

each L$^2$ is independently C$_{1-8}$ bivalent straight or branched hydrocarbon chain wherein 1-4 methylene units of the chain are independently and optionally replaced with —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, or —(R)NC(S)N(R)—; and n is independently 0, 1, 2, 3, 4, or 5.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic C$_3$-C$_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

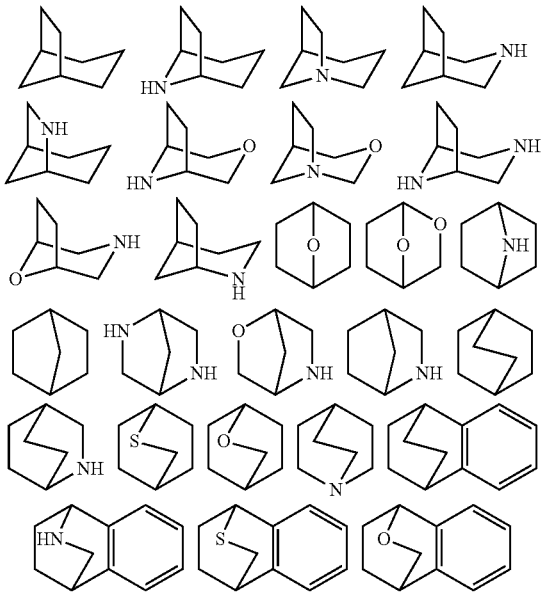

The term "lower alkyl" refers to a C$_{1-4}$ straight or branched alkyl group. Exemplary lower alkyl groups are methyl, ethyl, propyl, isopropyl, butyl, isobutyl, and tert-butyl.

The term "lower haloalkyl" refers to a C$_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent C$_{1-8}$ (or C$_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

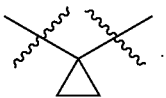

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH (OR°)₂; —(CH₂)₀₋₄SR°; —(CH₂)₀₋₄Ph, which may be substituted with R°; —(CH₂)₀₋₄O(CH₂)₀₋₁Ph which may be substituted with R°; —CH=CHPh, which may be substituted with R°; —(CH₂)₀₋₄O(CH₂)₀₋₁-pyridyl which may be substituted with R°; —NO₂; —CN; —N₃; —(CH₂)₀₋₄N(R°)₂; —(CH₂)₀₋₄N(R°)C(O)R°; —N(R°)C(S)R°; —(CH₂)₀₋₄N(R°)C(O)NR°₂; —N(R°)C(S)NR°₂; —(CH₂)₀₋₄N(R)C(O)OR°; —N(R°)N(R°)C(O)R°; —N(R°)N(R°)C(O)NR°₂; —N(R°)N(R°)C(O)OR°; —(CH₂)₀₋₄C(O)R°; —C(S)R°; —(CH₂)₀₋₄C(O)OR°; —(CH₂)₀₋₄C(O)SR°; —(CH₂)₀₋₄C(O)OSiR°₃; —(CH₂)₁₋₄OC(O)R°; —OC(O)(CH₂)₀₋₄SR—, SC(S)SR°; —(CH₂)₀₋₄SC(O)R°; —(CH₂)₀₋₄C(O)NR°₂; —C(S)NR°₂; —C(S)SR°; —SC(S)SR°; —(CH₂)₀₋₄C(O)NR°₂; —C(O)N(OR°)R°; —C(O)C(O)R°; —C(O)CH₂C(O)R°; —C(NOR°)R°; —(CH₂)₀₋₄SSR°; —(CH₂)₀₋₄S(O)₂R°; —(CH₂)₀₋₄S(O)₂OR°; —(CH₂)₀₋₄OS(O)₂R°; —S(O)₂NR°₂; —(CH₂)₀₋₄S(O)R°; —N(R°)S(O)₂NR°₂; —N(R°)S(O)₂R; —N(OR°)R°; —C(NH)NR°₂; —P(O)₂R°; —P(O)R°₂; —OP(O)R°₂; —OP(O)(OR°)₂; —SiR°₃; —(C₁₋₄ straight or branched alkylene)O—N(R°)₂; or —(C₁₋₄ straight or branched alkylene)C(O)O—N(R°)₂, wherein each R° may be substituted as defined below and is independently hydrogen, C₁₋₆ aliphatic, —CH₂Ph, —O(CH₂)₀₋₁Ph, —CH₂-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH₂)₀₋₂R●, -(haloR●), —(CH₂)₀₋₂OH, —(CH₂)₀₋₂OR●, —(CH₂)₀₋₂CH(OR●)₂; —O(haloR●), —CN, —N₃, —(CH₂)₀₋₂C(O)R●, —(CH₂)₀₋₂C(O)OH, —(CH₂)₀₋₂C(O)OR●, —(CH₂)₀₋₂SR●, —(CH₂)₀₋₂SH, —(CH₂)₀₋₂NH₂, —(CH₂)₀₋₂NHR●, —(CH₂)₀₋₂NR●₂, —NO₂, —SiR●₃, —OSiR●₃, —C(O)SR●, —(C₁₋₄ straight or branched alkylene)C(O)OR●, or —SSR● wherein each R● is unsubstituted or where preceded by "halo" is substituted only with one or more halogens, and is independently selected from C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*₂, =NNHC(O)R*, =NNHC(O)OR*, =NNHS(O)₂R*, =NR*, =NOR*, —O(C(R*2))₂₋₃O—, or —S(C(R*₂))₂₋₃S—, wherein each independent occurrence of R* is selected from hydrogen, C₁₋₆ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*₂)₂₋₀O—, wherein each independent occurrence of R* is selected from hydrogen, C₁₋₄ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R●, -(haloR●), —OH, —OR●, —O(haloR●), —CN, —C(O)OH, —C(O)OR●, —NH₂, —NHR●, —NR●₂, or —NO₂, wherein each R● is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†₂, —C(O)R†, —C(O)OR†, —C(O)C(O)R†, —C(O)CH₂C(O)R†, —S(O)₂R†, —S(O)₂NR†₂, —C(S)NR†₂, —C(NH)NR†₂, or —N(R†)S(O)₂R†; wherein each R† is independently hydrogen, C₁₋₆ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR●, —O(haloR●), —CN, —C(O)OH, —C(O)OR●, —NH₂, —NHR●, —NR●₂, or —NO₂, wherein each R● is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N⁺(C₁₋₄alkyl)₄ salts.

Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise depicted, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms.

As used herein, the term "inhibitor" is defined as a compound that binds to and/or inhibits PHGDH with measurable affinity. In certain embodiments, an inhibitor has an $IC_{50}$ and/or binding constant of less than about 100 μM, less than about 50 μM, less than about 1 μM, less than about 500 nM, less than about 100 nM, less than about 10 nM, or less than about 1 nM.

The terms "measurable affinity" and "measurably inhibit," as used herein, means a measurable change in PHGDH activity between a sample comprising a compound of the present invention, or composition thereof, and PHGDH, and an equivalent sample comprising PHGDH, in the absence of said compound, or composition thereof.

3. Description of Exemplary Embodiments

In certain embodiments, the present invention provides a compound of formula I:

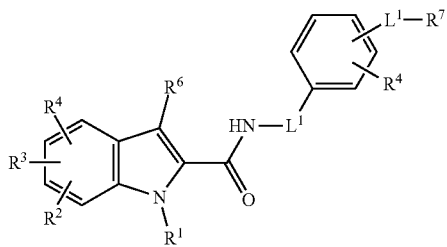

or a pharmaceutically acceptable salt thereof, wherein:
$R^1$ is hydrogen or $C_{1-4}$ alkyl;
each of $R^2$ and $R^3$ is independently halogen, —OR, —CN, $C_{1-6}$ aliphatic optionally substituted with 1, 2, or 3 halogens, or -L-R'; or $R^2$ and $R^3$ are optionally taken together with the carbon atoms to which they are attached and any intervening atoms to form a 5-8 membered partially unsaturated ring having 0-2 heteroatoms independently selected from nitrogen, oxygen, or sulfur;
$R^4$ is hydrogen, halogen, —OR$^5$, —CN, $C_{1-6}$ aliphatic optionally substituted with 1, 2, or 3 halogens, or -L-R';
each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
$R^5$ is hydrogen, —(CH$_2$)$_n$-phenyl, or $C_{1-6}$ alkyl optionally substituted with 1, 2, or 3 halogens;
each L is independently a $C_{1-6}$ bivalent straight or branched hydrocarbon chain wherein 1-4 methylene units of the chain are independently and optionally replaced with —O—, —C(O)—, —C(O)O—, —OC(O)—, —OC(O)N(R)—, —(R)NC(O)O—, —C(O)N(R)—, —(R)NC(O)—, —N(R)—, —N(R)C(O)N(R)—, —S—, —SO—, or —SO$_2$—;
each R' is independently hydrogen, $C_{1-6}$ aliphatic, or an optionally substituted 4-8 membered saturated or partially unsaturated monocyclic heterocyclic ring having 1-2 heteroatoms independently selected from nitrogen, oxygen, or sulfur;
$R^6$ is hydrogen or $C_{1-4}$ alkyl;
$R^7$ is hydrogen, —CO$_2$R, $C_{1-6}$ optionally substituted aliphatic group, or a bivalent 3-7 membered ring;
$L^1$ is a covalent bond or a $C_{1-8}$ bivalent straight or branched hydrocarbon chain wherein 1-5 methylene units of the chain are independently and optionally replaced with —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, —(R)NC(S)N(R)—, or -Cy-;
each -Cy- is independently a bivalent 6-membered arylene ring containing 0-2 nitrogen atoms, or a bivalent 5-membered heteroarylene ring with 1-4 heteroatoms independently selected from nitrogen, oxygen, or sulfur, or a bivalent partially unsaturated 8-10 membered bicyclic heterocyclene ring with 1-4 heteroatoms independently selected from nitrogen, oxygen, or sulfur, wherein -Cy- is optionally substituted with 1 or 2 substituents independently selected from $C_{1-4}$ alkyl or —OR;
$R^8$ is hydrogen, —CO$_2$R, or $C_{1-6}$ optionally substituted aliphatic;
$R^9$ is hydrogen, halogen, $C_{1-4}$ alkyl, —CN, —OR, —(CH$_2$)$_n$-(optionally substituted phenyl), or $L^2$-R$^8$;
each $L^2$ is independently $C_{1-8}$ bivalent straight or branched hydrocarbon chain wherein 1-4 methylene units of the chain are independently and optionally replaced with —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, or —(R)NC(S)N(R)—; and
n is independently 0, 1, 2, 3, 4, or 5.

In certain embodiments, the present invention provides a compound of formula I wherein said compound is other than compound 1-39 or 1-41.

As defined above and described herein, $R^1$ is hydrogen or $C_{1-4}$ alkyl. In some embodiments, $R^1$ is hydrogen. In some embodiments, R1 is $C_{1-4}$ alkyl. In some embodiments, $R^1$ is methyl. In some embodiments, $R^1$ is ethyl.

In some embodiments, $R^1$ is selected from those depicted in Table 1, below.

As defined above and described herein, $R^2$ is independently halogen, —OR, —CN, $C_{1-6}$ aliphatic optionally substituted with 1, 2, or 3 halogens, or -L-R'; or $R^2$ and $R^3$ are optionally taken together with the carbon atoms to which they are attached and any intervening atoms to form a 5-8 membered partially unsaturated ring having 0-2 heteroatoms independently selected from nitrogen, oxygen, or sulfur.

In some embodiments, $R^2$ is halogen. In some embodiments, $R^2$ is —OR. In some embodiments, $R^2$ is —CN. In some embodiments, $R^2$ is $C_{1-6}$ aliphatic optionally substituted with 1, 2, or 3, halogens. In some embodiments, $R^2$ is -L-R'. In some embodiments, $R^2$ and $R^3$ are taken together with the carbon atoms to which they are attached and any intervening atoms to form a 5-8 membered partially unsaturated ring having 0-2 heteroatoms independently selected from nitrogen, oxygen, or sulfur In some embodiments, $R^2$ is F, Cl, —CF$_3$, —OCF$_3$, —OCHF$_2$, —OCH$_2$Ph, —OCH$_3$, —CN, —CH$_3$,

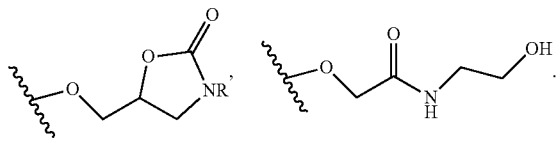

In some embodiments, $R^2$ is F or Cl. In some embodiments, $R^2$ is —OCH$_3$. In some embodiments, $R^2$ is —CH$_3$.

In some embodiments, $R^2$ is selected from those depicted in Table 1, below.

As defined above and described herein, $R^3$ is independently halogen, —OR, —CN, $C_{1-6}$ aliphatic optionally substituted with 1, 2, or 3 halogens, or -L-R'; or $R^2$ and $R^3$ are optionally taken together with the carbon atoms to which they are attached and any intervening atoms to form a 5-8 membered partially unsaturated ring having 0-2 heteroatoms independently selected from nitrogen, oxygen, or sulfur.

In some embodiments, $R^3$ is halogen. In some embodiments, $R^3$ is —OR. In some embodiments, $R^3$ is —CN. In some embodiments, $R^3$ is $C_{1-6}$ aliphatic optionally substituted with 1, 2, or 3, halogens. In some embodiments, $R^3$ is -L-R'. In some embodiments, $R^2$ and $R^3$ are taken together with the carbon atoms to which they are attached and any intervening atoms to form a 5-8 membered partially unsaturated ring having 0-2 heteroatoms independently selected from nitrogen, oxygen, or sulfur.

In some embodiments, $R^3$ is F, Cl, —CF$_3$, —OCF$_3$, —OCHF$_2$, —OCH$_2$Ph, —OCH$_3$, —CN, —CH$_3$,

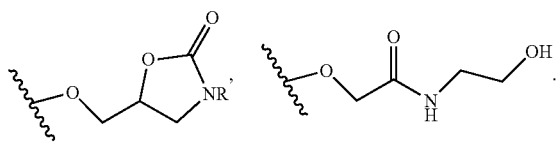

In some embodiments, $R^3$ is F or Cl. In some embodiments, $R^3$ is —OCH$_3$. In some embodiments, $R^3$ is —CH$_3$.

In some embodiments, $R^3$ is selected from those depicted in Table 1, below.

As defined above and described herein, $R^4$ is hydrogen, halogen, —OR$^5$, —CN, $C_{1-6}$ aliphatic optionally substituted with 1, 2, or 3 halogens, or -L-R'.

In some embodiments, $R^4$ is hydrogen. In some embodiments, $R^4$ is halogen. In some embodiments, $R^4$ is —OR$^5$. In some embodiments, $R^4$ is $C_{1-6}$ aliphatic optionally substituted with 1, 2, or 3 halogens. In some embodiments, $R^4$ is -L-R'.

In some embodiments, $R^4$ is F, Cl, —CF$_3$, —OCF$_3$, —OCHF$_2$, —OCH$_2$Ph, —OCH$_3$, —CN, —CH$_3$,

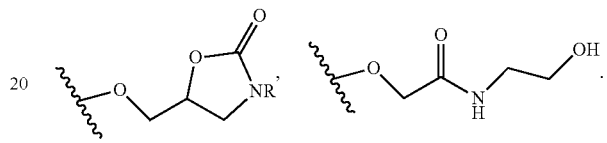

In some embodiments, $R^4$ is F or Cl. In some embodiments, $R^4$ is —OCH$_3$. In some embodiments, $R^4$ is —CH$_3$.

In some embodiments, $R^4$ is selected from those depicted in Table 1, below.

As defined above and described herein, each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

In some embodiments, R is hydrogen. In some embodiments, R is an optionally substituted $C_{1-6}$ aliphatic group. In some embodiments, R is an optionally substituted 3-8 membered saturated or partially unsaturated monocyclic carbocyclic ring. In some embodiments, R is an optionally substituted phenyl. In some embodiments, R is an optionally substituted 8-10 membered bicyclic aromatic carbocyclic ring. In some embodiments, R is an optionally substituted 4-8 membered saturated or partially unsaturated monocyclic heterocyclic ring having 1-2 heteroatoms independently selected from nitrogen, oxygen, or sulfur. In some embodiments, R is a 5-6 membered monocyclic heteroaromatic ring having 1-4 heteroatoms independently selected from nitrogen, oxygen, or sulfur. In some embodiments, R is an optionally substituted 8-10 membered bicyclic heteroaromatic ring having 1-5 heteroatoms independently selected from nitrogen, oxygen, or sulfur.

In some embodiments, R is selected from those depicted in Table 1, below.

As defined above and described herein, each L is independently a $C_{1-6}$ bivalent straight or branched hydrocarbon chain wherein 1-4 methylene units of the chain are independently and optionally replaced with —O—, —C(O)—, —C(O)O—, —OC(O)—, —OC(O)N(R)—, —(R)NC(O)O—, —C(O)N(R)—, —(R)NC(O)—, —N(R)—, —N(R)C(O)N(R)—, —S—, —SO—, or —SO$_2$—.

In some embodiments, L is a $C_{1-6}$ bivalent straight or branched hydrocarbon chain wherein 1-4 methylene units of the chain are independently replaced with —O—, —C(O)—, —C(O)O—, —OC(O)—, —OC(O)N(R)—, —(R)NC(O)O—, —C(O)N(R)—, —(R)NC(O)—, —N(R)—, —N(R)C(O)N(R)—, —S—, —SO—, or —SO$_2$—. In some embodiments, 1 or 2 methylene units of the chain are replaced with —O—. In some embodiments, 1 or 2 methylene units of the chain are replaced with —C(O)—. In some embodiments, 1 or 2 methylene units of the chain are replaced with —C(O)O—. In some embodiments, 1 or 2 methylene units of the chain are replaced with —C(O)O—. In some embodiments, 1 or 2 methylene units of the chain are replaced with —OC(O)—. In some embodiments, 1 or 2 methylene units of the chain are replaced with —OC(O)N(R)—. In some embodiments, 1 or 2 methylene units of the chain are replaced with —(R)NC(O)O—. In some embodiments, 1 or 2 methylene units are replaced with —C(O)N(R)—. In some embodiments, 1 or 2 methylene units of the chain are replaced with —(R)NC(O)—. In some embodiments, 1 or 2 methylene units of the chain are replaced with —N(R)—. In some embodiments, 1 or 2 methylene units of the chain are replaced with —N(R)C(O)N(R)—. In some embodiments, 1 or 2 methylene units of the chain are replaced with —S—. In some embodiments, 1 or 2 methylene units of the chain are replaced with —SO—. In some embodiments, 1 or 2 methylene units are replaced with —SO$_2$—. In some embodiments, 1 or 2 methylene units of the chain are independently replaced with —O—, —C(O)—, —C(O)O—, —OC(O)—, —OC(O)N(R)—, —(R)NC(O)O—, —C(O)N(R)—, —(R)NC(O)—, —N(R)—, —N(R)C(O)N(R)—, —S—, —SO—, or —SO$_2$—, wherein each R is independently hydrogen or methyl.

In some embodiments, L is a $C_{1-6}$ bivalent straight or branched hydrocarbon chain wherein 1, 2, or 3 methylene units of the chain are independently replaced with —O—, —C(O)—, —C(O)O—, —OC(O)—, —OC(O)N(R)—, —(R)NC(O)O—, —C(O)N(R)—, —(R)NC(O)—, —N(R)—, or —N(R)C(O)N(R)—, wherein R is hydrogen or methyl. In some embodiments, L is a $C_{1-6}$ bivalent straight or branched hydrocarbon chain wherein 1 or 2 methylene units of the chain are independently replaced with —O—, —C(O)—, —C(O)N(R)—, —(R)NC(O)—, or —N(R)—, wherein each R is independently hydrogen or methyl.

In some embodiments, L is —O—. In some embodiments, L is —O—CH$_2$—. In some embodiments, L is —O—CH$_2$—C(O)NH—.

In some embodiments, L is selected from those depicted in Table 1, below.

As defined above and described herein, each R' is independently hydrogen, $C_{1-6}$ aliphatic, or an optionally substituted 4-8 membered saturated or partially unsaturated monocyclic heterocyclic ring having 1-3 heteroatoms independently selected from nitrogen, oxygen, or sulfur.

In some embodiments, R' is hydrogen. In some embodiments, R' is $C_{1-6}$ aliphatic. In some embodiments, R' is an optionally substituted 4-8 membered saturated or partially saturated monocyclic heterocyclic ring having 1-3 heteroatoms independently selected from nitrogen, oxygen or sulfur.

In some embodiments, R' is

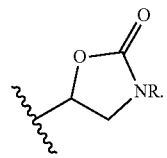

In some embodiments, R' is

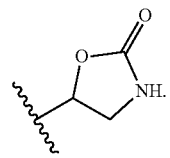 [SMILES: *C1CNC(=O)O1]

In some embodiments, R' is

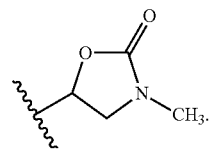 [SMILES: *C1CN(C)C(=O)O1]

In some embodiments, R' is selected from those depicted in Table 1, below.

As defined above and described herein, $R^5$ is hydrogen, —(CH$_2$)$_n$-phenyl, or $C_{1-6}$ alkyl optionally substituted with 1, 2, or 3 halogens.

In some embodiments, $R^5$ is hydrogen. In some embodiments, $R^5$ is —(CH$_2$)$_n$-phenyl. In some embodiments, $R^5$ is $C_{1-6}$ alkyl optionally substituted with 1, 2, or 3 halogens.

In some embodiments, $R^5$ is selected from those depicted in Table 1, below.

As defined above, and described herein, $R^6$ is hydrogen or $C_{1-4}$ alkyl. In some embodiments, $R^6$ is hydrogen. In some embodiments, $R^6$ is $C_{1-4}$ alkyl.

In some embodiments, $R^6$ is methyl.

In some embodiments, $R^6$ is selected from those depicted in Table 1, below.

As defined above, and described herein, $R^7$ is hydrogen, —CO$_2$R, optionally substituted $C_{1-6}$ aliphatic, or a bivalent 3-7 membered ring.

In some embodiments, $R^7$ is hydrogen. In some embodiments, $R^7$ is —CO$_2$R. In some embodiments, $R^7$ is $C_{1-6}$ aliphatic. In some embodiments, $R^7$ is a bivalent 3-7 membered ring.

In some embodiments, $R^7$ is hydrogen, methyl, ethyl, cyclopropyl, cyclobutyl, or —CO$_2$H.

In some embodiments $R^7$ is selected from those depicted in Table 1, below.

As defined above, and described herein, $L^1$ is a covalent bond or a $C_{1-8}$ bivalent straight or branched hydrocarbon chain wherein 1-5 methylene units of the chain are independently and optionally replaced with —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, —(R)NC(S)N(R)—, or -Cy-.

In some embodiments, $L^1$ is a covalent bond. In some embodiments, $L^1$ is a $C_{1-8}$ bivalent straight or branched hydrocarbon chain. In some embodiments, $L^1$ is a $C_{1-8}$ bivalent straight or branched hydrocarbon chain wherein 1-5 methylene units of the chain are independently replaced with —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, —(R)NC(S)N(R)—, or -Cy-. In some embodiments, 1, 2, or 3 methylene units of the chain are replaced with —O—. In some embodiments, 1, 2, or 3 methylene units of the chain are replaced with —C(O)—. In some embodiments, 1, 2, or 3 methylene units of the chain are replaced with —C(O)O— or —OC(O)—. In some embodiments, 1, 2, or 3 methylene units of the chain are replaced with —N(R)—. In some embodiments, 1, 2, or 3 methylene units of the chain are replaced with —C(O)N(R)— or —(R)NC(O)—. In some embodiments, 1, 2, or 3 methylene units of the chain are replaced with —OC(O)N(R)— or —(R)NC(O)O—. In some embodiments, 1, 2, or 3 methylene units of the chain are replaced with —N(R)C(O)N(R)—. In some embodiments, 1, 2, or 3 methylene units of the chain are replaced with —S—. In some embodiments, 1, 2, or 3 methylene units of the chain are replaced with —SO—. In some embodiments, 1, 2, or 3 methylene units of the chain are replaced with —SO$_2$—. In some embodiments, 1, 2, or 3 methylene units of the chain are replaced with —SO$_2$N(R)— or —(R)NSO$_2$—. In some embodiments, 1, 2, or 3 methylene units of the chain are replaced with —C(S)—. In some embodiments, 1, 2, or 3 methylene units of the chain are replaced with —C(S)O— or —OC(S)—. In some embodiments, 1, 2, or 3 methylene units of the chain are replaced with —C(S)N(R)— or —(R)NC(S)—. In some embodiments, 1, 2, or 3 methylene units of the chain are replaced with —(R)NC(S)N(R)—. In some embodiments, 1, 2, or 3 methylene units of the chain are replaced with -Cy-. In some embodiments, $L^1$ is a $C_{1-6}$ bivalent straight or branched hydrocarbon chain wherein 1, 2, or 3 methylene units of the chain are independently and optionally replaced with —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, —(R)NC(S)N(R)—, or -Cy-, wherein each R is independently hydrogen, —CH$_2$-phenyl, phenyl, —CH$_3$, —CH$_2$CH$_3$, cyclopentyl, cyclohexyl, —CH$_2$F, —CHF$_2$, —CF$_3$, —CH$_2$CHF$_2$, or —CH$_2$CF$_3$; or each R is independently hydrogen or methyl; or R is hydrogen.

In some embodiments, $L^1$ is a $C_{1-6}$ bivalent straight or branched hydrocarbon chain wherein 1, 2, 3, or 4 methylene units of the chain are independently and optionally replaced with —O—, —C(O)—, —C(O)O—, —OC(O)—, —NH—, —C(O)NH—, —NHC(O)—, —NHC(O)NH—, —SO$_2$—, or -Cy-.

In some embodiments, $L^1$ is a $C_{1-6}$ bivalent straight or branched hydrocarbon chain wherein 1, 2, or 3 methylene units of the chain are independently replaced with —O—, —C(O)—, —C(O)O—, —OC(O)—, —NH—, —C(O)NH—, —NHC(O)—, —NHC(O)NH—, —SO$_2$—, or -Cy-.

In some embodiments, $L^1$ is a $C_{1-6}$ bivalent straight or branched hydrocarbon chain wherein 1, 2, or 3 methylene units of the chain are independently replaced with —C(O)—, —NH—, —C(O)NH—, —NHC(O)—, —NHC(O)NH—, —SO$_2$—, or -Cy-.

In some embodiments, $L^1$ is a $C_{3-6}$ bivalent straight or branched hydrocarbon chain wherein 2 or 3 methylene units of the chain are independently replaced with —SO$_2$—, —SO$_2$NH—, —C(O)O—, —C(O)NH—, or —NHC(O)NH—. In some embodiments, $L^1$ is a $C_{3-6}$ bivalent branched hydrocarbon chain wherein 2 or 3 methylene units of the chain are independently replaced with —SO$_2$—, —SO$_2$NH—, —C(O)O—, —C(O)NH—, or —NHC(O)NH—.

In some embodiments, the methylene unit of $L^1$ is replaced with —SO$_2$—. In some embodiments, the methylene unit of $L^1$ is replaced with —SO$_2$NH—. In some embodiments, the methylene unit of $L^1$ is substituted with two methyl groups. In some embodiments, the methylene unit of $L^1$ is replaced with —C(O)NH—. In some embodiments, the methylene unit of $L^1$ is replaced with —SO$_2$— and the adjacent methylene unit is replaced with —NHC(O)NH—. In some embodiments, the methylene unit of $L^1$ is substituted with two methyl groups and the adjacent methylene unit is replaced with —NHC(O)NH—.

In some embodiments, $L^1$ is a covalent bond.

In some embodiments, $L^1$ is

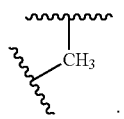

In some embodiments, $L^1$ is

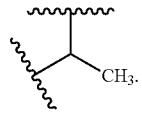 [SMILES: *C(*)C]

In some embodiments, $L^1$ is

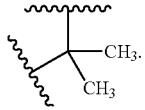

In some embodiments, $L^1$ is

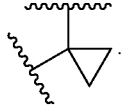

In some embodiments, $L^1$ is

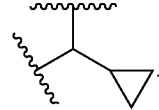 [SMILES: *C(*)C1CC1]

In some embodiments, $L^1$ is

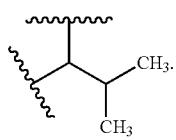

In some embodiments, $L^1$ is

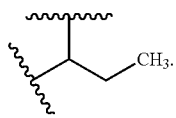

In some embodiments, $L^1$ is

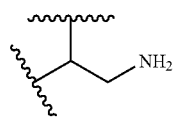

In some embodiments, $L^1$ is

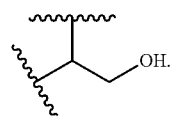

In some embodiments, $L^1$ is

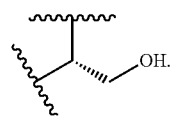

In some embodiments, $L^1$ is

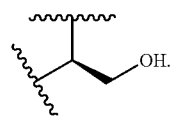

In some embodiments, $L^1$ is

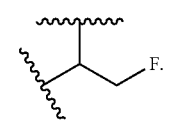

In some embodiments, $L^1$ is

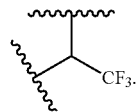

In some embodiments, $L^1$ is selected from those depicted in Table 1, below.

As defined above and described herein, each -Cy- is independently a bivalent 6-membered arylene ring containing 0-2 nitrogen atoms wherein the ring is optionally substituted with 1 or 2 substituents independently selected from $C_{1-4}$ alkyl or —OR, or a bivalent 5-membered heteroarylene ring with 1-4 heteroatoms independently selected from nitrogen, oxygen, or sulfur, or a bivalent partially unsaturated 8-10 membered bicyclic heterocyclene ring with 1-4 heteroatoms independently selected from nitrogen, oxygen, or sulfur.

In some embodiments, -Cy- is a bivalent 6-membered arylene ring containing 0-2 nitrogen atoms. In some embodiments, -Cy- is a bivalent 6-membered arylene ring containing 0-2 nitrogen atoms wherein the ring is substituted with 1 or 2 substituents independently selected from $C_{1-4}$ alkyl or —OR, wherein R is hydrogen or $C_{1-4}$ alkyl. In some embodiments, -Cy- is a bivalent 5-membered heteroarylene ring with 1-4 heteroatoms independently selected from nitrogen, oxygen, or sulfur. In some embodiments, -Cy- is a bivalent partially unsaturated 8-10 membered bicyclic heterocyclene ring with 1-4 heteroatoms independently selected from nitrogen, oxygen, or sulfur.

In some embodiments, -Cy- is

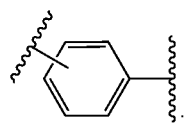

In some embodiments, -Cy- is selected from those depicted in Table 1, below.

In some embodiments, the present invention provides a compound of Formulae II-a, II-b, II-c, II-d, II-e, II-f, or II-g:

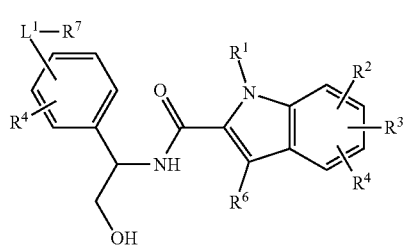

II-a

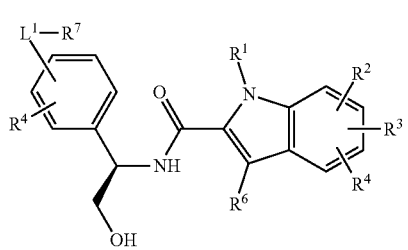

II-b

-continued
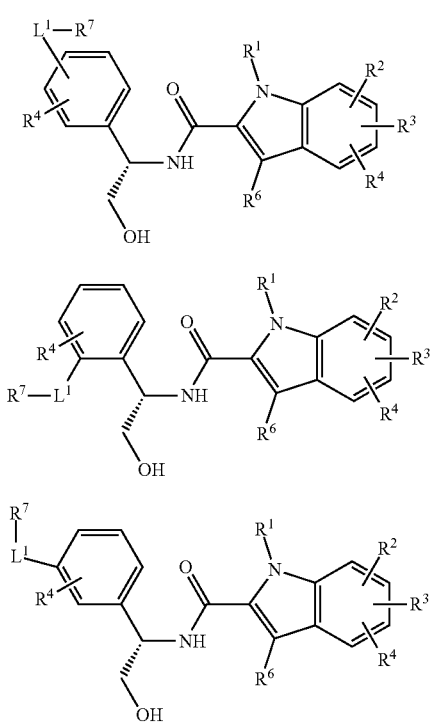
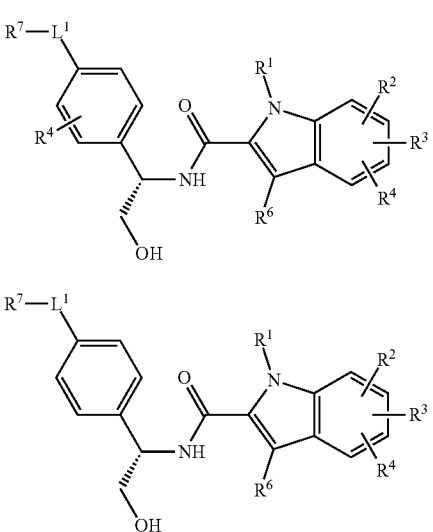
or a pharmaceutically acceptable salt thereof, wherein each of $R^1$, $R^2$, $R^3$, $R^4$, $R^5$, $R^6$, $R^7$, $R^8$, $R^9$, R, R', $L^1$, -Cy-, and n is defined above and described in embodiments herein.
Exemplary compounds of the invention are set forth in Table 1, below.
TABLE 1
Exemplary Compounds
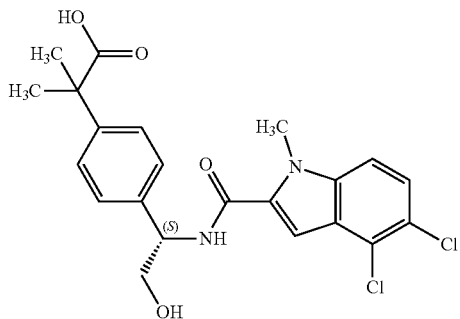
I-1
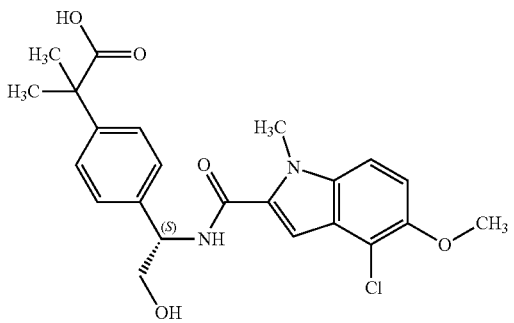
I-2

TABLE 1-continued
Exemplary Compounds
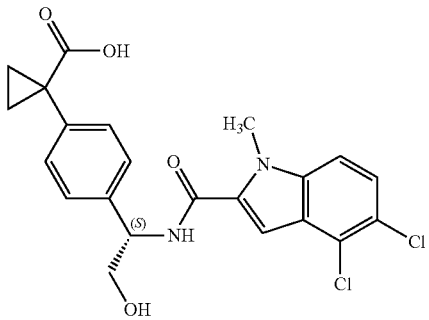
I-3
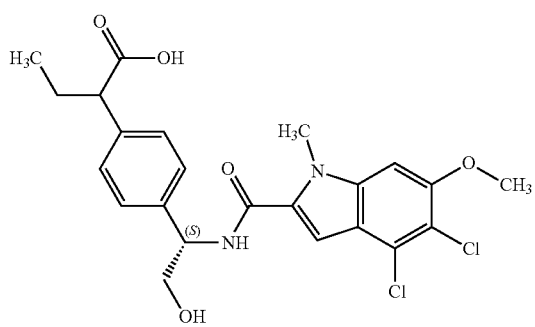
I-4
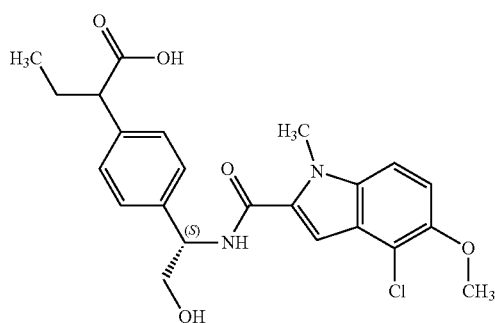
I-5
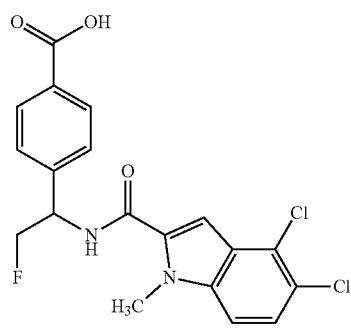 [SMILES: Cn1c(C(=O)NC(CF)c2ccc(C(=O)O)cc2)cc2c(Cl)c(Cl)ccc21]
I-6
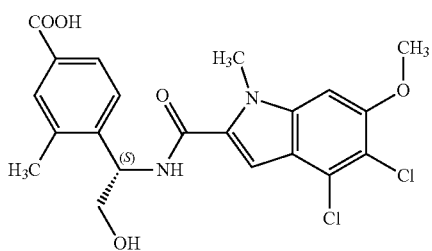
I-7

TABLE 1-continued
Exemplary Compounds
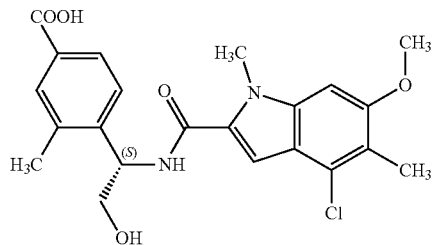
I-8
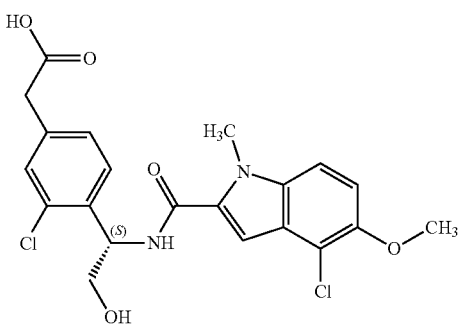
I-9
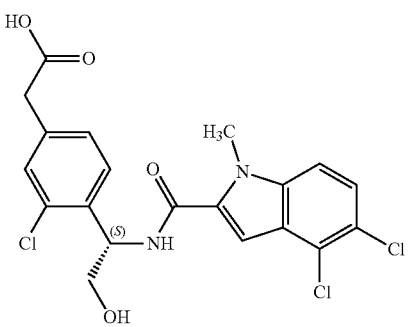
I-10
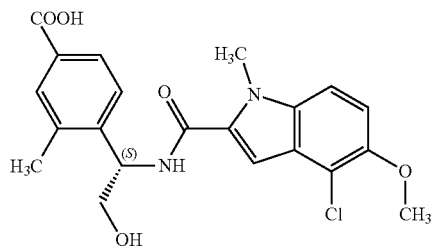
I-11
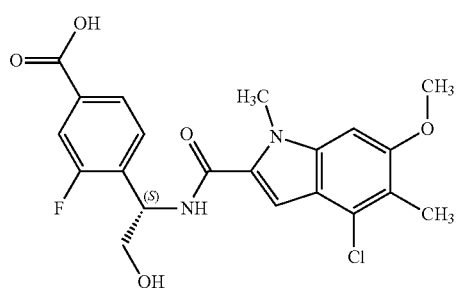
I-12

TABLE 1-continued
Exemplary Compounds
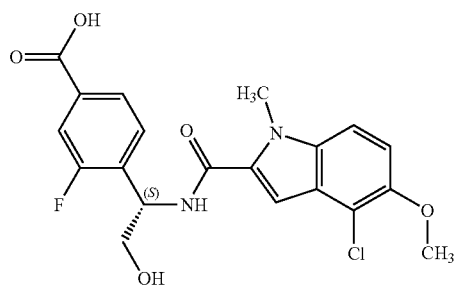
I-13
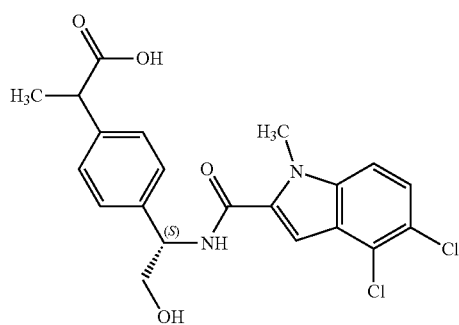
I-14
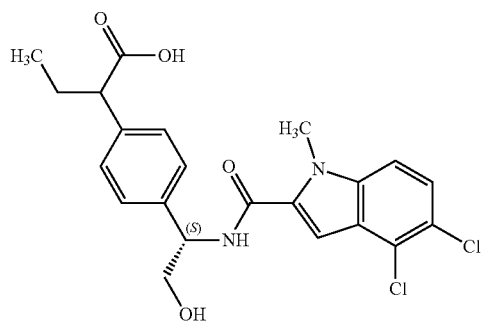
I-15
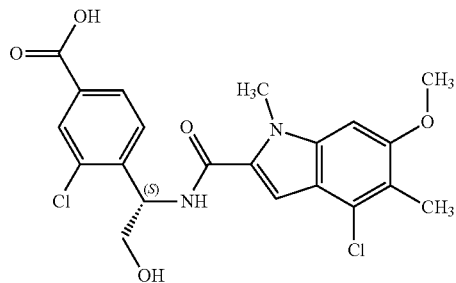
I-16
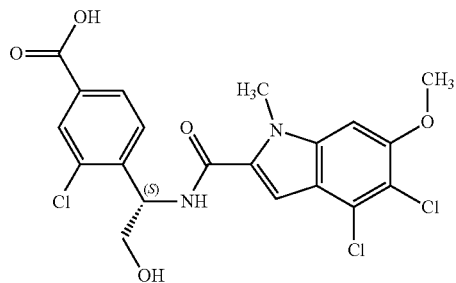
I-17

TABLE 1-continued
Exemplary Compounds
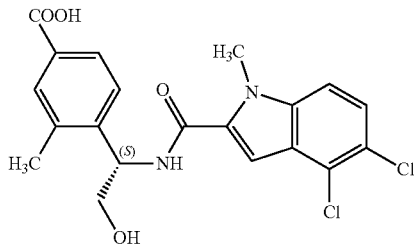
I-18
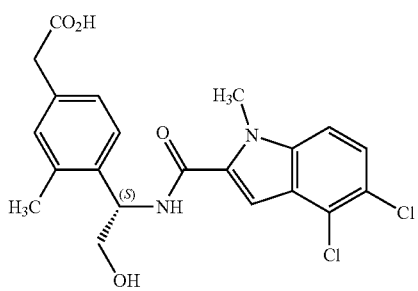
I-19
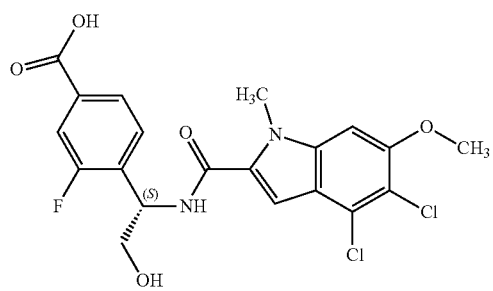
I-20
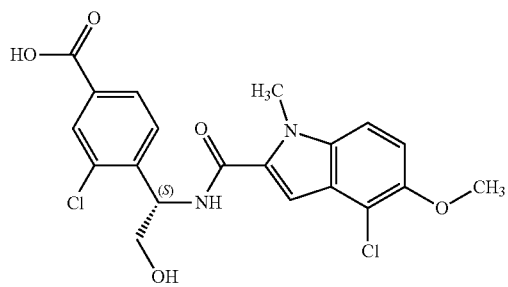
I-21
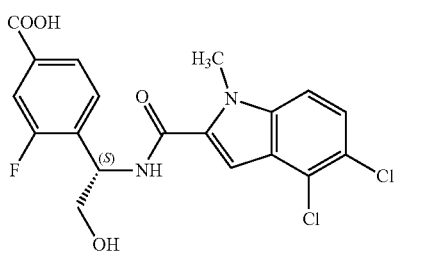
I-22

TABLE 1-continued
Exemplary Compounds
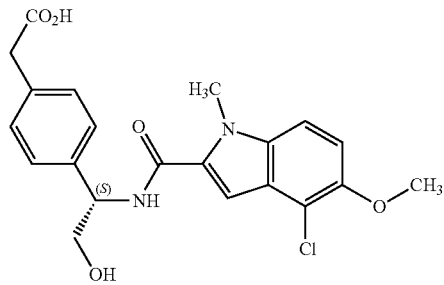
I-23
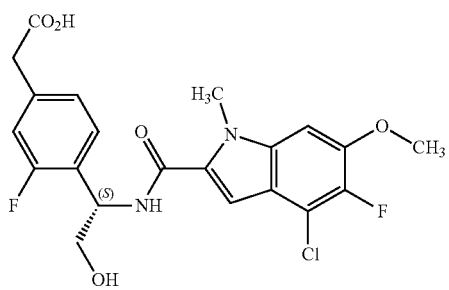
I-24
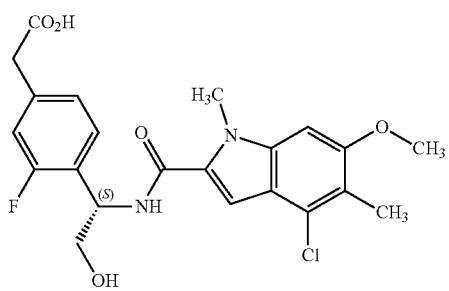
I-26
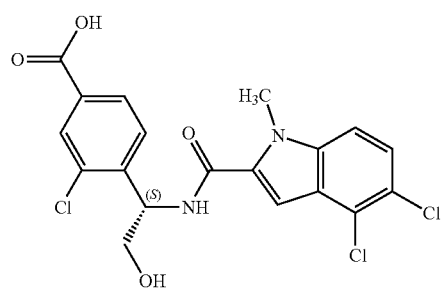
I-27
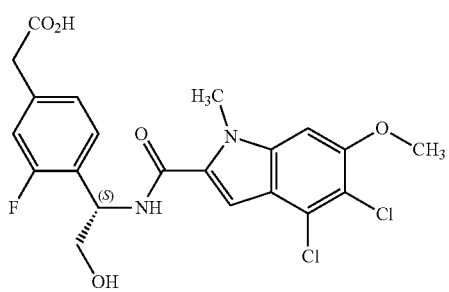
I-28

TABLE 1-continued
Exemplary Compounds
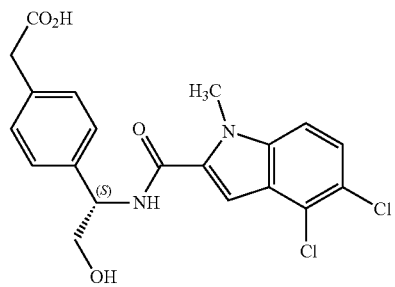
I-29
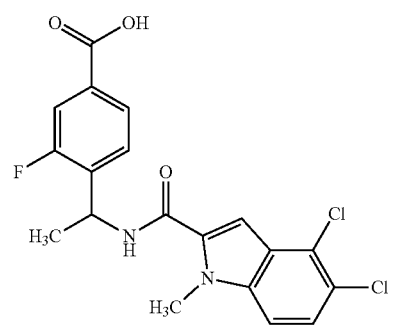 [SMILES: CC(NC(=O)c1cc2c(Cl)c(Cl)ccc2n1C)c1ccc(C(=O)O)cc1F]
I-30
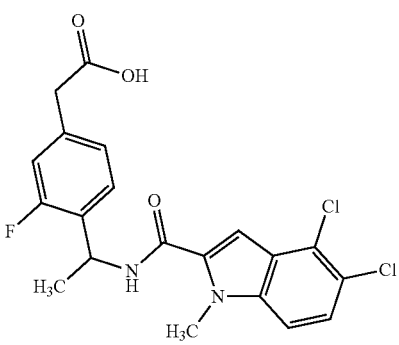 [SMILES: CC(NC(=O)c1cc2c(Cl)c(Cl)ccc2n1C)c1ccc(CC(=O)O)cc1F]
I-31
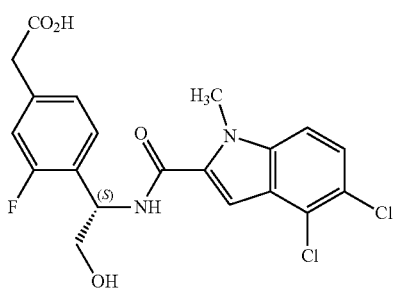
I-32
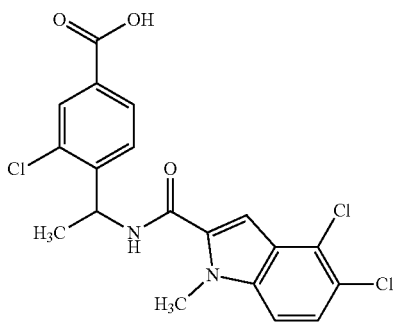 [SMILES: CC(NC(=O)c1cc2c(Cl)c(Cl)ccc2n1C)c1ccc(C(=O)O)cc1Cl]
I-33

TABLE 1-continued
Exemplary Compounds
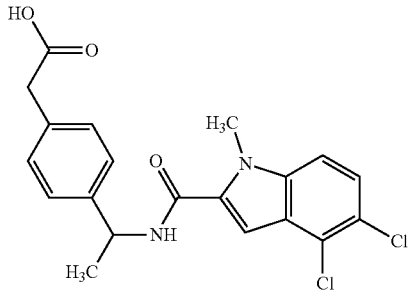 [SMILES: CC(NC(=O)c1cc2c(Cl)c(Cl)ccc2n1C)c1ccc(CC(=O)O)cc1]
I-34
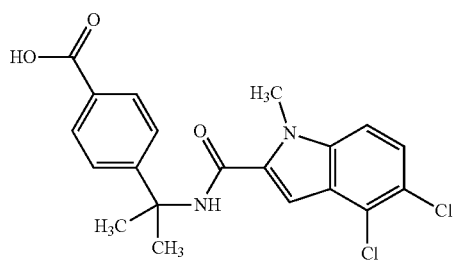 [SMILES: Cn1c(C(=O)NC(C)(C)c2ccc(C(=O)O)cc2)cc2c(Cl)c(Cl)ccc21]
I-35
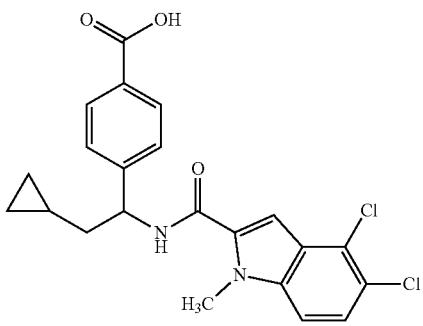 [SMILES: Cn1c(C(=O)NC(CC2CC2)c2ccc(C(=O)O)cc2)cc2c(Cl)c(Cl)ccc21]
I-36
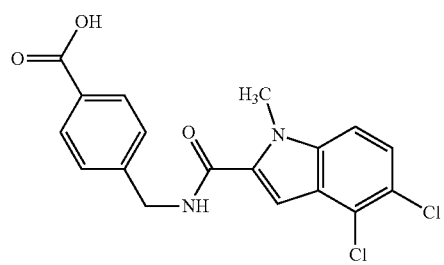 [SMILES: Cn1c(C(=O)NCc2ccc(C(=O)O)cc2)cc2c(Cl)c(Cl)ccc21]
I-37
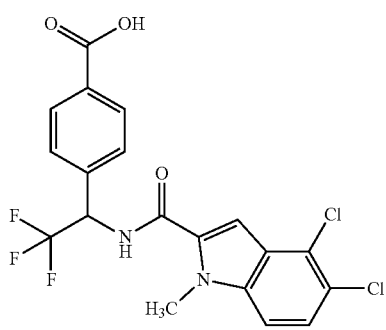 [SMILES: Cn1c(C(=O)NC(c2ccc(C(=O)O)cc2)C(F)(F)F)cc2c(Cl)c(Cl)ccc21]
I-38

TABLE 1-continued
Exemplary Compounds
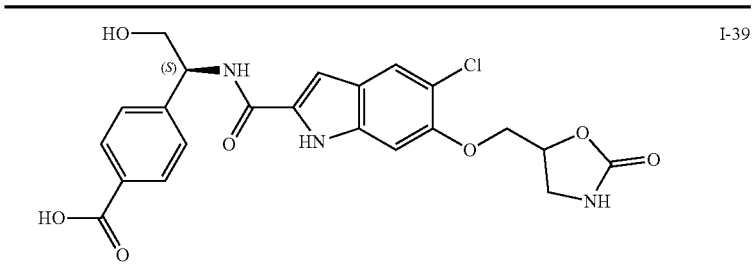
I-39
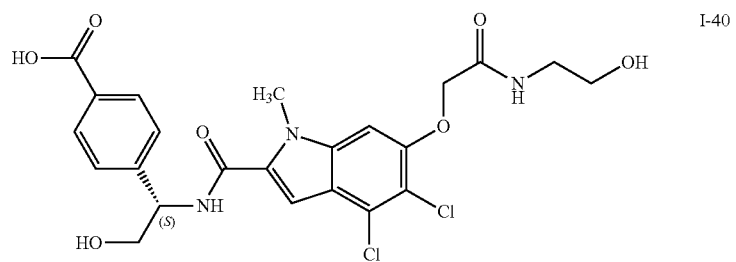
I-40
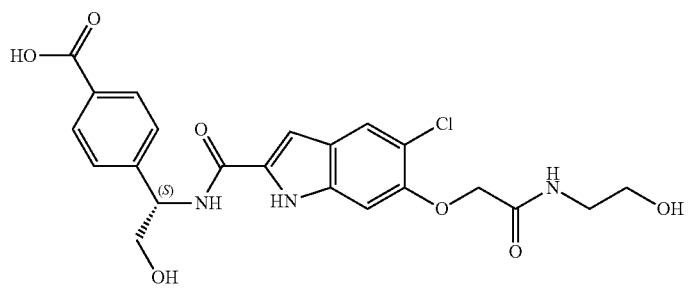
I-41
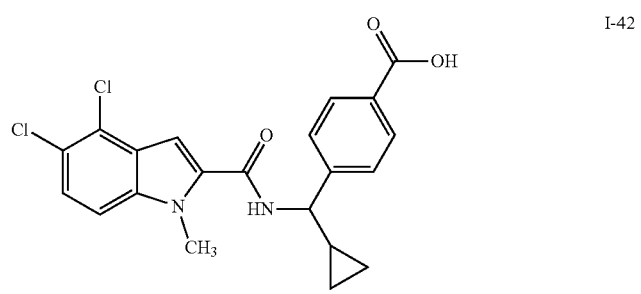
I-42
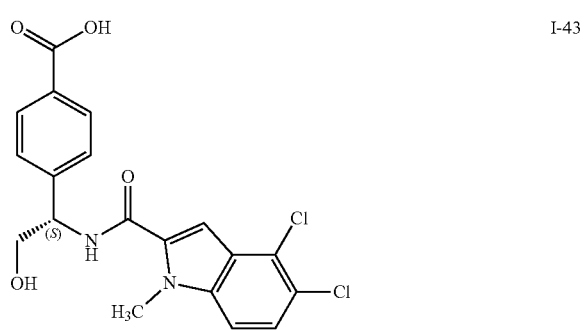
I-43

TABLE 1-continued

Exemplary Compounds

I-44, I-45, I-46, I-47, I-48

TABLE 1-continued

Exemplary Compounds

I-49

I-50

I-51

I-52

I-53

I-54 diastereomer 1

TABLE 1-continued

Exemplary Compounds

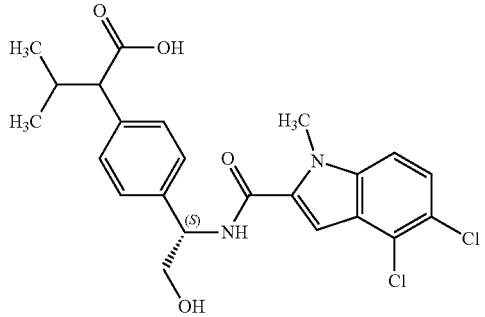

I-55 diastereomer 2

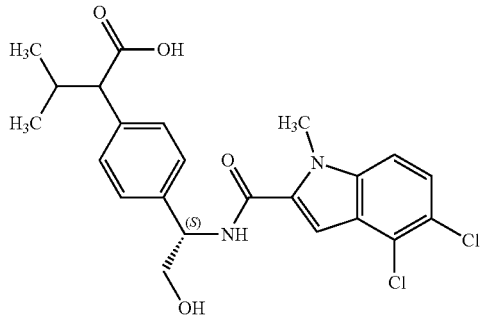

I-56 racemic

In certain embodiments, the present invention provides a compound depicted in Table 1, above, or a pharmaceutically acceptable salt thereof.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit PHGDH, or a mutant thereof, in a biological sample or in a patient. In certain embodiments, the amount of compound in compositions of this invention is such that is effective to measurably inhibit PHGDH, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of PHGDH, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of PHGDH or a mutant thereof.

The activity of a compound utilized in this invention as an inhibitor of PHGDH, or a mutant thereof, may be assayed in vitro, in vivo or in a cell line. In vitro assays include assays that determine inhibition of PHGDH, or a mutant thereof. Alternate in vitro assays quantitate the ability of the inhibitor to bind to PHGDH. Detailed conditions for assaying a compound utilized in this invention as an inhibitor of PHGDH, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of PHGDH and are therefore useful for treating one or more disorders associated with activity of PHGDH. Thus, in certain embodiments, the present invention provides a method for treating a PHGDH-mediated disorder comprising the step of administering to a patient in need thereof a compound of the present invention, or pharmaceutically acceptable composition thereof.

As used herein, the terms "PHGDH-mediated" disorders, diseases, and/or conditions as used herein means any disease or other deleterious condition in which PHGDH, or a mutant thereof, is known to play a role. Accordingly, another embodiment of the present invention relates to treating or lessening the severity of one or more diseases in which PHGDH, or a mutant thereof, are known to play a role.

In some embodiments, the present invention provides a method for treating one or more disorders, diseases, and/or conditions wherein the disorder, disease, or condition includes, but is not limited to, a cellular proliferative disorder.

Cellular Proliferative Disorders

The present invention features methods and compositions for the diagnosis and prognosis of cellular proliferative disorders (e.g., cancer) and the treatment of these disorders by targeting PHGDH of the serine biosynthetic pathway. Cellular proliferative disorders described herein include, e.g., cancer, obesity, and proliferation-dependent diseases. Such disorders may be diagnosed using methods known in the art.

Cancer

Cancer includes, in one embodiment, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). In some embodiments, the cancer is melanoma or breast cancer.

Cancers includes, in another embodiment, without limitation, mesothelioma, hepatobilliary (hepatic and billiary duct), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkin's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In some embodiments, the present invention provides a method for treating a tumor in a patient in need thereof, comprising administering to the patient any of the compounds, salts or pharmaceutical compositions described herein. In some embodiments, the tumor comprises any of the cancers described herein. In some embodiments, the tumor comprises melanoma cancer. In some embodiments, the tumor comprises breast cancer. In some embodiments, the tumor comprises lung cancer. In some embodiments the tumor comprises small cell lung cancer (SCLC). In some embodiments the tumor comprises non-small cell lung cancer (NSCLC).

In some embodiments, the tumor is treated by arresting further growth of the tumor. In some embodiments, the tumor is treated by reducing the size (e.g., volume or mass) of the tumor by at least 5%, 10%, 25%, 50%, 75%, 90% or 99% relative to the size of the tumor prior to treatment. In some embodiments, tumors are treated by reducing the quantity of the tumors in the patient by at least 5%, 10%, 25%, 50%, 75%, 90% or 99% relative to the quantity of tumors prior to treatment.

Other Proliferative Diseases

Other proliferative diseases include, e.g., obesity, benign prostatic hyperplasia, psoriasis, abnormal keratinization, lymphoproliferative disorders (e.g., a disorder in which there is abnormal proliferation of cells of the lymphatic system), chronic rheumatoid arthritis, arteriosclerosis, restenosis, and diabetic retinopathy. Proliferative diseases that are hereby incorporated by reference include those described in U.S. Pat. Nos. 5,639,600 and 7,087,648.

Inflammatory Disorders and Diseases

It has recently been reported that PHGDH gene expression, dictated by IL-2R signaling, is a crucial event for DNA synthesis during S phase of activated T cells. Jun do Y et al., *Cell Immunol.* 2014 February; 287(2):78-85. Compounds according to the invention are useful in the treatment of inflammatory or obstructive airways diseases, resulting, for example, in reduction of tissue damage, airways inflammation, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Compounds according to the invention are useful in the treatment of heteroimmune diseases. Examples of such heteroimmune diseases include, but are not limited to, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, such as therapy for or intended to restrict or abort symptomatic attack when it occurs, for example antiinflammatory or bronchodilatory. Prophylactic benefit in asthma may in particular be apparent in subjects prone to "morning dipping". "Morning dipping" is a recognized asthmatic syndrome, common to a substantial percentage of asthmatics and characterized by asthma attack, e.g. between the hours of about 4 to 6 am, i.e. at a time normally substantially distant form any previously administered symptomatic asthma therapy.

Compounds of the current invention can be used for other inflammatory or obstructive airways diseases and conditions to which the present invention is applicable and include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, but not limited to, acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

With regard to their anti-inflammatory activity, in particular in relation to inhibition of eosinophil activation, compounds of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is an disease of the skin. In some embodiments, the inflammatory disease of the skin is selected from contact dermatitits, atompic dermatitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, and other inflammatory or allergic conditions of the skin.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic juvenile idiopathic arthritis (SJIA), Cryopyrin Associated Periodic Syndrome (CAPS), and osteoarthritis.

In some embodiments the inflammatory disease which can be treated according to the methods of this invention is a TH17 mediated disease. In some embodiments the TH17 mediated disease is selected from Systemic lupus erythematosus, Multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Metabolic Disease

In some embodiments the invention provides a method of treating a metabolic disease. In some embodiments the metabolic disease is selected from Type 1 diabetes, Type 2 diabetes, metabolic syndrome or obesity.

The compounds and compositions, according to the method of the present invention, may be administered using any amount and any route of administration effective for treating or lessening the severity of a cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting PHGDH activity in a biological sample comprising the step of contacting said biological sample with a compound of this invention, or a composition comprising said compound.

According to another embodiment, the invention relates to a method of inhibiting PHGDH, or a mutant thereof, activity in a biological sample comprising the step of contacting said biological sample with a compound of this invention, or a composition comprising said compound. In certain embodiments, the invention relates to a method of irreversibly inhibiting PHGDH, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Another embodiment of the present invention relates to a method of inhibiting PHGDH in a patient comprising the step of administering to said patient a compound of the present invention, or a composition comprising said compound.

According to another embodiment, the invention relates to a method of inhibiting PHGDH, or a mutant thereof, activity in a patient comprising the step of administering to said patient a compound of the present invention, or a composition comprising said compound. According to certain embodiments, the invention relates to a method of irreversibly inhibiting PHGDH, or a mutant thereof, activity in a patient comprising the step of administering to said patient a compound of the present invention, or a composition comprising said compound. In other embodiments, the present invention provides a method for treating a disorder mediated by PHGDH, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethyl-amino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™ Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecin and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtubulin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; colchicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the Axl receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; ilmofosine; RO 318220 and RO 320432; GO 6976; Isis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2α, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S.

Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl) {2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Methods of Providing the Present Compounds

The compounds of this invention may be prepared or isolated in general by synthetic and/or semi-synthetic methods known to those skilled in the art for analogous compounds and by methods described in detail in the Examples, herein.

In the Schemes below, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 5$^{th}$ Edition, John Wiley & Sons, 2001, *Comprehensive Organic Transformations*, R. C. Larock, 2$^{nd}$ Edition, John Wiley & Sons, 1999, and *Protecting Groups in Organic Synthesis*, T. W. Greene and P. G. M. Wuts, 3$^{rd}$ edition, John Wiley & Sons, 1999, the entirety of each of which is hereby incorporated herein by reference.

As used herein, the phrase "leaving group" (LG) includes, but is not limited to, halogens (e.g. fluoride, chloride, bromide, iodide), sulfonates (e.g. mesylate, tosylate, benzenesulfonate, brosylate, nosylate, triflate), diazonium, and the like.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, 3$^{rd}$ edition, John Wiley & Sons, 1999, and Philip Kocienski, in "Protecting Groups", Georg Thieme Verlag Stuttgart, N.Y., 1994, the entireties of which is incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl) ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, 3$^{rd}$ edition, John Wiley & Sons, 1999, and Philip Kocienski, in "Protecting Groups", Georg Thieme Verlag Stuttgart, N.Y., 1994, the entireties of which is incorporated herein by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. See, for example, *"March's Advanced* Organic Chemistry", 5$^{th}$ Ed., Ed.: Smith, M. B. and March, J., John Wiley & Sons, New York: 2001, the entirety of which is incorporated herein by reference. Such interconversions may require one or more of the aforementioned techniques, and certain methods for synthesizing compounds of the invention are described below.

In one aspect, certain compounds of the present invention of formula I, or subformulae thereof, are generally prepared according to Scheme 1 set forth below:

Scheme 1

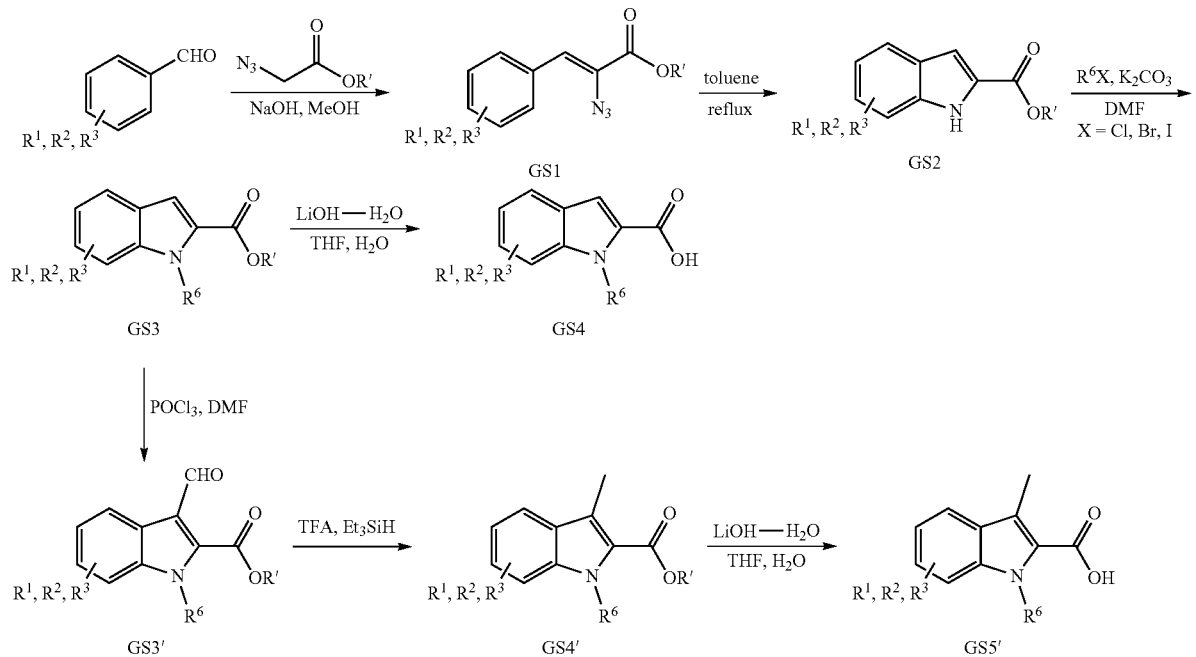

In Scheme 1 above, R' is a group such as $C_{1-6}$ aliphatic, 5- to 8-membered aromatic ring, or other functionality compatible with an ester; and $R^1$, $R^2$, $R^3$, and $R^6$ are selected consistent with formula I above and below and in classes and subclasses as described herein.

In one aspect, the present invention provides methods for preparing compounds of formula GS4 as described in Scheme 1. An optionally substituted benzaldehyde may be condensed with an azidoacetate in the presence of base such as sodium hydroxide or sodium methoxide to give intermediate GS1. Heating GS1 in a solvent such as toluene (e.g., at reflux) provides the indole-2-carboxylate ester. In some embodiments, the indole nitrogen is alkylated using an appropriate alkyl halide such as methyl or ethyl iodide and a suitable base such as, but not limited, to sodium hydride, potassium tert-butoxide, or potassium carbonate in a suitable solvent to provide GS3. In some embodiments, the ester of GS3 is hydrolyzed using a base such as LiOH, KOH or NaOH in a solvent such as a mixture of water and THF to provide an intermediate used in the synthesis of compounds of the invention of general structure GS4.

Alternatively, in some embodiments GS3 may be treated with appropriate reagents such as $POCl_3$ and DMF to give GS3'. In some embodiments, the aldehyde in GS3' is then reduced to a methyl group with appropriate reagents such as $Et_3SiH$ and TFA to give GS4'. Finally, in some embodiments, hydrolysis of the ester in GS4' provides an intermediate used in the synthesis of compounds of the invention of general structure GS5'.

In another aspect, compounds of the present invention of formula I, or subformulae thereof, are generally prepared according to Scheme 2 set forth below:

Scheme 2

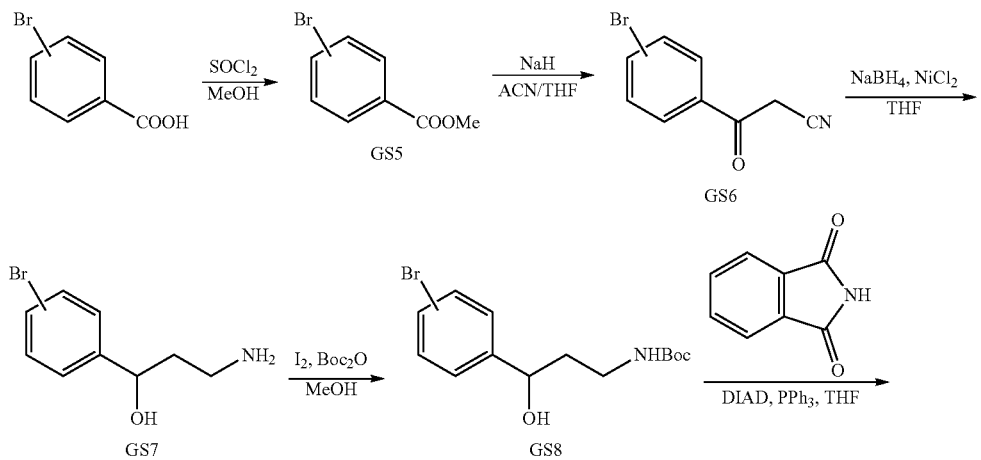

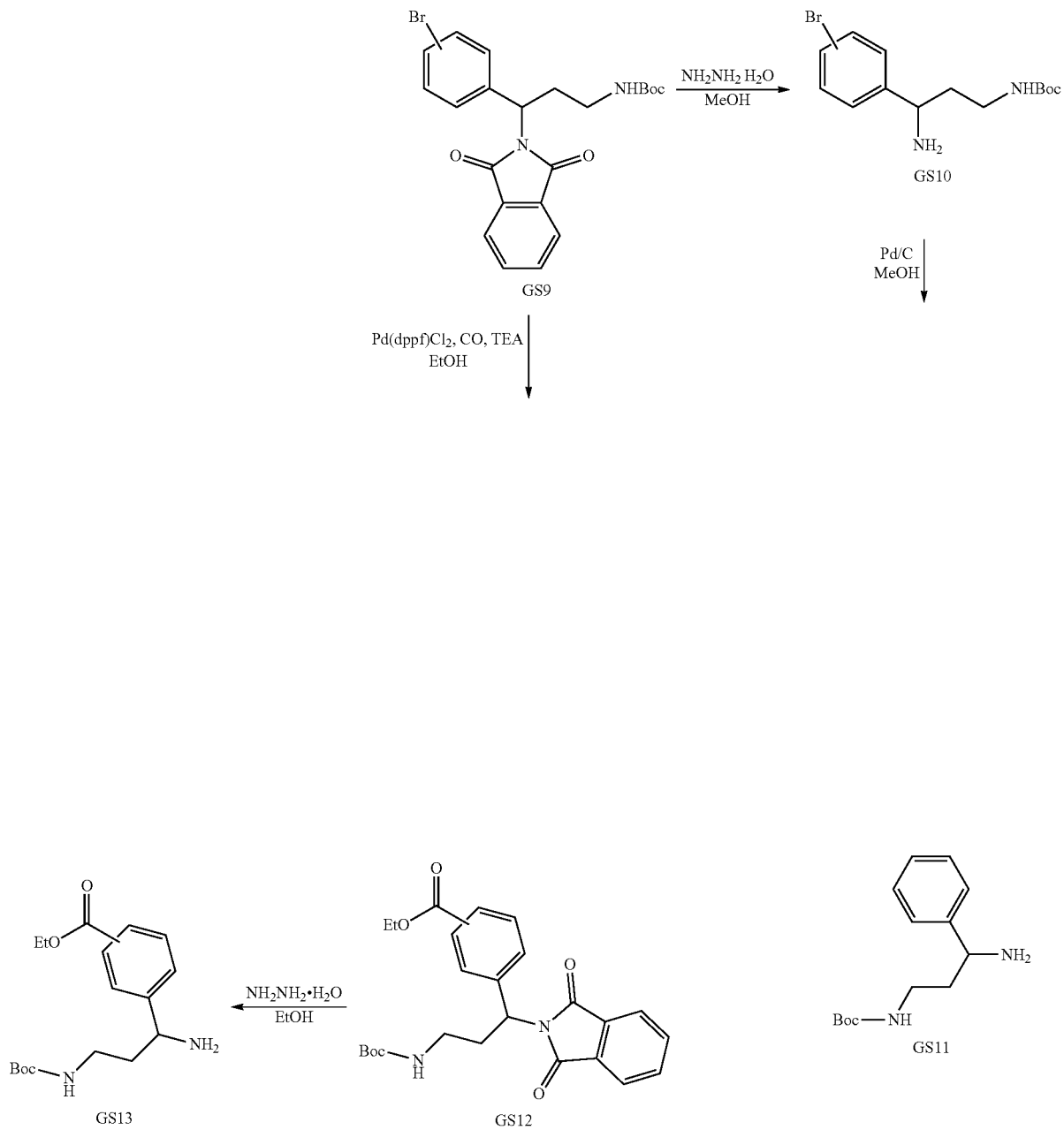

Optionally substituted benzoic acids (e.g. bromide or other halide-substituted) can be converted to the ester GS5 by reacting with reagents such as thionyl chloride in methanol. Heating GS5 in a mixture of acetonitrile and tetrahydrofuran with sodium hydride leads to GS6. Reduction with nickel chloride hexahydrate and sodium borohydride in tetrahydrofuran gives GS7. The amine can be protected under standard conditions with di-tert-butyl dicarbonate and iodine in methanol. The alcohol of GS8 can then be transformed to the indoline-dione by coupling with isoindoline-1,3-dione (phthalimide), diisopropyl azodicarboxylate (DIAD), and triphenylphosphine in tetrahydrofuran. Heating GS9 with hydrazine hydrate in an appropriate solvent such as methanol or ethanol leads to amine GS10. The bromide or other halide can then be removed with conditions such as hydrogenation with palladium/charcoal under hydrogen atmosphere (50 psi) in methanol to give GS11.

Alternatively, GS9 can be coupled with Pd(dppf)Cl$_2$*CH$_2$Cl$_2$ and triethylamine in ethanol in the presence of carbon monoxide (50 psi) to convert the bromide to ester GS12. The amine GS13 can then be formed as described for GS10.

In another aspect, compounds of the present invention of formula I, or subformulae thereof, are generally prepared according to Scheme 3 set forth below:

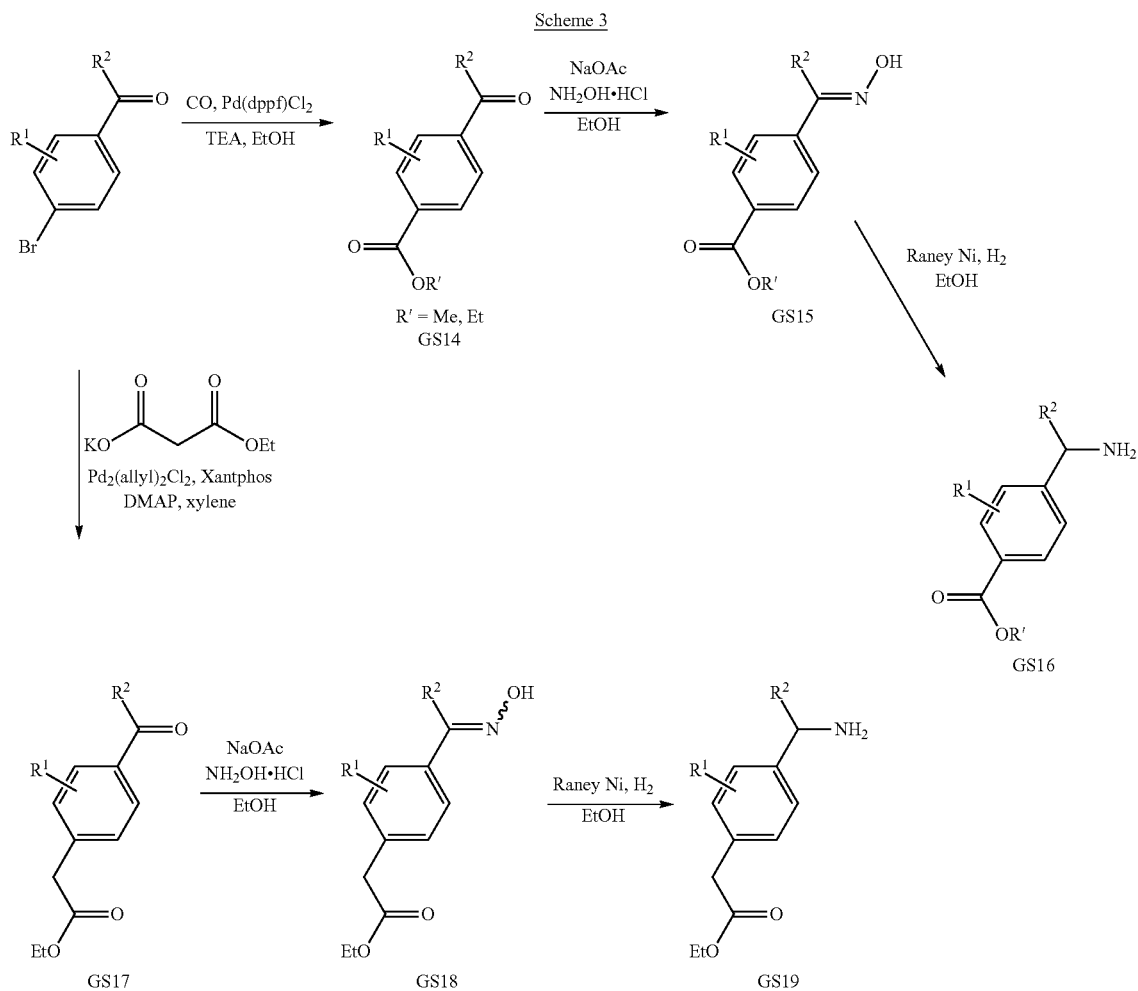

A variety of bromophenylketones in Scheme 3 (R1 is a group such as those disclosed in Table 1 R$^2$ can be one of various groups including CF$_3$, alkyl, cycloalkyl, or nitrogen containing C$_{1-6}$ alkyl and cycloalkyl) can be treated with a catalyst such as Pd(dppf)Cl$_2$ in an appropriate solvent such as ethanol or methanol in the presence of carbon monoxide (50 psi) with heating to form ester GS14. The carbonyl can then converted to oxime GS15 by treatment with appropriate reagents such as hydroxylamine hydrochloride and sodium acetate in ethanol with heating. GS15 can then be reduced under standard hydrogenation conditions such as Raney nickel under hydrogen atmosphere (50 psi) in ethanol to form GS16.

Alternatively, the bromophenylketone can be coupled with (3-ethoxy-3-oxo-propanoyl)oxypotassium by reacting with allyl(chloro)palladium, Xantphos, and DMAP in xylene to form GS17. The carbonyl can then be further elaborated to oxime GS18 and amine GS19 via the method described for GS15 and GS16, respectively.

In another aspect, compounds of the present invention of formula I, or subformulae thereof, are generally prepared according to Scheme 4 set forth below:

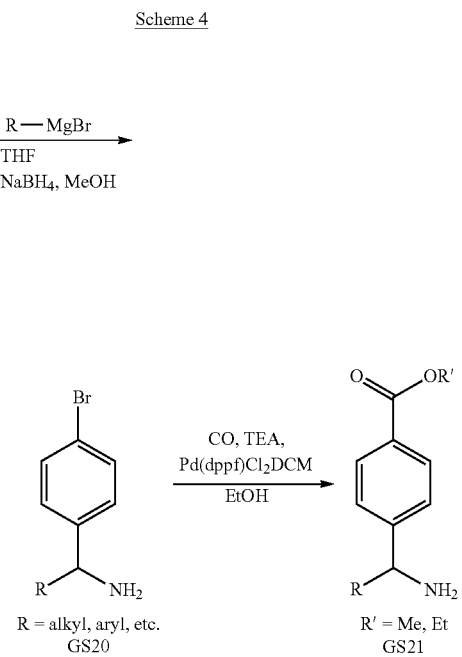

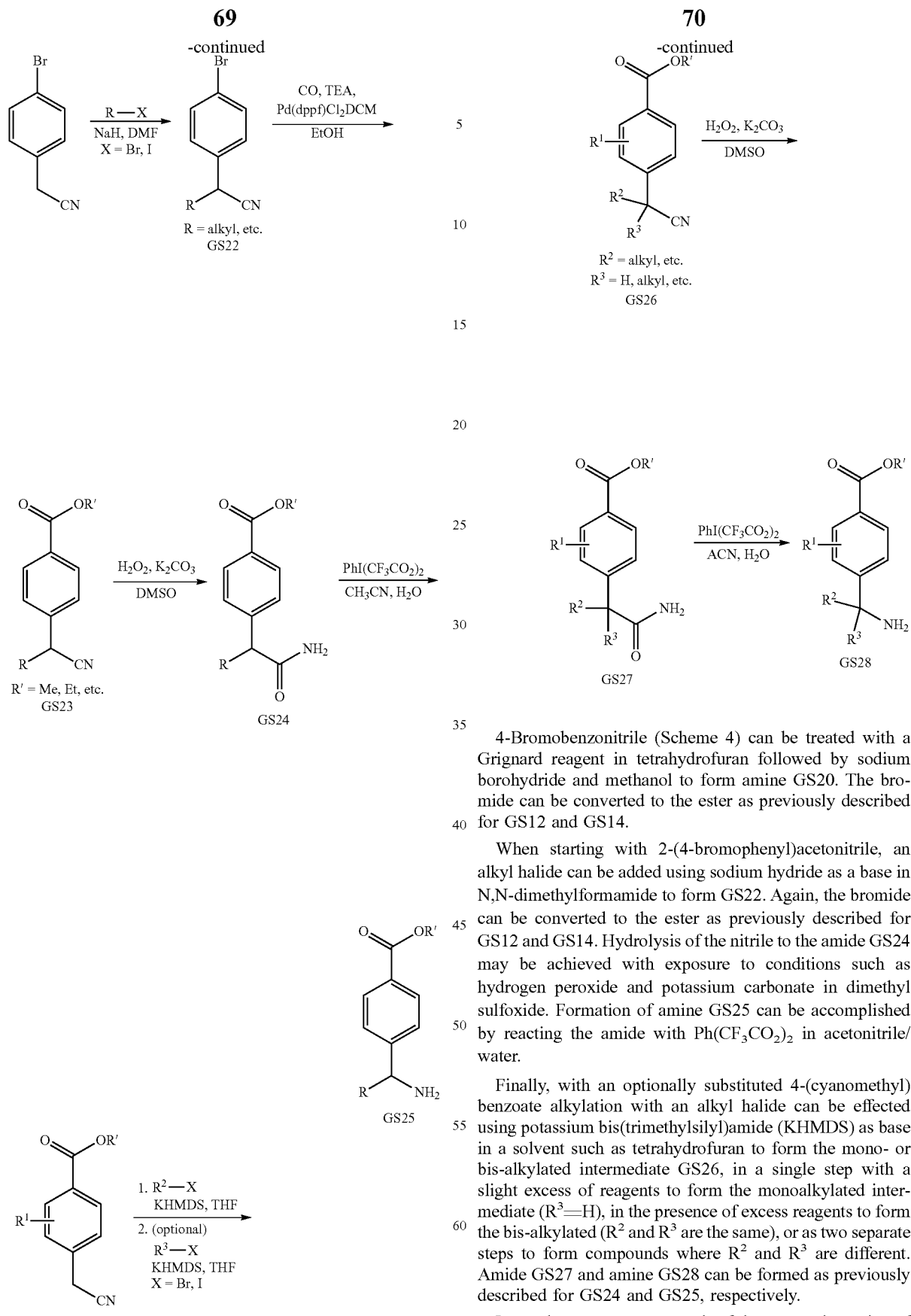

4-Bromobenzonitrile (Scheme 4) can be treated with a Grignard reagent in tetrahydrofuran followed by sodium borohydride and methanol to form amine GS20. The bromide can be converted to the ester as previously described for GS12 and GS14.

When starting with 2-(4-bromophenyl)acetonitrile, an alkyl halide can be added using sodium hydride as a base in N,N-dimethylformamide to form GS22. Again, the bromide can be converted to the ester as previously described for GS12 and GS14. Hydrolysis of the nitrile to the amide GS24 may be achieved with exposure to conditions such as hydrogen peroxide and potassium carbonate in dimethyl sulfoxide. Formation of amine GS25 can be accomplished by reacting the amide with $Ph(CF_3CO_2)_2$ in acetonitrile/water.

Finally, with an optionally substituted 4-(cyanomethyl)benzoate alkylation with an alkyl halide can be effected using potassium bis(trimethylsilyl)amide (KHMDS) as base in a solvent such as tetrahydrofuran to form the mono- or bis-alkylated intermediate GS26, in a single step with a slight excess of reagents to form the monoalkylated intermediate ($R^3$=H), in the presence of excess reagents to form the bis-alkylated ($R^2$ and $R^3$ are the same), or as two separate steps to form compounds where $R^2$ and $R^3$ are different. Amide GS27 and amine GS28 can be formed as previously described for GS24 and GS25, respectively.

In another aspect, compounds of the present invention of formula I, or subformulae thereof, are generally prepared according to Scheme 5 set forth below:

Scheme 5

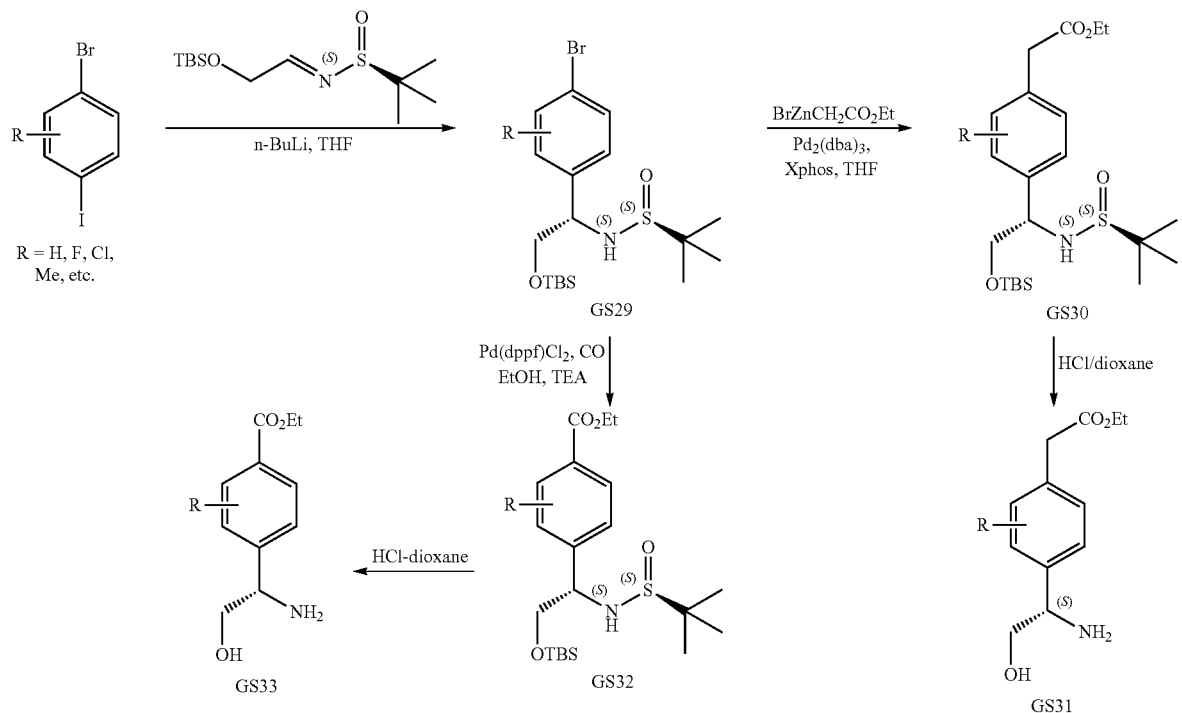

The corresponding substituted or unsubstituted 4-bromo-1-iodobenzene in Scheme 5 can be treated with n-butyllithium followed by (S,E)-N-(2-((tert-butyldimethyl silyl)oxy)ethylidene)-2-methylpropane-2-sulfinamide to form intermediate GS29. The bromide can then be coupled under appropriate conditions such as bromo-(2-ethoxy-2-oxo-ethyl)zinc using $Pd_2(dba)_3$ and XPhos in tetrahydrofuran with heating to give GS30. Deprotection is achieved under standard conditions using hydrochloric acid in dioxane or methanol to give GS31.

Alternatively, an ester may be installed at the bromine position of GS29 by treatment with $Pd(dppf)Cl_2 \cdot CH_2Cl_2$ and triethylamine in ethanol in the presence of CO gas (50 psi) to give GS32. Deprotection to form GS33 can be achieved as described for GS31.

In another aspect, compounds of the present invention of formula I, or subformulae thereof, are generally prepared according to Scheme 6 set forth below:

Scheme 6

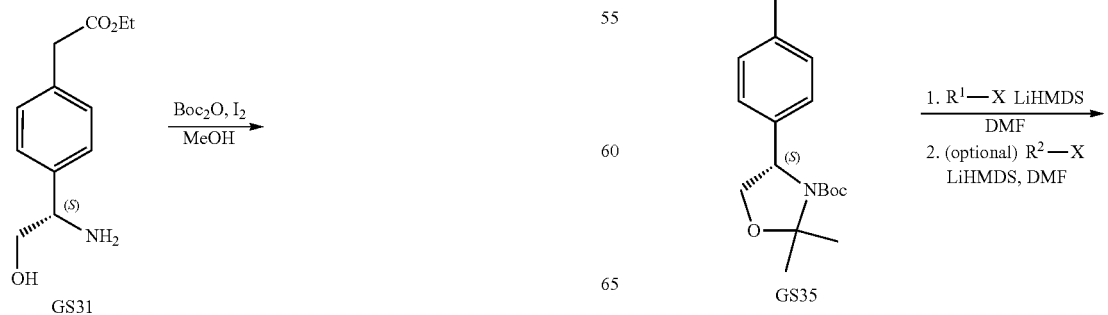

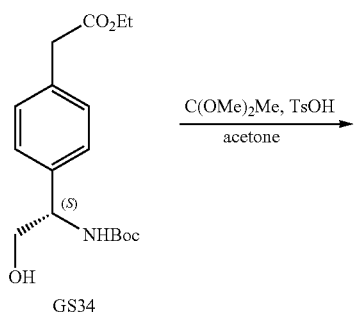

-continued

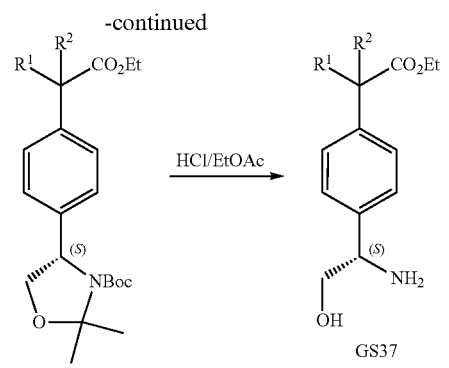

R¹ = alkyl
R² = H, alkyl
GS36

Intermediate GS31 in Scheme 6 can be treated with iodine and di-tert-butyl dicarbonate in dichloromethane to form protected amine GS34. Reacting GS34 with appropriate reagents such as 2,2-dimethoxypropane and p-toluenesulfonic acid (TsOH) in acetone gives GS35. GS35 can then be alkylated with a variety of alky halides with an appropriate base such as LiHMDS in an appropriate solvent such as N,N-dimethylformamide or tetrahydrofuran to give either the mono or bis alkylated product GS36. Deprotection with hydrogen chloride in ethyl acetate or dioxane gives amine GS37.

In another aspect, compounds of the present invention of formula I, or subformulae thereof, are generally prepared according to Scheme 7 set forth below:

-continued

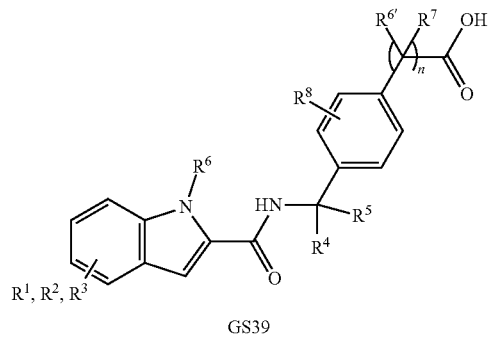

n = 0, 1
R' = Me, Et

In Scheme 7, $R^1$, $R^2$, $R^3$, $R^4$, $R^5$, $R^6$, $R^{6'}$, $R^7$, and $R^8$ are selected consistent with formula I, or subformulae thereof, as described above and below. Conversion of the acid group in GS4 in Scheme 7 to the acid chloride can be done using procedures well known to one skilled in the art. For example, the acid GS4 can be treated with oxalyl chloride or thionyl chloride with a catalytic amount of DMF in a solvent such as DCM. Reaction of the acid chloride intermediate with an amine of choice in the presence of a base such as triethylamine or diisopropylethylamine affords GS38. Hydrolysis of the ester can be achieved with lithium hydroxide in tetrahydrofuran and water to form the final acid product GS39.

In another aspect, compounds of the present invention of formula I, or subformulae thereof, are generally prepared according to Scheme 8 set forth below:

Scheme 7

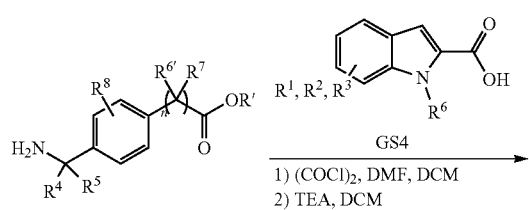

Scheme 8

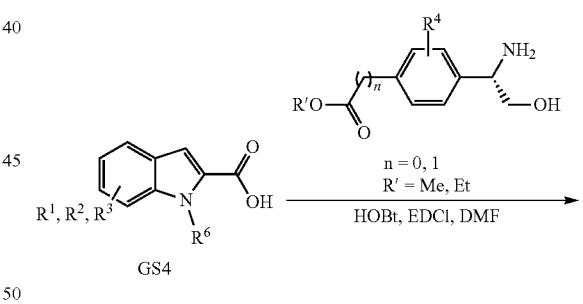

n = 0, 1
R' = Me, Et

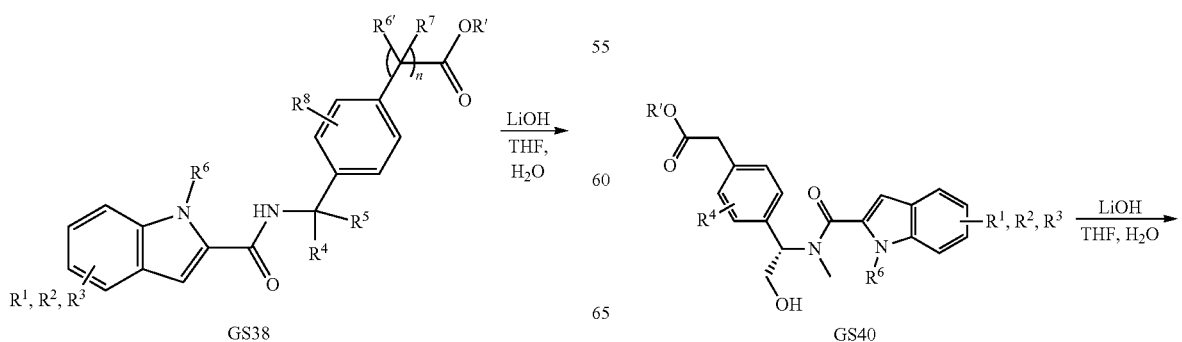

-continued

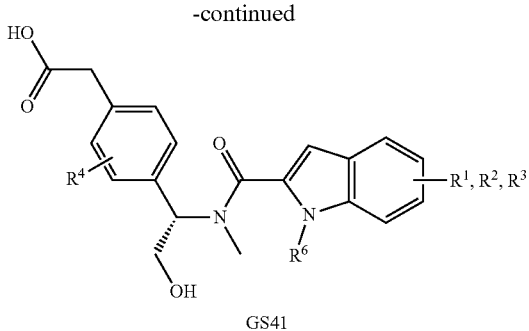

GS41

In Scheme 7, $R^1$, $R^2$, $R^3$, $R^4$, and $R^6$ are selected consistent with formula I, or subformulae thereof, as described above and below. Acid GS4 in Scheme 8 can be coupled with a variety of amines with EDCI and HOBt in DMF to form GS40. Hydrolysis of the ester to form GS41 can be effected as described for GS39 above.

In another aspect, compounds of the present invention of formula I, or subformulae thereof, are generally prepared according to Scheme 9 set forth below:

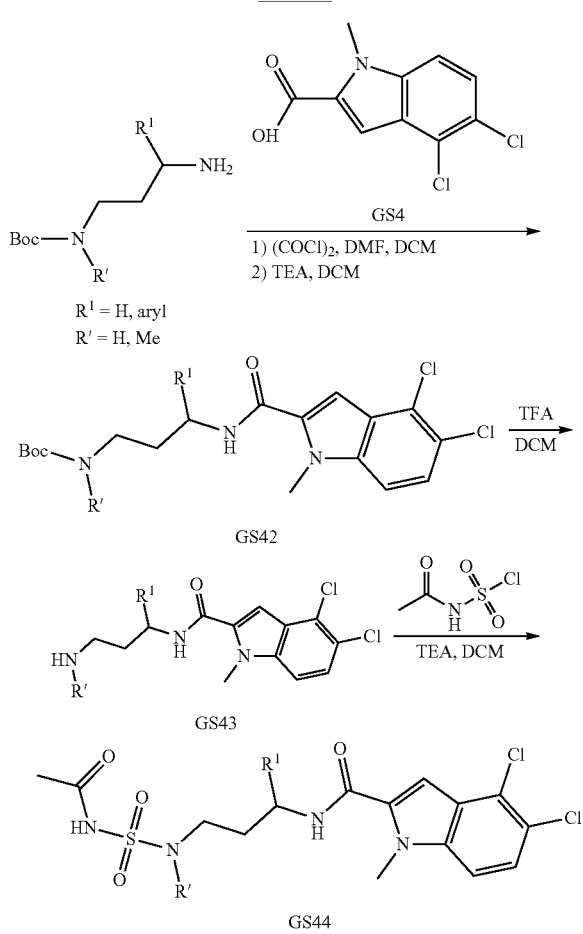

Acid GS4 in Scheme 9 can be coupled with a variety of amines to form product GS42 as previously described for GS38. Deprotection of the Boc with trifluoracetic acid in dichloromethane can be used to give amine GS43. The amine can then be coupled with N-acetylsulfamoyl chloride in dichloromethane to form final product GS44.

Abbreviations

Ac: acetyl
AcOH: acetic acid
ACN: acetonitrile
Ad: adamantyl
AIBN: 2,2'-azo bisisobutyronitrile
Anhyd: anhydrous
Aq: aqueous
BINAP: 2,2'-bis(diphenylphosphino)-1,1'-binaphthyl
$BH_3$: Borane
Bn: benzyl
Boc: tert-butoxycarbonyl
$Boc_2O$: di-tert-butyl dicarbonate
BPO: benzoyl peroxide
nBuOH: n-butanol
cSFC: chiral supercritical fluid chromatography
COD: cyclooctadiene
d: days
DAST: diethylaminosulfur trifluoride
dba: dibenzylideneacetone
DBU: 1,8-diazobicyclo[5.4.0]undec-7-ene
DCE: 1,2-dichloroethane
DCM: dichloromethane
DEA: diethylamine
DIBAL-H: diisobutylaluminum hydride
DIPEA or DIEA: N,N-diisopropylethylamine
DMA: N,N-dimethylacetamide
DME: 1,2-dimethoxyethane
DMAP: 4-dimethylaminopyridine
DMF: N,N-dimethylformamide
DMSO-dimethyl sulfoxide
DPPA: diphenylphosphoryl azide
dppf: 1,1'-bis(diphenylphosphino)ferrocene
EDC or EDCI: 1-(3-dimethylaminopropyl)-3-ethylcarbodiimide hydrochloride
ee: enantiomeric excess
ESI: electrospray ionization
EA: ethyl acetate
EtOAc: ethyl acetate
EtOH: ethanol
FA: formic acid
h: hours
HATU: N,N,N',N'-tetramethyl-O-(7-azabenzotriazol-1-yl)uronium hexafluorophosphate
HCl: hydrochloric acid
HPLC: high performance liquid chromatography
HOAc: acetic acid
IPA: isopropyl alcohol
KHMDS: potassium hexamethyldisilazide
$K_2CO_3$: potassium carbonate
LAH: lithium aluminum hydride
LDA: lithium diisopropylamide
LiHMDS: lithium bis(trimethylsilyl)amide
m-CPBA: meta-chloroperbenzoic acid
M: molar
MeCN: acetonitrile
MeOH: methanol
$Me_2S$: dimethyl sulfide
MeONa: sodium methoxide
MeI: iodomethane
min: minutes
mL: milliliters
mM: millimolar mmol: millimoles
MOMCl: methyl chloromethyl ether
MsCl: methanesulfonyl chloride
MTBE: methyl tert-butyl ether
NaNO$_2$: sodium nitrite
Na$_2$SO$_4$: sodium sulfate
NBS: N-bromosuccinimide
NCS: N-chlorosuccinimide
NaOH: sodium hydroxide
NMP: N-methylpyrrolidine
NMR: Nuclear Magnetic Resonance
° C.: degrees Celsius
Pd/C: Palladium on Carbon
Pd(OAc)$_2$: Palladium Acetate
PBS: phosphate buffered saline
PE: petroleum ether
POCl$_3$: phosphorus oxychloride
PPh$_3$: triphenylphosphine
Rel: relative
R.T. or rt: room temperature
sat: saturated
SEMCl: chloromethyl-2-trimethyl silylethyl ether
SFC: supercritical fluid chromatography
SOCl$_2$: thionyl chloride
tBuOK: potassium tert-butoxide
TBAB: tetrabutylammonium bromide
TEA: triethylamine
Tf: trifluoromethanesulfonate
TfAA: trifluoromethanesulfonic anhydride
TFA: trifluoroacetic acid
TIPS: triisopropylsilyl
THF: tetrahydrofuran
THP: tetrahydropyran
TLC: thin layer chromatography
TMEDA: tetramethylethylenediamine
pTSA: para-toluenesulfonic acid
Xantphos: 4,5-bis(diphenylphosphino)-9,9-dimethylxanthene The following examples are intended to illustrate the invention and are not to be construed as being limitations thereon. Unless otherwise stated, one or more tautomeric forms of compounds of the examples described hereinafter may be prepared in situ and/or isolated. All tautomeric forms of compounds of the examples described hereafter should be considered to be disclosed. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions are carried out under nitrogen or argon unless otherwise stated. Optical rotations were measured in MeOH.

Proton NMR ($^1$H NMR) is conducted in deuterated solvent. In certain compounds disclosed herein, one or more $^1$H shifts overlap with residual protio solvent signals; these signals have not been reported in the experimental provided hereinafter.

Analytical Instruments Table

| | |
|---|---|
| LCMS | Shimadzu UFLC MS: LCMS-2020 |
| | Agilent Technologies 1200 series MS: Agilent Technologies 6110 |
| | Agilent Technologies 1200 series MS: LC/MSD VL |
| NMR | BRUKER AVANCE III/400; Frequency (MHz) 400.13; Nucleus: 1H; Number of Transients: 8 |
| Prep-HPLC | Gilson GX-281 systems: instruments GX-A, GX-B, GX-C, GX-D, GX-E, GX-F, GX-G and GX-H |
| GCMS | SHIMADZU GCMS-QP2010 Ultra |
| Analytical cSFC | Agilent Technologies 1290 Infinity |
| Prep-cSFC | Waters SFC Prep 80 |

For Acidic LCMS Data:
LCMS was recorded on an Agilent 1200 Series LC/MSD or Shimadzu LCMS2020 equipped with electro-spray ionization and quadruple MS detector [ES+ve to give MH$^+$] and equipped with Chromolith Flash RP-18e 25*2.0 mm, eluting with 0.0375 vol % TFA in water (solvent A) and 0.01875 vol % TFA in acetonitrile (solvent B).

For Basic LCMS Data:
LCMS was recorded on an Agilent 1200 Series LC/MSD or Shimadzu LCMS 2020 equipped with electro-spray ionization and quadruple MS detector [ES+ve to give MH$^+$] and equipped with Xbridge C18, 2.1×50 mm columns packed with 5 mm C18-coated silica or Kinetex EVO C18 2.1×30 mm columns packed with 5 mm C18-coated silica, eluting with 0.05 vol % NH$_3$.H$_2$O in water (solvent A) and acetonitrile (solvent B).

Synthesis of Intermediates 4,5-Dichloro-1-methyl-indole-2-carboxylic Acid
(Intermediate A)

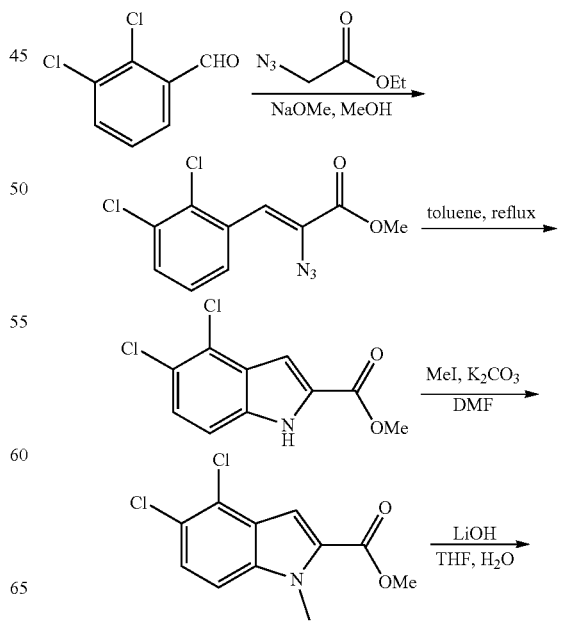

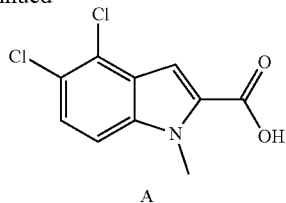

A

Step 1—Methyl (Z)-2-azido-3-(2,3-dichlorophenyl) prop-2-enoate

To a solution of sodium methoxide (11.1 g, 205 mmol) in anhydrous methanol (80 mL) was added a mixed solution of 2,3-dichlorobenzaldehyde (12.0 g, 68.5 mmol) and ethyl 2-azidoacetate (26.5 g, 205 mmol) in anhydrous methanol (80 mL) at −50° C. After stirring at −50° C. for 2 hrs, the mixture was warmed to rt, and stirred for 14 hrs. On completion, the suspension was poured onto ice and the azido derivative was collected by filtration, washed with cold water. The filter cake was dried in vacuo and purified by column chromatography (petroleum ether/ethyl acetate=10/1) to give the title compound. $^1$H NMR (400 MHz, CDCl$_3$) δ=8.06 (dd, J=1.3, 8.0 Hz, 1H), 7.45 (dd, J=1.4, 8.0 Hz, 1H), 7.30-7.24 (m, 2H), 3.97 (s, 3H).

Step 2—Methyl 4,5-dichloro-1H-indole-2-carboxylate

A solution of methyl (Z)-2-azido-3-(2,3-dichlorophenyl) prop-2-enoate (7.80 g, 28.6) in toluene (150 mL) was stirred at 120° C. for 16 hrs. On completion, the toluene was removed in vacuo to give a residue. The residue was purified by column chromatography (petroleum ether/ethyl acetate=12/1 to 5/1) to give the title compound. $^1$H NMR (400 MHz, DMSO-d$_6$) δ=12.52 (br. s., 1H), 7.47-7.41 (m, 2H), 7.12 (d, J=2.1 Hz, 1H), 3.90 (s, 3H).

Step 3—Methyl 4,5-dichloro-1-methyl-indole-2-carboxylate

To a solution of methyl 4,5-dichloro-1H-indole-2-carboxylate (4.50 g, 18.4 mmol) in N,N-dimethylformamide (40 mL) was added potassium carbonate (6.37 g, 46.1 mmol) and iodomethane (10.4 g, 73.7 mmol). The mixture was stirred at 60° C. for 16 hrs. On completion, the reaction mixture was concentrated in vacuo to remove solvent. The residue was diluted with water 30 mL and extracted with dichloromethane (3×15 mL). The combined organic layer was dried over sodium sulfate, filtered and concentrated in vacuo to give a residue. The residue was purified by column chromatography (petroleum ether/ethyl acetate=8/1 to 3/1) to give the title compound.

$^1$H NMR (400 MHz, DMSO-d$_6$) δ=7.69 (d, J=8.8 Hz, 1H), 7.53 (d, J=8.8 Hz, 1H), 7.22 (s, 1H), 4.05 (s, 3H), 3.89 (s, 3H).

Step 4—4,5-Dichloro-1-methyl-indole-2-carboxylic Acid

To a solution of methyl 4,5-dichloro-1-methyl-indole-2-carboxylate (4.10 g, 15.8 mmol) in a mixture solvent of tetrahydrofuran (40 mL) and water (10 mL) was added lithium hydroxide (1.14 g, 47.6 mmol). The mixture was stirred at rt for 16 hrs. On completion, the reaction mixture was concentrated in vacuo. The residue was acidified with 1M hydrochloric acid until pH=3. During which, a fine precipitate was formed and it was filtered and the filter cake was washed with water, dried under vacuum to give the title compound. $^1$H NMR (400 MHz, DMSO-d$_6$) δ=13.35 (br. s., 1H), 7.61 (d, J=8.8 Hz, 1H), 7.46 (d, J=8.8 Hz, 1H), 7.14 (s, 1H), 4.03 (s, 3H).

N-(2-((tert-butyldimethylsilyl)oxy)ethyl)-2-chloroacetamide (Intermediate B)

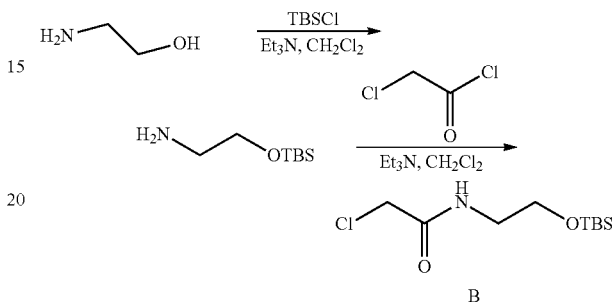

B

Step 1—2-((Tert-butyldimethylsilyl)oxy)ethanamine

To a solution of 2-aminoethanol (5.00 g, 81.8 mmol) and triethylamine (16.5 g, 163 mmol) in dichloromethane (80 mL) was added TBSCl (12.3 g, 81.8 mmol) at 0° C. After addition, the mixture was allowed to warm to rt slowly. After the mixture was stirred at rt for 12 hrs, the reaction mixture was concentrated under reduced pressure to give the residue which was purified by silica gel chromatography eluted with dichloromethane to give the title compound. $^1$H NMR (400 MHz, DMSO-d$_6$) δ=3.60 (t, J=5.6 Hz, 2H), 2.68 (t, J=5.6 Hz, 2H), 0.87 (s, 9H), 0.04 (s, 6H).

Step 2—N-(2-((tert-butyldimethylsilyl)oxy)ethyl)-2-chloroacetamide

To a solution of 2-((tert-butyldimethylsilyl)oxy) ethanamine (12.0 g, 59.5 mmol) and triethylamine (12.0 g, 119 mmol) in dichloromethane (300 mL) was added 2-chloroacetyl chloride (6.72 g, 59.5 mmol) and the reaction mixture was stirred at rt for 12 hrs. The reaction mixture was washed with water, dried over anhydrous sodium sulfate, filtered and concentrated to afford the crude product. The crude product was purified by column chromatography (petroleum ether/ethyl acetate=8/1 to 3:1) to give the title compound. $^1$H NMR (400 MHz, CDCl$_3$) δ=7.02 (br. s., 1H), 4.06 (s, 2H), 3.71 (t, J=5.2 Hz, 2H), 3.43 (q, J=5.2 Hz, 2H), 0.91 (s, 9H), 0.08 (s, 6H).

Ethyl 5-chloro-6-hydroxy-1H-indole-2-carboxylate (Intermediate C) and 6-(2-((2-((Tert-butyldimethylsilyl)oxy)ethyl)amino)-2-oxoethoxy)-5-chloro-1H-indole-2-carboxylic Acid (Intermediate D)

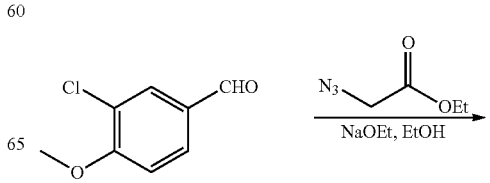

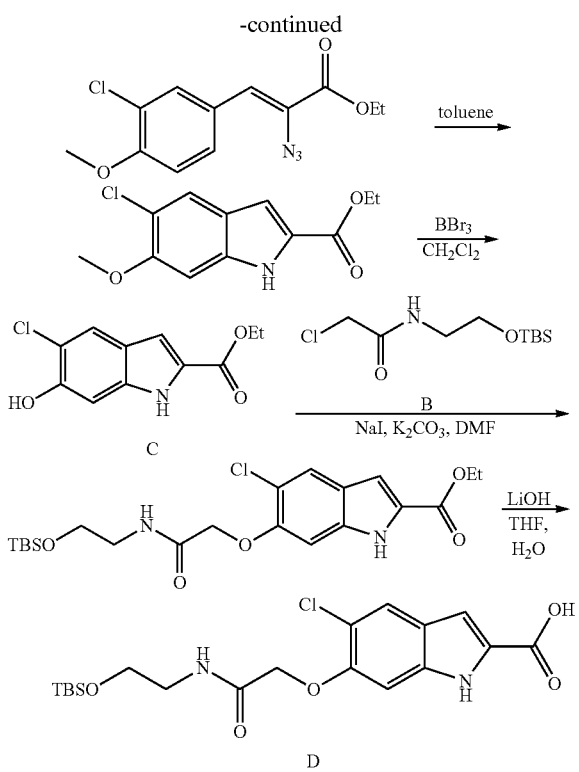

Step 1—Ethyl 2-azido-3-(3-chloro-4-methoxyphenyl)acrylate

Sodium ethoxide (2.02 g, 87.9 mmol) was added to ethanol (50 mL) at 0° C. After gas evolution ceased, 3-chloro-4-methoxybenzaldehyde (5.00 g, 29.3 mmol) and ethyl 2-azidoacetate (11.9 g, 87.9 mmol, 12.9 mL) in ethanol (50 mL) was added dropwise at −40° C. The mixture was then stirred at rt for 12 hours. The residue was adjusted to pH=7 with diluted hydrochloric acid solution (1 N) at 0° C., and then ethanol was removed under reduced pressure. The mixture was extracted with ethyl acetate (3×50 mL). The combined organic phase was dried over anhydrous sodium sulfate, filtered and concentrated in vacuum. The residue was purified by silica gel chromatography (petroleum ether/ethyl acetate=1/0 to 10/1) to give the title compound. $^1$H NMR (300 MHz, CDCl$_3$) δ=7.96 (d, J=2.4 Hz, 1H), 7.68 (dd, J=8.8, 2.0 Hz, 1H), 6.93 (d, J=8.8 Hz, 1H), 6.80 (s, 1H), 4.37 (q, J=7.2 Hz, 2H), 3.95 (s, 3H), 1.40 (t, J=7.2 Hz, 3H).

Step 2—Ethyl 5-chloro-6-methoxy-1H-indole-2-carboxylate (E,Z)-ethyl 2-azido-3-(3-chloro-4-methoxyphenyl)acrylate (4.87 g, 17.3 mmol) in toluene (80 mL) was heated to 110° C. for 9 hrs. The reaction mixture was concentrated under reduced pressure to give the crude product, which was purified by silica gel chromatography (petroleum ether/ethyl acetate=10/1 to 1/1) to give the title compound. $^1$H NMR (300 MHz, DMSO-d$_6$) δ=11.87 (br. s., 1H), 7.73 (s, 1H), 7.06 (d, J=1.6 Hz, 1H), 7.01 (s, 1H), 4.31 (q, J=7.2 Hz, 2H), 3.87 (s, 3H), 1.32 (t, J=7.2 Hz, 3H).

Step 3—Ethyl 5-chloro-6-hydroxy-1H-indole-2-carboxylate

To a solution of ethyl 5-chloro-6-methoxy-1H-indole-2-carboxylate (3.10 g, 12.2 mmol) in dichloromethane (60 mL) was added boron tribromide (9.18 g, 36.6 mmol, 3.53 mL) in dichloromethane (10 mL) at 0-rt for 5 hours. The reaction mixture was quenched by addition ethanol (20 mL) at 0° C., and then concentrated under reduced pressure. The residue was diluted with ethyl acetate (60 mL) and washed with water (30 mL). The organic phase was separated and dried over anhydrous sodium sulfate, filtered and concentrated under reduced pressure to afford the crude product, which was purified by column chromatography (petroleum ether/ethyl acetate=5/1 to 1/1) to give the title compound. $^1$H NMR (400 MHz, DMSO-d$_6$) δ=11.59 (br. s., 1H), 10.11 (s, 1H), 7.63 (s, 1H), 7.05-6.95 (m, 2H), 4.30 (q, J=7.2 Hz, 2H), 1.31 (t, J=7.2 Hz, 3H).

Step 4—Ethyl 6-[2-[2-[tert-butyl(dimethyl)silyl]oxyethylamino]-2-oxo-ethoxy]-5-chloro-1H-indole-2-carboxylate A mixture of ethyl 5-chloro-6-hydroxy-1H-indole-2-carboxylate (370 mg, 1.54 mmol), N-(2-((tert-butyldimethylsilyl)oxy)ethyl)-2-chloroacetamide (428 mg, 1.70 mmol), potassium carbonate (213 mg, 1.54 mmol) and sodium iodide (11.5 mg, 77.2 umol) in N,N-dimethylformamide (15 mL) was stirred at 90° C. for 12 hrs. The reaction mixture was concentrated under reduced pressure to give the crude product, which was purified by column chromatography (petroleum ether/ethyl acetate=5/1 to 1:1) to give the title compound. $^1$H NMR (300 MHz, CDCl$_3$) δ=9.49 (br. s., 1H), 7.69 (s, 1H), 7.30 (bs, 1H), 7.11 (d, J=1.2 Hz, 1H), 6.93 (s, 1H), 4.58 (s, 2H), 4.39 (q, J=7.2 Hz, 2H), 3.74 (t, J=5.0 Hz, 2H), 3.51 (q, J=5.6 Hz, 2H), 1.40 (t, J=7.2 Hz, 3H), 0.87 (s, 9H), 0.05 (s, 6H).

Step 5—6-(2-((2-((Tert-butyldimethylsilyl)oxy)ethyl)amino)-2-oxoethoxy)-5-chloro-1H-indole-2-carboxylic Acid A mixture of ethyl 6-(2-((2-((tert-butyldimethylsilyl)oxy)ethyl)amino)-2-oxoethoxy)-5-chloro-1H-indole-2-carboxylate (1.30 g, 1.57 mmol) and lithium hydroxide (300 mg, 12.5 mmol) in water (1 mL) and tetrahydrofuran (10 mL) was stirred at rt for 24 hours. The reaction mixture was adjusted to pH=6-7 with citric acid (0.1 mol/L) at 0° C., and then diluted with water (100 mL). A yellow solid was filtered and washed with water. The filtered cake was dissolved in dichloromethane/methanol=5/1 (50 mL), dried over anhydrous sodium sulfate, filtered and concentrated under reduced pressure to give the title compound. $^1$H NMR (300 MHz, DMSO-d$_6$) δ=11.40 (br. s., 1H), 7.75 (t, J=5.6 Hz, 1H), 7.64 (s, 1H), 7.00 (s, 1H), 6.73 (s, 1H), 4.54 (s, 2H), 3.63 (t, J=6.0 Hz, 2H), 3.29 (q, J=5.6 Hz, 2H), 0.85 (s, 9H), 0.03 (s, 6H).

4,5-Dichloro-6-methoxy-1-methyl-indole-2-carboxylic Acid (Intermediate E)

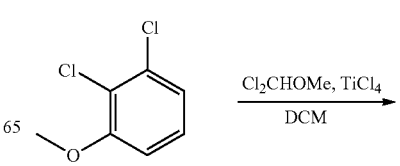

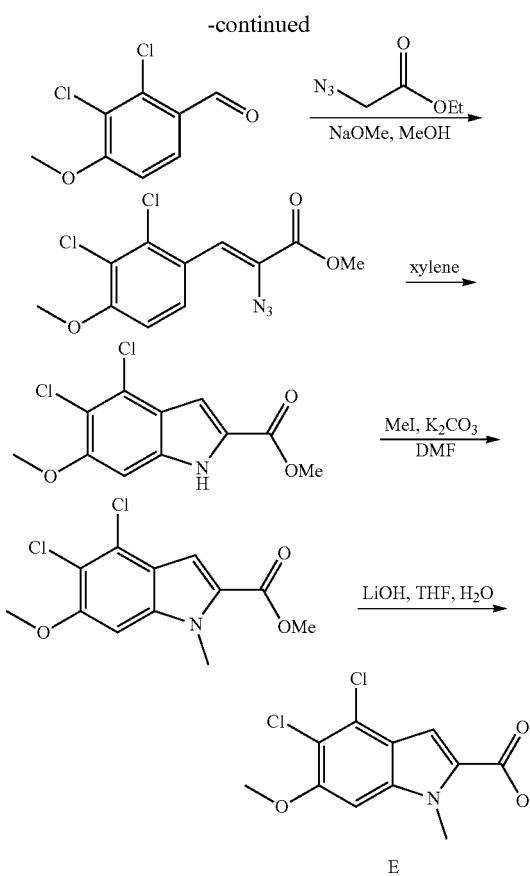

Step 1—2,3-Dichloro-4-methoxy-benzaldehyde

To a solution of 1,2-dichloro-3-methoxy-benzene (5.00 g, 28.2 mmol) in dichloromethane (30 mL) was added TiCl$_4$ (9.11 g, 48.0 mmol) dropwise at 0° C. under nitrogen. Then dichloro(methoxy)methane (3.25 g, 28.2 mmol) was added to the solution dropwise at 0° C. under nitrogen, and the solution was stirred at rt for 5 hrs. The residue was poured into water (200 mL). The aqueous phase was extracted with ethyl acetate (3×300 mL). The combined organic phase was washed with brine (3×200 mL), dried over anhydrous sodium sulfate, filtered and concentrated in vacuo. The residue was purified by silica gel chromatography (petroleum ether:ethyl acetate=100:1 to 10:1) to give the title compound. $^1$H NMR (400 MHz, CDCl$_3$): δ=10.36 (s, 1H), 7.89 (d, J=8.8 Hz, 1H), 7.97 (d, J=8.8 Hz, 1H), 4.01 (s, 3H).

Step 2—Methyl(Z)-2-azido-3-(2,3-dichloro-4-methoxy-phenyl)prop-2-enoate

To a solution of sodium methoxide (7.90 g, 146 mmol) in methanol (300 mL) was added 2,3-dichloro-4-methoxy-benzaldehyde (10.0 g, 48.8 mmol) in several portions at −20° C. under nitrogen, then ethyl 2-azidoacetate (18.9 g, 146.3 mmol) was added to the solution dropwise at -rt under nitrogen. The mixture was stirred at rt for 12 hrs. The mixture was poured into water (500 mL) and extracted with ethyl acetate (3×500 mL). The combined organic phase was washed with saturated brine (3×500 mL), dried over anhydrous sodium methoxide, filtered and concentrated in vacuo. The residue was purified by column chromatography (petroleum ether: ethyl acetate=100:1 to 1:1) to give the title compound. $^1$H NMR (400 MHz, CDCl$_3$)$^1$H NMR (400 MHz, CDCl$_3$) δ=8.19 (d, J=8.8 Hz, 1H), 7.29 (d, J=3.6 Hz, 1H), 6.93 (d, J=9.0 Hz, 1H), 3.98 (s, 3H), 3.96 (s, 3H).

Step 3—Methyl 4,5-dichloro-6-methoxy-1H-indole-2-carboxylate

Methyl (Z)-2-azido-3-(2,3-dichloro-4-methoxy-phenyl)prop-2-enoate (500 mg, 1.66 mmol) was added to xylene (100 mL) in one portion at 15° C., the solution was stirred at 120° C. for 12 hrs. The mixture was concentrated in vacuo. The residue was washed with petroleum ether:ethyl acetate (10:1, 50 mL) to give the title compound. $^1$H NMR (400 MHz, DMSO-d$_6$) δ=12.31 (br. s., 1H), 7.07 (d, J=1.2 Hz, 1H), 7.01 (s, 1H), 3.91 (s, 3H), 3.88 (s, 3H).

Step 4—4,5-Dichloro-6-methoxy-1-methyl-indole-2-carboxylate

To a solution of methyl 4,5-dichloro-6-methoxy-1H-indole-2-carboxylate (220 mg, 803 umol) in N,N-dimethylformamide (5 mL) was added potassium carbonate (333 mg, 2.41 mmol) and methyl iodide (342 mg, 2.41 mmol) in one portion at rt under nitrogen. The mixture was stirred at 50° C. for 12 hrs. The mixture was then poured into water (10 mL). The aqueous phase was extracted with ethyl acetate (3×20 mL) the combined organic phase was washed with brine (3×20 mL), dried over anhydrous sodium sulfate, filtered and concentrated in vacuo to give the title compound. $^1$H NMR (DMSO-d$_6$, 400 MHz): δ=7.31 (s, 1H), 7.15 (s, 1H), 4.03 (s, 3H), 3.97 (s, 3H), 3.86 (s, 3H).

Step 5—4,5-Dichloro-6-methoxy-1-methyl-indole-2-carboxylic Acid

To a solution of methyl 4,5-dichloro-6-methoxy-1-methyl-indole-2-carboxylate (200 mg, 694 umol) in a mixture solvent of tetrahydrofuran (10 mL) and water (10 mL) was added lithium hydroxide (49.8 mg, 2.08 mmol) in one portion at rt under nitrogen. The mixture was stirred at rt for 12 hrs. The mixture was concentrated in vacuo, the residue was adjusted to pH=3 with 3N hydrochloric acid (3 mL) which yielded a precipitate. The solid was filtered and concentrated in vacuum to give the title compound. $^1$H NMR (400 MHz, DMSO-d$_6$) δ=12.90 (br. s., 1H), 7.29 (s, 1H), 7.10 (s, 1H), 4.02 (s, 3H), 3.98 (s, 3H).

Methyl 6-[2-[2-[tert-butyl(dimethyl)silyl]oxyethylamino]-2-oxo-ethoxyl-4,5-dichloro-1-methyl-indole-2-carboxylate (Intermediate F)

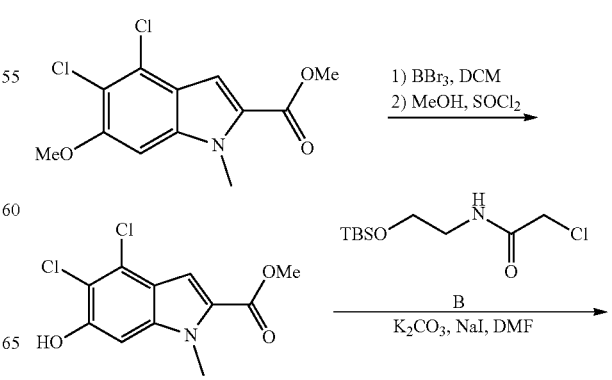

-continued

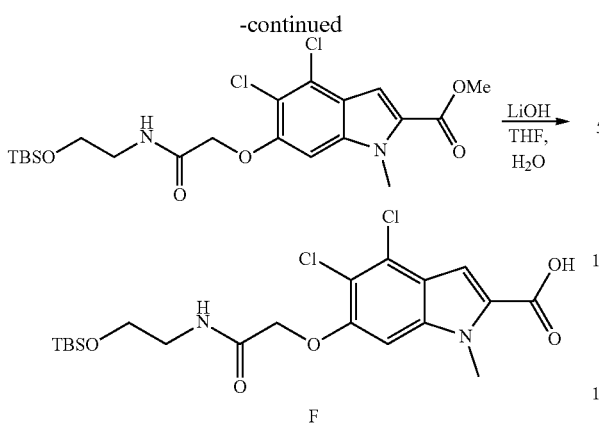

Step 1—Methyl 4,5-dichloro-6-hydroxy-1-methyl-indole-2-carboxylate

To a solution of methyl 4,5-dichloro-6-methoxy-1-methyl-indole-2-carboxylate (1.60 g, 5.55 mmol, synthesized via steps 1-4 of Intermediate E) in dichloromethane (20 mL) was added boron tribromide (2.78 g, 11.1 mmol, 1.07 mL) at 0° C., and then the mixture was stirred at rt for 16 hours. On completion, dichloromethane (20 mL) was added to the mixture and was then poured into water (30 mL). Then the mixture was filtered, the filtrate was extracted with dichloromethane (3×30 mL), and the combined organic phase was combined with the filter cake and concentrated to yield 4,5-dichloro-6-hydroxy-1-methyl-indole-2-carboxylic acid (2.00 g) as gray solid. To a solution of 4,5-dichloro-6-hydroxy-1-methyl-indole-2-carboxylic acid (1.44 g, 5.54 mmol) in methanol (20 mL) was added thionyl chloride (725 mg, 6.09 mmol) at 20-rt, and then the mixture was stirred at 50° C. for 16 hours. On completion, methanol (10 mL) was added and the mixture was then filtered. The filter cake was dried to give the title compound. $^1$H NMR (400 MHz, DMSO-$d_6$) δ=10.71 (br. s., 1H), 7.10 (s, 1H), 6.98 (s, 1H), 3.91 (s, 3H), 3.86 (s, 3H).

Step 2—Methyl 6-[2-[2-[tert-butyl(dimethyl)silyl]oxyethylamino]-2-oxo-ethoxy]-4,5-dichloro-1-methyl-indole-2-carboxylate To a solution of methyl 4,5-dichloro-6-hydroxy-1-methyl-indole-2-carboxylate (500 mg, 1.82 mmol) in DMF (5.00 mL) was added N-[2-[tertbutyl(dimethyl)silyl]oxyethyl]-2-chloro-acetamide (504 mg, 2.00 mmol, Intermediate BF), NaI (13.6 mg, 91.0 umol) and $K_2CO_3$ (251 mg, 1.82 mmol). The reaction mixture was stirred at 100° C. for 12 hours. On completion, the reaction mixture was filtered and the filtrate was concentrated under reduced pressure to give the crude product. The crude product was purified by column chromatography to give the title compound. $^1$H NMR (400 MHz, CDCl$_3$) δ=8.02 (s, 1H), 7.32 (s, 1H), 6.73 (s, 1H), 4.62 (s, 2H), 4.04 (s, 3H), 3.92 (s, 3H), 3.77 (t, J=5.0 Hz, 2H), 3.53 (q, J=5.6 Hz, 2H), 0.88 (s, 9H), 0.06 (s, 6H).

Step 3—Methyl 6-[2-[2-[tert-butyl(dimethyl)silyl]oxyethylamino]-2-oxo-ethoxy]-4,5-dichloro-1-methyl-indole-2-carboxylate To a solution of methyl 6-[2-[2-[tert-butyl(dimethyl)silyl]oxyethylamino]-2-oxo-ethoxy]-4,5-dichloro-1-methyl-indole-2-carboxylate (750 mg, 1.53 mmol) in a mixture solvent of H$_2$O (1.00 mL) and THF (7.00 mL) was added and LiOH (147 mg, 6.13 mmol). The reaction mixture was stirred at rt for 12 hours. On completion, the reaction solution was diluted with water (50 mL) and acidified with a citric acid solution (0.1 mol/L) until pH=6-7 at 0° C. A white precipitate formed, which was then filtered. The filter cake was dissolved in DCM/MeOH (5:1, 150 mL), dried over Na$_2$SO$_4$, filtered and concentrated under reduced pressure to give the title compound. LCMS: (ES$^+$) m/z (M+H)$^+$= 475.2, tR=0.980. $^1$H NMR (300 MHz, DMSO-$d_6$) δ=7.75 (t, J=5.7 Hz, 1H), 7.31 (s, 1H), 7.06 (s, 1H), 4.72 (s, 2H), 4.00 (s, 3H), 3.65 (t, J=5.8 Hz, 2H), 3.30 (q, J=5.8 Hz, 2H), 0.83 (s, 9H), 0.02 (s, 6H).

(±)-5-Chloro-6-[(2-oxooxazolidin-5-yl)methoxy]-1H-indole-2-carboxylic Acid (Intermediate G)

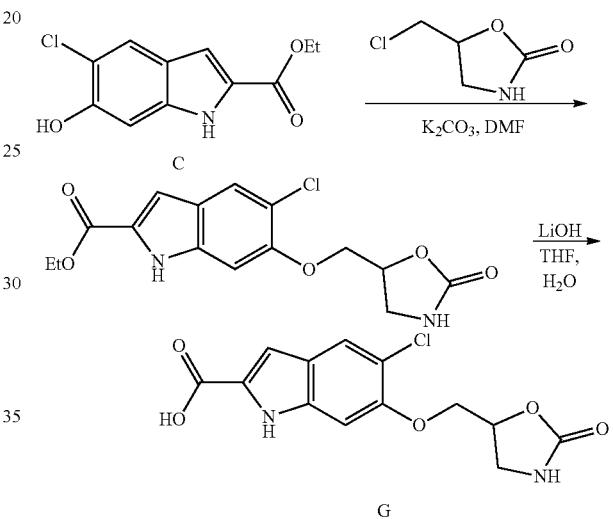

Step 1—(±)-Ethyl 5-chloro-6-[(2-oxooxazolidin-5-yl)methoxy]-1H-indole-2-carboxylate To a solution of ethyl 5-chloro-6-hydroxy-1H-indole-2-carboxylate (800 mg, 3.34 mmol) in dimethylformamide (20 mL) was added potassium carbonate (922 mg, 6.68 mmol) and (±)-5-(chloromethyl)oxazolidin-2-one (678 mg, 5.01 mmol, CAS #22625-57-6). The mixture was stirred at 100° C. for 12 hours. The reaction mixture was diluted with water and extracted with ethyl acetate (3×100 mL). The combined organic layers were washed with aqueous sodium chloride 100 mL (2×50 mL), dried over sodium sulfate, filtered and concentrated under reduced pressure to give a residue. The residue was purified by column chromatography (SiO$_2$, petroleum ether:ethyl acetate=3:1 to 0:1) to afford the title compound. $^1$H NMR (400 MHz, DMSO-$d_6$) δ=11.94 (br. s., 1H), 7.77 (s, 1H), 7.62 (br. s, 1H), 7.08 (s, 1H), 7.05 (s, 1H), 4.99-4.95 (m, 1H), 4.33 (q, J=7.2 Hz, 2H), 4.29-4.16 (m, 2H), 3.64-3.51 (m, 1H), 3.48-3.43 (m, 1H), 1.33 (t, J=7.2 Hz, 3H).

Step 2—(±)-5-Chloro-6-[(2-oxooxazolidin-5-yl)methoxy]-1H-indole-2-carboxylic Acid To a solution of (±)-ethyl 5-chloro-6-((2-oxooxazolidin-5-yl)methoxy)-1H-indole-2-carboxylate (300 mg, 885 umol) in tetrahydrofuran (5 mL) and water (2 mL) was added lithium hydroxide (74.3 mg, 1.77 mmol). The mixture was stirred at rt for 12 hours. The reaction mixture was quenched by aq. hydrochloric acid (1 M, 5 mL) at 0° C., and then diluted with water and extracted with ethyl acetate (3×50 mL). The combined organic layers were washed with aqueous sodium chloride (3×30 mL), dried over anhydrous sodium sulfate, filtered and concentrated under reduced pressure to give the title compound. $^1$H NMR (400 MHz, DMSO-d$_6$) δ=11.81 (s, 1H), 7.74 (s, 1H), 7.62 (s, 1H), 7.03 (s, 1H), 7.01 (s, 1H), 5.01-4.93 (m, 1H), 4.29-4.16 (m, 2H), 3.68-3.60 (m, 1H), 3.49-3.42 (m, 1H).

4-chloro-6-methoxy-1,5-dimethyl-indole-2-carboxylic Acid (Intermediate H)

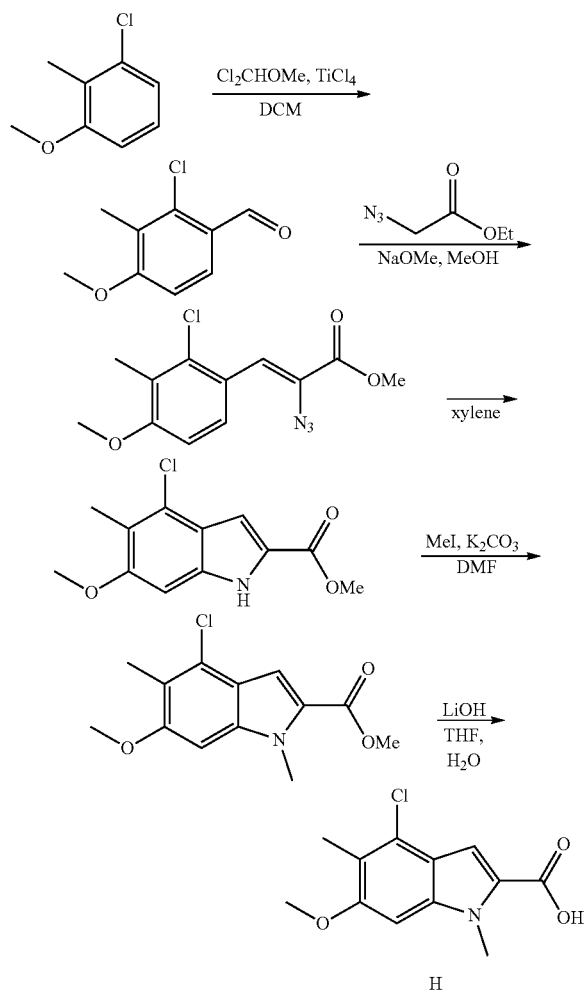

Step 1—2-Chloro-4-methoxy-3-methyl-benzaldehyde

To a solution of 1-chloro-3-methoxy-2-methyl-benzene (6.20 g, 39.6 mmol) in dichloromethane (60 mL) was added TiCl$_4$ (12.7 g, 67.3 mmol) dropwise at 0° C. under nitrogen. Then dichloro(methoxy)methane (4.55 g, 39.6 mmol) was added to the solution dropwise at 0° C. under nitrogen, and the solution was stirred at rt for 5 hrs. On completion, the reaction was poured into water (200 mL). The aqueous phase was extracted with ethyl acetate (3×300 mL). The combined organic phase was washed with brine (3×200 mL), dried over anhydrous sodium sulfate, filtered and concentrated in vacuo. The residue was purified by silica gel chromatography (petroleum ether:ethyl acetate=100:1 to 10:1) to give the title compound. $^1$H NMR (400 MHz, DMSO-d$_6$): δ=10.24 (s, 1H), 7.78-7.76 (d, J=8.8 Hz, 1H), 7.16-6.14 (d, J=8.8 Hz, 1H), 3.91 (s, 3H), 2.25 (s, 3H).

Step 2—Methyl (Z)-2-azido-3-(2-chloro-4-methoxy-3-methyl-phenyl)prop-2-enoate

To a solution of sodium methoxide (4.39 g, 81.3 mmol) in methanol (300 mL) was added 2-chloro-4-methoxy-3-methyl-benzaldehyde (5.00 g, 27.1 mmol) in several portions at −20° C. under nitrogen. Then ethyl 2-azidoacetate (10.5 g, 81.3 mmol) was added to the solution dropwise at −20° C. under nitrogen. The mixture was stirred at rt for 12 hrs. On completion, the mixture was poured into water (500 mL) and extracted with ethyl acetate (3×500 mL). The combined organic phase was washed with saturated brine (3×500 mL), dried over anhydrous sodium methoxide, filtered and concentrated in vacuo. The residue was purified by column chromatography (petroleum ether:ethyl acetate=100:1 to 1:1) to give the titled compound. LCMS: (ES$^+$) m/z (M+H)$^+$=282.02, tR=0.998.

Step 3—Methyl 4-chloro-6-methoxy-5-methyl-1H-indole-2-carboxylate

Methyl (Z)-2-azido-3-(2-chloro-4-methoxy-3-methyl-phenyl) prop-2-enoate (4.00 g, 14.2 mmol) was added to xylene (100 mL) in one portion at rt, then the solution was stirred at 120° C. for 12 hrs. The mixture was concentrated in vacuo. The residue was washed with petroleum ether:ethyl acetate (10:1, 50 mL) to give the title compound. $^1$H-NMR (400 MHz, DMSO-d$_6$): δ=12.02 (br. s., 1H), 7.01 (s, 1H), 6.86 (s, 1H), 3.86 (s, 3H), 3.85 (s, 3H), 2.26 (s, 3H).

Step 4—Methyl 4-chloro-6-methoxy-1,5-dimethyl-indole-2-carboxylate

To a solution of methyl 4-chloro-6-methoxy-5-methyl-1H-indole-2-carboxylate (3.00 g, 11.8 mmol) in N,N-dimethylformamide (10 mL) was added potassium carbonate (4.90 g, 35.5 mmol) and methyl iodide (5.04 g, 35.5 mmol) in one portion at rt under nitrogen. The mixture was stirred at 50° C. for 12 hrs. On completion, the residue was poured into water (10 mL). The aqueous phase was extracted with ethyl acetate (3×20 mL). The combined organic phase was washed with brine (3×20 mL), dried over anhydrous sodium sulfate, filtered and concentrated in vacuo to give the title compound. LCMS: (ES$^+$) m/z (M+H)$^+$=268.07, tR=0.778.

Step 5—4-chloro-6-methoxy-1,5-dimethyl-indole-2-carboxylic Acid

To a solution of methyl 4-chloro-6-methoxy-1,5-dimethyl-indole-2-carboxylate (3.00 g, 11.2 mmol) in a mixture solvent of tetrahydrofuran (10 mL) and water (10 mL) was added lithium hydroxide (269 g, 11.2 mmol) in one portion at rt under nitrogen. The mixture was stirred at rt for 12 hrs. On completion, the mixture was concentrated in vacuo, and the residue was adjusted to pH=0.3 with 3N hydrochloric acid (3 mL). The solid was filtered and concentrated in vacuum to give the title compound. ¹H NMR (400 MHz, DMSO-d₆) δ=7.06 (s, 2H), 3.99 (s, 3H), 3.90 (s, 3H), 2.26 (s, 3H).

4-Chloro-5-fluoro-6-methoxy-1-methyl-1H-indole-2-carboxylic Acid (Intermediate I)

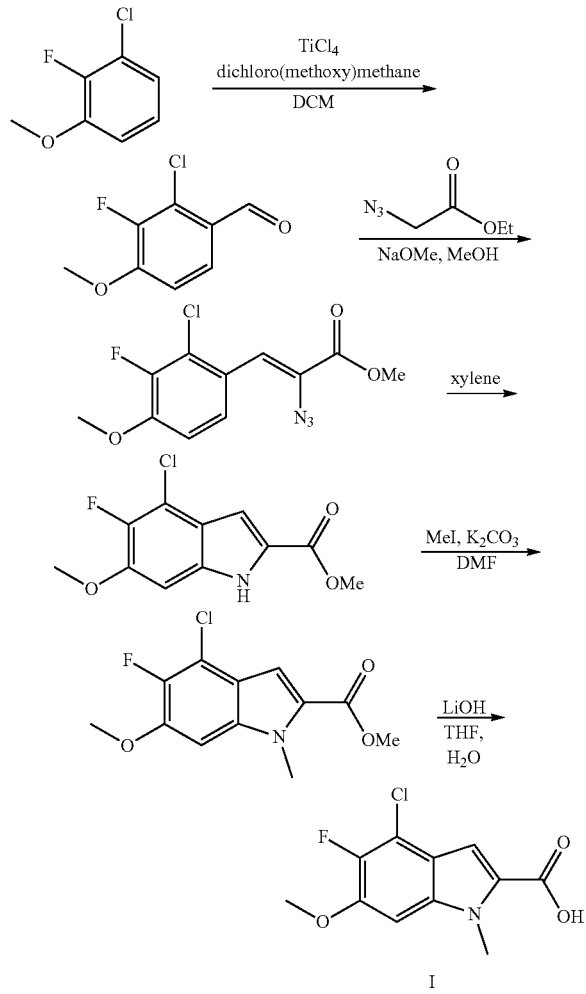

Step 1—2-Chloro-3-fluoro-4-methoxybenzaldehyde

To a mixture of 1-chloro-2-fluoro-3-methoxy-benzene (5.00 g, 31.1 mmol) in dichloromethane (40 mL) was added titanium tetrachloride (10.0 g, 52.9 mmol) dropwise at 0° C. under nitrogen. Dichloro(methoxy)methane (3.58 g, 31.1 mmol) was then added to the solution. Then the mixture was stirred at rt for 3 hours. On completion, the residue was poured into ice-water (50 mL) and extracted with ethyl acetate (50 mL). The combined organic layer was washed with brine (50 mL), dried with anhydrous sodium sulfate, filtered and concentrated in vacuo. The residue was purified by silica gel chromatography eluted with petroleum ether/ethyl acetate (20/1 to 3/1) to give the title compound. H NMR (400 MHz, DMSO-d₆) δ=10.15 (s, 1H), 7.74 (d, J=6.8 Hz, 1H), 7.37 (d, J=6.0 Hz, 1H), 3.98 (s, 3H).

Step 2—(Z)-methyl 2-azido-3-(2-chloro-3-fluoro-4-methoxyphenyl)acrylate

To a solution of sodium methoxide (1.72 g, 31.8 mmol) in methanol (25 mL) was added a solution of 2-chloro-3-fluoro-4-methoxy-benzaldehyde (2.00 g, 10.6 mmol) and ethyl azidoacetate (4.11 g, 31.8 mmol) in methanol (25 mL) at −20° C. under nitrogen. The mixture was stirred at rt for 5 hours. On completion, the mixture was poured into ice-water (50 mL) and a precipitate formed. The solution was filtered and the filter cake collected. The filter cake was then dissolved in dichloromethane and dried over anhydrous sodium sulfate, filtered and concentrated under reduced pressure to give the title compound. ¹H NMR (400 MHz, DMSO-d₆) δ=8.09 (dd, J=9.2, 1.9 Hz, 1H), 7.27 (t, J=8.8 Hz, 1H), 7.05 (s, 1H), 3.93 (s, 3H), 3.88 (s, 3H).

Step 3—Methyl 4-chloro-5-fluoro-6-methoxy-1H-indole-2-carboxylate (Z)-methyl-2-azido-3-(2-chloro-3-fluoro-4-methoxy-phenyl)prop-2-enoate (1.80 g, 6.30 mmol) was added to xylene (20 mL) in one portion at rt. The solution was stirred at 180° C. for 2.5 hours. On completion, the residue was cooled which yielded a precipitate. The solution was filtered to give the crude compound. The crude product was used directly in the next step without further purification.

Step 4—Methyl 4-chloro-5-fluoro-6-methoxy-1-methyl-1H-indole-2-carboxylate

To a solution of methyl 4-chloro-5-fluoro-6-methoxy-1H-indole-2-carboxylate (1.00 g, 3.88 mmol) in N,N-dimethylformamide (15 mL) was added potassium carbonate (1.61 g, 11.6 mmol) and iodomethane (1.65 g, 11.6 mmol) in one portion at rt under nitrogen, and the mixture was stirred at 50° C. for 4 hours. On completion, the residue was poured into ice-water (50 mL). The aqueous layer was extracted with ethyl acetate (50 mL) and the combined organic layer was washed with brine (30 mL), dried over anhydrous sodium sulfate, filtered and concentrated in vacuo to give the title compound. ¹H NMR (400 MHz, DMSO-d₆) δ=7.31 (d, J=6.8 Hz, 1H), 7.14 (s, 1H), 4.01 (s, 3H), 3.96 (s, 3H), 3.85 (s, 3H).

Step 5—4-Chloro-5-fluoro-6-methoxy-1-methyl-1H-indole-2-carboxylic Acid

To a solution of methyl 4-chloro-5-fluoro-6-methoxy-1-methyl-1H-indole-2-carboxylate (1.00 g) in anhydrous tetrahydrofuran (20.00 mL) and water (20.00 mL) was added lithium hydroxide (264 mg, 11.0 mmol) in one portion at rt under nitrogen. The solution was stirred for 2 hours at rt. On completion, the mixture was concentrated in vacuo to remove the tetrahydrofuran, then the residue was adjusted to pH=2 with hydrochloric acid (3 M) to give a precipitate. The solid was filtered and dried in vacuo to give the title compound. ¹H NMR (400 MHz, DMSO-d₆) δ=7.31 (d, J=6.4 Hz, 1H), 7.13 (s, 1H), 4.03 (s, 3H), 3.96 (s, 3H).

4-Chloro-5-methoxy-1-methyl-indole-2-carboxylic Acid (Intermediate J)

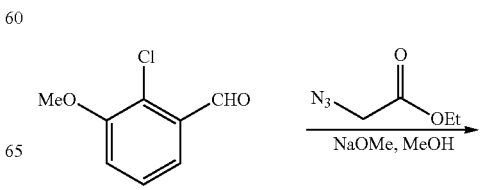

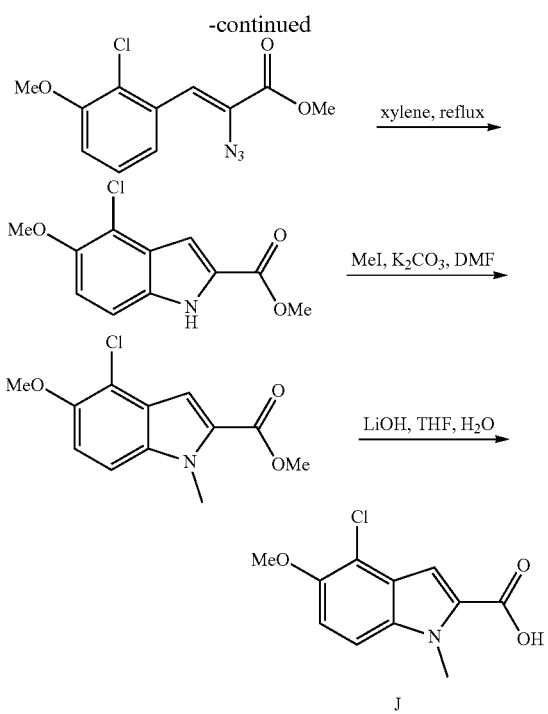

Step 1—Methyl-2-azido-3-(2-chloro-3-methoxy-phenyl)prop-2-enoate

To a solution of sodium methoxide (2.38 g, 43.9 mmol) in methanol (40 mL) was added 2-chloro-3-methoxy-benzaldehyde (2.50 g, 14.6 mmol) and ethyl 2-azidoacetate (4.73 g, 36.7 mmol) at −50° C. under nitrogen atmosphere. The mixture was stirred at the same temperature for 2 hrs, then warmed to rt and stirred for 14 hrs. On completion, the suspension was poured into ice and the azido derivative was collected by filtration and washed with cold water. The filter cake was dried over in vacuo to give the crude product. The crude product was purified by silica gel chromatography (petroleum ether:ethyl acetate=6:1) to give the title compound. $^1$H NMR (400 MHz, CDCl$_3$)$^1$H NMR (400 MHz, CDCl$_3$) δ=7.77 (dd, J=1.0, 8.0 Hz, 1H), 7.36 (s, 1H), 7.32-7.25 (m, 1H), 6.95 (dd, J=1.2, 8.4 Hz, 1H), 3.96 (s, 3H), 3.94 (s, 3H).

Step 2—Methyl-4-chloro-5-methoxy-1H-indole-2-carboxylate

Methyl-2-azido-3-(2-chloro-3-methoxy-phenyl)prop-2-enoate (2.00 g, 7.47 mmol) was dissolved in xylol (200 mL) and the mixture was stirred at 180° C. for 30 min. On completion, the reaction mixture was concentrated in vacuo to afford a residue. The residue was triturated with petroleum ether:ethyl acetate (10:1) to give the title compound. $^1$H NMR (400 MHz, DMSO-d$_6$) δ=12.16 (br. s., 1H), 7.40 (dd, J=0.4, 9.2 Hz, 1H), 7.24 (d, J=9.2 Hz, 1H), 7.04 (s, 1H), 3.89 (s, 3H), 3.86 (s, 3H).

Step 3—Methyl 4-chloro-5-methoxy-1-methyl-indole-2-carboxylate

To a solution of methyl 4-chloro-5-methoxy-1H-indole-2-carboxylate (920 mg, 3.84 mmol) in N,N-dimethylformamide (15 mL) was added potassium carbonate (1.33 g, 9.60 mmol) and iodomethane (2.18 g, 15.4 mmol). The resulting mixture was warmed to 60° C. and stirred for 3 hrs. On completion, the reaction mixture was concentrated in vacuo to afford a residue. The residue was diluted with water (30 mL) and extracted with dichloromethane (3×25 mL). The combined organic layer was dried over anhydrous sodium sulfate, filtered and concentrated in vacuo to give the title compound. $^1$H NMR (400 MHz, DMSO-d$_6$) δ=7.57 (d, J=9.2 Hz, 1H), 7.30 (d, J=9.2 Hz, 1H), 7.10 (s, 1H), 4.00 (s, 3H), 3.88 (s, 3H), 3.86 (s, 3H).

Step 4—4-Chloro-5-methoxy-1-methyl-indole-2-carboxylic Acid

To a solution of methyl 4-chloro-5-methoxy-1-methyl-indole-2-carboxylate (950 mg, 3.74 mmol) in tetrahydrofuran (16 mL) and water (4 mL) was added lithium hydroxide (268 mg, 11.2 mmol). The resulting mixture was stirred at rt for 3 hrs. On completion, the reaction mixture was concentrated in vacuo and the residue was acidified with 2N hydrochloric acid until pH=3. During which, a fine precipitate was formed. The precipitate was filtered and the filter cake was washed with water, dried in vacuo to give the title compound. $^1$H NMR (400 MHz, DMSO-d$_6$) δ=13.19 (br. s., 1H), 7.56 (d, J=9.2 Hz, 1H), 7.29 (d, J=9.2 Hz, 1H), 7.08 (s, 1H), 4.02 (s, 3H), 3.88 (s, 3H).

N-acetylsulfamoyl Chloride (Intermediate K)

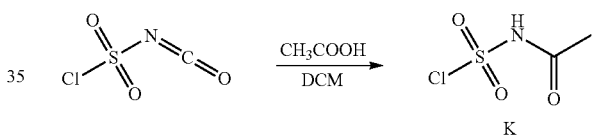

To a solution of N-(oxomethylene)sulfamoyl chloride (70.0 g, 495 mmol) in dichloromethane (50 mL) was added acetic acid (29.7 g, 495 mmol) dropwise at 0° C. The reaction was stirred at 0° C. for 3 hrs. On completion, the reaction was concentrated in vacuo, and the residue was washed with petroleum ether: ethyl acetate (10:1, 2×500 mL) to give the title compound (60.0 g, 77% yield) as a yellow solid. $^1$H NMR (400 MHz, DMSO-d$_6$) δ=2.11 (s, 3H).

(±)-Tert-butyl N-(3-amino-3-phenyl-propyl)carbamate (Intermediate L)

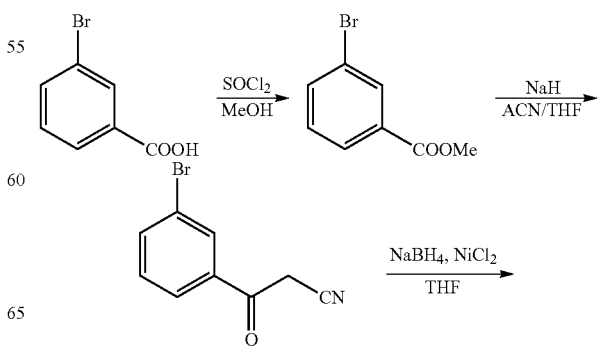

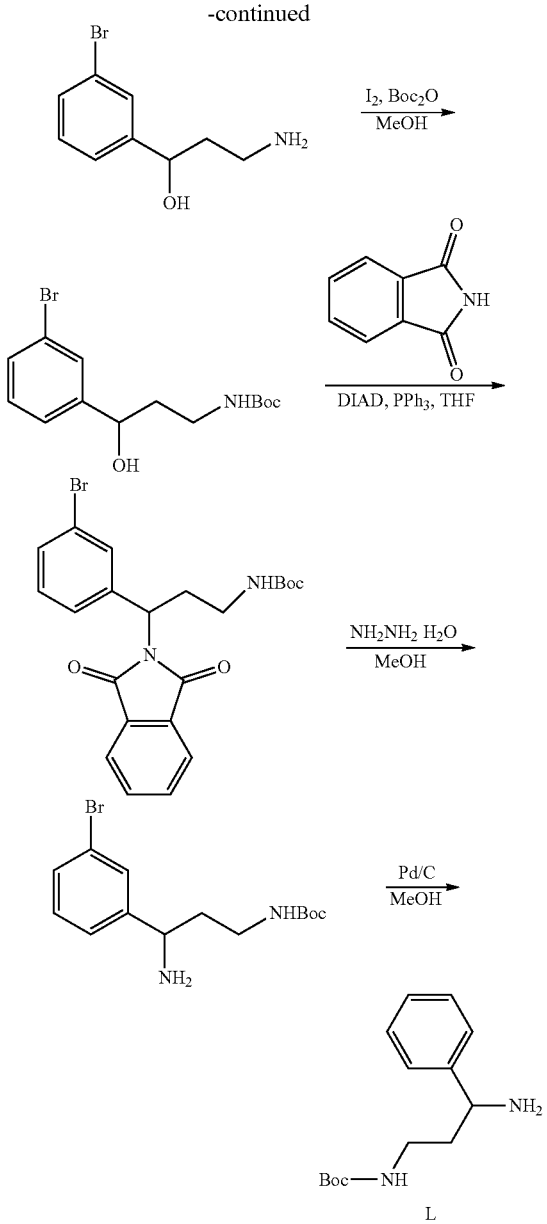

Step 1—Methyl 3-bromobenzoate

To a mixture of 3-bromobenzoic acid (85.0 g, 423 mmol) in methanol (700 mL) was added thionyl chloride (151 g, 1.27 mol) dropwise at rt under nitrogen atmosphere. The mixture was stirred at 62° C. for 16 hours. On completion, the reaction was concentrated in vacuo to give a residue. The residue was washed with saturated sodium bicarbonate (100 mL) and extracted with dichloromethane (2×100 mL). The organic layer was dried over sodium sulfate, concentrated in vacuo to give the title compound. $^1$H NMR (400 MHz, CDCl$_3$) δ=8.21 (s, 1H), 8.09-7.90 (m, 1H), 7.78-7.61 (m, 1H), 7.46-7.21 (m, 1H), 3.97 (s, 3H).

Step 2—3-(3-Bromophenyl)-3-oxo-propanenitrile

To a mixture of acetonitrile (7.78 g, 190 mmol, 9.97 mL) and anhydrous tetrahydrofuran (300 mL) was added sodium hydride (6.05 g, 151 mmol) portion-wise at rt under nitrogen atmosphere. Then methyl 3-bromobenzoate (25.0 g, 116 mmol) was added to the mixture and the resulting mixture was heated to 77° C. and stirred for 2 hours. On completion, the reaction was cooled to rt and hydrochloric acid solution (1 N, 400 mL) was added to the reaction. The aqueous was extracted with ethyl acetate (4×250 mL). The organic layer was washed with sodium bicarbonate (1.0 L), dried over sodium sulfate, and concentrated in vacuo to give the title compound. $^1$H NMR (400 MHz, CDCl$_3$) δ=8.07 (br. s., 1H), 7.94-7.76 (m, 2H), 7.44 (t, J=7.6 Hz, 1H), 4.10 (s, 2H).

Step 3—(±)-3-Amino-1-(3-bromophenyl)propan-1-ol

To a mixture of 3-(3-bromophenyl)-3-oxo-propanenitrile (5.00 g, 22.3 mmol) and nickel chloride hexahydrate (13.3 g, 55.8 mmol) in anhydrous tetrahydrofuran (100 mL) was added sodium borohydride (4.22 g, 112 mmol) portion-wise at 0° C. under nitrogen atmosphere. The mixture was warmed to rt and stirred for 2 hours. On completion, saturated ammonium chloride (10 mL) was added to the reaction and the mixture was dried over anhydrous sodium sulfate, filtrated and the residue was concentrated in vacuo to give the title compound. LCMS: (ES$^+$) m/z (M+H)$^+$= 230.0, tR=1.350.

Step 4—(±)-Tert-butyl N-[3-(3-bromophenyl)-3-hydroxy-propyl]carbamate

To a mixture of (±)-3-amino-1-(3-bromophenyl)-propan-1-ol (5.00 g, 21.73 mmol) in methanol (100 mL) was added iodine (552 mg, 2.17 mmol) and di-tert-butyl dicarbonate (14.2 g, 65.2 mmol) in one portion at rt under nitrogen atmosphere. The mixture was stirred at rt for 16 hours. On completion, the reaction was concentrated in vacuo to give a residue. The residue was purified by silica gel chromatography with dichloromethane:methanol=50:1 to give the title compound. LCMS: (ES$^+$) m/z (M+23)$^+$=352.0, tR=1.407.

Step 5—(±)-Tert-butyl N-[3-(3-bromophenyl)-3-(1,3-dioxoisoindolin-2-yl)propyl]carbamate To a mixture of (±)-tert-butyl N-[3-(3-bromophenyl)-3-hydroxy-propyl]carbamate (3.00 g, 9.08 mmol) and isoindoline-1,3-dione (1.34 g, 9.08 mmol) and triphenylphosphine (3.57 g, 13.6 mmol) in tetrahydrofuran (100 mL) was added diisopropyl azodicarboxylate (2.75 g, 13.6 mmol) dropwise at 0° C. under nitrogen atmosphere. The mixture was stirred at 0° C. for 30 mins, then warmed to rt and stirred for 15.5 hours. On completion, the reaction was washed with water and extracted with ethyl acetate (3×100 mL). The organic layer was combined and washed with brine, dried over anhydrous sodium sulfate and concentrated in vacuo to give a residue. The residue was purified by silica gel chromatography with petroleum ether:ethyl acetate (50:1 to 10:1) to give the title compound. LCMS: (ES$^+$) m/z (M+H)$^+$= 459.3, tR=1.319.

Step 6—(±)-Tert-butyl N-[3-amino-3-(3-bromophenyl)propyl]carbamate

To a mixture of (±)-tert-butyl N-[3-(3-bromophenyl)-3-(1,3-dioxoisoindolin-2-yl)propyl]carbamate (2.00 g, 4.35 mmol) in methanol (10.0 mL) was added hydrazine hydrate (872 mg, 17.4 mmol) in one portion at rt under nitrogen atmosphere. The mixture was stirred at 62° C. and stirred for 10 hours. On completion, the reaction was concentrated in vacuo. The residue was purified by Prep-HPLC (condition: water (0.05% ammonia hydroxide v/v)-acetonitrile; column: Phenomenex Gemini C18 250*50 10 um) to give the title compound. LCMS: (ES$^+$) m/z (M+H)$^+$=329.0, tR=2.598.

Step 7—(±)-Tert-butyl N-(3-amino-3-phenyl-propyl)carbamate

To a solution of (±)-tert-butyl N-[3-amino-3-(3-bromophenyl)propyl]carbamate (430 mg, 1.31 mmol) in methanol (50 mL) was added palladium-charcoal (500 mg) under nitrogen atmosphere. The suspension was degassed under vacuum and purged with H$_2$ several times, and the mixture was stirred under H$_2$ (50 psi) at rt for 10 hours. On completion, the reaction was concentrated in vacuo to give the title compound. LCMS: (ES$^+$) m/z (M+H)$^+$=251.1, tR=1.259.

(±)-Ethyl 3-[1-amino-3-(tert-butoxycarbonylamino)propyl]benzoate (Intermediate M)

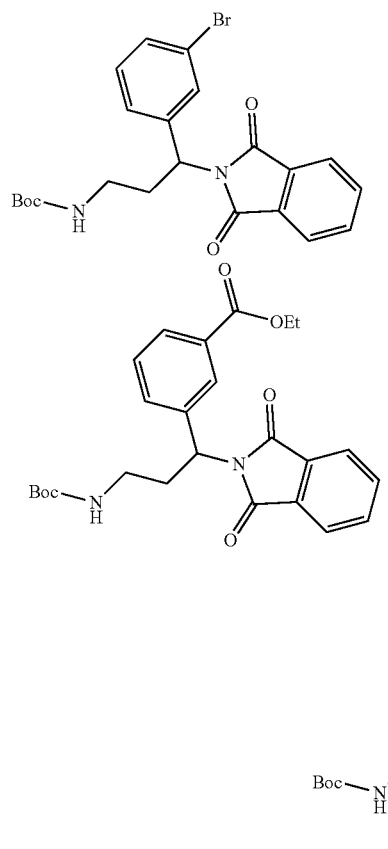

Step 1—(±)-Ethyl 3-[3-(tert-butoxycarbonylamino)-1-(1,3-dioxoisoindolin-2-yl)propyl]benzoate To a solution of (±)-tert-butyl N-[3-(3-bromophenyl)-3-(1,3-dioxoisoindolin-2-yl)propyl]carbamate (4.00 g, 8.71 mmol, synthesized via Steps 1-5 of Intermediate L) and Pd(dppf)Cl$_2$—CH$_2$Cl$_2$ (711 mg, 871 umol) in ethanol (60 mL) was added triethylamine (4.41 g, 43.5 mmol, 6.04 mL). The reaction mixture was stirred at 70° C. under carbon monoxide (50 psi) for 48 hours. The mixture was concentrated in vacuo to afford a residue. The residue was purified with silica gel chromatography (petroleum ether:ethyl acetate=8:1) to give the title compound. LCMS: (ES$^+$) m/z (M+H)$^+$=453.3, tR=0.963.

Step 2—(±)-Ethyl 3-[1-amino-3-(tert-butoxycarbonylamino)propyl]benzoate

To a mixture of (±)-ethyl 3-[3-(tert-butoxycarbonylamino)-1-(1,3-dioxoisoindolin-2-yl) propyl]benzoate (600 mg, 1.33 mmol) in ethanol (10 mL) was added hydrazine hydrate (208 mg, 4.16 mmol). Then the mixture was stirred at 80° C. for 2 hours. On completion, the reaction mixture was filtered. The filtrate was concentrated in vacuo. The residue was purified by column chromatography (petroleum ether:ethyl acetate=10:1 to dichloromethane:methanol=20:1) to give the title compound. LCMS: (ES$^+$) m/z (M+H)$^+$=323.2, tR=0.700. $^1$H NMR (400 MHz, CDCl$_3$) δ=7.91 (s, 1H), 7.86 (d, J=7.6 Hz, 1H), 7.45 (d, J=7.6 Hz, 1H), 7.34 (t, J=7.6 Hz, 1H), 5.20-4.89 (br. s, 2H), 4.31 (q, J=7.2 Hz, 2H), 3.97 (t, J=6.8 Hz, 1H), 3.28-2.96 (m, 2H), 1.86-1.73 (m, 2H), 1.37 (s, 9H), 1.33 (t, J=7.2 Hz, 3H).

Ethyl 4-[3-amino-1-[(4,5-dichloro-1-methyl-indole-2-carbonyl)-amino]-propyl]-benzoate (Intermediate N)

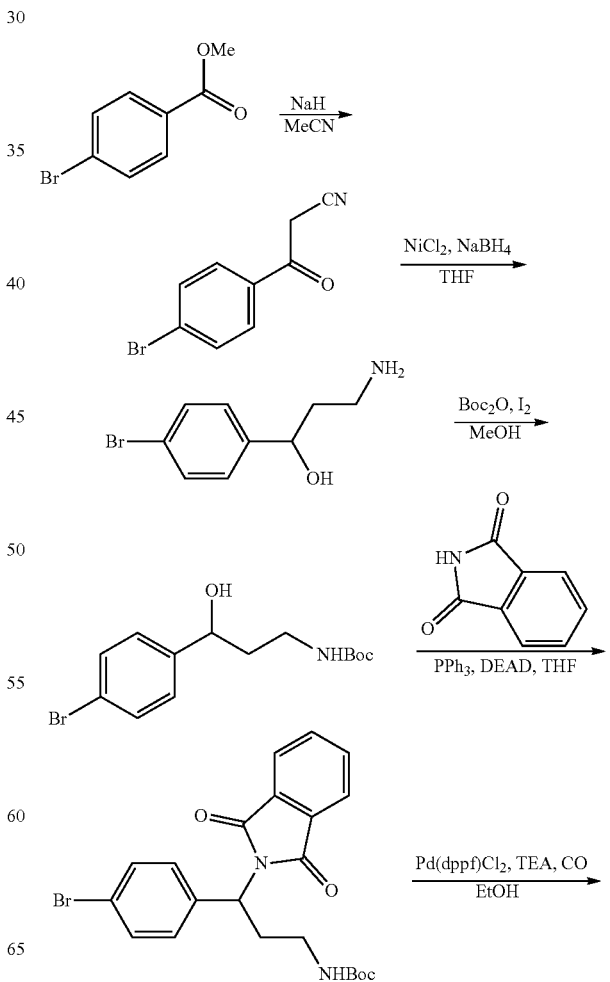

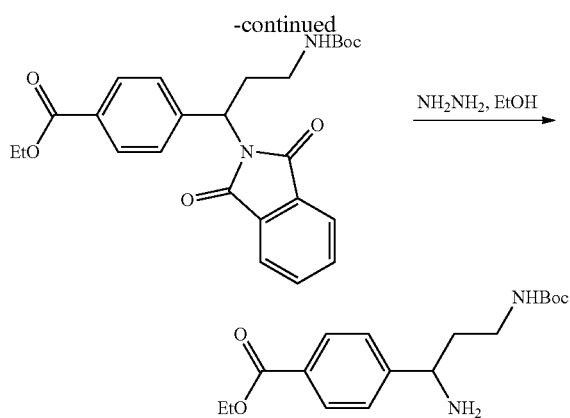

Step 1—3-(4-Bromophenyl)-3-oxo-propanenitrile

To a mixture of acetonitrile (1.40 g, 34.1 mmol) in anhydrous tetrahydrofuran (50 mL) was added sodium hydride (1.09 g, 27.2 mmol) portion-wise at rt under nitrogen. Then methyl 4-bromobenzoate (4.50 g, 20.9 mmol) was added to the mixture and then the resulting mixture was heated to 67° C. and stirred for 2 hours. On completion, the reaction was cooled to rt and 1 N hydrochloric acid solution (50 mL) was added. The aqueous layer was extracted with ethyl acetate (4×50 mL). The organic layer was washed with sodium bicarbonate (200 mL), dried over sodium sulfate, and concentrated in vacuo to give the title compound. $^1$H NMR (400 MHz, DMSO-$d_6$) δ=7.80 (d, J=8.0 Hz, 2H), 7.73 (d, J=8.0 Hz, 2H), 4.51 (s, 2H).

Step 2—3-Amino-1-(4-bromophenyl)propan-1-ol

To a mixture of 3-(4-bromophenyl)-3-oxo-propanenitrile (7.00 g, 31.2 mmol) and nickel chloride hexahydrate (18.6 g, 78.1 mmol) in anhydrous tetrahydrofuran (150 mL) was added sodium borohydride (5.91 g, 156 mmol) portion-wise at 0° C. under a nitrogen. The mixture was warmed to rt and stirred for 2 hours. On completion, ammonium chloride (10 mL) was added to the reaction and the mixture was extracted with EtOAc (3×100 mL). The organic layer was dried over anhydrous sodium sulfate, and filtered. The residue was concentrated in vacuo to give the title compound. LCMS: (ES$^+$) m/z (M+H)$^+$=230.0, tR=1.069.

Step 3—Tert-butyl N-[3-(4-bromophenyl)-3-hydroxy-propyl]carbamate

To a mixture of 3-amino-1-(4-bromophenyl)-propan-1-ol (8.85 g, 38.5 mmol) in methanol (300 mL) was added iodine (976 mg, 3.85 mmol) and di-tert-butyl dicarbonate (25.2 g, 115 mmol) in one portion at rt under a nitrogen. The mixture was stirred at rt and stirred for 16 hours. On completion, the reaction was concentrated in vacuo. The residue was purified by silica gel chromatography with dichloromethane:methanol=50:1 to give the title compound. LCMS: (ES$^+$) m/z (M-100)$^+$=230.0, tR=1.284.

Step 4—Tert-butyl N-[3-(4-bromophenyl)-3-(1,3-dioxoisoindolin-2-yl)propyl]carbamate To a mixture of tert-butyl N-[3-(4-bromophenyl)-3-hydroxy-propyl]carbamate (3.40 g, 10.3 mmol) and isoindoline-1,3-dione (1.52 g, 10.3 mmol) and triphenylphosphine (4.05 g, 15.5 mmol) in tetrahydrofuran (60 mL) was added diisopropyl azodicarboxylate (3.12 g, 15.5 mmol) dropwise at 0° C. under nitrogen. The mixture was stirred at 0° C. for 30 min, then warmed to rt and stirred for 15.5 hours. On completion, the reaction was quenched with water (5 mL) and extracted with ethyl acetate (3×50 mL). The organic layer was combined and washed with brine, dried over anhydrous sodium sulfate and concentrated in vacuo. The residue was purified by silica gel chromatography with petroleum ether:ethyl acetate (50:1 to 10:1) to give the title compound. $^1$H NMR (400 MHz, CDCl$_3$) δ=7.94-7.87 (m, 2H), 7.82-7.80 (m, 3H), 7.72 (dd, J=3.1, 5.4 Hz, 2H), 7.30-7.28 (m, 1H), 5.39 (dd, J=6.4, 10.0 Hz, 1H), 4.70 (br. s., 1H), 3.36-3.21 (m, 1H), 3.18-3.04 (m, 1H), 2.87-2.69 (m, 1H), 2.52-2.34 (m, 1H), 1.42 (s, 9H).

Step 5—Ethyl 4-[3-(tert-butoxycarbonyl amino)-1-(1,3-dioxoisoindolin-2-yl)propyl]benzoate To a solution of tert-butyl N-[3-(4-bromophenyl)-3-(1,3-dioxoisoindolin-2-yl)propyl]-carbamate (1.20 g, 2.61 mmol) and 1,1'-bis(diphenylphosphino)ferrocene-palladium(II)dichloride dichloromethane complex (213 mg, 261 umol) in ethanol (50.0 mL) was added triethylamine (1.32 g, 13.1 mmol) at rt. The mixture was bubbled with CO at 80° C. under 50 psi, then the mixture was stirred at 80° C. for 12 hrs. On completion, the reaction mixture was concentrated in vacuo. The residue was purified by silica gel chromatography with petroleum ether: ethyl acetate (20:1 to 10:1) to give the title compound. LCMS: (ES$^+$) m/z (M-100)$^+$=353.1, tR=1.548.

Step 6—Ethyl 4-[1-amino-3-(tert-butoxycarbonylamino)propyl]benzoate

To a mixture of ethyl 4-[3-(tert-butoxycarbonylamino)-1-(1,3-dioxoisoindolin-2-yl)propyl]benzoate (830 mg, 1.83 mmol) in ethanol (20 mL) was added hydrazine hydrate (366 mg, 7.32 mmol) in one portion at rt under nitrogen. The mixture was heated to 78° C. and stirred for 2 hours. On completion, the reaction was concentrated in vacuo. The residue was purified by silica gel chromatography with petroleum ether: ethyl acetate (40:1 to 20:1) to give the title compound. LCMS: (ES$^+$) m/z (M-55)$^+$=492.1, tR=1.761.

(±)-Ethyl 4-(1-amino-2-((tert-butoxycarbonyl)amino)ethyl)benzoate (Intermediate O)

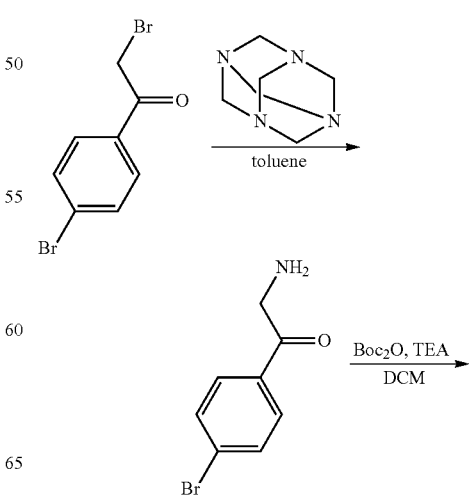

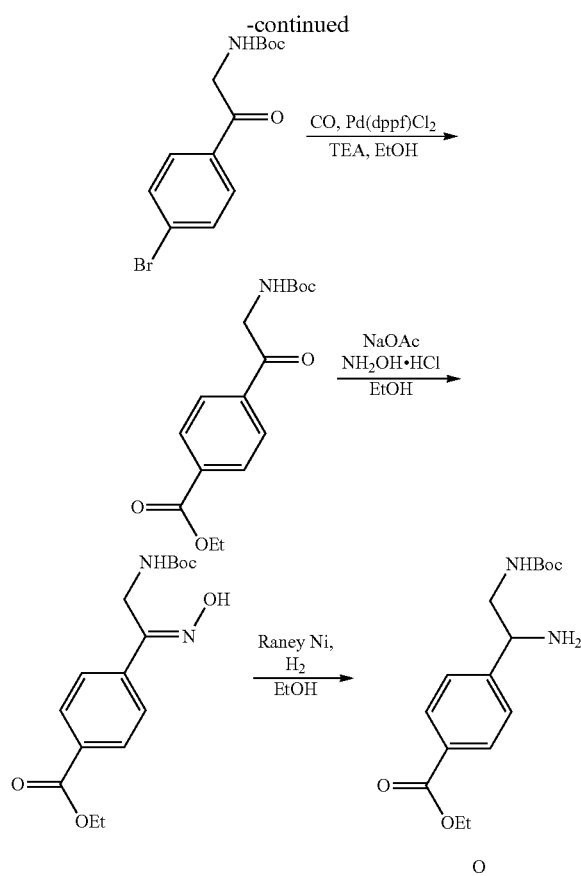

31.8 mmol) and Pd(dppf)Cl$_2$ (466 mg, 636.60 umol) in ethanol (37 mL) was stirred at 80° C. under carbon monoxide (50 psi) for 12 hrs. On completion, the mixture was concentrated, and the residue was purified by chromatography (petroleum ether:ethyl acetate=12:1 to 9:1) to give the title compound. LCMS: (ES$^+$) m/z (M+23)$^+$=330.2, tR=0.826.

Step 4—Ethyl 4-(2-((tert-butoxycarbonyl)amino)-1-(hydroxyimino)ethyl)benzoate

A mixture of ethyl 4-[2-(tert-butoxycarbonylamino)acetyl]benzoate (600 mg, 1.95 mmol), sodium acetate (640 mg, 7.80 mmol) and hydroxylamine hydrochloride (407 mg, 5.85 mmol) in ethanol (10 mL) was stirred at 80° C. for 1 h. On completion, the mixture was concentrated, and the residue was purified by chromatography (petroleum ether:ethyl acetate=8:1) to give the title compound. LCMS: (ES$^+$) m/z (M+23)$^+$=345.1, tR=0.779.

Step 5—(±)-Ethyl 4-(1-amino-2-((tert-butoxycarbonyl)amino)ethyl)benzoate

To a solution of ethyl 4-(2-((tert-butoxycarbonyl)amino)-1-(hydroxyimino)ethyl)benzoate (500 mg, 1.55 mmol) in ethanol (15 mL) was added Raney-Nickel (133 mg), and the mixture was stirred at rt under hydrogen (50 psi) for 3 hrs. On completion, the mixture was filtered, and the filtrate was concentrated in vacuo to give the title compound. LCMS: (ES$^+$) m/z (M+H)$^+$=309.1, tR=0.602.

(±)-Ethyl 4-[1-amino-3-[tert-butoxycarbonyl(methyl)amino]propyl]benzoate (Intermediate P)

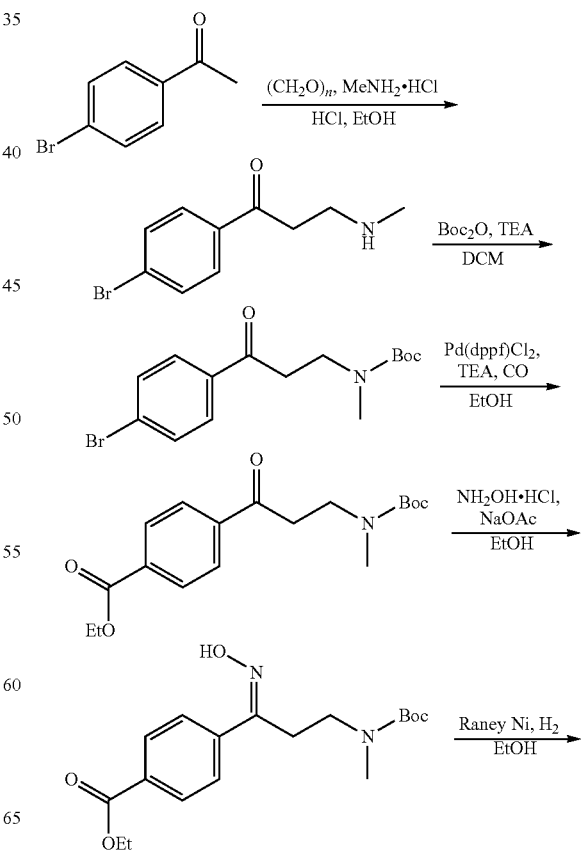

Step 1—2-Amino-1-(4-bromophenyl)ethanone

A mixture of hexamethylenetetramine (3.28 g, 23.4 mmol) and 2-bromo-1-(4-bromophenyl) ethanone (6.50 g, 23.4 mmol) in toluene (70 mL) was stirred at 40° C. for 12 hrs. On completion, the solid was collected by filtration, then suspended in a mixture of ethanol (50 mL) and concentrated hydrochloric acid (15 mL). The mixture was stirred for 0.5 hrs and then filtered. The solid was washed with ethanol (20 mL) to give the title compound. LCMS: (ES$^+$) m/z (M+H)$^+$=214.0, tR=0.171.

Step 2—Tert-butyl (2-(4-bromophenyl)-2-oxoethyl)carbamate

To the solution of 2-amino-1-(4-bromophenyl)ethanone (4.00 g, 16.0 mmol) and triethylamine (3.23 g, 31.9 mmol) in dichloromethane (100 mL) was added di-tert-butyl dicarbonate (4.18 g, 19.2 mmol). The mixture was stirred at rt for 1 hr. On completion, the mixture was poured into water (30 mL), and the aqueous phase was extracted with dichloromethane (3×30 mL). The combined organic layers were dried over anhydrous sodium sulfate, filtered, and concentrated. The residue was purified by column chromatography (petroleum ether:ethyl acetate=20:1 to 9:1) to give the title compound. LCMS: (ES$^+$) m/z (M+Na)$^+$=336.0, tR=0.807.

Step 3—Ethyl 4-(2-((tert-butoxycarbonyl)amino)acetyl)benzoate

A mixture of tert-butyl N-[2-(4-bromophenyl)-2-oxoethyl]carbamate (2.00 g, 6.37 mmol), triethylamine (3.22 g, -continued

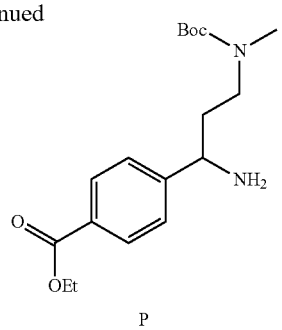

P

Step 1—1-(4-Bromophenyl)-3-(methylamino)propan-1-one

A mixture of 1-(4-bromophenyl)ethanone (10.0 g, 50.2 mmol), paraformaldehyde (5.43 g, 60.3 mmol), methylamine hydrochloride (3.73 g, 55.2 mmol), and concentrated hydrochloric acid (27.5 mg, 25.0 uL) in ethanol (50 mL) was heated in a sealed flask at 110° C. for 20 hrs. On completion, the reaction mixture was directly concentrated in vacuo and the residue was triturated with ethyl acetate (100 mL) to give the title compound. $^1$H NMR (400 MHz, MeOD-$d_4$) δ=7.98 (d, J=8.4 Hz, 2H), 7.74 (d, J=8.4 Hz, 2H), 3.57-3.52 (m, 2H), 3.46-3.40 (m, 2H), 2.79 (s, 3H).

Step 2—Tert-butyl N-[3-(4-bromophenyl)-3-oxopropyl]-N-methyl-carbamate

To a solution of 1-(4-bromophenyl)-3-(methylamino)propan-1-one (7.40 g, 26.5 mmol, hydrochloride) in anhydrous dichloromethane (80 mL) was added triethylamine (8.06 g, 79.9 mmol). At this point di-tert-butyl dicarbonate (11.6 g, 53.1 mmol) was added dropwise. The mixture was stirred at rt for 3 hrs. On completion, the reaction mixture was quenched with ice water (30 mL), then diluted with water (100 mL) and extracted with dichloromethane (3×100 mL). The combined organic layers were dried over anhydrous sodium sulfate, filtered and concentrated in vacuo. The residue was purified by column chromatography (SiO$_2$, petroleum ether: ethyl acetate=50:1 to 20:1) to give the title compound. $^1$H NMR (400 MHz, CDCl$_3$) δ=7.76 (d, J=8.4 Hz, 2H), 7.54 (d, J=8.4 Hz, 2H), 3.55 (t, J=7.0 Hz, 2H), 3.15-3.04 (m, 2H), 2.83 (s, 3H), 1.37 (s, 9H).

Step 3—Ethyl 4-[3-[tert-butoxycarbonyl(methyl)amino]propanoyl]benzoate

To a solution of tert-butyl N-[3-(4-bromophenyl)-3-oxopropyl]-N-methyl-carbamate (3.00 g, 8.77 mmol) in ethanol (100 mL) was added Pd(dppf)Cl$_2$ (1.28 g, 1.75 mmol) and triethylamine (4.44 g, 43.8 mmol) under nitrogen. The suspension was degassed under vacuum and purged with carbon monoxide several times. The mixture was stirred under carbon monoxide (50 psi) at 80° C. for 16 hrs. On completion, the reaction mixture was filtered and the filtrate was concentrated in vacuo to give a residue. The residue was purified by column chromatography (petroleum ether:ethyl acetate=50:1 to 15:1) to give the title compound. $^1$H NMR (400 MHz, CDCl$_3$) δ=8.06 (d, J=8.0 Hz, 2H), 7.94 (d, J=8.0 Hz, 2H), 4.34 (q, J=7.2 Hz, 2H), 3.57 (t, J=7.2 Hz, 2H), 3.21-3.09 (m, 2H), 2.84 (s, 3H), 1.37 (s, 9H), 1.32 (t, J=7.2 Hz, 3H).

Step 4—Ethyl 4-[(E and Z)—C-[2-[tert-butoxycarbonyl(methyl)amino]ethyl]-N-hydroxy-carbonimidoyl]-benzoate To a mixture of ethyl 4-[3-[tert-butoxycarbonyl(methyl)amino]propanoyl]benzoate (2.00 g, 5.96 mmol) in ethanol (15 mL) was added hydroxylamine hydrochloride (2.07 g, 29.8 mmol) and sodium acetate (2.45 g, 29.8 mmol). The mixture was stirred at 100° C. under nitrogen for 3 hrs. On completion, the reaction mixture was concentrated in vacuo. The residue was diluted with ice water (10 mL) and extracted with dichloromethane (3×10 mL). The combined organic layers were dried over anhydrous sodium sulfate, filtered and concentrated in vacuo to afford the title compound. $^1$H NMR (400 MHz, CDCl$_3$) δ=8.30-8.11 (m, 1H), 7.97 (d, J=8.4 Hz, 2H), 7.79-7.66 (m, 2H), 4.32 (q, J=7.2 Hz, 2H), 3.55-3.45 (m, 2H), 3.10-2.99 (m, 2H), 2.91-2.75 (m, 3H), 1.40 (s, 9H), 1.35 (t, J=7.2 Hz, 3H).

Step 5—(±)-Ethyl 4-[1-amino-3-[tert-butoxycarbonyl(methyl)amino]propyl]benzoate To a solution of ethyl 4-[(E and Z)—C-[2-[tert-butoxycarbonyl(methyl)amino]ethyl]-N-hydroxy-carbon-imidoyl]benzoate (1.00 g, 2.85 mmol) in ethanol (30 mL) was added Raney-Nickel (10%, 100 mg) under nitrogen. The suspension was degassed under vacuum and purged with hydrogen gas atmosphere several times. The mixture was stirred under hydrogen gas atmosphere (50 psi) at rt for 3 hrs. On completion, the reaction mixture was filtered and the filtrate was concentrated in vacuo to give the title compound. LCMS: (ES$^+$) m/z (M+H)$^+$=337.2, tR=0.812.

(±)-Methyl 4-(1-amino-2,2,2-trifluoroethyl)benzoate (Intermediate Q)

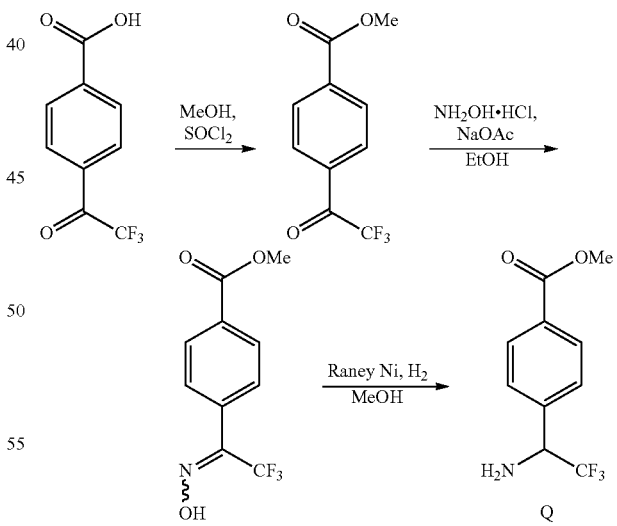

Step 1—Methyl 4-(2,2,2-trifluoroacetyl)benzoate

To a solution of 4-(2,2,2-trifluoroacetyl)benzoic acid (322 mg, 1.48 mmol) in methanol (5 mL) was added thionyl chloride (528 mg, 4.44 mmol) dropwise at 0° C. The mixture was stirred at rt for 16 hours. The reaction mixture was concentrated in vacuo. The residue was dissolved in dichloromethane (10 mL) and washed with saturated aqueous sodium bicarbonate (3×5 mL). The organic layer was then dried over sodium sulfate, filtered and concentrated in vacuo to give the title compound which was used crude in the next step.

Step 2—Methyl 4-(2,2,2-trifluoro-1-(hydroxyimino)ethyl)benzoate

To a solution of methyl 4-(2,2,2-trifluoroacetyl)benzoate (336 mg, 1.45 mmol) in ethanol (5 mL) was added potassium acetate (426 mg, 4.35 mmol) and hydroxylamine hydrochloride (302 mg, 4.35 mmol). The reaction mixture was stirred at 78° C. for 1 hour. The reaction mixture was concentrated in vacuo. The residue was dissolved in dichloromethane (30 mL), washed with water (10 mL) and brine (3×10 mL), dried over sodium sulfate, filtered and concentrated in vacuo. The residue was purified by chromatography (petroleum ether:ethyl acetate=50:1 to 20:1) to give the title compound. LCMS: (ES$^+$) m/z (M+H)$^+$=248.2, tR=0.808. $^1$H NMR (400 MHz, CDCl$_3$) δ=8.15 (d, J=8.4 Hz, 1H), 8.10 (d, J=8.4 Hz, 1H), 7.59 (dd, J=3.6 Hz, J=8 Hz, 2H), 3.97 (s, 3H).

Step 3—(±)-Methyl 4-(1-amino-2,2,2-trifluoroethyl)benzoate

To a solution of methyl 4-(2,2,2-trifluoro-1-(hydroxyimino)ethyl)benzoate (320 mg, 1.29 mmol) in methanol (5 mL) was added Raney-Nickel (11.0 mg, 129 umol) under hydrogen (50 psi). The reaction mixture was stirred at rt for 3 hours. On completion, the reaction mixture was filtered and concentrated in vacuo to give the title compound. LCMS: (ES$^+$) m/z (M+H)$^+$=234.2, tR=0.573.

(S)-methyl 4-(1-amino-2-hydroxyethyl)benzoate (Intermediate R)

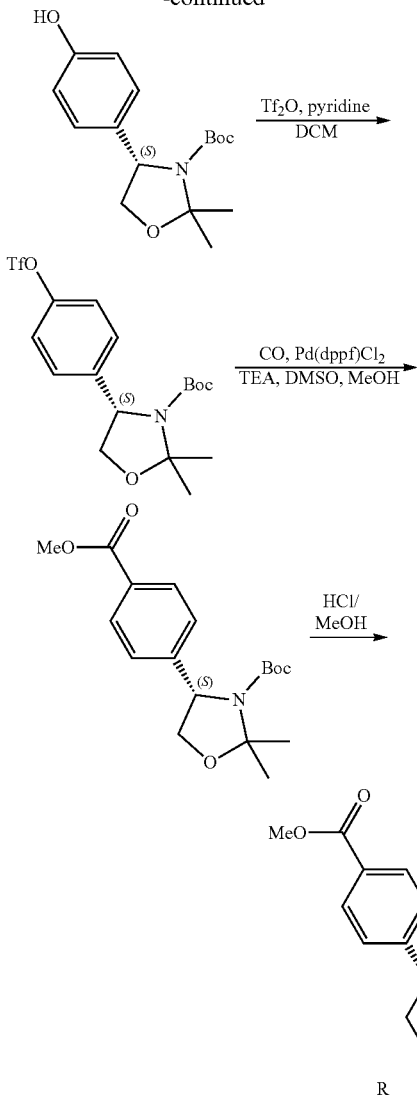

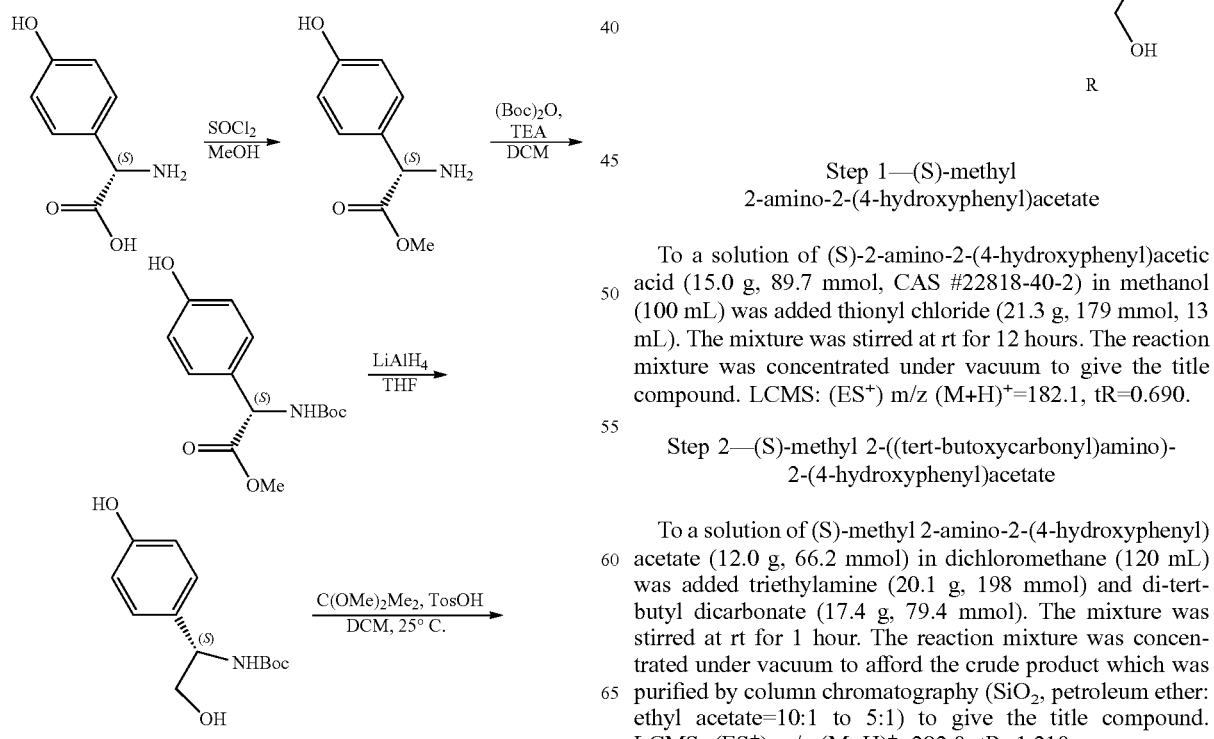

Step 1—(S)-methyl 2-amino-2-(4-hydroxyphenyl)acetate

To a solution of (S)-2-amino-2-(4-hydroxyphenyl)acetic acid (15.0 g, 89.7 mmol, CAS #22818-40-2) in methanol (100 mL) was added thionyl chloride (21.3 g, 179 mmol, 13 mL). The mixture was stirred at rt for 12 hours. The reaction mixture was concentrated under vacuum to give the title compound. LCMS: (ES$^+$) m/z (M+H)$^+$=182.1, tR=0.690.

Step 2—(S)-methyl 2-((tert-butoxycarbonyl)amino)-2-(4-hydroxyphenyl)acetate

To a solution of (S)-methyl 2-amino-2-(4-hydroxyphenyl)acetate (12.0 g, 66.2 mmol) in dichloromethane (120 mL) was added triethylamine (20.1 g, 198 mmol) and di-tert-butyl dicarbonate (17.4 g, 79.4 mmol). The mixture was stirred at rt for 1 hour. The reaction mixture was concentrated under vacuum to afford the crude product which was purified by column chromatography (SiO$_2$, petroleum ether:ethyl acetate=10:1 to 5:1) to give the title compound. LCMS: (ES$^+$) m/z (M+H)$^+$=282.0, tR=1.210.

Step 3—(S)-tert-butyl (2-hydroxy-1-(4-hydroxyphenyl)ethyl)carbamate

To a solution of (S)-methyl 2-((tert-butoxycarbonyl)amino)-2-(4-hydroxyphenyl)acetate (16.0 g, 56.9 mmol) in tetrahydrofuran (500 mL) was added lithium aluminum hydride (4.32 g, 113 mmol). The mixture was stirred at rt for 1 hour. The reaction mixture was quenched by addition sodium sulfate decahydrate and filtered. The filtrate was concentrated under vacuum to afford the crude product. The residue was purified by column chromatography ($SiO_2$, petroleum ether:ethyl acetate=3:1 to 1:1) to give the title compound.

Step 4—(S)-tert-butyl 4-(4-hydroxyphenyl)-2,2-dimethyloxazolidine-3-carboxylate To a solution of (S)-tert-butyl (2-hydroxy-1-(4-hydroxyphenyl)ethyl)carbamate (10.0 g, 39.4 mmol) in dichloromethane (100 mL) was added p-toluenesulfonic acid (679 mg, 3.95 mmol) and 2,2-dimethoxypropane (82.2 g, 789 mmol). The mixture was stirred at rt for 12 hours. The reaction mixture was concentrated in vacuo to give the title compound. $^1$H NMR (400 MHz, $CDCl_3$) δ=7.08 (d, J=8.8 Hz, 2H), 6.71-6.64 (m, 2H), 4.80-4.65 (m, 1H), 4.19-4.15 (m, 1H), 3.78-3.76 (m, 1H), 1.68-1.64 (m, 3H), 1.52 (s, 3H), 1.26-1.15 (m, 9H).

Step 5—(S)-tert-butyl 2,2-dimethyl-4-(4-(((trifluoromethyl)sulfonyl)oxy)phenyl)oxazolidine-3-carboxylate To a solution of (S)-tert-butyl 4-(4-hydroxyphenyl)-2,2-dimethyloxazolidine-3-carboxylate (5.00 g, 17.0 mmol) in dichloromethane (50 mL) was added pyridine (13.5 g, 170 mmol) and then trifluoromethanesulfonic anhydride (5.77 g, 20.4 mmol). The mixture was stirred at 0° C. for 2 hours. The reaction mixture solution was quenched with water (10 mL) and diluted with dichloromethane (50 mL). Then the organic layer was separated and dried over anhydrous sodium sulfate and filtered. The filtrate was concentrated under vacuum to afford the crude product as a brown oil. The crude product was purified by column chromatography ($SiO_2$, petroleum ether:ethyl acetate=5:1) to give the title compound. $^1$H NMR (400 MHz, $CDCl_3$) δ=7.71 (d, J=8.0 Hz, 2H), 7.39 (d, J=8.0 Hz, 2H), 4.97-4.81 (m, 1H), 4.33-4.26 (m, 1H), 3.87-3.65 (m, 1H), 1.78-1.72 (m, 3H), 1.47 (s, 3H), 1.36-1.15 (m, 9H).

Step 6—(S)-tert-butyl 4-(4-(methoxycarbonyl)phenyl)-2,2-dimethyloxazolidine-3-carboxylate To a solution of (S)-tert-butyl 2,2-dimethyl-4-(4-(((trifluoromethyl)sulfonyl)oxy)-phenyl)oxazolidine-3-carboxylate (5.00 g, 11.7 mmol) in methanol (50 mL) and dimethyl sulfoxide (50 mL) was added $Pd(dppf)Cl_2$ (859 mg, 1.18 mmol) and triethylamine (2.38 g, 23.5 mmol). The mixture was stirred at 70° C. for 12 hours in carbon monoxide atmosphere under 50 psi. The crude product was purified by column chromatography ($SiO_2$, petroleum ether:ethyl acetate=5:1) to give the title compound. $^1$H NMR (400 MHz, $CDCl_3$) δ=7.99 (d, J=8.0 Hz, 2H), 7.35 (d, J=8.0 Hz, 2H), 4.97-4.83 (m, 1H), 4.33-4.28 (m, 1H), 3.91 (s, 3H), 3.85-3.83 (m, 1H), 1.78-1.72 (m, 3H), 1.61 (s, 3H), 1.45-1.18 (m, 9H).

Step 7—(S)-methyl 4-(1-amino-2-hydroxyethyl)benzoate

A solution of (S)-tert-butyl 4-(4-(methoxycarbonyl)phenyl)-2,2-dimethyloxazolidine-3-carboxylate (150 mg, 447 umol) in 4N HCl/MeOH (3 mL) was stirred at rt for 1 hour. The reaction solution was concentrated in vacuo to give the title compound. LCMS: ($ES^+$) m/z $(M+H)^+$=196.1, tR=0.681.

(±)-Methyl 4-(1-aminoethyl)benzoate (Intermediate S)

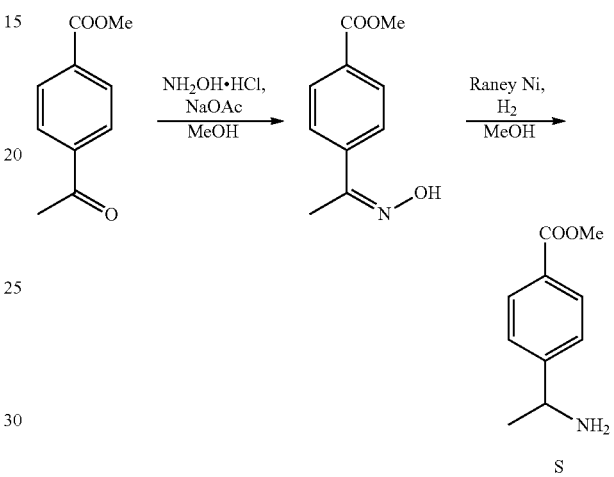

Step 1—Methyl 4-(1-(hydroxyimino)ethyl)benzoate

The mixture of methyl 4-acetylbenzoate (2.00 g, 11.2 mmol), hydroxylamine hydrochloride (1.56 g, 22.5 mmol) and sodium acetate (2.76 g, 33.7 mmol) in ethanol (40 mL) was stirred at 70° C. for 2 hrs. On completion, the mixture was filtered. The solid was collected by filtration, washed with water (30 mL), and dried in vacuo to give the title compound. LCMS: ($ES^+$)m/z $(M+H)^+$=194.1, tR=0.643.

Step 2—(±)-Methyl 4-(1-aminoethyl)benzoate

To a solution of methyl 4-(1-(hydroxyimino)ethyl)benzoate (800 mg, 4.14 mmol) in methanol (30 mL) was added Raney-Nickel (700 mg). The reaction mixture was stirred under hydrogen (50 psi) at rt for 4 hrs. On completion, the mixture was filtered. The filtrate was concentrated in vacuo to give the title compound. $^1$H NMR (400 MHz, DMSO-$d_6$) δ=7.90 (d, J=8.4 Hz, 2H), 7.52 (d, J=8.0 Hz, 2H), 4.06 (q, J=6.8 Hz, 1H), 3.84 (s, 3H), 1.25 (d, J=6.8 Hz, 3H).

Ethyl 4-[amino(cyclopropyl)methyl]benzoate (Intermediate T)

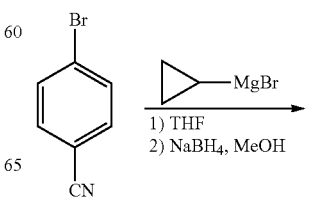

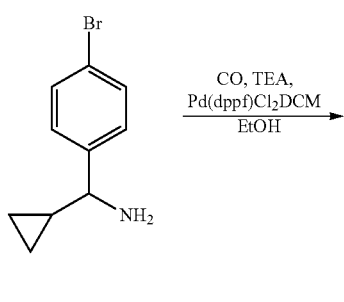

Step 1—(±)-(4-Bromophenyl)-cyclopropyl-methanamine

A solution of 4-bromobenzonitrile (1.30 g, 7.14 mmol) in anhydrous tetrahydrofuran (5 mL) was added over a period of 15 mins to a 0.5 M solution of bromo(cyclopropyl) magnesium (42 mL) in anhydrous tetrahydrofuran chilled in an ice bath. After stirring the resulting solution at 0° C. for 5.5 hours, anhydrous methanol (20 mL) was added over a period of 15 mins. Then sodium borohydride (540 mg, 14.2 mmol) was added in portions and the resulting mixture was warmed to rt and stirred for 14 hours. On completion, the reaction mixture was concentrated in vacuo. The residue was diluted with saturated sodium bicarbonate solution (30 mL) and extracted with dichloromethane (3×30 mL). The combined organic layers were extracted with 1 M hydrochloric acid (2×30 mL), then the aqueous phase was collected and basified with 4 M aqueous sodium hydroxide solution until pH=8-9. The aqueous phase was again extracted with dichloromethane (3×30 mL), and the combined organic layers were dried with anhydrous sodium sulfate, filtered and concentrated in vacuo to give the title compound. $^1$H NMR (400 MHz, CDCl$_3$) δ=7.47 (d, J=8.4 Hz, 2H), 7.31 (d, J=8.4 Hz, 2H), 3.19 (d, J=8.5 Hz, 1H), 1.68 (s, 2H), 1.11-1.00 (m, 1H), 0.67-0.58 (m, 1H), 0.53-0.45 (m, 1H), 0.38-0.31 (m, 1H), 0.31-0.24 (m, 1H).

Step 2—Ethyl 4-[amino(cyclopropyl)methyl]benzoate

To a solution of (4-bromophenyl)-cyclopropyl-methanamine (900 mg, 3.98 mmol) in ethanol (40 mL) was added Pd(dppf)Cl$_2$.DCM (582 mg, 796 umol) and triethylamine (2.01 g, 19.9 mmol) under nitrogen gas. The suspension was degassed under vacuum and purged with carbon monoxide several times. The mixture was stirred under carbon monoxide (50 psi) at 80° C. for 16 hours. On completion, the reaction mixture was filtered and the filtrate was concentrated in vacuo. The residue was purified by column chromatography (SiO$_2$, dichloromethane:methanol=50:1 to 20:1) to give the title compound. $^1$H NMR (400 MHz, CDCl$_3$) δ=7.96 (d, J=8.4 Hz, 2H), 7.54 (d, J=8.4 Hz, 2H), 4.30 (q, J=7.2 Hz, 2H), 3.55 (d, J=9.6 Hz, 1H), 1.43-1.35 (m, 1H), 1.30 (t, J=7.2 Hz, 3H), 0.63-0.50 (m, 3H), 0.32-0.21 (m, 1H).

(±)-Ethyl 4-(1-amino-2-cyclopropyl-ethyl)benzoate (Intermediate U)

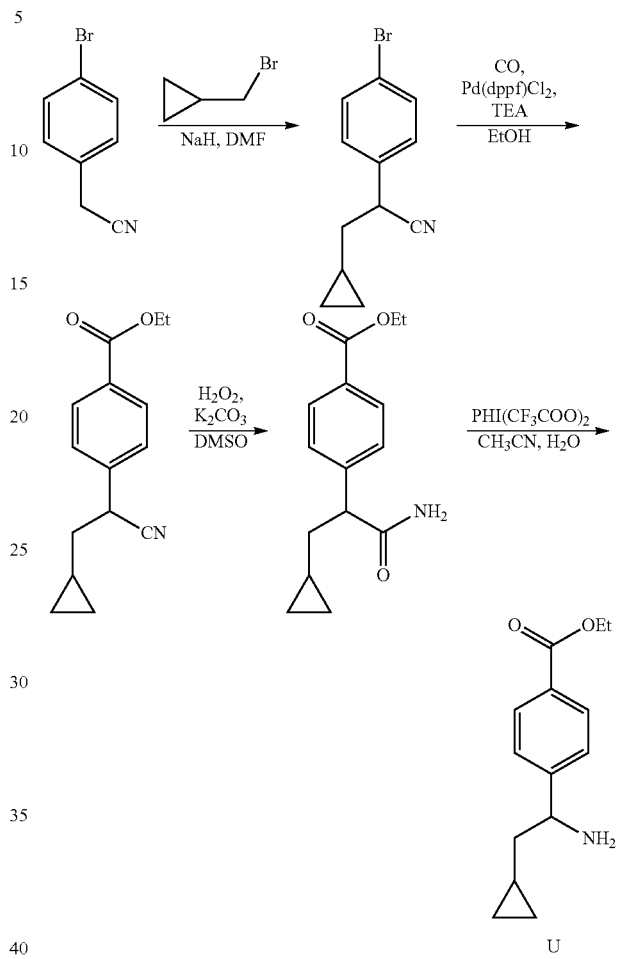

Step 1—(±)-2-(4-Bromophenyl)-3-cyclopropyl-propanenitrile

To a suspension of sodium hydride (673 mg, 16.8 mmol, 60% purity) in N,N-dimethylformamide (30 mL) was added a solution of 2-(4-bromophenyl)acetonitrile (3.00 g, 15.3 mmol) in N,N-dimethylformamide (15 mL) at 0° C. The reaction mixture was stirred at 0° C. for 1 h. Then bromomethylcyclopropane (2.07 g, 15.3 mmol) was added. The mixture was stirred at rt for 3 hrs. On completion, the mixture was diluted with water (30 mL) and extracted with ethyl acetate (3×15 mL). The combined organic layers were washed with water (3×15 mL), dried over sodium sulfate, filtered and concentrated in vacuo. The residue was purified by chromatography (petroleum ether:ethyl acetate=30:1 to 10:1) to give the title compound. $^1$H NMR (400 MHz, CDCl$_3$) δ=7.51 (d, J=8.4 Hz, 2H), 7.22 (d, J=8.4 Hz, 2H), 3.82 (dd, J=6.4, 8.0 Hz, 1H), 1.84-1.91 (m, 2H), 0.53-0.62 (m, 3H), 0.14-0.20 (m, 2H).

Step 2—(±)-Ethyl 4-(1-cyano-2-cyclopropyl-ethyl)benzoate

To a solution of (±)-2-(4-bromophenyl)-3-cyclopropyl-propanenitrile (2.66 g, 10.6 mmol) in ethanol (30 mL) was added triethylamine (5.38 g, 53.1 mmol) and Pd(dppf)Cl$_2$ (868 mg, 1.06 mmol). The reaction mixture was stirred under carbon monoxide (50 psi) at 60° C. for 20 hrs. On completion, the mixture was concentrated in vacuo. The residue was purified by chromatography (petroleum ether: ethyl acetate=50:1 to 20:1) to give the title compound. LCMS: (ES$^+$) m/z (M+H)$^+$=244.1, tR=0.888.

Step 3—(±)-Ethyl 4-[2-amino-1-(cyclopropylmethyl)-2-oxo-ethyl]benzoate

To a solution of (±)-ethyl 4-(1-cyano-2-cyclopropyl-ethyl)benzoate (200 mg, 822 umol) and potassium carbonate (45.5 mg, 328 umol) in dimethyl sulfoxide (6 mL) was added hydrogen peroxide (745 mg, 6.57 mmol 30% solution). The reaction mixture was stirred at rt for 3 hrs. On completion, the mixture was diluted with saturated sodium thiosulfate (20 mL) and extracted with ethyl acetate (3×30 mL). The combined organic layers were washed with brine (3×30 mL), dried over anhydrous sodium sulfate and concentrated. The residue was purified by chromatography (petroleum ether:ethyl acetate=30:1 to 2:1) to give the title compound. LCMS: (ES$^+$) m/z (M+H)$^+$=262.2, tR=0.766.

Step 4—(±)-Ethyl 4-(1-amino-2-cyclopropyl-ethyl)benzoate

To the solution of (±)-ethyl 4-[2-amino-1-(cyclopropylmethyl)-2-oxo-ethyl]benzoate (200 mg, 765 umol) in water (2 mL) and acetonitrile (2 mL) was added [bis(trifluoroacetoxy)iodo]benzene (360 mg, 857 umol). The reaction mixture was stirred at rt for 16 hrs. On completion, the mixture was concentrated in vacuo to remove the organic solvent. The aqueous phase was diluted with water (10 mL), acidified with hydrochloric acid (1 N), and washed with ethyl acetate (3×20 mL). The aqueous phase was basified with saturated aqueous sodium bicarbonate until pH=9, and extracted with ethyl acetate (3×20 mL). The combined organic layers were dried over anhydrous sodium sulfate, filtered and concentrated in vacuo to give the title compound. LCMS: (ES$^+$) m/z (M-NH$_2$)$^+$=217.2, tR=0.649.

Ethyl 4-(1-amino-1-methyl-ethyl)benzoate (Intermediate V)

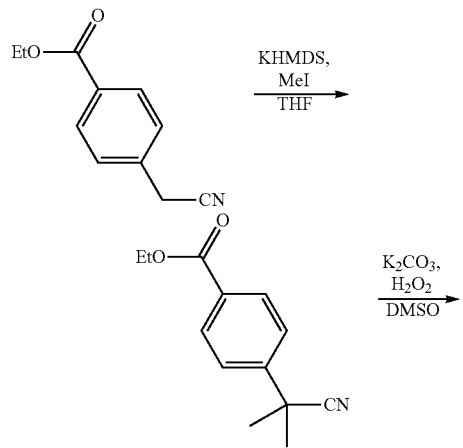

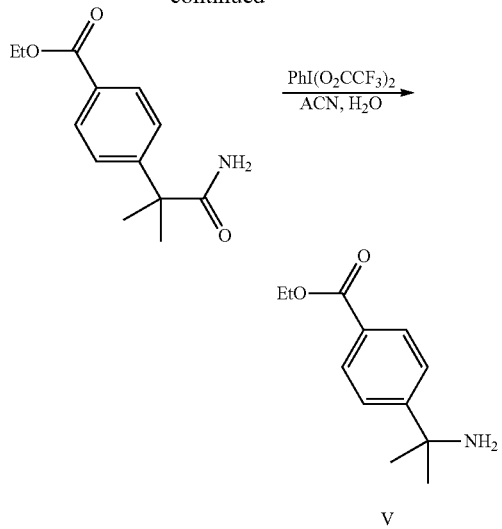

Step 1—Ethyl 4-(1-cyano-1-methyl-ethyl)benzoate

To a solution of ethyl 4-(cyanomethyl)benzoate (2.50 g, 13.2 mmol) in anhydrous tetrahydrofuran (80 mL) was added potassium bis(trimethylsilyl)amide (1 M, 52.8 mL) at −10° C. After the reaction mixture was stirred at −10° C. for 30 min, methyl iodide (9.38 g, 66.0 mmol) was added. The reaction mixture was warmed to rt and stirred for 3.5 hrs. On completion, the mixture was quenched with saturated aqueous ammonium chloride (50 mL), extracted with dichloromethane (3×50 mL), dried and concentrated. The residue was purified by chromatography (petroleum ether:ethyl acetate=10:1) to give the title compound. LCMS: (ES$^+$) m/z (M+H)$^+$=218.2, tR=0.819.

Step 2—Ethyl 4-(2-amino-1,1-dimethyl-2-oxo-ethyl)benzoate

To a solution of ethyl 4-(1-cyano-1-methyl-ethyl)benzoate (2.20 g, 10.1 mmol) and potassium carbonate (560 mg, 4.05 mmol) in dimethyl sulfoxide (22 mL) was added hydrogen peroxide (3.45 g, 30.3 mmol, 30% purity). The reaction mixture was stirred at 60° C. for 16 hrs. On completion, the mixture was diluted with water (250 mL). The solid was collected by filtration, and then dried in vacuo to give the title compound. $^1$H NMR (400 MHz, CDCl$_3$) δ=7.93 (d, J=8.0 Hz, 2H), 7.38 (d, J=8.0 Hz, 2H), 4.29 (q, J=7.2 Hz, 2H), 1.51 (s, 6H), 1.24 (t, J=7.2 Hz, 3H).

Step 3—Ethyl 4-(1-amino-1-methyl-ethyl)benzoate

To a mixture of ethyl 4-(2-amino-1,1-dimethyl-2-oxo-ethyl)benzoate (1.80 g, 7.65 mmol) in acetonitrile (35 mL) and water (35 mL) was added [bis(trifluoroacetoxy)iodo]benzene (3.95 g, 9.18 mmol). The reaction mixture was stirred at rt for 18 hrs. On completion, the mixture was concentrated in vacuo. The residue was diluted with water (30 mL) and extracted with dichloromethane (2×20 mL). The combined organic layers were dried over anhydrous sodium sulfate, filtered and concentrated in vacuo to give the title compound. LCMS: (ES$^+$) m/z (M-NH$_2$)$^+$=191.2, tR=0.560.

(±)-Tert-butyl 2-(4-(1-aminoethyl)phenyl)acetate (Intermediate W)

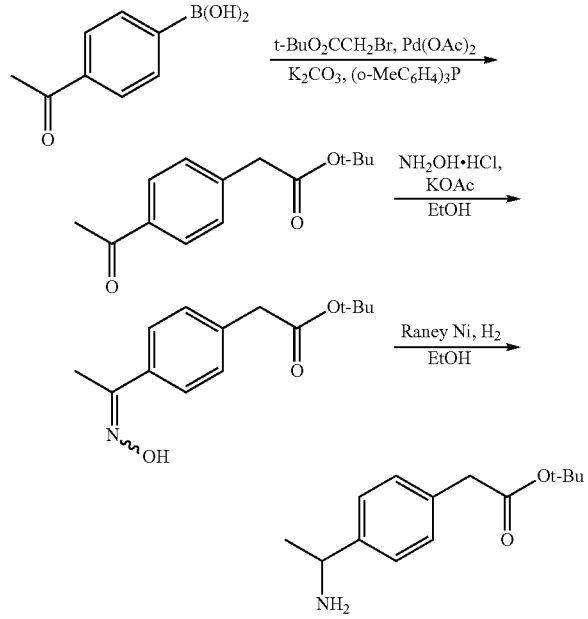

Step 1—Tert-butyl 2-(4-acetylphenyl)acetate

To a solution of tert-butyl 2-bromoacetate (4.00 g, 20.5 mmol) in tetrahydrofuran (70 mL) was added palladium acetate (138 mg, 615 umol), tri(o-methylphenyl)phosphine (624 mg, 2.05 mmol) and potassium carbonate (15.3 g, 111 mmol). Then a solution of (4-acetylphenyl)boronic acid (4.04 g, 24.6 mmol) in tetrahydrofuran (70 mL) and water (2 mL) was added dropwise. The mixture was stirred at rt for 18 hours. On completion, the residue was diluted with ethyl acetate (50 mL), washed with water (50 mL) and brine (40 mL). The combined organic layers were dried over sodium sulfate, filtered and concentrated in vacuo. The residue was purified by chromatography (petroleum ether:ethyl acetate=25:1 to 20:1) to give the title compound. $^1$H NMR (400 MHz, CDCl$_3$) δ=7.83 (d, J=8.4 Hz, 2H), 7.28 (d, J=8.4 Hz, 2H), 3.51 (s, 2H), 2.49 (s, 3H), 1.36 (s, 9H).

Step 2—Tert-butyl 2-(4-(1-(hydroxyimino)ethyl)phenyl)acetate

To a solution of tert-butyl 2-(4-acetylphenyl)acetate (1.30 g, 5.55 mmol) in ethanol (20 mL) was added hydroxylamine hydrochloride (1.93 g, 27.8 mmol) and potassium acetate (2.72 g, 27.8 mmol). The mixture was stirred at 80° C. for 1 hour. On completion, the reaction mixture was concentrated in vacuo. The residue was diluted with ethyl acetate (10 mL) and washed with water (10 mL) followed by brine (10 mL). The organic layer was dried over sodium sulfate, filtered and concentrated in vacuo to give the title compound. $^1$H NMR (400 MHz, DMSO-d$_6$) δ=11.15 (brs., 1H), 7.60 (d, J=8.0 Hz, 2H), 7.26 (d, J=8.0 Hz, 2H), 3.57 (s, 2H), 2.14 (s, 3H), 1.40 (s, 9H).

Step 3—(±)-Tert-butyl 2-(4-(1-aminoethyl)phenyl)acetate

To a solution of tert-butyl 2-(4-(1-(hydroxyimino)ethyl)phenyl)acetate (500 mg, 2.01 mmol) in ethanol (15 mL) was added Raney-Nickel under nitrogen. The suspension was stirred under hydrogen (50 psi) at rt for 2 hours. On completion, the reaction mixture was concentrated in vacuo to give the title compound. $^1$H NMR (400 MHz, DMSO-d$_6$) δ=7.30 (d, J=8.0 Hz, 2H), 7.16 (d, J=8.0 Hz, 2H), 3.96 (m, 1H), 3.50 (s, 2H), 1.40 (s, 9H), 1.23 (d, J=6.8 Hz, 3H).

Methyl 3-amino-3-methyl-butanoate (Intermediate X)

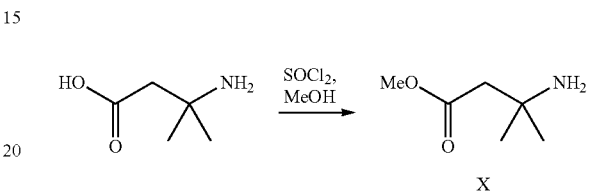

To a solution of 3-amino-3-methyl-butanoic acid (1.00 g, 8.54 mmol) in methanol (20.0 mL) was added sulfur dichloride (508 mg, 4.27 mmol) dropwise at rt. The solution was then stirred at 50° C. for 12 hrs. On completion, the reaction was concentrated in vacuo to give the title compound.

(±)-Ethyl 4-(1-aminoethyl)-3-fluorobenzoate (Intermediate Y)

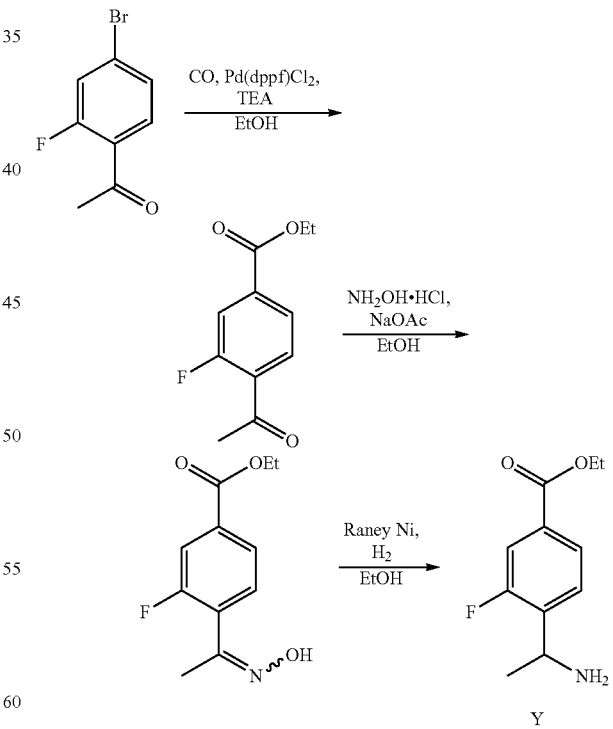

Step 1—Ethyl 4-acetyl-3-fluorobenzoate

A mixture of 1-(4-bromo-2-fluoro-phenyl)ethanone (3.00 g, 13.8 mmol), Pd(dppf)Cl$_2$ (1.13 g, 1.38 mmol) and triethylamine (6.99 g, 69.1 mmol) in ethanol (30 mL) was stirred under carbon monoxide (50 psi) at 70° C. for 16 hrs. On completion, the mixture was concentrated in vacuo. The residue was purified by column chromatography (petroleum ether:ethyl acetate=30:1) to give the title compound. $^1$H NMR (400 MHz, CDCl$_3$) δ=7.97-7.87 (m, 2H), 7.82 (dd, J=1.2, 11.2 Hz, 1H), 4.43 (q, J=7.2 Hz, 2H), 2.69 (s, 3H), 1.43 (t, J=7.2 Hz, 3H).

Step 2—Ethyl 3-fluoro-4-(1-(hydroxyimino)ethyl)benzoate

To a solution of ethyl 4-acetyl-3-fluoro-benzoate (500 mg, 2.38 mmol) in ethanol (20 mL) was added hydroxylamine hydrochloride (827 mg, 11.9 mmol) and sodium acetate (976 mg, 11.9 mmol). The reaction mixture was stirred at 80° C. for 2 hrs. On completion, the mixture was concentrated in vacuo. The residue was poured into ice-water (20 mL), and the aqueous phase was extracted with ethyl acetate (3×20 mL). The combined organic layers were washed with brine (2×10 mL), dried over anhydrous sodium sulfate, filtered and concentrated in vacuo to give the title compound. LCMS: (ES$^+$) m/z (M+H)$^+$=226.2, tR=0.813.

Step 3—(±)-Ethyl 4-(1-aminoethyl)-3-fluorobenzoate

To a solution of ethyl 3-fluoro-4-(1-(hydroxyimino)ethyl) benzoate (600 mg, 2.66 mmol) in ethanol (30 mL) was added Raney-Nickel (22.8 mg, 266 umol) under nitrogen. The mixture was stirred under hydrogen (30 psi) at rt for 16 hrs. On completion, the mixture was concentrated in vacuo to give the title compound. $^1$H NMR (400 MHz, CDCl$_3$) δ=7.83 (dd, J=1.2, 8.0 Hz, 1H), 7.73-7.64 (m, 1H), 7.57-7.46 (m, 1H), 4.49-4.31 (m, 3H), 1.43 (t, J=7.6 Hz, 3H), 1.30 (d, J=5.6 Hz, 3H).

(±)-Ethyl 2-[4-(1-aminoethyl)-3-fluoro-phenyl]acetate (Intermediate Z)

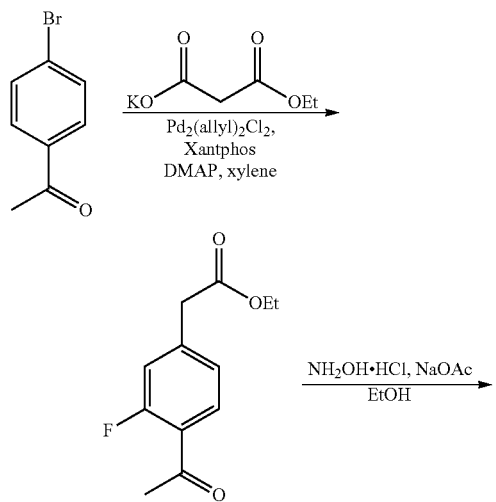

Step 1—Ethyl 2-(4-acetyl-3-fluoro-phenylacetate

To a solution of 1-(4-bromo-2-fluoro-phenyl)ethanone (1.80 g, 8.29 mmol) in xylene (20 mL) was added allyl (chloro)palladium (303 mg, 829 umol), Xantphos (479 mg, 829 umol), N,N-4-dimethylaminopyridine (101 mg, 829 umol), (3-ethoxy-3-oxo-propanoyl)oxypotassium (1.41 g, 8.29 mmol) in one portion at rt. The reaction mixture was stirred at 80° C. for 12 hrs. On completion, the mixture was concentrated in vacuo. The residue was diluted with water (10 mL) and extracted with ethyl acetate (3×30 mL). The combined organic layers were washed with water (2×20 mL), dried over anhydrous sodium sulfate, and concentrated in vacuo. The residue was purified by chromatography (petroleum:ethyl acetate=100:1 to 10:1) to give the title compound. $^1$H NMR (400 MHz, DMSO-d$_6$) δ=8.00-7.83 (m, 1H), 7.81-7.74 (m, 1H), 7.34-7.18 (m, 1H), 4.11 (q, J=6.4 Hz, 2H), 3.80 (s, 2H), 2.63 (s, 3H), 1.27 (t, J=6.4 Hz, 3H).

Step 2—Ethyl 2-(3-fluoro-4-(1-(hydroxyimino) ethyl)phenyl)acetate

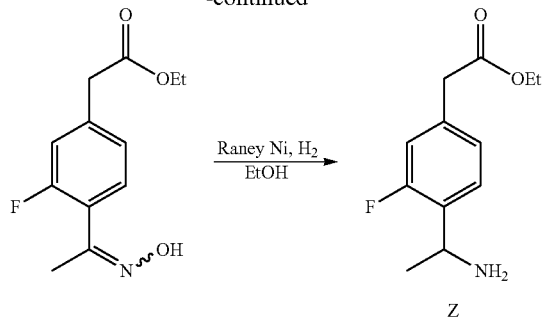

To a solution of ethyl 2-(4-acetyl-3-fluoro-phenyl) acetate (100 mg, 446 umol) in ethanol (20 mL) was added hydroxylamine hydrochloride (93.0 mg, 1.34 mmol) and sodium acetate (110 mg, 1.34 mmol) in one portion at rt. The reaction mixture was stirred at 80° C. for 2 hrs. On completion, the mixture was quenched with water (20 mL) and extracted with ethyl acetate (3×30 mL). The combined organic layers were washed with water (3×30 mL), dried over anhydrous sodium sulfate, and concentrated in vacuo to give the title compound (100 mg, 94% yield) as a yellow solid. LCMS: (ES$^+$) m/z (M+H)$^+$=240.0, tR=0.661.

Step 3—(±)-Ethyl 2-[4-(1-aminoethyl)-3-fluoro-phenyl]acetate

To a solution of ethyl 2-(3-fluoro-4-(1-(hydroxyimino) ethyl)phenyl)acetate (100 mg, 418 umol) in ethanol (20 mL) was added Raney-Nickel (717 mg, 1.67 mmol) under nitrogen. The reaction mixture was stirred under hydrogen (30 psi) at rt for 12 hrs. On completion, the mixture was filtered, and the filtrate was concentrated in vacuo. The residue was purified by chromatography (petroleum ether:ethyl acetate=100:1 to 1:1) to give the title compound. LCMS: (ES$^+$) m/z (M+H)$^+$=226.1, tR=0.608.

(±)-Methyl 4-(1-aminoethyl)-3-chlorobenzoate (Intermediate AA)

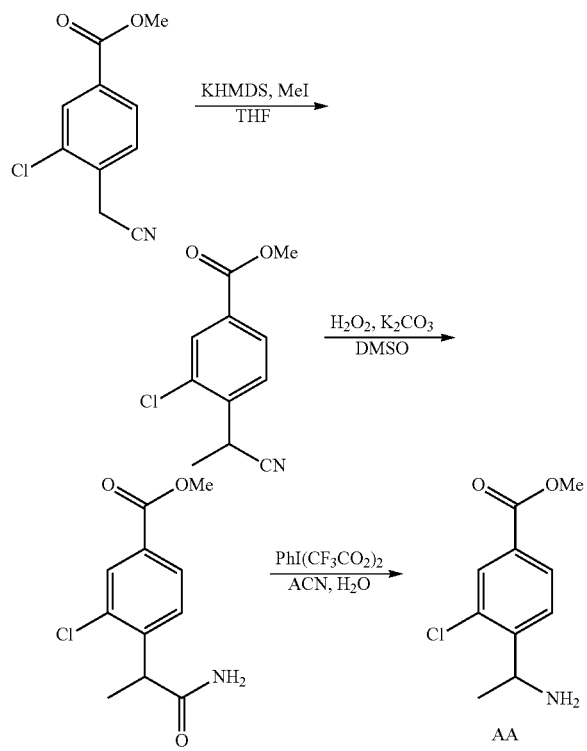

Step 1—(±)-Methyl 3-chloro-4-(1-cyanoethyl)benzoate

To a solution of methyl 3-chloro-4-(cyanomethyl)benzoate (1.00 g, 4.77 mmol) in tetrahydrofuran (10 mL) was added potassium bis(trimethylsilyl)amide (1 M, 5.7 mL) at 0° C. The mixture was stirred at 0° C. for 0.5 h. Then methyl iodide (677 mg, 4.77 mmol) was added and the reaction mixture was stirred at rt for 0.5 h. On completion, the mixture was concentrated in vacuo to give the title compound. $^1$H NMR (400 MHz, CDCl$_3$) δ=7.96 (s, 1H), 7.85 (d, J=8.0 Hz, 1H), 7.52 (d, J=8.0 Hz, 1H), 4.28-4.19 (m, 1H), 3.78 (s, 3H), 1.50 (d, J=7.2 Hz, 3H).

Step 2—(±)-Methyl 4-(1-amino-1-oxopropan-2-yl)-3-chlorobenzoate

To a solution of methyl 3-chloro-4-(1-cyanoethyl)benzoate (1.10 g, 4.92 mmol) and potassium carbonate (272 mg, 1.97 mmol) in dimethyl sulfoxide (15 mL) was added hydrogen peroxide (5.58 g, 49.2 mmol, 30% solution). The reaction mixture was stirred at rt for 2 hrs. On completion, the mixture was quenched by saturated aqueous sodium sulfite (10 mL) and extracted with ethyl acetate (3×30 mL). The combined organic layers were washed with water (3×50 mL) and brine (50 mL), dried over anhydrous sodium sulfate, filtered and concentrated in vacuo to give the title compound. LCMS: (ES$^+$) m/z (M+H)$^+$=242.1, tR=0.721.

Step 3—(±)-Methyl 4-(1-aminoethyl)-3-chlorobenzoate

To a mixture of (±)-methyl 4-(2-amino-1-methyl-2-oxoethyl)-3-chloro-benzoate (1.42 g, 5.88 mmol) in acetonitrile (15 mL) and water (15 mL) was added [bis(trifluoroacetoxy)iodo]benzene (2.78 g, 6.46 mmol) in one portion. The mixture was stirred at rt for 16 hrs. On completion, the mixture was quenched with hydrochloric acid (1 N) and extracted with ethyl acetate (3×20 mL). The aqueous layer was basified with sodium bicarbonate until pH=9 and extracted with dichloromethane (2×20 mL). The combined organic layers were dried over anhydrous sodium sulfate, filtered and concentrated in vacuo to give the title compound. LCMS: (ES$^+$) m/z (M-NH$_2$)$^+$=197.2, tR=0.581. $^1$H NMR (400 MHz, CDCl$_3$) δ=8.03 (d, J=1.6 Hz, 1H), 7.95 (dd, J=1.6, 8.0 Hz, 1H), 7.66 (d, J=8.0 Hz, 1H), 4.61 (q, J=6.7 Hz, 1H), 3.94 (s, 3H), 1.42 (d, J=6.8 Hz, 3H).

(±)-Ethyl 4-(1-amino-2-fluoro-ethyl)benzoate (Intermediate AB)

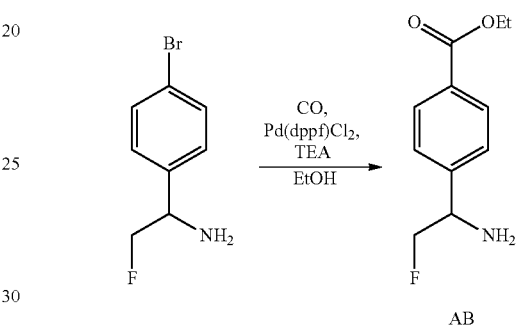

To a solution of (±)-1-(4-bromophenyl)-2-fluoro-ethanamine (200 mg, 917 umol) and triethylamine (371 mg, 3.67 mmol) in ethanol (15.0 mL) was added Pd(dppf)Cl$_2$.CH$_2$Cl$_2$ (97.4 mg, 119 umol) under nitrogen. The mixture was stirred under carbon monoxide (50 psi) at 80° C. for 16 hours. On completion, the reaction mixture was filtered and the filtrate was concentrated in vacuo. The residue was purified by silica gel chromatography (petroleum ether:ethyl acetate=2:1 to 1:1) to give the title compound. LCMS (ES$^+$): 212.1 m/z (M+H)$^+$, tR=1.196 min.

(S)-Ethyl 2-(4-(1-amino-2-hydroxyethyl)phenyl) acetate (Intermediate AC)

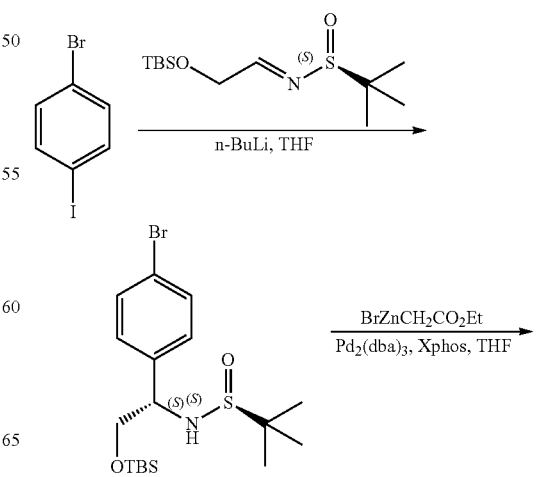

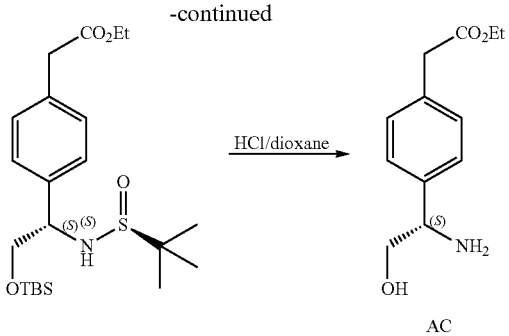

Step 1—N-[(1S)-1-(4-bromophenyl)-2-[tert-butyl (dimethyl)silyl]oxy-ethyl]-2-methyl-propane-2-sulfinamide To a solution of 4-bromo-1-iodobenzene (10.2 g, 36.0 mmol) in tetrahydrofuran (100 mL) was added n-butyllithium (15.9 mL, 2.5 M) at −78° C. The mixture was stirred at −78° C. for 1 h, then (S,E)-N-(2-((tert-butyldimethylsilyl)oxy)ethylidene)-2-methylpropane-2-sulfinamide (10.0 g, 36.0 mmol, synthesized via Steps 1-3 of Intermediate AF) was added. The reaction mixture was stirred at rt for 12 hrs. On completion, the mixture was quenched with saturated aqueous ammonium chloride (250 mL) and extracted with ethyl acetate (3×100 mL). The combined organic layers were washed with brine (2×100 mL), dried over anhydrous sodium sulfate, then filtered. The filtrate was concentrated in vacuo. The residue was purified by chromatography (petroleum ether: ethyl acetate=5:1 to 1:1) to give the title compound. $^1$H NMR (400 MHz, CDCl$_3$) δ=7.47 (d, J=8.4 Hz, 2H), 7.2 (d, J=8.4 Hz, 2H), 4.42 (dd, J=2.0, 8.8 Hz, 1H), 4.20 (s, 1H), 3.77-3.64 (m, 2H), 3.55-3.48 (m, 1H), 1.23 (s, 9H), 0.91 (s, 9H), 0.06 (d, J=7.78 Hz, 6H).

Step 2—Ethyl-2-[4-[(1S)-2-[tert-butyl(dimethyl)silyl]oxy-1-(tert-butyl sulfinylamino)ethyl]-phenyl]acetate To a solution of (S)—N—((S)-1-(4-bromophenyl)-2-((tert-butyldimethylsilyl)oxy)ethyl)-2-methylpropane-2-sulfinamide (2.00 g, 4.60 mmol) and bromo-(2-ethoxy-2-oxo-ethyl)zinc (1 M, 23.00 mL) in tetrahydrofuran (100 mL) was added Pd$_2$(dba)$_3$ (421.50 mg, 460.00 umol) and XPhos (438.86 mg, 920 umol). The mixture was stirred at 80° C. for 1 h. On completion, the reaction mixture was concentrated in vacuo. The residue was purified by chromatography (petroleum ether:ethyl acetate=10:1 to 3:1) to give the title compound. $^1$H NMR (400 MHz, CDCl$_3$) δ=7.34-7.25 (m, 4H), 4.54 (dd, J=2.4, 9.2 Hz, 1H), 4.30 (d, J=1.4 Hz, 1H), 4.18 (q, J=7.2 Hz, 2H), 3.78 (dd, J=4.0, 10 Hz, 1H), 3.65-3.58 (m, 3H), 1.26 (t, J=7.2 Hz, 3H), 1.25 (s, 9H), 0.93 (s, 9H), 0.08 (d, J=7.6 Hz, 6H).

Step 3—(S)-Ethyl 2-(4-(1-amino-2-hydroxyethyl)phenyl)acetate

A mixture of ethyl 2-[4-[(1S)-2-[tert-butyl(dimethyl)silyl]oxy-1-[[(S)-tert-butylsulfinyl]amino]ethyl]-3-fluoro-phenyl]acetate (1.10 g, 2.49 mmol) in hydrogen chloride/dioxane (10 mL, 4 M) was stirred at rt for 12 hrs. On completion, the reaction mixture was concentrated in vacuo, the residue was diluted with water (20 mL) and washed with ethyl acetate (3×20 mL). The aqueous phase was basified with saturated aqueous sodium bicarbonate until pH=9, and extracted with ethyl acetate (100 mL). The organic layer was washed with brine (20 ml), dried over anhydrous sodium sulfate and filtered. The filtrate was concentrated in vacuo to give the title compound. $^1$H NMR (400 MHz, CDCl$_3$) δ=7.32-7.27 (m, 4H), 4.17 (q, J=7.2 Hz, 2H), 4.06 (dd, J=7.6, 4.2 Hz, 1H), 3.78-3.72 (m, 1H), 3.62 (s, 2H), 3.56 (dd, J=10.4, 8.4 Hz, 1H), 1.28 (t, J=7.2 Hz, 3H).

(S)-Ethyl 2-(4-(1-amino-2-hydroxyethyl)-3-fluorophenyl)acetate (Intermediate AD)

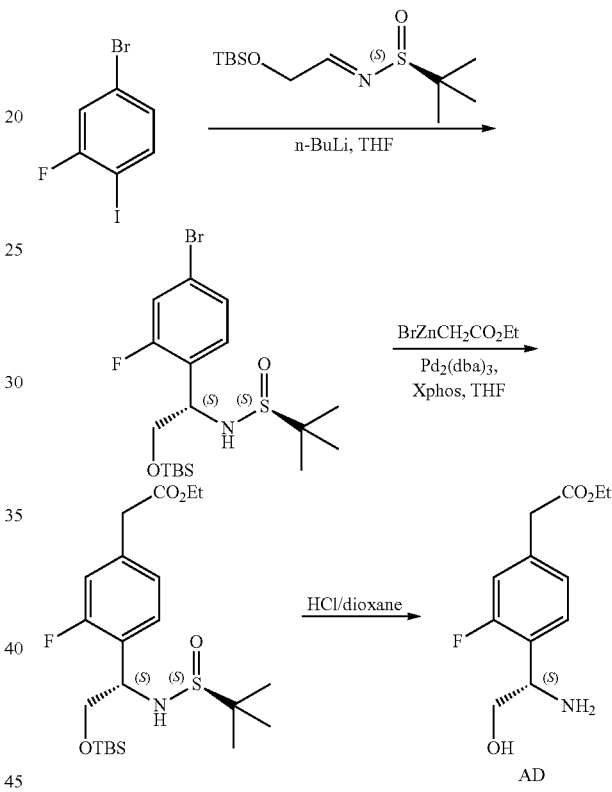

Step 1—(S)—N—((S)-1-(4-Bromo-2-fluorophenyl)-2-((tert-butyldimethylsilyl)oxy)ethyl)-2-methylpropane-2-sulfinamide To a solution of 4-bromo-2-fluoro-1-iodobenzene (10.0 g, 33.2 mmol) in tetrahydrofuran (100 mL) was added n-butyllithium (13.2 mL, 2.5 M) at −78° C. The mixture was stirred at −78° C. for 1 h, then (S,E)-N-(2-((tert-butyldimethylsilyl)oxy)ethylidene)-2-methylpropane-2-sulfinamide (9.22 g, 33.2 mmol, synthesized via Steps 1-3 of Intermediate AF) was added. The reaction mixture was stirred at −78° C. for 2 hrs. On completion, the mixture was quenched with saturated aqueous ammonia chloride (50 mL) and extracted with ethyl acetate (3×100 mL). The combined organic layers were washed with brine (20 ml), dried over anhydrous sodium sulfate, then filtered. The residue was purified by chromatography (petroleum ether:ethyl acetate=10:1) to give the title compound. $^1$H NMR (400 MHz, CDCl$_3$) δ=7.26-7.22 (m, 3H), 4.84-4.82 (m, 1H), 4.24 (d, J=2.8 Hz, 1H), 3.81 (dd, J=4.0, 10.0 Hz, 1H), 3.50 (d, J=4.0 Hz, 1H), 1.24 (s, 9H), 0.89 (s, 9H), 0.04 (d, J=17.6 Hz, 6H).

Step 2—Ethyl 2-[4-[(1S)-2-[tert-butyl(dimethyl)silyl]oxy-1-[[(S)-tert-butylsulfinyl]amino]ethyl]-3-fluoro-phenyl]acetate To a solution of (S)—N—((S)-1-(4-Bromo-2-fluorophenyl)-2-((tert-butyldimethylsilyl)oxy)ethyl)-2-methylpropane-2-sulfinamide (10.0 g, 22.1 mmol) and bromo-(2-ethoxy-2-oxo-ethyl)zinc (55 mL, 0.5 M) in tetrahydrofuran (150 mL) was added Pd$_2$(dba)$_3$ (1.01 g, 1.11 mmol) and XPhos (526 mg, 1.11 mmol). The mixture was stirred at 70° C. for 1 h. On completion, the reaction mixture was quenched with water (100 mL) and extracted with ethyl acetate (500 mL). The combined organic layers were dried over anhydrous sodium sulfate and then filtered. The filtrate was concentrated in vacuo. The residue was purified by chromatography (petroleum ether:ethyl acetate=10:1) to give the title compound. $^1$H NMR (400 MHz, CDCl$_3$) δ=7.36-7.29 (m, 1H), 7.06-7.00 (m, 2H), 4.88-4.85 (m, 1H), 4.26-4.25 (m, 1H), 4.20-4.15 (q, J=7.6 Hz, 2H), 3.88-3.87 (m, 1H), 3.69-3.68 (m, 1H), 3.60 (s, 2H), 1.26 (t, J=5.2 Hz, 3H), 1.25 (s, 9H), 0.90 (s, 9H), 0.08 (d, J=9.6 Hz, 6H).

Step 3—(S)-Ethyl 2-(4-(1-amino-2-hydroxyethyl)-3-fluorophenyl)acetate

A mixture of ethyl 2-[4-[(1S)-2-[tert-butyl(dimethyl)silyl]oxy-1-[[(S)-tert-butylsulfinyl]amino]ethyl]-3-fluoro-phenyl]acetate (4.00 g, 9.10 mmol) in hydrogen chloride/dioxane (40 mL) was stirred at rt for 2 hrs. On completion, the reaction mixture was concentrated in vacuo, the residue was diluted with water and washed with ethyl acetate (100 mL). The aqueous phase was basified with saturated aqueous sodium bicarbonate until pH=9, and extracted with ethyl acetate (100 mL). The organic layer was washed with brine (20 ml), dried over anhydrous sodium sulfate and filtered. The filtrate was concentrated in vacuo to give the title compound. $^1$H NMR (400 MHz, DMSO-d$_6$) δ=7.50-7.46 (m, 1H), 7.07-7.02 (m, 2H), 4.84 (s, 2H), 4.14-4.06 (m, 3H), 3.66 (s, 1H), 3.47 (m, 1H), 3.36-3.29 (m, 1H), 1.19 (t, J=3.2 Hz, 3H).

Ethyl 4-[(1S)-1-amino-2-hydroxy-ethyl]-3-fluoro-benzoate (Intermediate AE)

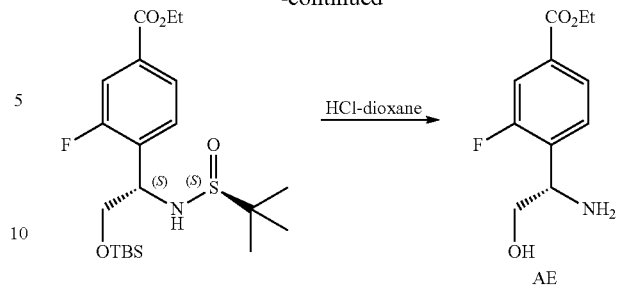

Step 1: Ethyl 4-[(1S)-2-[tert-butyl(dimethyl)silyl]oxy-1-[[(S)-tert-butylsulfinyl]amino]ethyl]-3-chloro-benzoate To a solution of N-[(1S)-1-(4-bromo-2-chloro-phenyl)-2-[tert-butyl(dimethyl)silyl]oxy-ethyl]-2-methyl-propane-2-sulfinamide (5.00 g, 10.7 mmol, synthesized via Step 1 of Intermediate AD) in ethanol (50 mL) was added TEA (3.24 g, 32.0 mmol), and Pd(dppf)Cl$_2$·CH$_2$Cl$_2$ (870 mg, 1.07 mmol). Then the mixture was stirred under CO gas (50 Psi) at 90° C. for 12 hrs. The reaction mixture was then filtered, and concentrated in vacuo. The residue was purified by chromatography on silica gel (petroleum ether: ethyl acetate=50/1 to 10:1) to give the title compound. $^1$H NMR (400 MHz, CDCl$_3$) δ=8.04 (d, J=1.2 Hz, 1H), 7.92 (d, J=8.4 Hz, 1H), 7.53 (d, J=8.4 Hz, 1H), 5.08 (td, J=3.6, 6.8 Hz, 1H), 4.43-4.35 (m, 3H), 3.98 (dd, J=4.0, 10.4 Hz, 1H), 3.64 (dd, J=7.2, 10.0 Hz, 1H), 1.40 (t, J=7.2 Hz, 3H), 1.26 (s, 9H), 0.89 (s, 9H), 0.08 (s, 3H), -0.01 (s, 3H).

Step 2—Ethyl 4-[(1S)-1-amino-2-hydroxy-ethyl]-3-fluoro-benzoate

Ethyl 4-[(1S)-2-[tert-butyl(dimethyl)silyl]oxy-1-[[(S)-tert-butylsulfinyl]amino]ethyl]-3-fluoro-benzoate (200 mg, 448 umol) was dissolved in hydrochloric/dioxane (5 mL). The mixture was stirred at rt for 2 hrs. On completion, the reaction mixture was concentrated in vacuo. The residue was diluted with water (5 mL) and extracted with ethyl acetate (10 mL). The aqueous layer was adjusted with aqueous sodium bicarbonate to pH=9, then extracted with dichloromethane (50 mL). The organic layer was concentrated in vacuo, dried over anhydrous sodium sulfate, filtered and concentrated in vacuo to give the title compound. LCMS (ES$^+$) m/z (M+H)$^+$: 228.1, tR=0.51 min.

Ethyl 4-[(1S)-1-amino-2-hydroxy-ethyl]-3-chloro-benzoate (Intermediate AF)

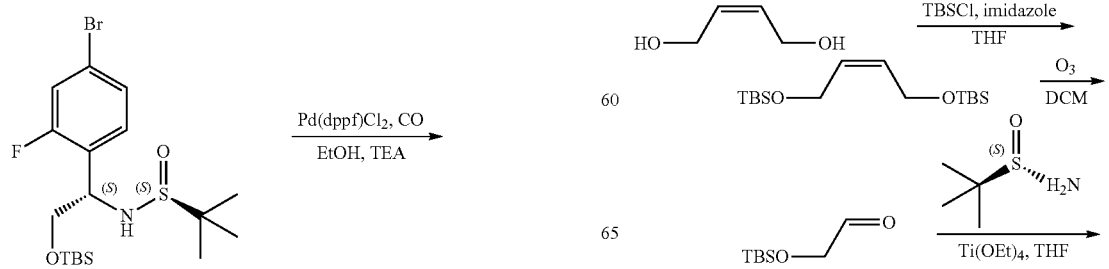

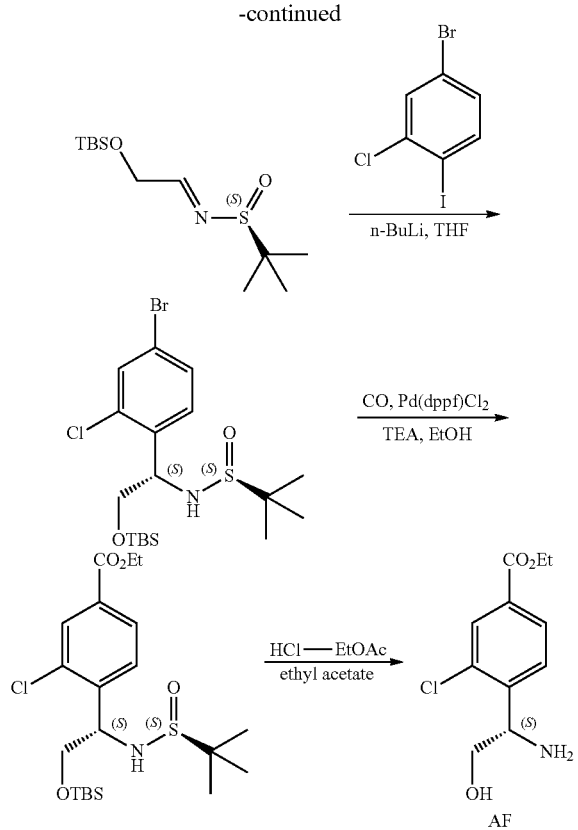

Step 1—Tert-butyl-[(Z)-4-[tert-butyl(dimethyl)silyl]oxybut-2-enoxy]-dimethyl-silane To a solution of (Z)-but-2-ene-1,4-diol (100 g, 1.14 mol) and imidazole (194 g, 2.85 mol) in tetrahydrofuran (1.50 L) was added tert-butyldimethylsilyl chloride (429 g, 2.85 mol) in tetrahydrofuran (600 mL) dropwise at 0° C. for 1 hr, and the reaction was stirred at rt for 12 hrs. On completion, the resulting mixture was filtered and the filtrate was concentrated. The residue was diluted with water (500 mL) and the resulting mixture was extracted with ethyl acetate (3×1000 mL). The combined organic layers were washed with brine (3×600 mL), dried over anhydrous sodium sulfate, filtered and concentrated in vacuo to give a residue. The residue was purified by chromatography on silica gel with petroleum to give the title compound (360 g, 95% yield) as yellow oil. $^1$H NMR (400 MHz, CDCl$_3$) δ=5.58-5.51 (m, 2H), 4.23 (t, J=10.8 Hz, 4H), 0.89 (s, 18H), 0.06 (s, 12H).

Step 2—2-[Tert-butyl(dimethyl)silyl]oxyacetaldehyde

A solution of tert-butyl-[(Z)-4-[tert-butyl(dimethyl)silyl]oxybut-2-enoxy]-dimethyl-silane (358 g, 1.13 mol) in dichloromethane (2 L) was cooled to −78° C. and ozone was bubbled through until the solution turned blue. On completion, nitrogen was bubbled at a very high rate, until the blue color disappeared. Then dimethyl sulfide (351 g, 5.65 mol) was added in portions and the mixture was warmed to rt for 12 hrs. The mixture was removed by evaporation and the residue was diluted with brine (1000 mL), extracted with ethyl acetate (3×1000 mL) and dried over anhydrous sodium sulfate, filtered and concentrated. The residue was purified by chromatography on silica gel (petroleum ether) to give the title compound. $^1$H NMR (400 MHz, CDCl$_3$) δ=9.72 (s, 1H), 4.23 (s, 2H), 0.95 (s, 9H), 0.12 (s, 6H).

Step 3—(S,E)-N-(2-((tert-butyldimethylsilyl)oxy)ethylidene)-2-methylpropane-2-sulfinamide To a solution of 2-[tert-butyl(dimethyl)silyl]oxyacetaldehyde (120 g, 688 mmol) and (S)-2-methylpropane-2-sulfinamide (87.6 g, 722 mmol) in tetrahydrofuran (1.5 L) was added tetraethoxytitanium (235 g, 1.03 mol). The mixture was stirred at rt for 12 hrs. On completion, the mixture was slowly poured into water (1 L) and then filtered, the filtrate was concentrated in vacuo. The resulting residue was extracted with ethyl acetate (3×600 mL), the organic layer was washed with water (3×400 mL), dried over anhydrous sodium sulfate, filtered and concentrated. The residue was purified by chromatography on silica gel (petroleum ether:ethyl acetate=50:1 to 10:1) to give the title compound. $^1$H NMR (400 MHz, CDCl$_3$) δ=8.05 (t, J=3.0 Hz, 1H), 4.53 (d, J=3.0 Hz, 2H), 1.19 (s, 9H), 0.91 (s, 9H), 0.09 (s, 6H).

Step 4—(S)—N—((S)-1-(4-bromo-2-chlorophenyl)-2-((tert-butyldimethylsilyl)oxy)ethyl)-2-methylpropane-2-sulfinamide To a solution of 4-bromo-2-chloro-1-iodo-benzene (12.5 g, 39.6 mmol) in tetrahydrofuran (200 mL) was added n-butyllithium (2.42 g, 37.8 mmol) at −78° C. under nitrogen atmosphere, and (S,E)-N-(2-((tert-butyldimethylsilyl)oxy)ethylidene)-2-methylpropane-2-sulfinamide (10.0 g, 36.0 mmol) in tetrahydrofuran (100 mL) was added into the mixture dropwise, the reaction was stirred at this temperature for 3 hrs. On completion, the reaction mixture was quenched with saturated ammonium chloride (20 mL) and the mixture was extracted with ethyl acetate (3×300 mL). The combined organic layers were washed with brine (3×100 mL), dried over anhydrous sodium sulfate, filtered and concentrated under reduced pressure. The residue was purified by chromatography on silica gel (petroleum ether:ethyl acetate=20:1 to 5:1) to give the title compound. $^1$H NMR (400 MHz, CDCl$_3$) δ=7.55 (d, J=2.0 Hz, 1H), 7.42-7.38 (m, 1H), 7.35-7.31 (m, 1H), 4.99 (td, J=3.6, 7.2 Hz, 1H), 4.34 (d, J=3.2 Hz, 1H), 3.93 (dd, J=4.0, 10.4 Hz, 1H), 3.59 (dd, J=7.2, 10.4 Hz, 1H), 1.26 (s, 9H), 0.9 (s, 9H), 0.09 (s, 3H), 0.02 (s, 3H).

Step 5—Ethyl 4-[(1S)-2-[tert-butyl(dimethyl)silyl]oxy-1-[[(S)-tert-butylsulfinyl]amino]ethyl]-3-chlorobenzoate To a solution of (S)—N—((S)-1-(4-bromo-2-chlorophenyl)-2-((tert-butyldimethylsilyl)oxy)ethyl)-2-methylpropane-2-sulfinamide (5.00 g, 10.6 mmol) in ethanol (50 mL) was added triethylamine (3.24 g, 31.9 mmol), Pd(dppf)Cl$_2$.CH$_2$Cl$_2$ (870 mg, 1.07 mmol) and the mixture was stirred under carbon monoxide (50 psi) at 90° C. for 12 hrs. On completion, the mixture was concentrated in vacuo. The resulting residue was purified by chromatography on silica gel (petroleum ether:ethyl acetate=50:1 to 10:1) to give the title compound. $^1$H NMR (400 MHz, CDCl$_3$) δ=8.03 (d, J=1.2 Hz, 1H), 7.91 (d, J=8.4 Hz, 1H), 7.52 (d, J=8.4 Hz, 1H), 5.07 (d, J=6.8 Hz, 1H), 4.42-4.33 (m, 3H), 4.01-3.92 (m, 1H), 3.63 (t, J=10.0 Hz, 1H), 1.39 (t, J=7.2 Hz, 3H), 1.25 (s, 9H), 0.88 (s, 9H), 0.07 (s, 3H), −0.02 (s, 3H).

Step 6—Ethyl 4-[(1S)-1-amino-2-hydroxy-ethyl]-3-chloro-benzoate

A mixture of ethyl 4-[(1S)-2-[tert-butyl(dimethyl)silyl]oxy-1-[[(S)-tert-butylsulfinyl]amino]ethyl]-3-chloro-benzoate (700 mg, 1.51 mmol) in ethyl acetate (5 mL) was added hydrogen chloride in ethyl acetate (4 M, 0.5 mL) and the mixture was stirred at rt for 2 hrs. On completion, the reaction was concentrated in vacuo. The residue was extracted with dichloromethane (3×20 mL), washed with sodium bicarbonate (2×10 mL), and the organic layer was dried over anhydrous sodium sulfate, filtered and concentrated to give the title compound. $^1$H NMR (400 MHz, CDCl$_3$) δ=8.01 (s, 1H), 7.92 (d, J=8.4 Hz, 1H), 7.58 (d, J=8.4 Hz, 1H), 4.56 (m, 1H), 4.36 (q, J=7.6 Hz, 2H), 3.84 (m, 1H), 3.35 (t, J=7.6 Hz, 1H), 1.38 (t, J=6.8 Hz, 3H).

2-[4-[(1S)-1-amino-2-hydroxy-ethyl]-3-chloro-phenyl]acetate (Intermediate AG)

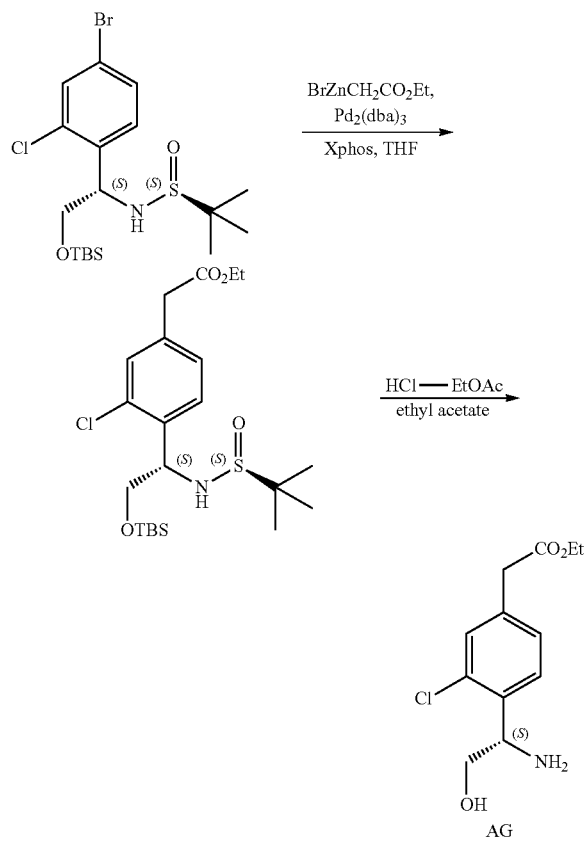

Step 1—Ethyl 4-[(1S)-2-[tert-butyl(dimethyl)silyl]oxy-1-[[(S)-tert-butylsulfinyl]amino]ethyl]-3-chloro-benzoate To a solution of N-[(1S)-1-(4-bromo-2-chloro-phenyl)-2-[tert-butyl(dimethyl)silyl]oxy-ethyl]-2-methyl-propane-2-sulfinamide (3.50 g, 7.46 mmol, synthesized via Steps 1-4 of Intermediate AF) in tetrahydrofuran (60 mL) was added bis(dibenzylideneacetone)palladium (429 mg, 746 umol) and 2-(dicylohexylphosphino)-2,4,6-triisoprpylbiphenyl (355 mg, 746 umol). Bromo-(2-ethoxy-2-oxo-ethyl)zinc (0.5 M in tetrahydrofuran, 37.3 mL, 18.6 mmol) was added under nitrogen atmosphere, and the mixture was stirred at 80° C. for 12 hrs. On completion, the reaction was filtered, and the filtrate was mixed with water and extracted with ethyl acetate (3×50 mL). The organic layer was washed with water (3×40 mL), dried over anhydrous sodium sulfate, filtered and concentrated in vacuo. The resulting residue was purified by chromatography on silica gel (petroleum ether:ethyl acetate=50:1 to 10:1) to give the title compound. $^1$H NMR followed the pilot run (400 MHz, CDCl$_3$) δ=7.39 (d, J=8.0 Hz, 1H), 7.30 (d, J=1.0 Hz, 1H), 7.17 (d, J=8.0 Hz, 1H), 5.02-4.99 (m, 1H), 4.32 (d, J=2.4 Hz, 1H), 4.16 (q, J=7.2 Hz, 2H), 3.92 (d, J=10.4 Hz, 1H), 3.57 (s, 2H), 1.27 (t, J=7.2 Hz, 3H) 1.23 (s, 9H), 0.89 (s, 9H), 0.07 (s, 3H), 0.00 (s, 3H).

Step 2—2-[4-[(1S)-1-amino-2-hydroxy-ethyl]-3-chloro-phenyl]acetate

To a mixture of ethyl 4-[(1S)-2-[tert-butyl(dimethyl)silyl]oxy-1-[[(S)-tert-butylsulfinyl]amino]ethyl]-3-chloro-benzoate (700 mg, 1.51 mmol) in ethyl acetate (15 mL) was added hydrogen chloride (4 M in ethyl acetate, 5 mL) and the mixture was stirred at rt for 2 hrs. On completion, the reaction was concentrated in vacuo to give a residue, the residue was extracted with dichloromethane (3×20 mL) and washed with saturated sodium bicarbonate (2×10 mL). The organic layer was dried over anhydrous sodium sulfate, filtered and concentrated to give the title compound. LCMS (ES$^+$) m/z (M+H)$^+$: 258.2, tR=0.488 min.

Ethyl 4-[(1S)-1-amino-2-hydroxy-ethyl]-3-methyl-benzoate (Intermediate AH)

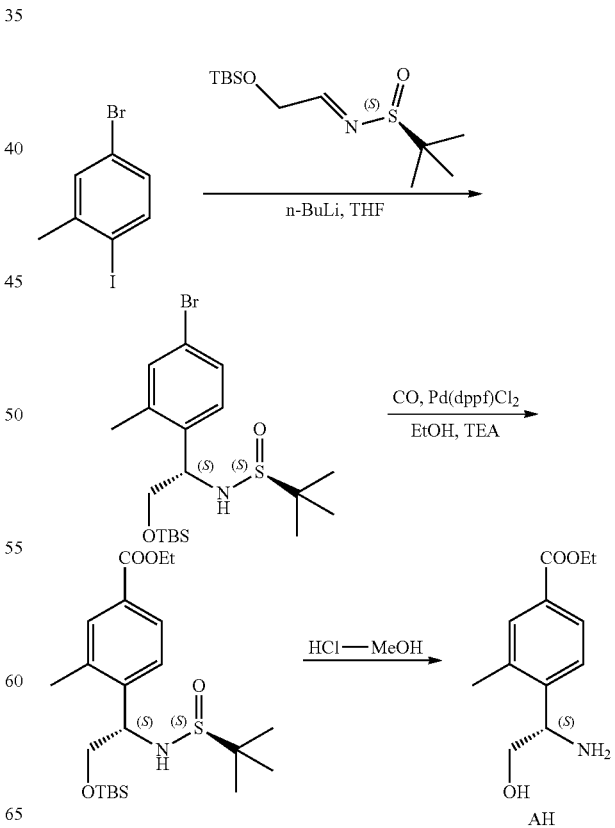

Step 1—N-[(1S)-1-(4-bromo-2-methyl-phenyl)-2-[tert-butyl(dimethyl)silyl]oxy-ethyl]-2-methyl-propane-2-sulfinamide To a solution of 4-bromo-1-iodo-2-methyl-benzene (20.0 g, 67.4 mmol) in anhydrous tetrahydrofuran (200 mL) was added n-butyllithium (2.5 M, 28 mL) at −70° C. under nitrogen. Then (S)—N-[2-[tert-butyl(dimethyl)silyl]oxyethylidene]-2-methyl-propane-2-sulfinamide (18.7 g, 67.3 mmol, synthesized via Steps 1-3 of Intermediate AF) was added to the solution at −70° C. under nitrogen, and the reaction was stirred at −70° C. for 2 hrs. On completion, 10 mL water was added into the solution dropwise. Then the solution was extracted with ethyl acetate (3×20 mL), washed with water (3×20 mL), dried over anhydrous sodium sulfate, and concentrated in vacuo. The residue was purified by silica gel (petroleum ether:ethyl acetate=100:10-10:1) to give the title compound. $^1$H NMR (400 MHz, CDCl$_3$) δ=7.35-7.31 (m, 2H), 7.27-7.23 (m, 1H), 4.27 (s, 1H), 3.75 (dd, J=4.1, 10.2 Hz, 1H), 3.58 (dd, J=9.2, 10.0 Hz, 1H), 2.41 (s, 3H), 1.24 (s, 9H), 0.93 (s, 9H), 0.09 (d, J=7.0 Hz, 6H).

Step 2—Ethyl 4-[(1S)-2-[tert-butyl(dimethyl)silyl]oxy-1-[[(S)-tert-butylsulfinyl]amino]ethyl]-3-methyl-benzoate To a solution of N-[(1S)-1-(4-bromo-2-methyl-phenyl)-2-[tert-butyl(dimethyl)silyl]oxy-ethyl]-2-methyl-propane-2-sulfinamide (200 mg, 446 umol) in ethanol (20 mL) was added Pd(dppf)Cl$_2$ (163 mg, 223 umol) and triethylamine (1.13 g, 11.1 mmol) in one portion at rt. The suspension was degassed in vacuo and purged with carbon monoxide. The mixture was stirred under carbon monoxide (50 psi) at rt for 12 hours. On completion, the reaction was concentrated in vacuo, and the residue was purified by column chromatography on silica gel (petroleum ether:ethyl acetate=100:1-10:1) to give the title compound. LCMS: (ES$^+$) m/z (M+H)$^+$= 442.2. tR=0.568.

Step 3—Ethyl 4-[(1S)-1-amino-2-hydroxy-ethyl]-3-methyl-benzoate

To a solution of ethyl 4-[(1S)-2-[tert-butyl(dimethyl)silyl]oxy-1-[[(S)-tert-butylsulfinyl]amino]ethyl]-3-methyl-benzoate (250 mg, 566 umol) in methanol (20 mL) was added hydrochloric/methanol (4 M, 1.42 mL) at rt, and the reaction was stirred at rt for 2 hrs. On completion the reaction was concentrated in vacuo to give the title compound. LCMS: (ES$^+$) m/z (M-NH$_2$)$^+$=207.2. tR=0.647.

Ethyl 2-[4-[(1S)-1-amino-2-hydroxy-ethyl]-3-methyl-phenyl]acetate (Intermediate AI)

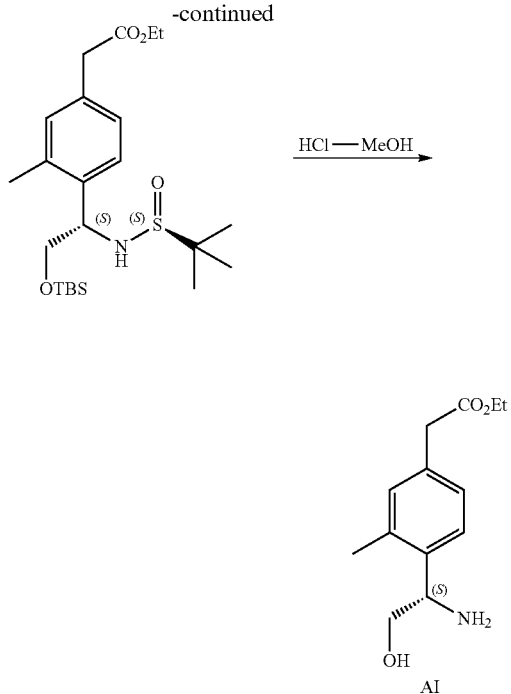

Step 1—Ethyl 2-[4-[(1S)-2-[tert-butyl(dimethyl)silyl]oxy-1-[[(S)-tert-butyl sulfinyl]amino]ethyl]-3-methyl-phenyl]acetate To a solution of N-[(1S)-1-(4-bromo-2-methyl-phenyl)-2-[tert-butyl(dimethyl)silyl]oxy-ethyl]-2-methyl-propane-2-sulfinamide (2.00 g, 4.46 mmol, synthesized via Step 1 of Intermediate AH) in anhydrous tetrahydrofuran (50 mL) was added Pd$_2$(dba)$_3$ (408 mg, 446 umol) and XPhos (213 mg, 446 umol) under nitrogen in one portion. Then bromo-(2-ethoxy-2-oxo-ethyl)zinc (0.7 M, 38.23 mL) was added to the solution dropwise, and the reaction was stirred at 70° C. for 3 hrs. On completion, 20 mL water was added into the solution, then extracted with ethyl acetate (3×50 mL). The combined organic extract was washed with water (3×50 mL), dried over anhydrous sodium sulfate, filtered and concentrated in vacuo. The residue was purified by column chromatography (petroleum ether:ethyl acetate=500:1-1:1) to give the title compound. $^1$H NMR (400 MHz, CDCl$_3$) δ=7.24 (d, J=8.0 Hz, 1H), 7.06-6.98 (m, 2H), 4.70 (ddd, J=1.6, 4.0, 9.2 Hz, 1H), 4.20 (d, J=1.2 Hz, 1H), 4.08 (q, J=7.2 Hz, 2H), 3.66 (dd, J=4.0, 10.4 Hz, 1H), 3.48 (s, 2H), 2.32 (s, 3H), 1.19 (t, J=7.1 Hz, 3H), 1.15 (s, 9H), 0.84 (s, 9H), 0.01 (d, J=7.0 Hz, 6H).

Step 2—Ethyl 2-[4-[(1S)-1-amino-2-hydroxy-ethyl]-3-methyl-phenyl]acetate

To a solution of ethyl 2-[4-[(1S)-2-[tert-butyl(dimethyl)silyl]oxy-1-[[(S)-tert-butylsulfinyl]amino]ethyl]-3-methyl-phenyl]acetate (250 mg, 549 umol) in methanol (20 mL) was added hydrochloric acid/methanol (4 M, 1.37 mL) in one portion, and the reaction was stirred at rt for 1 hr. On completion the reaction was concentrated in vacuo to give the title compound. LCMS: (ES$^+$) m/z (M+H)$^+$=238.1, tR=0.541.

Tert-butyl (4S)-4-[4-(2-ethoxy-2-oxo-ethyl)phenyl]-2,2-dimethyl-oxazolidine-3-carboxylate (Intermediate AJ)

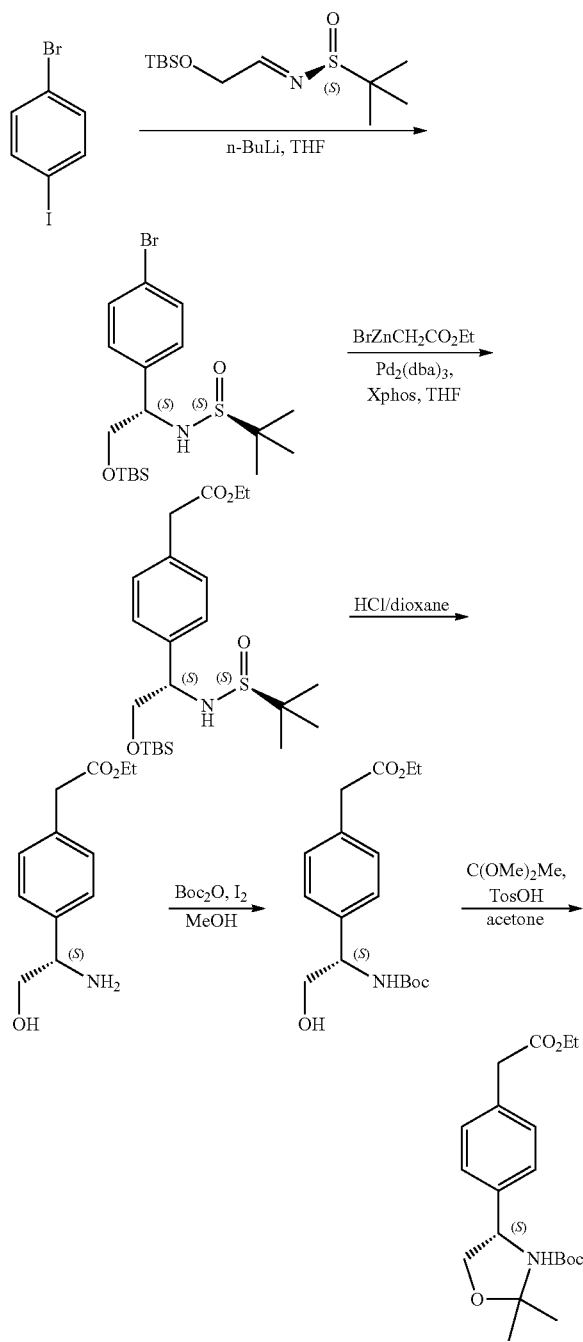

Step 1—N-[(1S)-1-(4-bromophenyl)-2-[tert-butyl(dimethyl)silyl]oxy-ethyl]-2-methyl-propane-2-sulfinamide To a solution of 1-bromo-4-iodo-benzene (22.0 g, 77.7 mmol) in anhydrous tetrahydrofuran (60 mL) was added n-butyllithium (2.5 M, 31.1 mL) at −60° C. under $N_2$. The mixture was stirred at −60° C. for 30 mins. Then (S)—N-[2-[tert-butyl(dimethyl)silyl]oxyethylidene]-2-methyl-propane-2-sulfinamide (21.5 g, 77.7 mmol, synthesized via Steps 1-3 of Intermediate AF) dissolved in tetrahydrofuran (30 mL) was added dropwise. Finally, the mixture was warmed to rt and stirred at rt for 2 hrs. On completion, the reaction mixture was quenched with saturated ammonium chloride solution (100 mL) and extracted with ethyl acetate (3×200 mL). The combined organic layers were washed with brine (300 mL), dried over anhydrous sodium sulfate, filtered and concentrated in vacuo. The resulting residue was purified by column chromatography (petroleum ether:ethyl acetate=15:1 to 5:1) to give the title compound. $^1$H NMR (400 MHz, $CDCl_3$) δ=7.39 (d, J=8.4 Hz, 2H), 7.15 (d, J=8.4 Hz, 2H), 4.42 (ddd, J=1.6, 4.0, 8.8 Hz, 1H), 4.20 (s, 1H), 3.69 (dd, J=4.1, 10.0 Hz, 1H), 3.55-3.48 (m, 1H), 1.16 (s, 9H), 0.83 (s, 9H), -0.01 (d, J=8.0 Hz, 6H).

Step 2—Ethyl 2-[4-[(1S)-2-[tert-butyl(dimethyl)silyl]oxy-1-[[(S)-tert-butylsulfinyl]amino]ethyl]phenyl]acetate A mixture of N-[(1S)-1-(4-bromophenyl)-2-[tert-butyl(dimethyl)silyl]oxy-ethyl]-2-methyl-propane-2-sulfinamide (16.5 g, 37.9 mmol), bromo-(2-ethoxy-2-oxo-ethyl)zinc (0.5 M, 151 mL), $Pd_2(dba)_3$ (3.48 g, 3.80 mmol), and Xphos (2.72 g, 5.70 mmol) in tetrahydrofuran (60 mL) was degassed and purged with nitrogen gas for 3 times, and then the mixture was stirred at 70° C. for 3 hours under nitrogen gas atmosphere. On completion, the reaction mixture was quenched by addition of ice water (120 mL), and extracted with ethyl acetate (3×200 mL). The combined organic layers were washed with brine (2×150 mL), dried over anhydrous sodium sulfate, filtered and concentrated in vacuo. The resulting residue was purified by column chromatography (petroleum ether: ethyl acetate=20:1 to 5:1) to give the title compound. $^1$H NMR (400 MHz, $CDCl_3$) δ=7.26-7.22 (m, 2H), 7.22-7.18 (m, 2H), 4.50-4.42 (m, 1H), 4.22 (s, 1H), 4.10 (q, J=7.2 Hz, 2H), 3.71 (dd, J=4.0, 10.0 Hz, 1H), 3.57-3.51 (m, 3H), 1.20 (t, J=7.2 Hz, 3H), 1.17 (s, 9H), 0.85 (s, 9H), 0.01 (s, 3H), -0.01 (s, 3H).

Step 3—Ethyl 2-[4-[(1S)-1-amino-2-hydroxy-ethyl]phenyl]acetate

Ethyl 2-[4-[(1S)-2-[tert-butyl(dimethyl)silyl]oxy-1-[[(S)-tert-butylsulfinyl]amino]ethyl]phenyl]acetate (9.50 g, 21.5 mmol) was dissolved in 4 M hydrogen chloride/dioxane solution (57 mL). The mixture was stirred at rt for 1 hr. The reaction mixture was then concentrated in vacuo and the residue was diluted with water (20 mL) and washed with dichloromethane (3×20 mL). The inorganic layer was basified with an aqueous saturated sodium bicarbonate to pH>7, then extracted with dichloromethane (3×20 mL). The combined organic layer was dried over anhydrous sodium sulfate, filtered and concentrated in vacuo to give the title compound. $^1$H NMR (400 MHz, $CDCl_3$) δ=7.32-7.24 (m, 4H), 4.15 (q, J=7.2 Hz, 2H), 4.06-3.99 (m, 1H), 3.75-3.68 (m, 1H), 3.60 (s, 2H), 3.54 (dd, J=8.4, 10.4 Hz, 1H), 2.34 (br. s., 3H), 1.27 (t, J=7.2 Hz, 3H).

Step 4—Ethyl 2-[4-[(1S)-1-(tert-butoxycarbonylamino)-2-hydroxy-ethyl]phenyl]acetate To a solution of ethyl 2-[4-[(1S)-1-amino-2-hydroxy-ethyl]phenyl]acetate (3.00 g, 13.4 mmol) in anhydrous dichloromethane (20 mL) was added iodine (341 mg, 1.34 mmol). Next, di-tert-butyl dicarbonate (2.93 g, 13.44 mmol) was added dropwise. The mixture was stirred at rt for 1 hr. On completion, the reaction mixture was quenched with ice saturated sodium sulphite solution (50 ml) and extracted with dichloromethane (3×50 mL). The collected organic phase was dried over anhydrous sodium sulfate, filtered and concentrated in vacuo. The residue was purified by column chromatography (dichloromethane:methanol=100:1 to 50:1) to give the title compound. $^1$H NMR (400 MHz, CDCl$_3$) δ=7.32-7.25 (m, 4H), 5.25 (s, 1H), 4.78 (s, 1H), 4.17 (q, J=7.2 Hz, 2H), 3.85 (s, 2H), 3.62 (s, 2H), 2.34 (s, 1H), 1.45 (s, 9H), 1.28 (t, J=7.2 Hz, 3H).

Step 5—Tert-butyl (4S)-4-[4-(2-ethoxy-2-oxo-ethyl)phenyl]-2,2-dimethyl-oxazolidine-3-carboxylate To a solution of ethyl 2-[4-[(1S)-1-(tert-butoxycarbonylamino)-2-hydroxy-ethyl]phenyl]acetate (3.20 g, 9.90 mmol) in acetone (30 mL) was added p-toluenesulfonic acid (170 mg, 990 umol) and 2,2-dimethoxypropane (20.6 g, 198 mmol). The mixture was stirred at rt for 2 hrs. On completion, the reaction mixture was concentrated in vacuo. The residue was purified by column chromatography (petroleum ether: ethyl acetate=20:1 to 10:1) to give the title compound. $^1$H NMR (400 MHz, CDCl$_3$) δ=7.31-7.22 (m, 4H), 4.98-4.75 (m, 1H), 4.28 (dd, J=6.8, 9.0 Hz, 1H), 4.16 (q, J=7.2 Hz, 2H), 3.92-3.83 (m, 1H), 3.61 (s, 2H), 1.82-1.71 (m, 3H), 1.62 (s, 3H), 1.48 (s, 3H), 1.26 (t, J=7.2 Hz, 3H), 1.21 (s, 6H).

(±)-Ethyl 2-[4-[(1S)-1-amino-2-hydroxy-ethyl]phenyl]propanoate (Intermediate AK)

Step 1—(±) Tert-butyl (4S)-4-[4-(2-ethoxy-1-methyl-2-oxo-ethyl)phenyl]-2,2-dimethyl-oxazolidine-3-carboxylate To a solution of (±)-tert-butyl (4S)-4-[4-(2-ethoxy-2-oxo-ethyl)phenyl]-2,2-dimethyl-oxazolidine-3-carboxylate (280 mg, 770 umol) in anhydrous tetrahydrofuran 4 mL was added LiHMDS (1 M, 847 uL) dropwise at 0° C. The mixture was stirred at 0° C. for 30 mins, and then iodomethane (109 mg, 770 umol) dissolved in tetrahydrofuran 1 mL was added dropwise. Finally, the mixture was warmed to rt and stirred at rt for 2.5 hrs. On completion, the reaction mixture was poured into 10 mL of ice saturated ammonium chloride solution and extracted with ethyl acetate (3×15 mL). The organic phase was collected, dried over anhydrous sodium sulfate, concentrated in vacuo. The resulting residue was purified by column chromatography (petroleum ether: ethyl acetate=20:1 to 10:1) to give the title compound. $^1$H NMR (400 MHz, CDCl$_3$) δ=7.27 (m., 4H), 5.01-4.74 (m, 1H), 4.29 (dd, J=6.8, 8.8 Hz, 1H), 4.20-4.04 (m, 2H), 3.88 (d, J=8.4 Hz, 1H), 3.75-3.67 (m, 1H), 1.81-1.71 (m, 3H), 1.62 (s, 3H), 1.53-1.45 (m, 6H), 1.29-1.13 (m, 9H).

Step 2—(±)-Ethyl 2-[4-[(1S)-1-amino-2-hydroxy-ethyl]phenyl]propanoate (±)-Tert-butyl (4S)-4-[4-(2-ethoxy-1-methyl-2-oxo-ethyl)phenyl]-2,2-dimethyl-oxazolidine-3-carboxylate (150 mg, 397 umol) was dissolved in 4 M of hydrogen chloride dioxane solution (13.6 mL). The mixture was stirred at rt for 1 hr. On completion, the reaction mixture was concentrated in vacuo to get the title compound. LCMS: (ES$^+$) m/z (M+H)$^+$=238.1, tR=0.486.

(±)-Ethyl 2-[4-[(1S)-1-amino-2-hydroxy-ethyl]phenyl]butanoate (Intermediate AL)

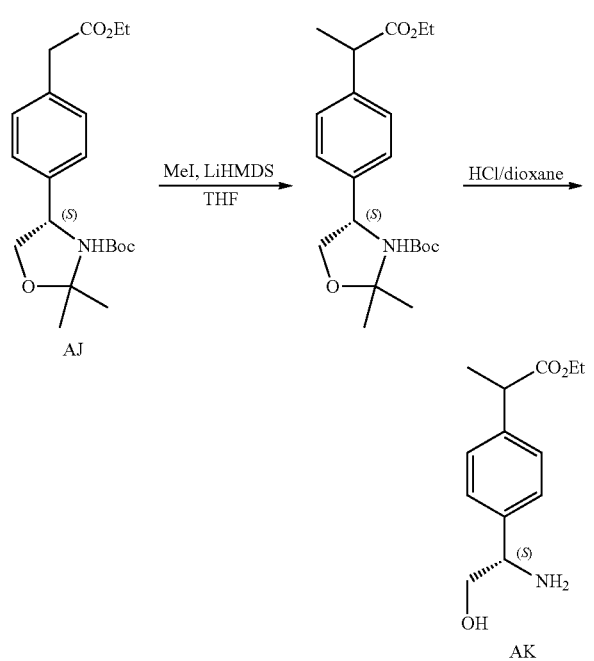

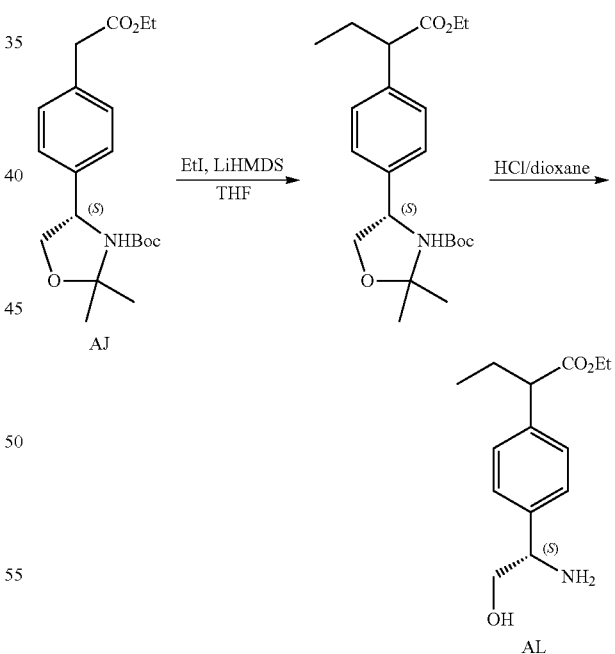

Step 1—(±)-Tert-butyl (4S)-4-[4-(1-ethoxycarbonyl-propyl)phenyl]-2,2-dimethyl-oxazolidine-3-carboxylate To a solution of tert-butyl (4S)-4-[4-(2-ethoxy-2-oxo-ethyl)phenyl]-2,2-dimethyl-oxazolidine-3-carboxylate (600 mg, 1.65 mmol) in anhydrous tetrahydrofuran (8 mL) was added LiHMDS (1 M, 2.47 mL) dropwise at 0° C. The mixture was stirred at 0° C. for 30 mins, then iodoethane (283 mg, 1.82 mmol) dissolved in tetrahydrofuran (2 mL) was added dropwise. Finally, the mixture was warmed to rt and stirred for 2.5 hrs. On completion, the reaction mixture was poured into 20 mL of cold saturated ammonium chloride solution, and extracted with ethyl acetate (3×20 mL). The organic phase was separated, dried over anhydrous sodium sulfate, and concentrated in vacuo. The resulting residue was purified by column chromatography (petroleum ether: ethyl acetate=20:1 to 10:1) to give the title compound. $^1$H NMR (400 MHz, CDCl$_3$) δ=7.19-7.11 (m, 4H), 4.91-4.63 (m, 1H), 4.20 (dd, J=6.8, 8.8 Hz, 1H), 4.10-3.98 (m, 2H), 3.79 (d, J=8.4 Hz, 1H), 3.35 (t, J=7.7 Hz, 1H), 2.08-1.88 (m, 1H), 1.77-1.60 (m, 4H), 1.53 (s., 3H), 1.40 (br. s., 3H), 1.17-1.04 (m, 9H), 0.81 (t, J=7.2 Hz, 3H).

Step 2—(±)-Ethyl 2-[4-[(1S)-1-amino-2-hydroxy-ethyl]phenyl]butanoate (±)-Tert-butyl (4S)-4-[4-(1-ethoxycarbonylpropyl)phenyl]-2,2-dimethyl-oxazolidine-3-carboxylate (340 mg, 868 umol) was dissolved in 4 M of hydrogen chloride dioxane solution (10 mL). The mixture was stirred at rt for 3 hrs. On completion, the reaction mixture was concentrated in vacuo to give the title compound. LCMS: (ES$^+$) m/z (M+H)$^+$=252.1, tR=0.532.

Ethyl 2-[4-[(1S)-1-amino-2-hydroxy-ethyl]phenyl]-2-methyl-propanoate (Intermediate AM)

770 mmol) in dimethyl formamide (20 mL), was added lithium bis(trimethylsilyl)amide (1 M, 7.70 mL, 7.70 mmol) dropwise at 0° C. The mixture was stirred at rt for 0.5 hr, then methyl iodide (1.09 g, 7.70 mol) in dimethyl formamide (1 mL) was added dropwise, and the reaction was stirred at this temperature for 2 hrs. On completion, the mixture was diluted with saturated ammonium chloride (20 mL), and extracted with ethyl acetate (3×20 mL). The combined organic layer was washed with brine (4×20 mL), dried over anhydrous sodium sulfate, filtered and concentrated. The resulting residue was purified by chromatography on silica gel (petroleum ether:ethyl acetate=20:1 to 8:1) to give the title compound. $^1$H NMR (400 MHz, CDCl$_3$) δ=7.31-7.25 (m, 4H), 4.94 (m, 1H), 4.26 (d, J=8.8 Hz, 1H), 4.10 (q, J=7.2 Hz, 2H), 3.87 (d, J=4.4 Hz, 1H), 1.78-1.69 (m, 3H), 1.62-1.57 (m, 6H), 1.56 (s, 3H), 1.47 (s, 3H), 1.16 (s, 9H).

Step 2—Ethyl 2-[4-[(1S)-1-amino-2-hydroxy-ethyl]phenyl]-2-methyl-propanoate

To a solution of tert-butyl (4S)-4-[4-(2-ethoxy-1,1-dimethyl-2-oxo-ethyl)phenyl]-2,2-dimethyl-oxazolidine-3-carboxylate (200 mg, 510 umol) in dichloromethane (20 mL) was added hydrogen chloride (4 M in ethyl acetate, 2 mL), and the mixture was stirred at rt for 1 hr. On completion, the mixture was concentrated in vacuo to give a residue, and the residue was diluted with water (5 mL) and extracted with ethyl acetate (2×10 mL). The aqueous phase was then basified with sodium bicarbonate, and extracted with ethyl acetate (2×10 mL). The organic layer was dried over anhydrous sodium sulfate, filtered and concentrated to give the title compound that was used crude in the next step.

Ethyl 1-[4-[(1S)-1-amino-2-hydroxy-ethyl]phenyl]cyclopropanecarboxylate (Intermediate AN)

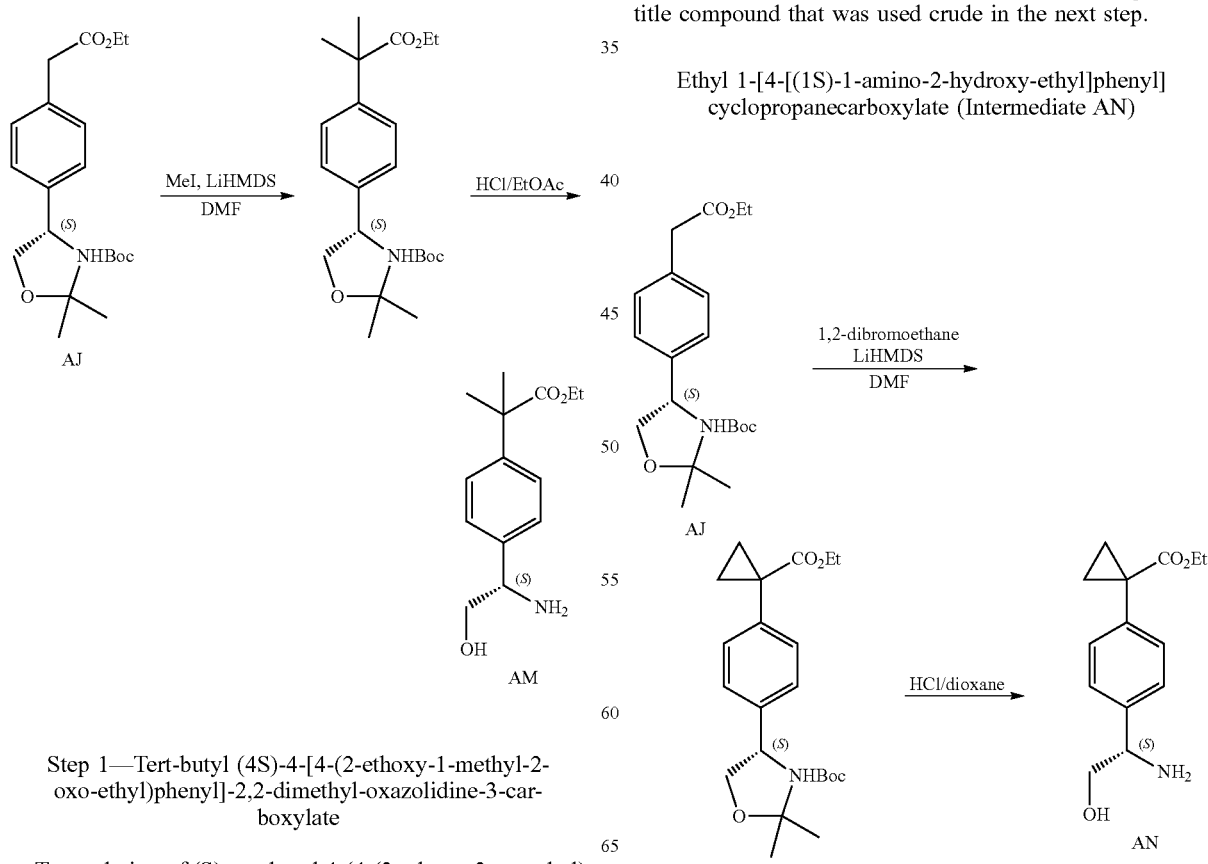

Step 1—Tert-butyl (4S)-4-[4-(2-ethoxy-1-methyl-2-oxo-ethyl)phenyl]-2,2-dimethyl-oxazolidine-3-carboxylate To a solution of (S)-tert-butyl 4-(4-(2-ethoxy-2-oxoethyl)phenyl)-2,2-dimethyloxazolidine-3-carboxylate (280 mg,

Step 1—Tert-butyl (4S)-4-[4-(1-ethoxycarbonylcyclopropyl)phenyl]-2,2-dimethyl-oxazolidine-3-carboxylate To a solution of tert-butyl (4S)-4-[4-(2-ethoxy-2-oxoethyl)phenyl]-2,2-dimethyl-oxazolidine-3-carboxylate (400 mg, 1.10 mmol) in anhydrous N, N-dimethylformamide (4 mL) was added LiHMDS (1 M, 4.40 mL) dropwise at 0° C. The mixture was stirred at 0° C. for 30 mins, and then 1,2-dibromoethane (371 mg, 1.98 mmol) dissolved in anhydrous N, N-dimethylformamide (2 mL) was added dropwise. Finally, the mixture was warmed to rt and stirred at rt for 2.5 hrs. On completion, the reaction mixture was poured into 20 mL of cold a saturated ammonium chloride solution, and extracted with ethyl acetate (3×20 mL). The organic phase was collected, dried over anhydrous sodium sulfate, and concentrated in vacuo to get a residue. The residue was purified by column chromatography (petroleum ether:ethyl acetate=20:1 to 10:1) to give the title compound. $^1$H NMR (400 MHz, CDCl$_3$) δ=7.33-7.21 (m, 4H), 5.00-4.74 (m, 1H), 4.29 (dd, J=6.8, 8.8 Hz, 1H), 4.20-4.04 (m, 2H), 3.88 (d, J=3.6 Hz, 1H), 1.82-1.71 (m, 3H), 1.63-1.55 (m, 6H), 1.49 (s, 3H), 1.31-1.07 (m, 10H).

Step 2—Ethyl 1-[4-[(1S)-1-amino-2-hydroxy-ethyl]phenyl]cyclopropanecarboxylate Tert-butyl (4S)-4-[4-(1-ethoxycarbonylcyclopropyl)phenyl]-2,2-dimethyl-oxazolidine-3-carboxylate (210 mg, 539 umol) was dissolved in 4 M of hydrogen chloride dioxane solution (10 mL). The mixture was stirred at rt for 3 hr. On completion, the reaction mixture was concentrated in vacuo to get the title compound. LCMS: (ES$^+$) m/z (M+H)$^+$=250.3, tR=0.532.

(±)-Ethyl 2-[4-[(1S)-1-amino-2-hydroxy-ethyl]phenyl]-3-methyl-butanoate (Intermediate AO)

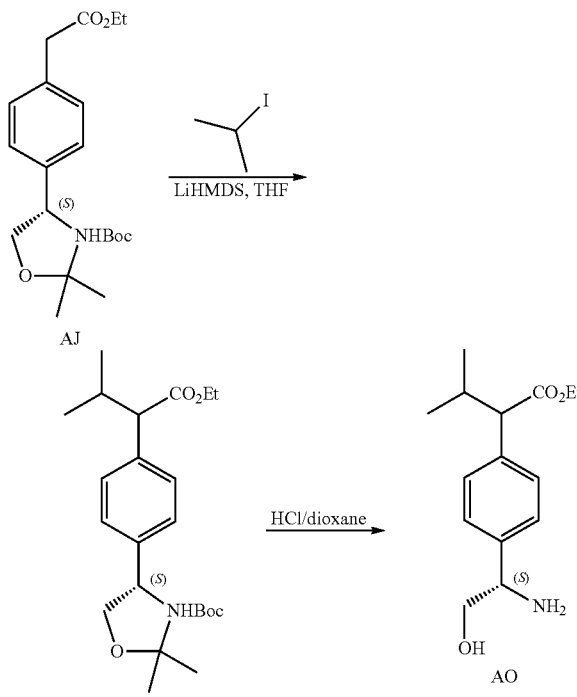

Step 1—(±)-Tert-butyl (4S)-4-[4-(1-ethoxycarbonyl-2-methyl-propyl)phenyl]-2,2-dimethyl-oxazo-lidine-3-carboxylate To a solution of tert-butyl (4S)-4-[4-(2-ethoxy-2-oxoethyl)phenyl]-2,2-dimethyl-oxazolidine-3-carboxylate (6.00 g, 16.5 mmol) in anhydrous tetrahydrofuran (75 mL) was added LiHMDS (1 M, 21.4 mL) dropwise at 0° C., and the mixture was stirred at 0° C. for 30 min. Iodopropane (3.65 g, 21.4 mmol) in anhydrous tetrahydrofuran (15 mL) was added dropwise. The mixture was then warmed to rt and stirred for 2.5 hrs. The reaction mixture was then poured into 120 mL of cold saturated ammonium chloride solution, and extracted with ethyl acetate (3×120 mL). The organic phase was collected, dried over anhydrous sodium sulfate, and concentrated in vacuo. The resulting residue was purified by column chromatography (petroleum ether: ethyl acetate=20:1 to 10:1) to give the title compound. $^1$H NMR (400 MHz, CDCl$_3$) δ=7.32-7.27 (m, 2H), 7.27-7.21 (m, 2H), 5.00-4.72 (m, 1H), 4.28 (dd, J=6.8, 9.2 Hz, 1H), 4.21-4.02 (m, 2H), 3.92-3.80 (m, 1H), 3.13 (d, J=10.5 Hz, 1H), 2.41-2.25 (m, 1H), 1.81-1.70 (m, 3H), 1.61 (br. s., 3H), 1.48 (br. s., 3H), 1.21 (t, J=7.0 Hz, 3H), 1.16 (s, 6H), 1.04 (d, J=6.4 Hz, 3H), 0.70 (d, J=6.7 Hz, 3H).

Step 2—(±)-Ethyl 2-[4-[(1S)-1-amino-2-hydroxy-ethyl]phenyl]-3-methyl-butanoate (±)-Tert-butyl (4S)-4-[4-(1-ethoxycarbonyl-2-methyl-propyl)phenyl]-2,2-dimethyl-oxazolidine-3-carboxylate (5.60 g, 13.8 mmol) was dissolved in 4 M of hydrogen chloride dioxane solution (40 mL). The mixture was stirred at rt for 16 hrs. On completion, the reaction mixture was concentrated in vacuo to get the title compound (HCl salt). LCMS: (ES$^+$) m/z (M+H)$^+$=266.2, tR=1.190.

(±)-(2-Ethoxy-2-oxoethyl)zinc(II) bromide (Intermediate AP)

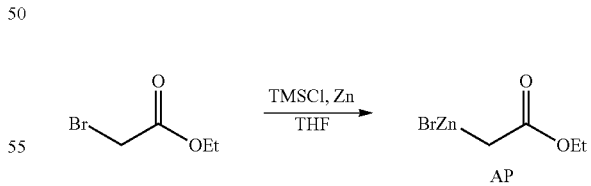

To a mixture of zinc powder (11.8 g, 180 mmol) in anhydrous tetrahydrofuran (44 mL) was added chlorotrimethylsilane (976 mg, 8.98 mmol) in one portion at 30° C. under nitrogen. Then a solution of ethyl 2-bromoacetate (15.0 g, 89.8 mmol) in anhydrous tetrahydrofuran (110 mL) was added dropwise over 0.5 hour at 40-50° C. After the addition, the resulting mixture was stirred at 40° C. for 1 hour. The resulting solution was used in the next step directly.

General Methods

Example 1 (Method 1)—(±)-N-[3-(acetylsulfamoylamino)-1-phenyl-propyl]-4,5-dichloro-1-methyl-indole-2-carboxamide

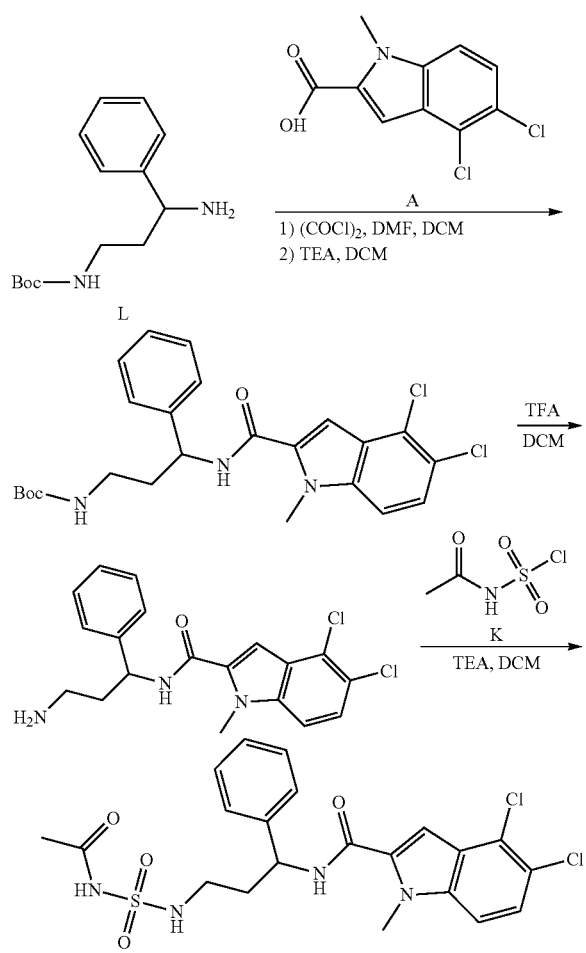

Step 1—(±)-Tert-butyl N-[3-[(4,5-dichloro-1-methyl-indole-2-carbonyl)amino]-3-phenyl-propyl]carbamate To a mixture of 4,5-dichloro-1-methyl-indole-2-carboxylic acid (120 mg, 492 umol) in dichloromethane (15.0 mL) and N,N-dimethyl formamide (719 ug, 9.83 umol) was added oxalyl chloride (256 mg, 2.02 mmol) dropwise at 0° C. under nitrogen atmosphere. The reaction mixture was stirred at rt for 2 hours. On completion, the reaction solution was concentrated in vacuo to give 4,5-dichloro-1-methyl-indole-2-carbonyl chloride (140 mg, crude). To a mixture of (±)-tert-butyl N-(3-amino-3-phenyl-propyl)carbamate (100 mg, 399 umol) and triethylamine (121 mg, 1.20 mmol) in dichloromethane (10.0 mL) was added 4,5-dichloro-1-methyl-indole-2-carbonyl chloride (126 mg, 479 umol) in a solution of dichloromethane (5.00 mL) dropwise at rt under nitrogen atmosphere. The mixture was stirred at rt and stirred for 6 hours. On completion, the reaction was washed with water (5 mL) and extracted with dichloromethane (2×10 mL). The combined organic layer was dried over anhydrous sodium sulfate and concentrated in vacuo to give the title compound. LCMS: (ES$^+$) m/z (M-56)$^+$=420.0, tR=1.750.

Step 2—(±)-N-(3-amino-1-phenyl-propyl)-4,5-dichloro-1-methyl-indole-2-carboxamide To a mixture of (±)-tert-butyl N-[3-[(4,5-dichloro-1-methyl-indole-2-carbonyl)amino]-3-phenyl-propyl]carbamate (200 mg, 420 umol) in dichloromethane (10.0 mL) was added trifluoroacetic acid (1.53 g, 13.4 mmol) in one portion at rt under nitrogen atmosphere. The mixture was stirred at rt for 30 min. On completion, the reaction was concentrated in vacuo to give the title compound (300 mg, 80% yield) as brown oil. LCMS (ES$^+$) m/z (M+H)$^+$: 376.1, tR=0.657.

Step 3—(±)-N-[3-(acetylsulfamoylamino)-1-phenyl-propyl]-4,5-dichloro-1-methyl-indole-2-carboxamide To a mixture of (±)-N-(3-amino-1-phenyl-propyl)-4,5-dichloro-1-methyl-indole-2-carboxamide (290 mg, 771 umol) and triethylamine (234 mg, 2.31 mmol) in dichloromethane (15.0 mL) was added N-acetylsulfamoyl chloride (182 mg, 1.16 mmol) dropwise at 0° C. under nitrogen atmosphere. The mixture was stirred at 0° C. for 30 min. On completion, the reaction was concentrated in vacuo. The residue was purified by Prep-HPLC (condition: 0.05% ammonia-ACN; column: Phenomenex Gemini C18 250*50 10u) to give the title compound. LCMS (ES$^+$) m/z (M+H)$^+$: 497.2, tR=0.918 min. $^1$H NMR (400 MHz, DMSO-d$_6$) δ=11.29-10.73 (m, 1H), 9.08 (d, J=8.4 Hz, 1H), 7.60 (d, J=8.8 Hz, 2H), 7.47-7.38 (m, 3H), 7.38-7.30 (m, 3H), 7.28-7.20 (m, 1H) 5.14-5.04 (m, 1H), 3.96 (s, 3H), 2.92 (t, J=6.78 Hz, 2H), 2.03-2.10 (m, 1H), 2.02-1.95 (m, 1H), 1.92 (s, 3H).

Example 2—N-[3-(acetylsulfamoylamino)propyl]-4,5-dichloro-1-methyl-indole-2-carboxamide

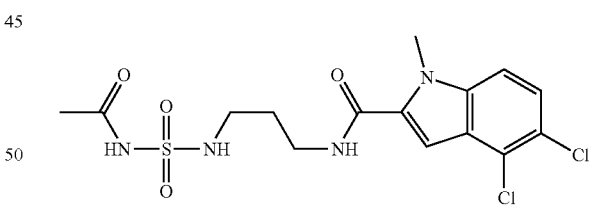

N-[3-(acetylsulfamoylamino)propyl]-4,5-dichloro-1-methyl-indole-2-carboxamide was synthesized via Method 1 with acid A and tert-butyl N-(3-aminopropyl)carbamate (CAS #75178-96-0). For Step 2, HCl in methanol was used for deprotection instead of TFA. The final residue was purified by pre-HPLC (Condition: 10 mM NH$_4$HCO$_3$-MeOH; Column: Welch Ultimate AQ-C18 150*30 mm; Particle size: 5 um) to give the title compound. LCMS: (ES$^+$) m/z (M+H)$^+$=421.1, tR=0.798. $^1$H NMR (400 MHz, DMSO-d$_6$) δ=11.36 (s, 1H), 8.70 (t, J=5.6 Hz, 1H), 7.66 (t, J=5.6 Hz, 1H), 7.62 (d, J=8.8 Hz, 1H), 7.46 (d, J=8.8 Hz, 1H), 7.17 (s, 1H), 4.02 (s, 3H), 3.29 (q, J=6.8 Hz, 2H), 2.95 (q, J=6.8 Hz, 2H), 1.97 (s, 3H), 1.74 (q, J=6.8 Hz, 2H).

Example 3—N-[3-[acetylsulfamoyl(methyl)amino]propyl]-4,5-dichloro-1-methyl-indole-2-carboxamide

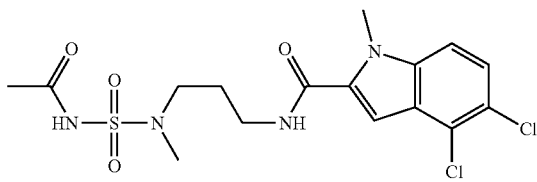

N-[3-[acetylsulfamoyl(methyl)amino]propyl]-4,5-dichloro-1-methyl-indole-2-carboxamide was synthesized via Method 1 with acid A and tert-butyl N-(3-aminopropyl)-N-methyl-carbamate (CAS #150349-36-3). For Step 2, HCl in ethyl acetate was used for deprotection instead of TFA. The final residue was purified by prep-HPLC (Condition: 0.225% FA-ACN Column: Phenomenex Synergi Max-RP 250*80 10u) to give the title compound. LCMS: (ES$^+$) m/z (M+Na)$^+$=457.0, tR=0.819. $^1$H NMR (400 MHz, DMSO-$d_6$) δ=8.69 (t, J=5.6 Hz, 1H), 7.61 (d, J=8.8 Hz, 1H), 7.44 (d, J=8.91 Hz, 1H), 7.16 (s, 1H), 4.00 (s, 3H), 3.28 (d, J=6.0 Hz, 2H), 3.23 (t, J=7.2 Hz, 2H), 2.82 (s, 3H), 1.95 (s, 3H) 1.80 (q, J=7.2 Hz, 2H).

Example 4—(±)-3-[3-(Acetylsulfamoylamino)-1-[(4,5-dichloro-1-methyl-indole-2-carbonyl)amino]propyl]benzoic Acid

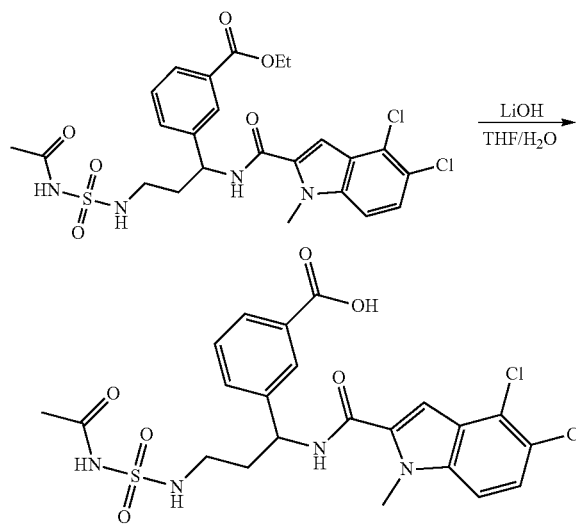

To a mixture of (±)-ethyl 3-[3-(acetylsulfamoylamino)-1-[(4,5-dichloro-1-methyl-indole-2-carbonyl)amino]propyl]benzoate (110 mg, 193 umol, synthesized via Method 1 with acid A and amine M) in a mixture of tetrahydrofuran (2 mL) and water (2 mL) was added lithium hydroxide (32.4 mg, 772 umol) and the mixture was stirred at rt for 12 hrs. On completion, the mixture was concentrated in vacuo. The residue was purified by prep-HPLC (condition: 0.225% FA-ACN; column: Phenomenex Synergi C18 150*25*10 um) to give the title compound. LCMS: (ES$^+$) m/z (M+H)$^+$=541.1, tR=0.858. $^1$H NMR (400 MHz, DMSO-$d_6$) δ=9.15 (d, J=8.0 Hz, 1H), 8.04 (s, 1H), 7.83 (d, J=7.6 Hz, 1H), 7.69-7.53 (m, 3H), 7.52-7.42 (m, 2H), 7.33 (s, 1H), 5.22-5.08 (m, 1H), 3.96 (s, 3H), 2.94 (br. s., 2H), 2.15-2.05 (m, 1H), 2.04-1.95 (m, 1H), 1.92 (s, 3H).

Example 5—(±)-N-[3-(acetylsulfamoylamino)-1-[3-(hydroxymethyl)phenyl]propyl]-4,5-dichloro-1-methyl-indole-2-carboxamide

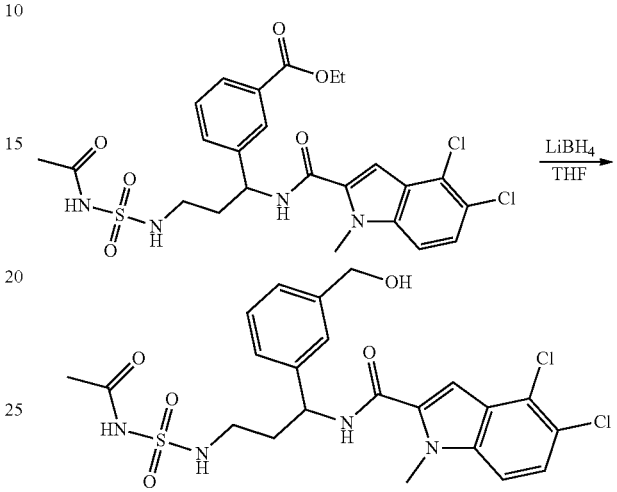

To a mixture of ethyl 3-[3-(acetylsulfamoylamino)-1-[(4,5-dichloro-1-methyl-indole-2-carbonyl)amino]propyl]benzoate (90.0 mg, 158 umol, synthesized via Method 1 with acid A and amine M) in a mixture of tetrahydrofuran (6 mL) was added lithium borohydride (13.0 mg, 632 umol). Then the reaction mixture was stirred at rt for 12 hrs. On completion, the mixture was quenched with 1.0 N hydrochloric acid and concentrated. The residue was purified by prep-HPLC (condition: 0.225% FA-ACN; Column: Phenomenex Synergi C18 150*25*10 um) to give the title compound. LCMS: (ES$^+$) m/z (M+H)$^+$=527.1, tR=0.846. $^1$H NMR (400 MHz, DMSO-$d_6$) δ=9.08 (d, J=8.4 Hz, 1H), 8.31 (s, 1H), 7.61 (d, J=8.8 Hz, 1H), 7.45 (d, J=8.8 Hz, 1H), 7.37 (s, 1H), 7.34-7.25 (m, 4H), 7.19 (d, J=6.4 Hz, 1H), 5.13-5.01 (m, 1H), 4.50 (s, 2H), 3.97 (s, 3H), 2.88 (br. s., 2H), 2.05 (dd, J=8.0, 14.3 Hz, 1H), 2.00-1.90 (m, 1H), 1.85 (s, 3H).

Example 6—4-[3-(Acetylsulfamoylamino)-1-(4,5-dichloro-1-methyl-indole-2-carbonyl)amino]propyl]benzoic Acid

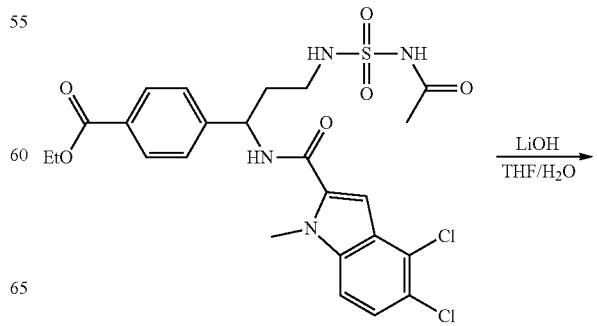

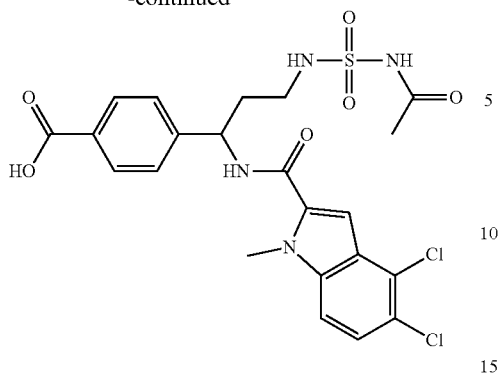

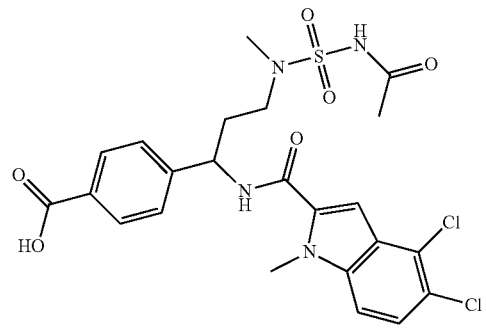

To a mixture of ethyl 4-[3-(acetylsulfamoylamino)-1-[(4,5-dichloro-1-methyl-indole-2-carbonyl)amino]propyl]benzoate (380 mg, 214 umol, synthesized via Method 1 with acid A and amine N, where for Step 2 HCl in MeOH was used for the deprotection instead of TFA) in tetrahydrofuran (10 mL) and water (5 mL) was added LiOH (25.6 mg, 1.07 mmol) in one portion at rt under nitrogen. The mixture was stirred at rt for 12 hours. On completion, the reaction was acidified with 2 N hydrochloric acid (2 mL) to pH=6-7. The residue was purified by prep-HPLC (condition: 0.1% TFA-ACN; Phenomenex Synergi C18 100*21.2 mm*4 um) to give the title compound. LCMS (ES$^+$): 541.1 m/z (M+H)$^+$, tR=0.775 min. $^1$H NMR (400 MHz, DMSO-d$_6$) δ=11.31 (s, 1H), 9.14 (d, J=8.4 Hz, 1H), 7.93 (d, J=8.4 Hz, 2H), 7.75 (t, J=5.6 Hz, 1H), 7.60 (d, J=8.8 Hz, 1H), 7.52 (d, J=8.4 Hz, 2H), 7.45 (d, J=8.8 Hz, 1H), 7.33 (s, 1H), 5.10-5.20 (m, 1H), 3.95 (s, 3H), 3.00-2.90 (m, 2H), 2.14-1.96 (m, 2H), 1.93 (s, 3H).

Example 7—(±)-4-[3-[Acetylsulfamoyl(methyl)amino]-1-[(4,5-dichloro-1-methyl-indole-2-carbonyl)-amino]propyl]benzoic Acid

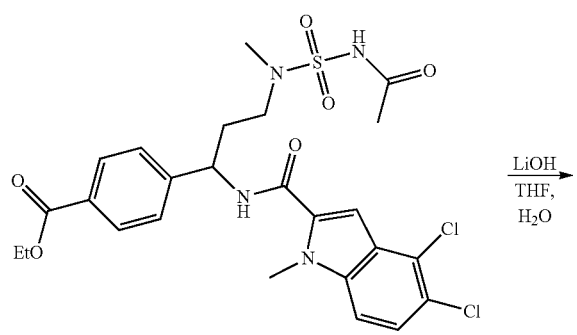

To a solution of (±)-ethyl 4-[3-[acetylsulfamoyl(methyl)amino]-1-[(4,5-dichloro-1-methyl-indole-2-carbonyl)amino]propyl]benzoate (150 mg, 257 umol, synthesized via Method 1 with acid A and amine P, where HCl in MeOH was used for the deprotection in Step 2) in tetrahydrofuran (6 mL) and water (3 mL) was added lithium hydroxide (24.6 mg, 1.03 mmol). The mixture was stirred at rt for 12 hrs. On completion, the reaction mixture was concentrated in vacuo to remove the solvent and the residue was acidified with 1 M hydrochloric acid to the pH=3. Then, the mixture was concentrated in vacuo. The crude product was purified by prep-HPLC (0.1% TFA-ACN, YMC-Actus ODS-AQ 150*30 mm; Particle size: 5 um) to give the title compound. LCMS: (ES$^+$) m/z (M+H)$^+$=555.2, tR=0.821. $^1$H NMR (400 MHz, DMSO-d$_6$) δ=12.89 (br. s., 1H), 11.41 (br. s., 1H), 9.17 (d, J=8.4 Hz, 1H), 7.94 (d, J=8.4 Hz, 2H), 7.60 (d, J=8.8 Hz, 1H), 7.55 (d, J=8.4 Hz, 2H), 7.44 (d, J=8.8 Hz, 1H), 7.32 (s, 1H), 5.15-5.07 (m, 1H), 3.95 (s, 3H), 3.33-3.20 (m, 2H), 2.84 (s, 3H), 2.18-2.01 (m, 2H), 1.94 (s, 3H).

Example 8 (Method 2)—4-[(1S)-1-[[5-Chloro-6-[2-(2-hydroxyethylamino)-2-oxo-ethoxy]-1H-indole-2-carbonyl amino]-2-hydroxy-ethyl]benzoic Acid

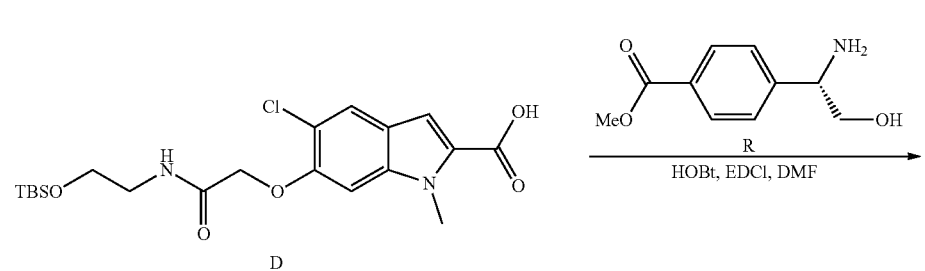

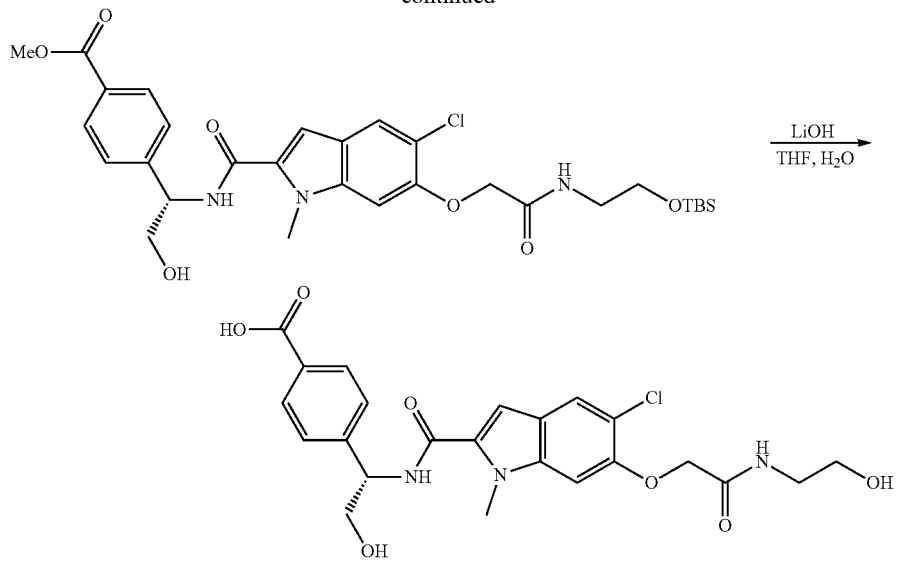

Step 1—Methyl 4-[(1S)-1-[[6-[2-[2-[tert-butyl(dimethyl)silyl]oxyethylamino]-2-oxo-ethoxy]-5-chloro-1H-indole-2-carbonyl]amino]-2-hydroxy-ethyl]benzoate To a solution of 6-(2-((2-((tert-butyldimethylsilyl)oxy)ethyl)amino)-2-oxoethoxy)-5-chloro-1H-indole-2-carboxylic acid (137 mg, 702 umol) in dimethylformamide (2 mL) was added EDCI (107 mg, 562 umol) and HOBt (75.9 mg, 562 umol) and (S)-methyl 4-(1-amino-2-hydroxyethyl)benzoate (200 mg, 468 umol) sequentially. The mixture was stirred at rt for 3 hrs. The reaction mixture was quenched with 50 mL of water and extracted with ethyl acetate (3×50 mL). The combined organic layers were washed with aqueous sodium chloride (100 mL), dried over sodium sulfate, filtered and concentrated in vacuo. The residue was purified by column chromatography (SiO₂, petroleum ether:ethyl acetate=3:1 to 0:1) to afford the title compound. ¹H NMR (400 MHz, DMSO-d₆) δ=11.58 (s, 1H), 8.75 (d, J=8.0 Hz, 1H), 7.93 (d, J=8.0 Hz, 2H), 7.78 (s, 1H), 7.73 (t, J=5.5 Hz, 1H), 7.55 (d, J=8.0 Hz, 2H), 7.24 (s, 1H), 7.02 (s, 1H), 5.18-5.12 (m, 1H), 5.05 (t, J=5.8 Hz, 1H), 4.58 (s, 2H), 3.84 (s, 3H), 3.73 (dd, J=10.0, 5.6 Hz, 2H), 3.64 (t, J=6.0 Hz, 2H), 3.29 (d, J=6.0 Hz, 2H), 0.85 (s, 9H), 0.03 (s, 6H).

Step 2—4-[(1S)-1-[[5-Chloro-6-[2-(2-hydroxyethylamino)-2-oxo-ethoxy]-1H-indole-2-carbonyl]amino]-2-hydroxy-ethyl]benzoic Acid To a solution of (S)-methyl 4-(1-(6-(2-((2-((tert-butyldimethylsilyl)oxy)ethyl)amino)-2-oxoethoxy)-5-chloro-1H-indole-2-carboxamido)-2-hydroxyethyl)benzoate (100 mg, 165 umol) in tetrahydrofuran (1 mL) and water (200 uL) was added lithium hydroxide (13.8 mg, 331 umol). The mixture was stirred at rt for 2 hours. The reaction mixture was concentrated in vacuo. The residue was diluted with water and adjusted to pH=2-3 with hydrochloric acid (1 M, 1 mL). The residue was purified by prep-HPLC (Condition: water (0.225% FA)-ACN; Column: Phenomenex Synergi C18 150*30 mm*4 um) and lyophilized to afford the title compound. LCMS (ES⁺): 476.1 m/z (M+H)⁺, tR=0.657. ¹H NMR (400 MHz, DMSO-d₆) δ=11.64 (s, 1H), 8.80 (d, J=8.4 Hz, 1H), 7.90 (d, J=8.0 Hz, 3H), 7.77 (s, 1H), 7.50 (d, J=8.4 Hz, 2H), 7.24 (s, 1H), 6.99 (s, 1H), 5.19-5.02 (m, 2H), 4.76 (br. s., 1H), 4.58 (s, 2H), 3.77-3.68 (m, 2H), 3.48-3.44 (m, 2H), 3.24 (d, J=5.6 Hz, 2H).

Method 2 Table: Compounds synthesized via Method 2 with corresponding acids and amines

| Example # | Structure | Intermediate Acid | Intermediate Amine | LCMS (ES+) m/z (M + H)⁺ | HNMR (400 MHz, DMSO-d₆) δ |
|---|---|---|---|---|---|
| 9 | HO-...NH...Cl...O...NH (4-[(1S)-1-({5-chloro-6-[(2-oxo-1,3-oxazolidin-5-yl)methoxy]-1H-indol-2-yl}formamido)-2-hydroxyethyl]benzoic acid) | G | (S)-methyl 4-(1-amino-2-hydroxy-ethyl)-benzoate | 474.0 | 11.67 (s, 1H), 8.82 (d, J = 8.0 Hz, 1H), 7.90 (d, J = 8.0 Hz, 2H), 7.76 (s, 1H), 7.62 (s, 1H), 7.49 (d, J = 8.2 Hz, 2H), 7.24 (s, 1H), 7.05 (s, 1H), 5.20-5.02 (m, 2H), 4.99-4.93 (m, 1H), 4.23 (d, J = 3.0 Hz, 1H), 4.20-4.15 (m, 1H), 3.76-3.68 (m, 2H), 3.63 (t, J = 8.9 Hz, 1H), 3.45 (br. s., 1H) |

-continued

Method 2 Table: Compounds synthesized via Method 2 with corresponding acids and amines

| Example # | Structure | Intermediate Acid | Intermediate Amine | LCMS (ES+) m/z (M + H)+ | HNMR (400 MHz, DMSO-d$_6$) δ |
|---|---|---|---|---|---|
| 10[a] | 4[(1S)-1-[(4,5-dichloro-1-methyl-1H-indol-2-yl)-formamido]-2-hydroxyethyl]benzoic acid | A | R | 407.0 | 9.09 (d, J = 8.0 Hz, 2H), 7.92 (d, J = 8.0 Hz, 2H), 7.61 (d, J = 8.8 Hz, 1H), 7.56 (d, J = 8 Hz, 2H), 7.45 (d, J = 8.8 Hz, 1H), 7.43 (s, 1H), 5.15-5.09 (m, 1H), 3.97 (s, 3H), 3.78-3.67 (m, 2H) |
| 11[b] | 2-{4-[(1S)-1-[(4,5-dichloro-1-methyl-1H-indol-2-yl)-formamido]-2-hydroxyethyl]phenyl}acetic acid | A | AC | 421.2 | 12.35 (br. s., 1H), 9.02 (d, J = 8.0 Hz, 1H), 7.66 (d, J = 8.8 Hz, 1H), 7.51 (d, J = 8.8 Hz, 1H), 7.44 (s, 1H), 7.41 (d, J = 8.03 Hz, 2H), 7.28 (d, J = 8.0 Hz, 2H), 5.14-5.08 (m, 1H), 5.04 (t, J = 5.52 Hz, 1H), 4.03 (s, 3H), 3.82-3.75 (m, 1H), 3.74-3.68 (m, 1H), 3.59 (s, 2H) |
| 12[c] | 2-{4-[(1S)-1-[(4,5-dichloro-1-methyl-1H-indol-2-yl)formamido]-2-hydroxyethyl]-3-fluorophenyl}acetic acid | A | AD | 439.0 | 9.03 (d, J = 8.0 Hz, 1H), 7.61 (d, J = 8.8 Hz, 1H), 7.47-7.42 (m, 3H), 7.10-7.07 (m, 2H), 5.38-5.32 (m, 1H), 5.12 (s, 1H), 3.97 (s, 3H), 3.71-3.66 (m, 2H), 3.57 (s, 2H) |
| 13[c] | 3-chloro-4-[(1S)-1-[(4,5-dichloro-1-methyl-1H-indol-2-yl)formamido]-2-hydroxyethyl]benzoic acid | A | AF | 441.1, 443.0 | 13.23 (br. s., 1H), 9.15 (d, J = 7.6 Hz, 1H), 7.94-7.86 (m, 2H), 7.70 (d, J = 8.0 Hz, 1H), 7.61 (d, J = 8.8 Hz, 1H), 7.49-7.42 (m, 2H), 5.48 (d, J = 6.8 Hz, 1H), 5.19 (t, J = 5.6 Hz, 1H), 3.95 (s, 3H), 3.69 (t, J = 6.0 Hz, 2H) |

Method 2 Table: Compounds synthesized via Method 2 with corresponding acids and amines

| Example # | Structure | Intermediate Acid | Intermediate Amine | LCMS (ES+) m/z (M + H)+ | HNMR (400 MHz, DMSO-$d_6$) δ |
|---|---|---|---|---|---|
| 14[d] | 2-{3-chloro-4-[(1S)-1-[(4,5-dichloro-1-methyl-1H-indol-2-yl)formamido]-2-hydroxyethyl]phenyl}-acetic acid | A | AG | 455.1 | 12.43 (br. s., 1H), 9.07 (d, J = 7.6 Hz, 1H), 7.61 (d, J = 9.0 Hz, 1H), 7.51 (d, J = 8.0 Hz, 1H), 7.48-7.42 (m, 2H), 7.34 (s, 1H), 7.22 (d, J = 8.0 Hz, 1H), 5.44 (q, J = 6.8 Hz, 1H), 5.14 (t, J = 6.0 Hz, 1H), 3.96 (s, 3H), 3.64 (t, J = 6.0 Hz, 2H), 3.58 (s, 2H) |
| 15[d] | 2-{4-[(1S)-1-[(4,5-dichloro-6-methoxy-1-methyl-1H-indol-2-yl)formamido]-2-hydroxyethyl]-3-fluorophenyl}acetic acid | E | AD | 469.0 | 8.88 (d, J = 8 Hz, 1H), 7.47-7.43 (m, 1H), 7.37 (s, 1H), 7.27 (s, 1H), 7.10-7.07 (m, 2H), 5.36-5.31 (m, 1H), 5.09 (s, 1H), 3.97 (s, 3H), 3.95 (s, 3H), 3.70-3.64 (m, 2H), 3.58 (s, 2H) |
| 16[e] | 2-{4-[(1S)-1-[(4-chloro-5-methoxy-1-methyl-1H-indol-2-yl)formamido]-2-hydroxyethyl]-phenyl}acetic acid | J | AC | 417.1 | 8.87 (d, J = 8.0 Hz, 1H), 7.50 (d, J = 8.8 Hz, 1H), 7.35 (d, J = 8.0 Hz, 2H), 7.27 (s, 1H), 7.24-7.17 (m, 3H), 5.08-5.01 (m, 2H), 3.94 (s, 3H), 3.88 (s, 3H), 3.70-3.65 (m, 2H), 3.53 (s, 2H) |
| 17[d] | 3-chloro-4-[(1S)-1-[(4-chloro-5-methoxy-1-methyl-1H-indol-2-yl)formamido]-2-hydroxyethyl]benzoic acid | J | AF | 437.2 | 13.22 (br. s., 1H), 9.05 (d, J = 7.6 Hz, 1H), 7.97-7.84 (m, 2H), 7.70 (d, J = 8.0 Hz, 1H), 7.51 (d, J = 8.8 Hz, 1H), 7.35 (s, 1H), 7.22 (d, J = 8.8 Hz, 1H), 5.48 (d, J = 6.8 Hz, 1H), 5.17 (t, J = 5.6 Hz, 1H), 3.92 (s, 3H), 3.88 (s, 3H), 3.69 (t, J = 5.6 Hz, 2H) |

-continued

Method 2 Table: Compounds synthesized via Method 2 with corresponding acids and amines

| Example # | Structure | Intermediate Acid | Intermediate Amine | LCMS (ES+) m/z (M + H)+ | HNMR (400 MHz, DMSO-d$_6$) δ |
|---|---|---|---|---|---|
| 18[d] | 2-{3-chloro-4-[(1S)-1-[4-chloro-5-methoxy-1-methyl-1H-indol-2-yl)formamido]-2-hydroxyethyl]phenyl}acetic acid | J | AG | 451.0 | 9.17 (d, J = 7.8 Hz, 1H), 7.49 (d, J = 9.0 Hz, 1H), 7.38 (d, J = 8.0 Hz, 1H), 7.35 (s, 1H), 7.25 (s, 1H), 7.21 (d, J = 9.0 Hz, 1H), 7.12 (d, J = 7.8 Hz, 1H), 5.39 (d, J = 6.3 Hz, 2H), 3.92 (s, 3H), 3.87 (s, 3H), 3.58 (d, J = 6.0 Hz, 2H), 3.23 (s, 2H) |
| 19[d] | 3-chloro-4-[(1S)-1-[(4,5-dichloro-6-methoxy-1-methyl-1H-indol-2-yl)formamido]-2-hydroxyethyl]benzoic acid | E | AF | 471.1 | 13.25 (br. s., 1H), 9.01 (d, J = 7.5 Hz, 1H), 7.95-7.85 (m, 2H), 7.69 (d, J = 7.8 Hz, 1H), 7.41 (s, 1H), 7.27 (s, 1H), 5.47 (q, J = 6.6 Hz, 1H), 5.18 (t, J = 5.9 Hz, 1H), 3.96 (s, 3H), 3.95 (s, 3H), 3.71-3.63 (m, 2H) |
| 20[f] | 3-chloro-4-[(1S)-1-[(4-chloro-6-methoxy-1,5-dimethyl-1H-indol-2-yl)formamido]-2-hydroxyethyl]benzoic acid | H | AF | 451.2 | 13.35 (br. s., 1H), 8.91 (d, J = 7.5 Hz, 1H), 7.97-7.86 (m, 2H), 7.69 (d, J = 8.0 Hz, 1H), 7.35 (s, 1H), 7.05 (s, 1H), 5.46 (d, J = 7.0 Hz, 1H), 5.16 (t, J = 6.0 Hz, 1H), 3.92 (s, 3H), 3.895 (s, 3H),, 3.68 (t, J = 6.0 Hz, 2H), 2.28 (s, 3H) |

[a]Step 1 was run at rt for 12 hours. Step 2 was run at rt for 5 hours. The final product was purified by prep-TLC (SiO$_2$, dichloromethane:methanol = 4:1). [b]Step 1 was performed at rt for 12 hrs. [c]Step 2 was performed at rt for 12 hrs. [d]Steps 1 & 2 were run at rt for 12 hrs. [e]Steps 1 & 2 were run at rt for 1 hr. [f]Step 1 was run at rt for 2 hrs & Step 2 was run at rt for 12 hrs.

Example 21—4-[(1S)-1-[[4,5-Dichloro-6-[2-(2-hydroxyethylamino)-2-oxo-ethoxy]-1-methyl-indole-2-carbonyl]amino]-2-hydroxy-ethyl]benzoic Acid

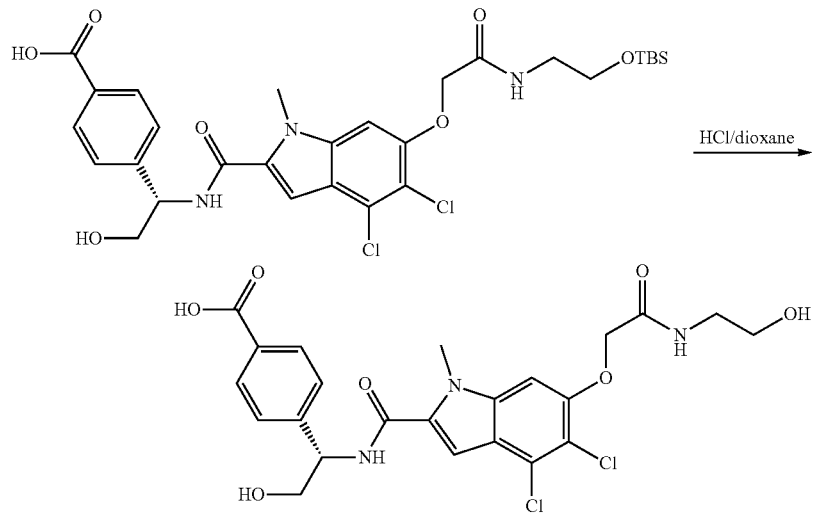

A solution of (S)-4-(1-(6-(2-((2-((tert-butyldimethylsilyl)oxy)ethyl)amino)-2-oxoethoxy)-4,5-dichloro-1-methyl-1H-indole-2-carboxamido)-2-hydroxyethyl)benzoic acid (100 mg, 139 umol, synthesized via Method 2 with acid F and (S)-methyl 4-(1-amino-2-hydroxyethyl)benzoate) in hydrogen chloride/dioxane (10 mL) was stirred at rt for 1 hour. The reaction mixture was concentrated under reduced pressure to remove hydrogen chloride/dioxane. The residue was diluted with 1 mL water and adjusted pH=2-3 with 1 M hydrochloric acid (1 mL). The residue was purified by prep-HPLC (Condition: water (0.225% FA)-ACN; Column: Phenomenex Synergi C18 150*30 mm*4 um) and lyophilized to afford the title compound. LCMS: (ES$^+$) m/z (M+H)$^+$=524.3, tR=0.697. $^1$H NMR (400 MHz, DMSO-d$_6$) δ=8.96 (d, J=7.6 Hz, 1H). 7.96-7.87 (m, 3H), 7.49 (d, J=8.4 Hz, 2H), 7.37 (s, 1H), 7.27 (s, 1H), 5.14-4.98 (m, 2H), 4.72 (s, 2H), 3.93 (s, 3H), 3.78-3.64 (m, 3H), 3.48 (s, 2H), 3.26 (s, 2H).

Example 22 (Method 3)—(±)-4-(1-(4,5-Dichloro-1-methyl-1H-indole-2-carboxamido)-2,2,2-trifluoroethyl)benzoic Acid

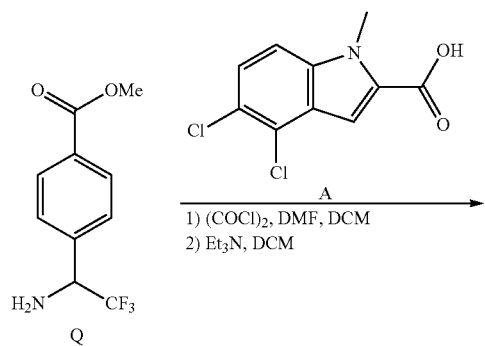

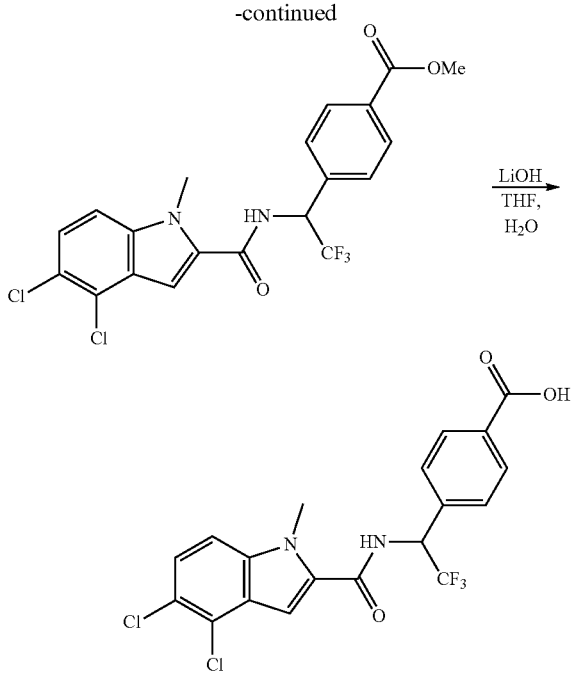

Step 1—(±)-Methyl 4-(1-(4,5-dichloro-1-methyl-1H-indole-2-carboxamido)-2,2,2-trifluoroethyl)benzoate To a solution of 4,5-dichloro-1-methyl-1H-indole-2-carboxylic acid (125 mg, 0.514 mmol) in dichloromethane (5 mL) was added oxalyl chloride (196 mg, 1.54 mmol) and a drop of N,N-dimethylformamide at 0° C. The mixture was stirred at rt for 1 hour. On completion, the reaction was concentrated in vacuo. The residue was dissolved in dichloromethane (10 mL) and added into a solution of triethylamine (156 mg, 1.54 mmol) and methyl 4-(1-amino-2,2,2- trifluoro-ethyl)benzoate (120 mg, 514 umol) in dichloromethane (10 mL). The reaction mixture was stirred at rt for 16 hours. On completion, the mixture was concentrated in vacuo. The residue was purified by silica gel column chromatography (petroleum ether:ethyl acetate=30:1 to 5:1) to give the title compound. LCMS: (ES$^+$) m/z (M+H)$^+$=459.0, tR=1.006.

Step 2—(±)-4-(1-(4,5-Dichloro-1-methyl-1H-indole-2-carboxamido)-2,2,2-trifluoroethyl)benzoic Acid To a solution of methyl 4-[1-[(4,5-dichloro-1-methyl-indole-2-carbonyl)amino]-2,2,2-trifluoro-ethyl]benzoate (44.0 mg, 95.8 umol) in tetrahydrofuran (3 mL) and water (1 mL) was added lithium hydroxide (6.88 mg, 287 umol). The mixture was stirred at rt for 16 hours. On completion, the mixture was acidified by aqueous hydrochloric acid (2 N) until pH=3, and concentrated in vacuo. The residue was purified by prep-HPLC [Instrument: GX-A; Column: Phenomenex Gemini 150*25 mm*10 um; Mobile phase: 23-53% acetonitrile in water (add 0.05% ammonium hydroxide)] to give title compound. LCMS: (ES$^+$) m/z (M−H)$^−$=442.9, tR=1.025. $^1$H NMR (400 MHz, DMSO-d$_6$) δ=9.78 (d, J=9.6 Hz, 1H), 7.97 (d, J=8.0 Hz, 2H), 7.73 (d, J=8.0 Hz, 2H), 7.65 (d, J=8.8 Hz, 1H), 7.52 (s, 1H), 7.49 (d, J=8.8 Hz, 1H), 6.17-6.09 (m, 1H), 4.00 (s, 3H).

Method 3 Table: Compounds synthesized via Method 3 with the corresponding acids and amines

| Example # | Structure | Intermediate Acid | Intermediate Amine | LCMS (ES+) m/z (M + H)$^+$ | HNMR (400 MHz, DMSO-d$_6$) δ |
|---|---|---|---|---|---|
| 9 | 4-[(1S)-1-({5-chloro-6-[(2-oxo-1,3-oxazolidin-5-yl)methoxy]-1H-indol-2-yl}formamido)-2-hydroxyethyl]benzoic acid | G | (S)-methyl 4-(1-amino-2-hydroxy-ethyl)-benzoate | 474.0 | 11.67 (s, 1H), 8.82 (d, J = 8.0 Hz, 1H), 7.90 (d, J = 8.0 Hz, 2H), 7.76 (s, 1H), 7.62 (s, 1H), 7.49 (d, J = 8.2 Hz, 2H), 7.24 (s, 1H), 7.05 (s, 1H), 5.20-5.02 (m, 2H), 4.99-4.93 (m, 1H), 4.23 (d, J = 3.0 Hz, 1H), 4.20-4.15 (m, 1H), 3.76-3.68 (m, 2H), 3.63 (t, J = 8.9 Hz, 1H), 3.45 (br. s., 1H) |
| 10$^a$ | 4-[(1S)-1-[(4,5-dichloro-1-methyl-1H-indol-2-yl)-formamido]-2-hydroxyethyl]benzoic acid | A | R | 407.0 | 9.09 (d, J = 8.0 Hz, 2H), 7.92 (d, J = 8.0 Hz, 2H), 7.61 (d, J = 8.8 Hz, 1H), 7.56 (d, J = 8 Hz, 2H), 7.45 (d, J = 8.8 Hz, 1H), 7.43 (s, 1H), 5.15-5.09 (m, 1H), 3.97 (s, 3H), 3.78-3.67 (m, 2H) |
| 11$^b$ | 2-{4-[(1S)-1-[(4,5-dichloro-1-methyl-1H-indol-2-yl)-formamido]-2-hydroxyethyl]phenyl}acetic acid | A | AC | 421.2 | 12.35 (br. s., 1H), 9.02 (d, J = 8.0 Hz, 1H), 7.66 (d, J = 8.8 Hz, 1H), 7.51 (d, J = 8.8 Hz, 1H), 7.44 (s, 1H), 7.41 (d, J = 8.03 Hz, 2H), 7.28 (d, J = 8.0 Hz, 2H), 5.14-5.08 (m, 1H), 5.04 (t, J = 5.52 Hz, 1H), 4.03 (s, 3H), 3.82-3.75 (m, 1H), 3.74-3.68 (m, 1H), 3.59 (s, 2H) |

-continued

Method 3 Table: Compounds synthesized via Method 3 with the corresponding acids and amines

| Example # | Structure | Intermediate Acid | Intermediate Amine | LCMS (ES+) m/z (M + H)+ | HNMR (400 MHz, DMSO-d$_6$) δ |
|---|---|---|---|---|---|
| 12$^c$ | 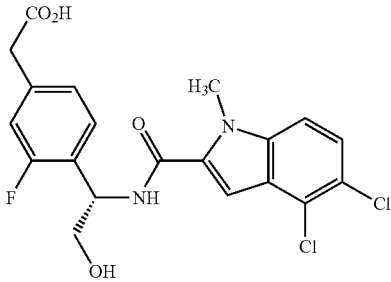<br>2-{4-[(1S)-1-[(4,5-dichloro-1-methyl-1H-indol-2-yl)formamido]-2-hydroxyethyl]-3-fluorophenyl}acetic acid | A | AD | 439.0 | 9.03 (d, J = 8.0 Hz, 1H), 7.61 (d, J = 8.8 Hz, 1H), 7.47-7.42 (m, 3H), 7.10-7.07 (m, 2H), 5.38-5.32 (m, 1H), 5.12 (s, 1H), 3.97 (s, 3H), 3.71-3.66 (m, 2H), 3.57 (s, 2H) |
| 13$^c$ | 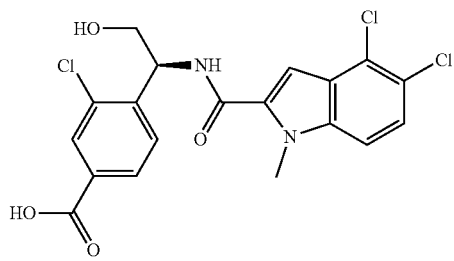<br>3-chloro-4-[(1S)-1-[(4,5-dichloro-1-methyl-1H-indol-2-yl)formamido]-2-hydroxyethyl]benzoic acid | A | AF | 441.1, 443.0 | 13.23 (br. s., 1H), 9.15 (d, J = 7.6 Hz, 1H), 7.94-7.86 (m, 2H), 7.70 (d, J = 8.0 Hz, 1H), 7.61 (d, J = 8.8 Hz, 1H), 7.49-7.42 (m, 2H), 5.48 (d, J = 6.8 Hz, 1H), 5.19 (t, J = 5.6 Hz, 1H), 3.95 (s, 3H), 3.69 (t, J = 6.0 Hz, 2H) |
| 14$^d$ | 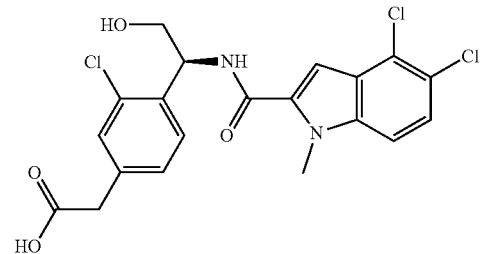<br>2-{3-chloro-4-[(1S)-1-[(4,5-dichloro-1-methyl-1H-indol-2-yl)formamido]-2-hydroxyethyl]phenyl}-acetic acid | A | AG | 455.1 | 12.43 (br. s., 1H), 9.07 (d, J = 7.6 Hz, 1H), 7.61 (d, J = 9.0 Hz, 1H), 7.51 (d, J = 8.0 Hz, 1H), 7.48-7.42 (m, 2H), 7.34 (s, 1H), 7.22 (d, J = 8.0 Hz, 1H), 5.44 (q, J = 6.8 Hz, 1H), 5.14 (t, J = 6.0 Hz, 1H), 3.96 (s, 3H), 3.64 (t, J = 6.0 Hz, 2H), 3.58 (s, 2H) |
| 15$^d$ | 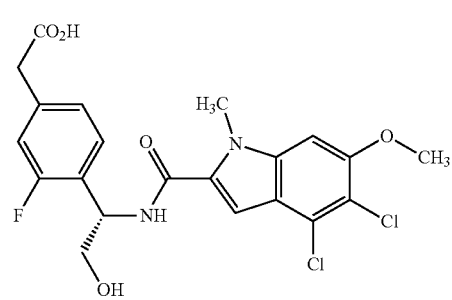<br>2-{4-[(1S)-1-[(4,5-dichloro-6-methoxy-1-methyl-1H-indol-2-yl)formamido]-2-hydroxyethyl]-3-fluorophenyl}acetic acid | E | AD | 469.0 | 8.88 (d, J = 8 Hz, 1H), 7.47-7.43 (m, 1H), 7.37 (s, 1H), 7.27 (s, 1H), 7.10-7.07 (m, 2H), 5.36-5.31 (m, 1H), 5.09 (s, 1H), 3.97 (s, 3H), 3.95 (s, 3H), 3.70-3.64 (m, 2H), 3.58 (s, 2H) |

-continued

Method 3 Table: Compounds synthesized via Method 3 with the corresponding acids and amines

| Example # | Structure | Intermediate Acid | Intermediate Amine | LCMS (ES+) m/z (M + H)+ | HNMR (400 MHz, DMSO-$d_6$) δ |
|---|---|---|---|---|---|
| 16[c] | 2-{4-[(1S)-1-[(4-chloro-5-methoxy-1-methyl-1H-indol-2-yl)formamido]-2-hydroxyethyl]-phenyl}acetic acid | J | AC | 417.1 | 8.87 (d, J = 8.0 Hz, 1H), 7.50 (d, J = 8.8 Hz, 1H), 7.35 (d, J = 8.0 Hz, 2H), 7.27 (s, 1H), 7.24-7.17 (m, 3H), 5.08-5.01 (m, 2H), 3.94 (s, 3H), 3.88 (s, 3H), 3.70-3.65 (m, 2H), 3.53 (s, 2H) |
| 17[d] | 3-chloro-4-[(1S)-1-[(4-chloro-5-methoxy-1-methyl-1H-indol-2-yl)formamido]-2-hydroxyethyl]benzoic acid | J | AF | 437.2 | 13.22 (br. s., 1H), 9.05 (d, J = 7.6 Hz, 1H), 7.97-7.84 (m, 2H), 7.70 (d, J = 8.0 Hz, 1H), 7.51 (d, J = 8.8 Hz, 1H), 7.35 (s, 1H), 7.22 (d, J = 8.8 Hz, 1H), 5.48 (d, J = 6.8 Hz, 1H), 5.17 (t, J = 5.6 Hz, 1H), 3.92 (s, 3H), 3.88 (s, 3H), 3.69 (t, J = 5.6 Hz, 2H) |
| 18[d] | 2-{3-chloro-4-[(1S)-1-[(4-chloro-5-methoxy-1-methyl-1H-indol-2-yl)formamido]-2-hydroxyethyl]phenyl}acetic acid | J | AG | 451.0 | 9.17 (d, J = 7.8 Hz, 1H), 7.49 (d, J = 9.0 Hz, 1H), 7.38 (d, J = 8.0 Hz, 1H), 7.35 (s, 1H), 7.25 (s, 1H), 7.21 (d, J = 9.0 Hz, 1H), 7.12 (d, J = 7.8 Hz, 1H), 5.39 (d, J = 6.3 Hz, 2H), 3.92 (s, 3H), 3.87 (s, 3H), 3.58 (d, J = 6.0 Hz, 2H), 3.23 (s, 2H) |
| 19[d] | 3-chloro-4-[(1S)-1-[(4,5-dichloro-6-methoxy-1-methyl-1H-indol-2-yl)formamido]-2-hydroxyethyl]benzoic acid | E | AF | 471.1 | 13.25 (br. s., 1H), 9.01 (d, J = 7.5 Hz, 1H), 7.95-7.85 (m, 2H), 7.69 (d, J = 7.8 Hz, 1H), 7.41 (s, 1H), 7.27 (s, 1H), 5.47 (q, J = 6.6 Hz, 1H), 5.18 (t, J = 5.9 Hz, 1H), 3.96 (s, 3H), 3.95 (s, 3H), 3.71-3.63 (m, 2H) |

| Example # | Structure | Intermediate Acid | Intermediate Amine | LCMS (ES+) m/z (M + H)+ | HNMR (400 MHz, DMSO-d6) δ |
|---|---|---|---|---|---|
| 20[f] | 3-chloro-4-[(1S)-1-[(4-chloro-6-methoxy-1,5-dimethyl-1H-indol-2-yl)formamido]-2-hydroxyethyl]benzoic acid | H | AF | 451.2 | 13.35 (br. s., 1H), 8.91 (d, J = 7.5 Hz, 1H), 7.97-7.86 (m, 2H), 7.69 (d, J = 8.0 Hz, 1H), 7.35 (s, 1H), 7.05 (s, 1H), 5.46 (d, J = 7.0 Hz, 1H), 5.16 (t, J = 6.0 Hz, 1H), 3.92 (s, 3H), 3.895 (s, 3H),, 3.68 (t, J = 6.0 Hz, 2H), 2.28 (s, 3H) |

[a]Step 2 was run at 50° C. for 4 hrs. [b]Step 2 was run at 60° C. for 24 hrs. [c]Step 2 was run at 60° C. for 16 hrs. [d]Step 2 was not performed, no hydrolysis necessary. [e]Step 1 was run at 0° C. for 1 hr. [f]Step 1 was run at rt for 1 hr. [g]Step 2 was run at rt for 24 hrs. [h]Step 1 was run at rt for 1 hr. Step 2 was run at 90° C. for 12 hrs. [i]Steps 1 & 2 were run at rt for 1 hr. [j]Step 1 was run at rt for 1 hr & Step 2 was run at rt for 12 hrs.

Example 47—(±)-4-(2-Amino-1-(4,5-dichloro-1-methyl-1H-indole-2-carboxamido)ethyl)benzoic Acid

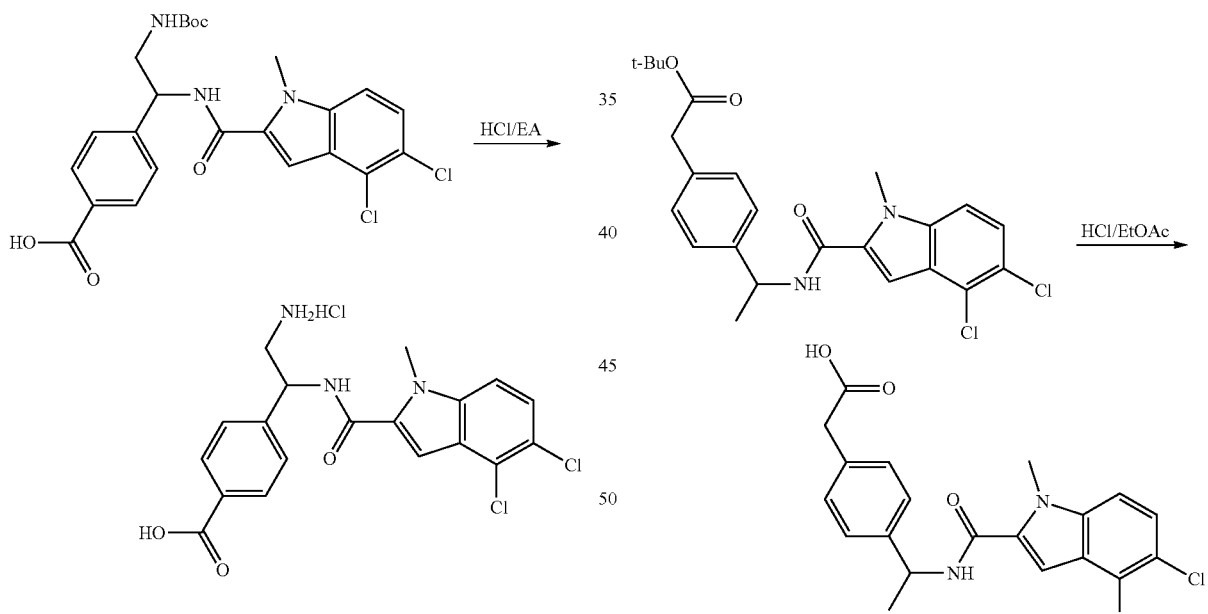

A solution of (±)-4-[2-(tert-butoxycarbonylamino)-1-[(4,5-dichloro-1-methyl-indole -2-carbonyl)amino]ethyl]benzoic acid (70.0 mg, 138 umol, synthesized via Method 3 with acid A and amine O) in hydrochloric acid/ethyl acetate (4 M, 3.5 mL) was stirred at rt for 1 hr. On completion, the mixture was concentrated and the residue was purified by prep-HPLC [Instrument: GX-E; Column: Phenomenex Synergi C18 150*30 mm*4 um; Mobile phase: 25-45% acetonitrile in water (added 0.05% hydrochloric acid)] to give the title compound. LCMS: (ES+) m/z (M+H)+=406.0, tR=0.657. $^1$H NMR (400 MHz, DMSO-d6) δ=9.43 (d, J=8.0 Hz, 1H), 7.97 (d, J=8.4 Hz, 2H), 7.63 (d, J=8.8 Hz, 1H), 7.58 (d, J=8.4 Hz, 2H), 7.53 (s, 1H), 7.47 (d, J=8.8 Hz, 1H), 5.46-5.35 (m, 1H), 3.97 (s, 3H), 3.23 (d, J=9.2 Hz, 2H).

Example 48—(±)-2-(4-(1-(4,5-Dichloro-1-methyl-1H-indole-2-carboxamido)ethyl)phenyl) Acetic Acid To a solution of (±)-tert-butyl 2-[4-[1-[(4,5-dichloro-1-methyl-indole-2-carbonyl)amino]ethyl]phenyl]acetate (50.0 mg, 108 umol, synthesized via Step 1 of Method 3 with acid A and amine W) in ethyl acetate (1 mL) was added hydrogen chloride/ethyl acetate (4 M, 5 mL). The mixture was stirred at rt for 5 hours. On completion, the mixture was concentrated in vacuo. The residue was purified by Prep-HPLC (acetonitrile/water, 0.05% TFA) to give the title compound. LCMS (ES+) m/z (M+H)+=405.0, tR=1.119. $^1$H NMR (400 MHz, DMSO-d6) δ=9.06 (d, J=8.2 Hz, 1H), 7.60 (d, J=8.8 Hz, 1H), 7.44 (d, J=8.8 Hz, 1H), 7.36 (s, 1H), 7.34 (d, J=2.1

Hz, 2H), 7.23 (d, J=8.2 Hz, 2H), 5.15 (m, 1H), 3.98 (s, 3H), 3.54 (s, 2H), 1.49 (d, J=7.0 Hz, 3H).

Example 49—N-(3-amino-1,1-dimethyl-3-oxo-propyl)-4,5-dichloro-1-methyl-indole-2-carboxamide

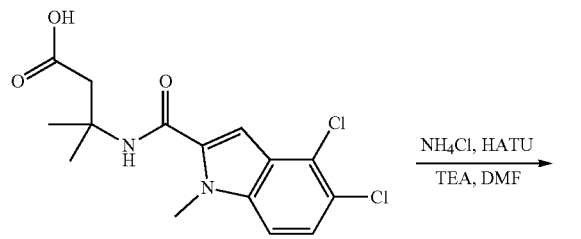

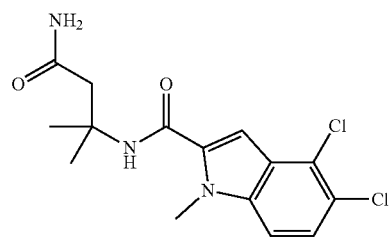

To a solution of 3-[(4,5-dichloro-1-methyl-indole-2-carbonyl)amino]-3-methyl-butanoic acid (100 mg, 291 umol, synthesized via Method 3 with acid A and amine X) in N,N-dimethylformamide (3.00 mL) was added HATU (222 mg, 583 umol), triethylamine (88.5 mg, 874 umol) and ammonium chloride (31.2 mg, 583 umol) in one portion at rt, and the reaction was stirred at rt for 12 hrs. The reaction was diluted with ethyl acetate (50 mL), washed with water (3×20 mL), dried over anhydrous sodium sulfate, and concentrated. The residue was purified by prep-HPLC (0.1% trifluoroacetic acid-ACN; Welch Ultimate AQ-C18 150*30 mm*5 um) to give the title compound. LCMS: (ES$^+$) m/z (M+H)$^+$=342.1, tR=0.974. $^1$H NMR (400 MHz, DMSO-d$_6$) δ=8.55 (s, 1H), 8.61-8.59 (d, J=8.8 Hz, 1H), 7.50 (br. s., 1H), 8.45-7.42 (d, J=8.8 Hz, 1H), 7.46 (s, 1H), 7.40 (br. s., 1H), 3.98 (s, 3H), 3.56 (s, 2H), 1.47 (s, 6H).

Example 50—(±)-2-[4-[(1S)-1-1(4,5-dichloro-1-methyl-indole-2-carbonyl)amino]-2-hydroxy-ethyl]phenyl]butanoic Acid

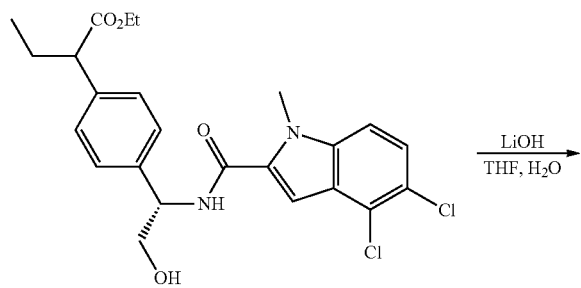

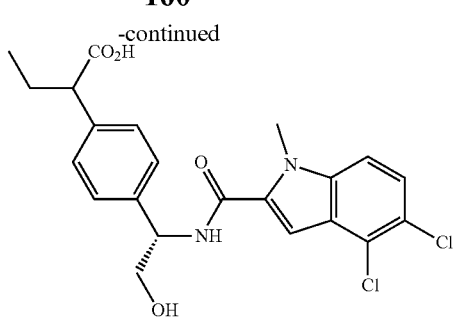

To a solution of (±)-ethyl 2-[4-[(1S)-1-[(4,5-dichloro-1-methyl-indole-2-carbonyl)amino]-2-hydroxy-ethyl]phenyl]butanoate (120 mg, 251 umol, synthesized via Step 1 of Method 3 with acid A and amine AL, where Step 1 was run at rt for 1 hr not 16 hrs) in water (2 mL) and tetrahydrofuran (3 mL) was added lithium hydroxide (48.1 mg, 2.01 mmol). The mixture was stirred at rt for 16 hrs. On completion, the reaction mixture was concentrated in vacuo and the residue was acidified with 1 M hydrochloric acid until pH=7. Then, the mixture was concentrated in vacuo. The crude product was purified by prep-HPLC (Condition: water (0.05% ammonia hydroxide v/v)-ACN, Column: Boston pH-lex 150*25*10 um) to give the title compound. LCMS: (ES$^+$) m/z (M+H)$^+$=449.1, tR=0.857. $^1$H NMR (400 MHz, DMSO-d$_6$) δ=9.84-9.34 (m, 1H), 7.64-7.47 (m, 2H), 7.42 (dd, J=2.8, 8.8 Hz, 1H), 7.28-7.14 (m, 4H), 6.00-5.37 (m, 1H), 5.02-4.84 (m, 1H), 3.97 (d, J=2.0 Hz, 3H), 3.51 (br. s., 1H), 3.06 (d, J=7.6 Hz, 1H), 1.93 (dd, J=7.2, 13.2 Hz, 1H), 1.48 (td, J=6.4, 13.0 Hz, 1H), 0.85-0.74 (m, 3H).

Example 51—(±)-2-[4-[(1S)-1-[(4-chloro-5-methoxy-1-methyl-indole-2-carbonyl)amino]-2-hydroxy-ethyl]phenyl]butanoic Acid To a solution of (±)-ethyl 2-[4-[(1S)-1-[(4-chloro-5-methoxy-1-methyl-indole-2-carbonyl)amino]-2-hydroxy-ethyl]phenyl]butanoate (140 mg, 296 umol, synthesized via Step 1 of Method 3 with acid J and amine AL, where Step 1 was run at rt for 1 hr not 16 hrs) in water (2 mL) and tetrahydrofuran (3 mL) was added lithium hydroxide (56.7 mg, 2.37 mmol). The mixture was stirred at rt for 16 hrs. On completion, the reaction mixture was concentrated in vacuo and the residue was acidified with 1 M hydrochloric acid until pH=7. At this point the mixture was concentrated in vacuo. The crude product was purified by prep-HPLC (Condition: water (0.1% TFA)-ACN, Column: YMC-Actus ODS-AQ 150*30*5 um) to give the title compound. LCMS: (ES$^+$) m/z (M+H)$^+$=445.3, tR=0.812. $^1$H NMR (400 MHz, DMSO-d$_6$) δ=12.29 (br. s., 1H), 8.87 (d, J=8.0 Hz, 1H), 7.51 (d, J=8.8 Hz, 1H), 7.37 (d, J=8.0 Hz, 2H), 7.29-7.23 (m, 3H), 7.22 (d, J=9.2 Hz, 1H), 5.09-5.01 (m, 1H), 4.97 (br. s., 1H), 3.95 (s, 3H), 3.88 (s, 3H), 3.76-3.62 (m, 2H), 3.42-3.37 (m, 1H), 2.01-1.89 (m, 1H), 1.70-1.58 (m, 1H), 0.83 (t, J=7.3 Hz, 3H).

Example 52—(±)-2-[4-[(1S)-1-(4,5-dichloro-6-methoxy-1-methyl-indole-2-carbonyl)amino]-2-hydroxy-ethyl]phenyl]butanoic Acid

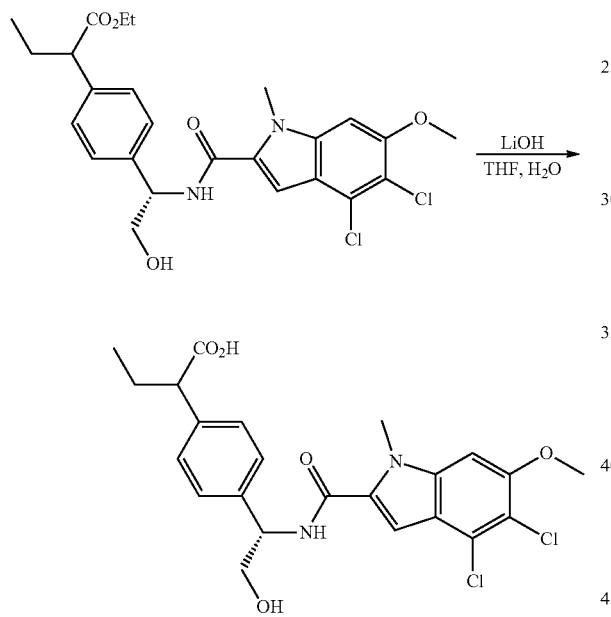

To a solution of (±)-ethyl 2-[4-[(1S)-1-[(4,5-dichloro-6-methoxy-1-methyl-indole-2-carbonyl)amino]-2-hydroxy-ethyl]phenyl]butanoate (150 mg, 295 umol, synthesized via Step 1 of Method 3 with acid E and amine AL, where Step 1 was run at rt for 1 hr not 16 hrs) in water (2 mL) and tetrahydrofuran (3 mL) was added lithium hydroxide (56.6 mg, 2.36 mmol). The mixture was stirred at rt for 16 hrs. On completion, the reaction mixture was concentrated in vacuo and the residue was acidified with 1 M hydrochloric acid until pH=7. Then, the mixture was concentrated in vacuo. The crude product was purified by prep-HPLC (Condition: water (0.1% TFA)-ACN, Column: YMC-Actus ODS-AQ 150*30*5 um) to give the title compound. LCMS: (ES$^+$) m/z (M+H)$^+$=479.2, tR=0.858. $^1$H NMR (400 MHz, DMSO-d$_6$) δ=12.29 (br. s., 1H), 8.83 (d, J=8.0 Hz, 1H), 7.39-7.33 (m, 3H), 7.28-7.23 (m, 3H), 5.08-5.00 (m, 1H), 4.97 (t, J=5.6 Hz, 1H), 3.98 (s, 3H), 3.96 (s, 3H), 3.75-3.60 (m, 2H), 3.38 (t, J=7.6 Hz, 1H), 2.02-1.89 (m, 1H), 1.69-1.58 (m, 1H), 0.83 (t, J=7.2 Hz, 3H).

Compounds Synthesized Via Other Methods

Example 53—(±)-2-[4-[(1S)-1-[(4,5-dichloro-1-methyl-indole-2-carbonyl)amino]-2-hydroxy-ethyl]phenyl]-3-methyl-butanoic acid

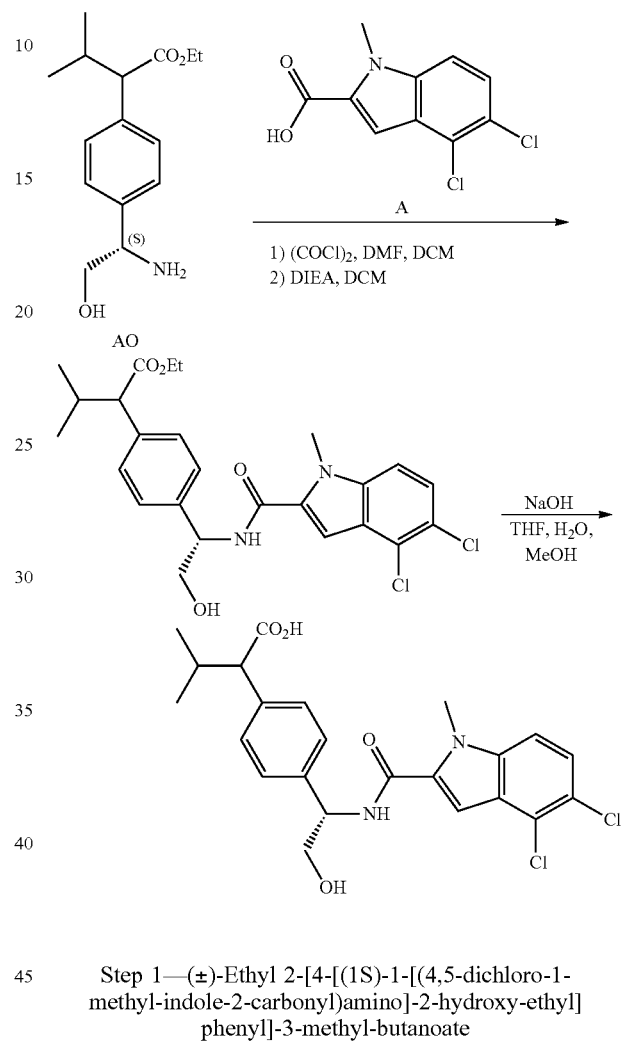

Step 1—(±)-Ethyl 2-[4-[(1S)-1-[(4,5-dichloro-1-methyl-indole-2-carbonyl)amino]-2-hydroxy-ethyl]phenyl]-3-methyl-butanoate To a solution of 4,5-dichloro-1-methyl-indole-2-carboxylic acid (2.50 g, 10.2 mmol) in anhydrous dichloromethane 60 mL was added a catalytic amount of N, N-dimethylformamide. The mixture was then cooled to 0° C. and oxalyl chloride (3.90 g, 30.7 mmol) was added dropwise. Afterwards, the reaction mixture was warmed to rt and stirred for 1 hr. On completion, the reaction mixture was concentrated in vacuo to give crude 4,5-dichloro-1-methyl-indole-2-carbonyl chloride, which was used into the next step without further purification. To a solution of (±)-ethyl 2-[4-[(1S)-1-amino-2-hydroxy-ethyl]phenyl]-3-methyl-butanoate (2.95 g, 11.1 mmol) in anhydrous dichloromethane 75 mL was added diisopropylethylamine (3.91 g, 30.2 mmol, 5.28 mL). Then, the mixture was cooled to 0° C. and 4,5-dichloro-1-methyl-indole-2-carbonyl chloride (2.65 g, 10.0 mmol) dissolved in anhydrous dichloromethane (75 mL) was added. The mixture was allowed to reach rt and stirred for 1 hr. On completion, the reaction mixture was washed with 0.5 M hydrochloride acid aqueous solution (150 mL) and ice water (2×150 mL). The organic phase was collected, dried over anhydrous sodium sulfate, filtered, and concentrated in vacuo. The residue was purified by column chromatography (petroleum ether: ethyl acetate=5:1 to 1:1) to give the title compound. LCMS: (ES$^+$) m/z (M+H)$^+$=491.3, tR=0.970. $^1$H NMR (400 MHz, CDCl$_3$) δ=7.41-7.37 (m, 2H), 7.37-7.32 (m, 3H), 7.21 (d, J=8.8 Hz, 1H), 7.04 (d, J=7.2 Hz, 1H), 7.00 (s, 1H), 5.26 (td, J=4.8, 7.2 Hz, 1H), 4.23-4.03 (m, 3H), 4.02 (s, 3H), 3.17 (d, J=10.4 Hz, 1H), 2.52 (m, 1H), 2.41-2.28 (m, 1H), 1.25 (t, J=7.2 Hz, 3H), 1.05 (d, J=6.4 Hz, 3H), 0.73 (d, J=6.4 Hz, 3H).

Step 2—( )-2-[4-[(1S)-1-[(4,5-dichloro-1-methyl-indole-2-carbonyl)amino]-2-hydroxy-ethyl]phenyl]-3-methyl-butanoic Acid To a solution of (±)-ethyl 2-[4-[(1S)-1-[(4,5-dichloro-1-methyl-indole-2-carbonyl)amino]-2-hydroxy-ethyl]phenyl]-3-methyl-butanoate (3.00 g, 6.10 mmol) in water (40 mL), tetrahydrofuran (60 mL) and methanol (40 mL) was added sodium hydroxide (1.22 g, 30.5 mmol). The mixture was stirred at 70° C. for 3 hrs. On completion, the reaction mixture was concentrated in vacuo to remove the organic solvent and the residue was acidified with 1 M hydrochloride acid to adjust the pH=7. Then, the mixture was concentrated in vacuo. The crude product was purified by prep-HPLC (column: Phenomenex Gemini C18 250*50 mm*10 um; mobile phase: [water (0.05% ammonia hydroxide v/v)-ACN]; ACN %: 10 ACN %-35 ACN %) to give the title compound. LCMS: (ES$^+$) m/z (M+H)$^+$=463.0, tR=0.975. $^1$H NMR (400 MHz, DMSO-d$_6$) δ=9.03 (br. s., 1H), 7.61 (d, J=8.8 Hz, 1H), 7.45 (d, J=8.8 Hz, 1H), 7.41 (d, J=2.0 Hz, 1H), 7.34 (d, J=8.0 Hz, 2H), 7.28 (d, J=8.0 Hz, 2H), 5.10-5.01 (m, 1H), 3.98 (s, 3H), 3.71-3.63 (m, 2H), 3.04 (d, J=10.4 Hz, 1H), 2.26-2.11 (m, 1H), 0.99 (d, J=6.4 Hz, 3H), 0.62 (d, J=6.4 Hz, 3H).

Example 54 & 55—(2R or 2S)-2-[4-[(1S)-1-[(4,5-dichloro-1-methyl-indole-2-carbonyl)amino]-2-hydroxy-ethyl]phenyl]-3-methyl-butanoic Acid & (2S or 2R)-2-14-[(1S)-1-[(4,5-dichloro-1-methyl-indole-2-carbonyl)amino]-2-hydroxy-ethyl]phenyl]-3-methyl-butanoic Acid

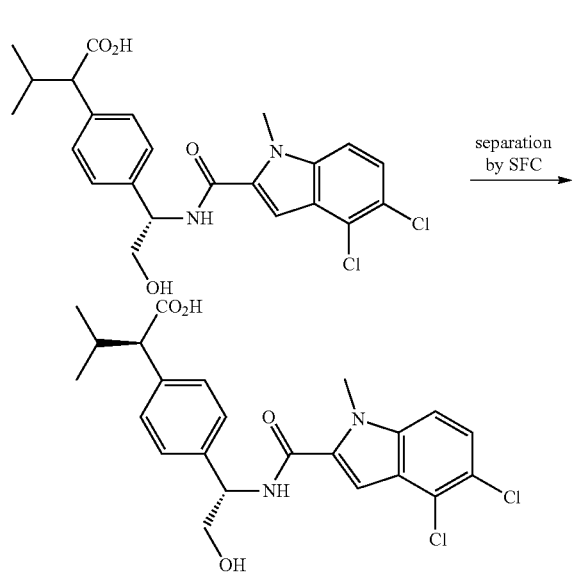

separation by SFC

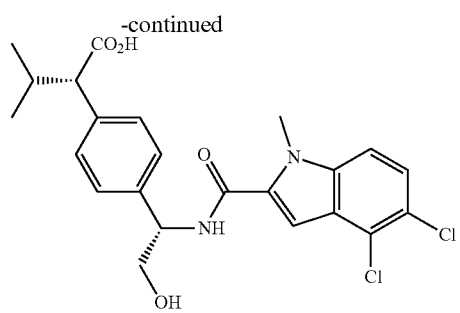

(±)-2-[4-[(1S)-1-[(4,5-dichloro-1-methyl-indole-2-carbonyl)amino]-2-hydroxy-ethyl]phenyl]-3-methyl-butanoic acid (1.80 g, 3.88 mmol, Example 53) was separated by SFC (Column: OD (250 mm*30 mm, 10 um); Mobile phase: A: CO$_2$ and B: ethanol (0.1% Ammonia); Isocratic: ethanol 25%) to give two enantiomers.

(2R or 2S)-2-[4-[(1S)-1-[(4,5-dichloro-1-methyl-indole-2-carbonyl)amino]-2-hydroxy-ethyl]phenyl]-3-methyl-butanoic acid (Example 54) Peak 1: (362 mg, 40% yield) was obtained as a white solid. cSFC analytical tR: 2.852 min., ee: 100%; LCMS: (ES$^+$) m/z (M+H)$^+$=463.0, tR=0.896. $^1$H NMR (400 MHz, DMSO-d$_6$) δ=8.99 (d, J=8.0 Hz, 1H), 7.61 (d, J=8.8 Hz, 1H), 7.45 (d, J=8.8 Hz, 1H), 7.40 (s, 1H), 7.39-7.35 (d, J=8.0 Hz, 2H), 7.30-7.26 (d, J=8.0 Hz, 2H), 5.10-5.03 (m, 1H), 3.98 (s, 3H), 3.76-3.61 (m, 2H), 3.08 (d, J=10.4 Hz, 1H), 2.19 (qd, J=6.4, 10.4 Hz, 1H), 0.99 (d, J=6.4 Hz, 3H), 0.63 (d, J=6.4 Hz, 3H).

(2S or 2R)-2-[4-[(1S)-1-[(4,5-dichloro-1-methyl-indole-2-carbonyl)amino]-2-hydroxy-ethyl]phenyl]-3-methyl-butanoic acid (Example 55) Peak 2: (349 mg, 39% yield) was obtained as a white solid. cSFC analytical tR: 2.981 min., ee: 97%; LCMS: (ES$^+$) m/z (M+H)$^+$=463.0, tR=0.890. $^1$H NMR (400 MHz, DMSO-d$_6$) δ=8.99 (d, J=8.0 Hz, 1H), 7.61 (d, J=8.8 Hz, 1H), 7.45 (d, J=8.8 Hz, 1H), 7.40 (s, 1H), 7.39-7.35 (d, J=8.0 Hz, 2H), 7.30-7.26 (d, J=8.0 Hz, 2H), 5.09-5.03 (m, 1H), 3.98 (s, 3H), 3.75-3.62 (m, 2H), 3.06 (d, J=10.4 Hz, 1H), 2.19 (qd, J=6.4, 10.4 Hz, 1H), 0.99 (d, J=6.4 Hz, 3H), 0.62 (d, J=6.4 Hz, 3H).

Example 56: 3-Phosphoglycerate Dehydrogenase (PHGDH) Diaphorase Coupled Assay

Full length (FL) 3-Phosphoglycerate Dehydrogenase (PHGDH) Diaphorase coupled assay (500 uM NAD)

PHGDH activity was determined by detecting the NADH produced during the reaction. Diaphorase was used to catalyze the oxidation of NADH with the concomitant reduction of resazurin to the fluorescent product resorufin. Resorufin fluorescence quantitatively reflected the production of NADH by the PHGDH reaction. To drive the forward reaction, two enzymes in the serine synthesis pathway subsequent to PHGDH, Phosphoserine aminotransferase (PSAT1) and phosphoserine phosphatase (PSPH) were also added to the reaction.

Briefly, serial dilution of compounds were incubated in a volume of 20 μl in 384 well plates with the assay mixture containing 5 nM PHGDH, 500 nM PSAT1, 500 nM PSPH, 500 μM NAD$^+$, 80 uM 3-phosphoglycerate, 1 mM glutamate, 57 uM Resazurin and 0.2 mg/ml Diaphorase in assay buffer containing 50 mM Trisethanoloamine (TEA) pH8.0, 10 mM MgCl$_2$, 0.01% Tween-20 and 0.05% Bovine Serum Albumin (BSA). The plate was then incubated at 30° C. for 60 minutes and resorufin fluorescence was measured at emission wavelength 598 nm following excitation at 525 nm. The positive control consisted of the complete reaction mixture with 4% DMSO and was set to 0% inhibition. The negative control consisted of the reaction mix lacking PHGDH with 4% DMSO and was set to 100% inhibition. Percent inhibition with the compounds was then calculated by normalizing the fluorescence observed at a given compound concentration to the positive and negative controls. $IC_{50}$ was calculated by plotting the % inhibition versus concentration and using hyperbolic fit to determine compound concentration corresponding to 50% inhibition.

Example 57: Full Length (FL) 3-Phosphoglycerate Dehydrogenase (PHGDH) Diaphorase Coupled Assay (20 uM NAD)

Serial dilution of compounds were incubated in a volume of 20 µl in 384 well plates with the assay mixture containing 10 nM PHGDH, 500 nM PSAT1, 500 nM PSPH, 20 µM $NAD^+$, 80 uM 3-phosphoglycerate, 1 mM glutamate, 57 uM Resazurin and 0.2 mg/ml Diaphorase in assay buffer containing 50 mM Trisethanoloamine (TEA) pH8.0, 10 mM $MgCl_2$, 0.01% Tween-20 and 0.05% Bovine Serum Albumin (BSA). The plate was then incubated at 30° C. for 60 minutes and resorufin fluorescence was measured at emission wavelength 598 nm following excitation at 525 nm. The positive control consisted of the complete reaction mixture with 4% DMSO and was set to 0% inhibition. The negative control consisted of the reaction mix lacking PHGDH with 4% DMSO and was set to 100% inhibition. Percent inhibition with the compounds was then calculated by normalizing the fluorescence observed at a given compound concentration to the positive and negative controls. $IC_{50}$ was calculated by plotting the % inhibition versus concentration and using hyperbolic fit to determine compound concentration corresponding to 50% inhibition.

Table 2 shows the activity of selected compounds of this invention in the full-length PHGDH activity inhibition assay. The compound numbers correspond to the compound numbers in Table 1 and in the Examples ("e" numbers), above. Compounds having an activity designated as "A" provided an $IC_{50}$ of 0.01-1 µM; compounds having an activity designated as "B" provided an $IC_{50}$ of 1-5 µM; and compounds having an activity designated as "C" provided an $IC_{50}$ of 5-10 µM and compounds having an activity designated as "D" provided an $IC_{50}$>10 µM. "NA" stands for "not assayed."

TABLE 2

| Compound/ Example # | PHGDH Activity Inhibition Data | |
| --- | --- | --- |
| | FL Diaphorase 500 µM NAD | FL Diaphorase 20 µM NAD |
| I-1 e39 | A | NA |
| I-2 e41 | A | NA |
| I-3 e40 | A | NA |
| I-4 e52 | A | NA |
| I-5 e51 | A | NA |
| I-6 e31 | A | NA |
| I-7 e45 | A | NA |
| I-8 e46 | A | NA |
| I-9 e18 | A | NA |
| I-10 e14 | A | NA |
| I-11 e44 | A | NA |
| I-12 e43 | A | NA |
| I-13 e42 | A | NA |
| I-14 e37 | A | NA |

TABLE 2-continued

| Compound/ Example # | PHGDH Activity Inhibition Data | |
| --- | --- | --- |
| | FL Diaphorase 500 µM NAD | FL Diaphorase 20 µM NAD |
| I-15 e50 | A | NA |
| I-16 e20 | A | NA |
| I-17 e19 | A | NA |
| I-18 e35 | A | NA |
| I-19 e36 | A | NA |
| I-20 e38 | A | NA |
| I-21 e17 | A | NA |
| I-22 e32 | A | NA |
| I-23 e16 | A | NA |
| I-24 e34 | A | NA |
| I-26 e33 | A | NA |
| I-27 e13 | A | NA |
| I-28 e15 | A | NA |
| I-29 e11 | A | NA |
| I-30 e28 | A | NA |
| I-31 e29 | A | NA |
| I-32 e12 | A | NA |
| I-33 e30 | A | NA |
| I-34 e48 | A | NA |
| I-35 e27 | B | NA |
| I-36 e25 | B | NA |
| I-37 e26 | B | NA |
| I-38 e22 | B | NA |
| I-39 e9 | A | NA |
| I-40 e21 | A | NA |
| I-41 e8 | A | NA |
| I-42 e24 | B | NA |
| I-43 e10 | A | NA |
| I-44 e23 | A | NA |
| I-45 e7 | — | A |
| I-46 e47 | — | A |
| I-47 e6 | NA | A |
| I-48 e5 | NA | B |
| I-49 e4 | NA | A |
| I-50 e1 | NA | B |
| I-51 e3 | NA | C |
| I-52 e2 | — | B |
| I-53 e49 | NA | D |
| I-54 e54 peak 1 | A | NA |
| I-55 e55 peak 2 | A | NA |
| I-56 e53 | A | NA |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

I claim:
1. A compound of formula I:

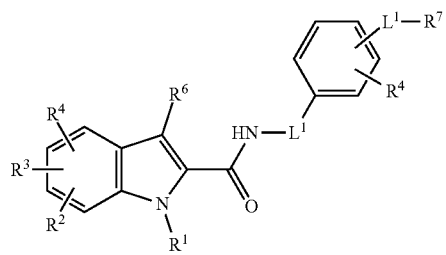

or a pharmaceutically acceptable salt thereof, wherein:

$R^1$ is methyl;

$R^2$ is F, Cl, —CF$_3$, —OCF$_3$, —OCHF$_2$, —OCH$_2$Ph, —OCH$_3$, —CN, —CH$_3$,

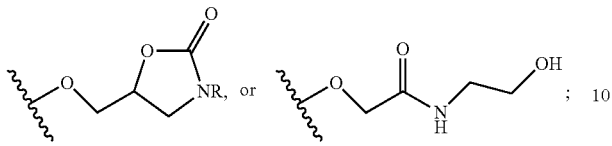

$R^3$ is halogen, —OR, —CN, or C$_{1-6}$ aliphatic optionally substituted with 1, 2, or 3 halogens; or $R^2$ and $R^3$ are optionally taken together with the carbon atoms to which they are attached and any intervening atoms to form a 5-8 membered partially unsaturated ring having 0-2 heteroatoms independently selected from nitrogen, oxygen, or sulfur;

$R^4$ is hydrogen, halogen, —OR$^5$, —CN, or C$_{1-6}$ aliphatic optionally substituted with 1, 2, or 3 halogens;

each R is independently hydrogen or an optionally substituted group selected from C$_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

$R^5$ is hydrogen, —(CH$_2$)$_n$-phenyl, or C$_{1-6}$ alkyl optionally substituted with 1, 2, or 3 halogens;

$R^6$ is hydrogen or C$_{1-4}$ alkyl;

$R^7$ is hydrogen or —CO$_2$R;

$L^1$ is a C$_{1-8}$ bivalent straight or branched hydrocarbon chain wherein 1-5 methylene units of the chain are independently and optionally replaced with —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, —(R)NC(S)N(R)—, or -Cy-;

each -Cy- is independently a bivalent 6-membered arylene ring containing 0-2 nitrogen atoms, or a bivalent 5-membered heteroarylene ring with 1-4 heteroatoms independently selected from nitrogen, oxygen, or sulfur, or a bivalent partially unsaturated 8-10 membered bicyclic heterocyclene ring with 1-4 heteroatoms independently selected from nitrogen, oxygen, or sulfur, wherein -Cy- is optionally substituted with 1 or 2 substituents independently selected from C$_{1-4}$ alkyl or —OR; and n is independently 0, 1, 2, 3, 4, or 5.

2. The compound according to claim 1, wherein $R^2$ is F, Cl, —OCF3, —OCF2, —OCH2Ph, —OCH3 or —CN.

3. The compound according to claim 1, wherein $R^3$ is halogen or —OR.

4. The compound according to claim 1, wherein R2 is F or Cl and R3 is halogen.

5. The compound according to claim 4, wherein $R^4$ is hydrogen.

6. The compound according to claim 1, wherein $R^5$ is hydrogen, —(CH$_2$)$_n$-phenyl, or C$_{1-6}$ alkyl optionally substituted with 1, 2, or 3 halogens.

7. The compound according to claim 1, wherein $L^1$ is

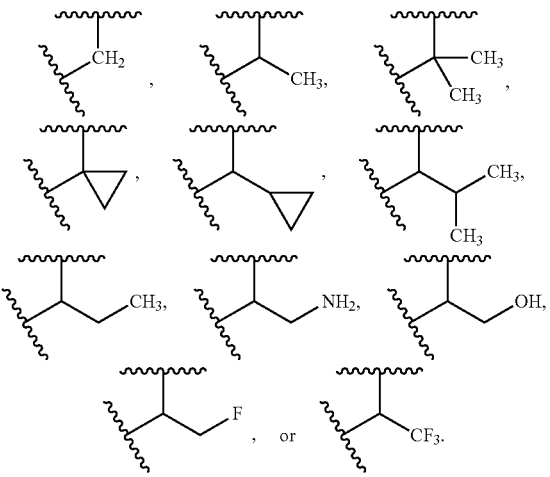

8. The compound according to claim 7, wherein $L^1$ is

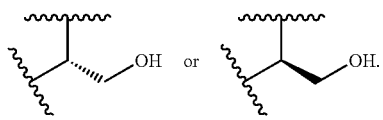

9. The compound according to claim 1, wherein said compound is of Formulae II-a, II-b, II-c, II-d, II-e, II-f, or II-g:

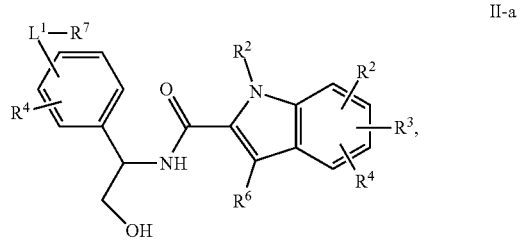

II-a

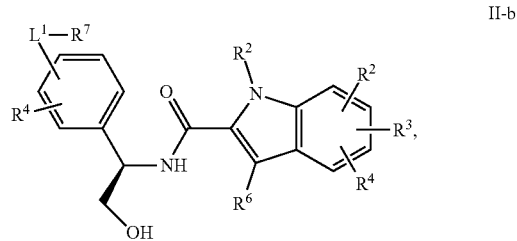

II-b

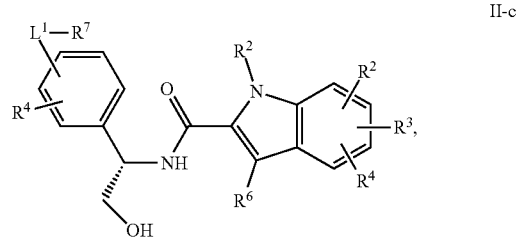

II-c

-continued
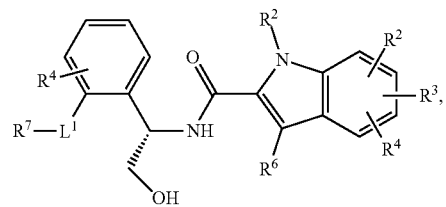
II-d
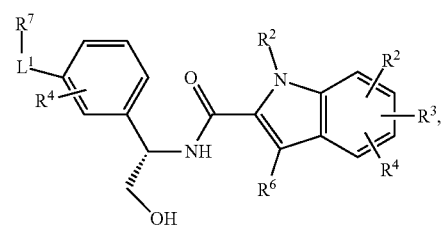
II-e
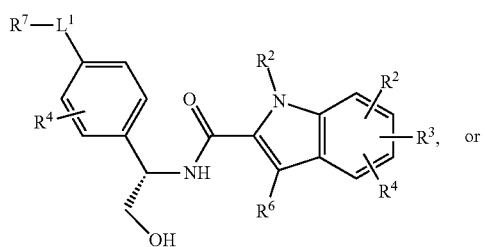
II-f
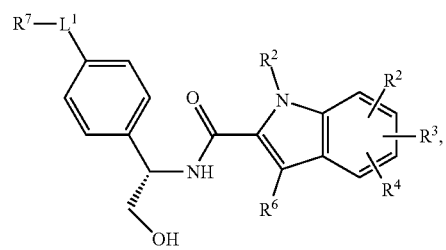
II-g
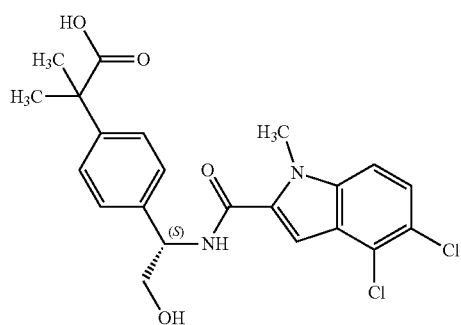
or a pharmaceutically acceptable salt thereof.
10. A compound selected from:
I-1
-continued
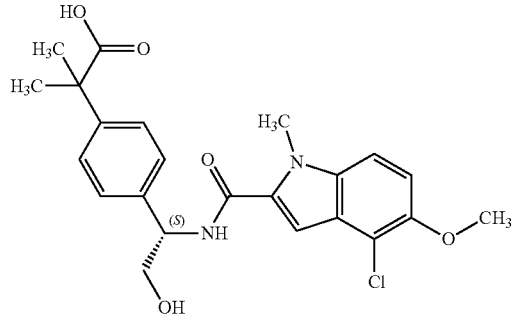
I-2
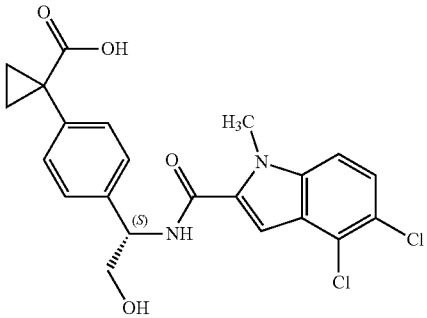
I-3
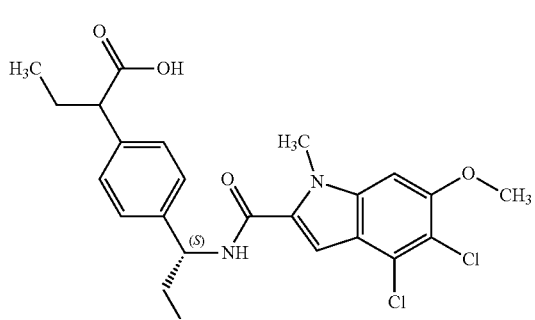
I-4
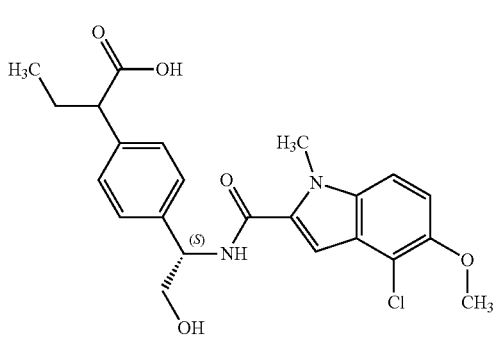
I-5
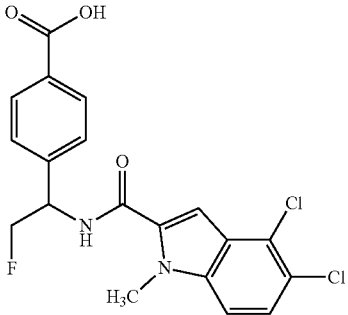
I-6

-continued
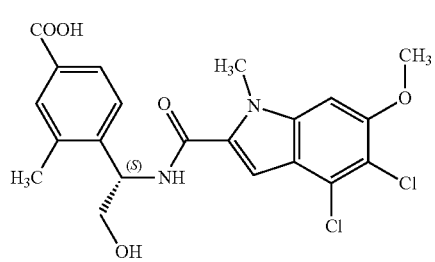
I-7
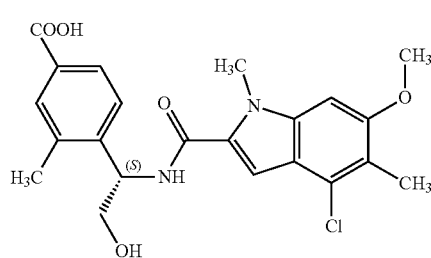
I-8
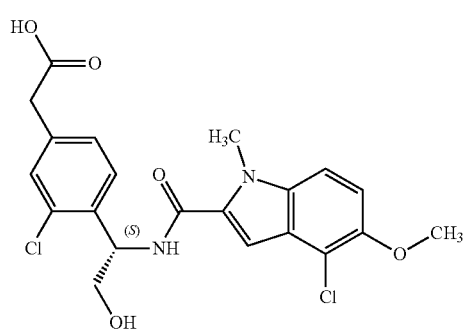
I-9
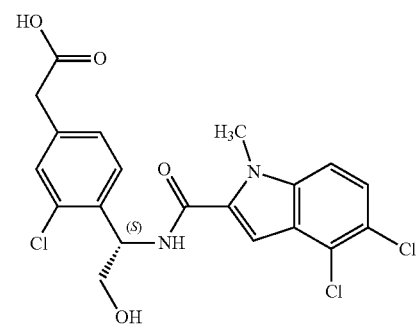
I-10
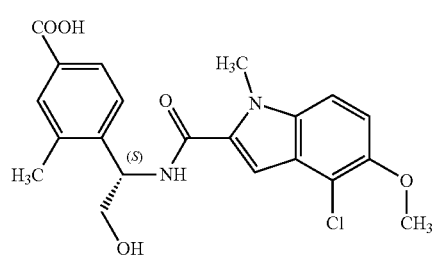
I-11
-continued
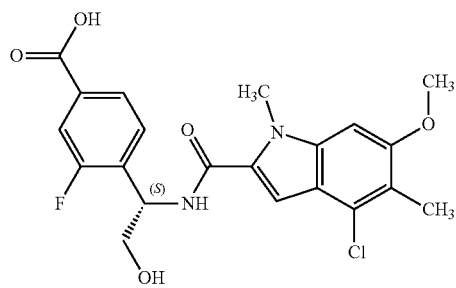
I-12
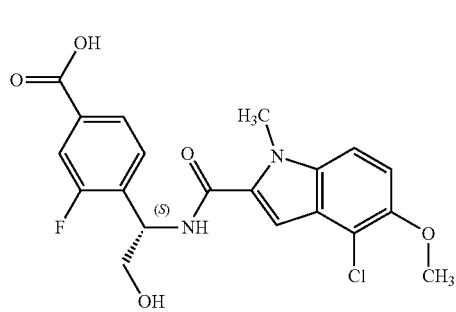
I-13
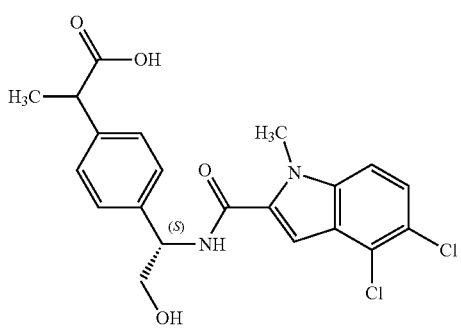
I-14
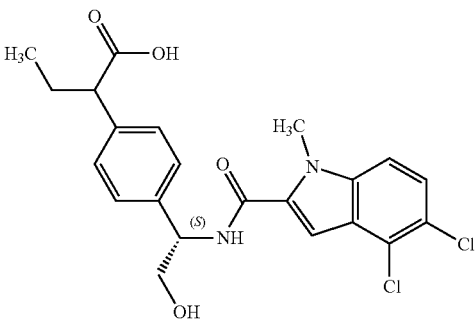
I-15
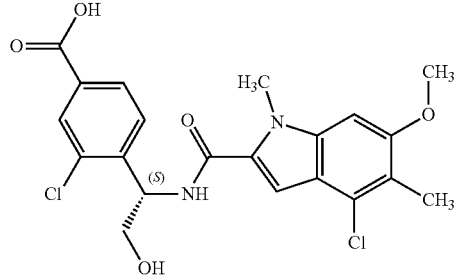
I-16

-continued
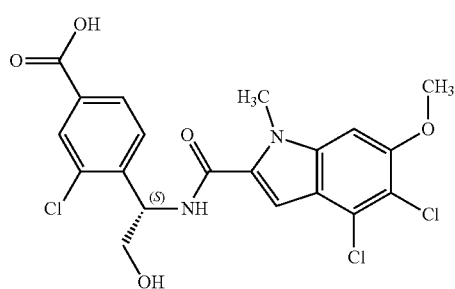 I-17
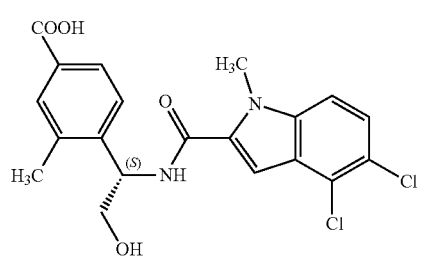 I-18
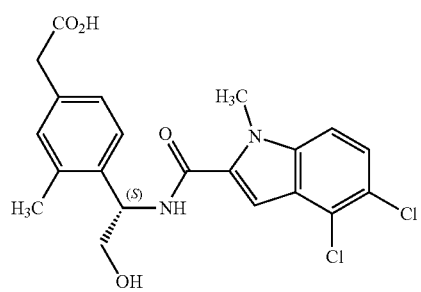 I-19
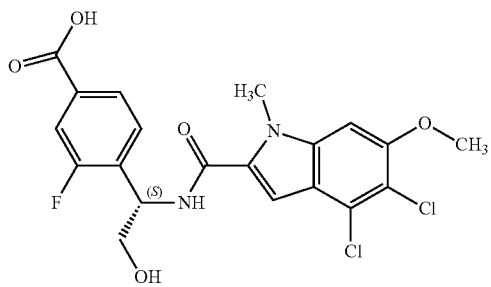 I-20
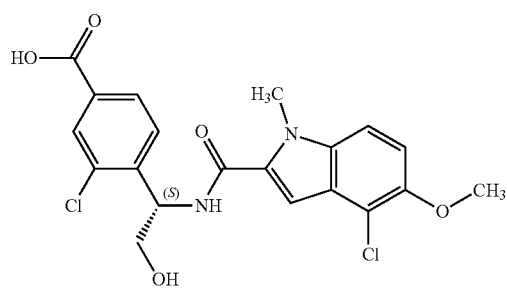 I-21
-continued
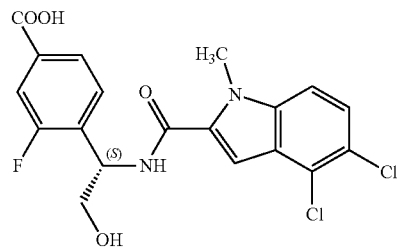 I-22
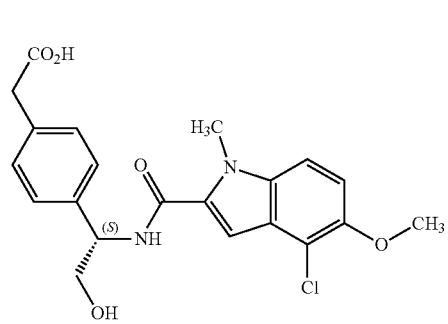 I-23
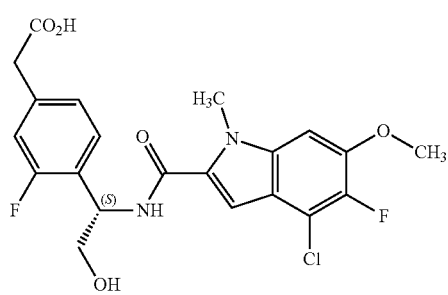 I-24
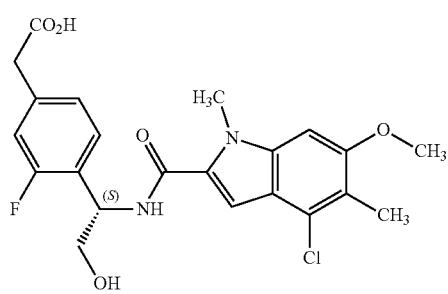 I-26
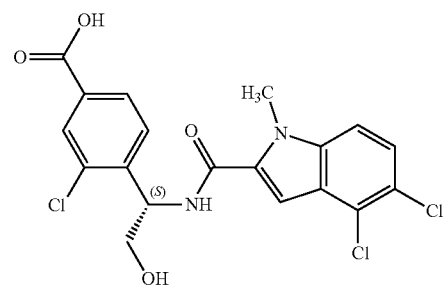 I-27

I-28 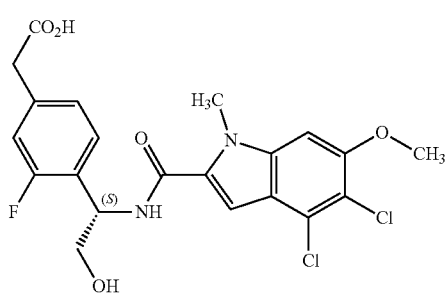
I-29 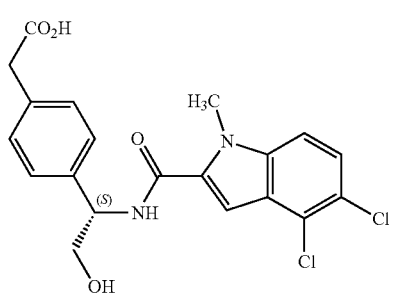
I-30 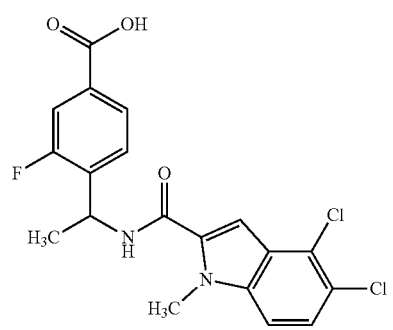
I-31 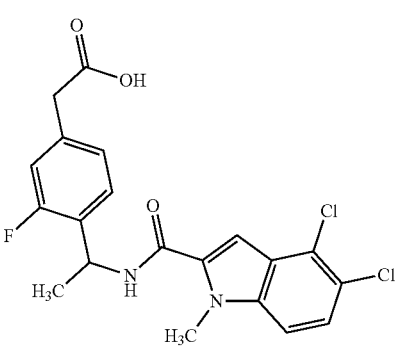
I-32 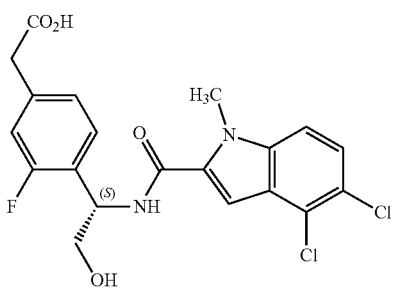
I-33 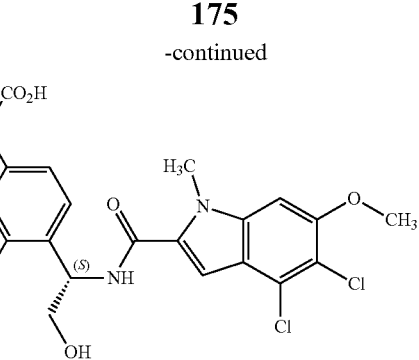
I-34 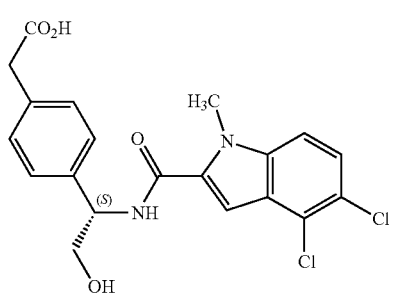
I-35 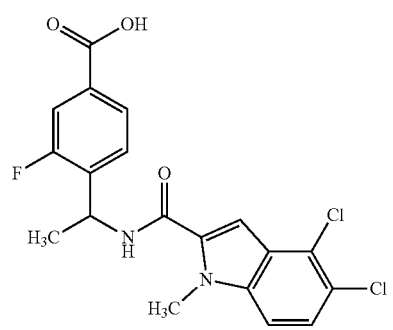
I-36 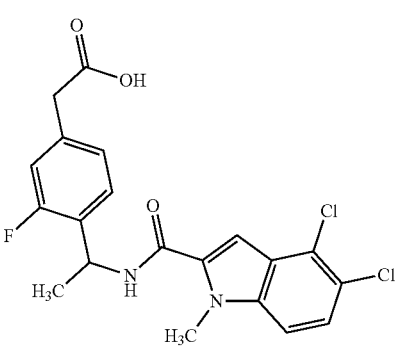
I-37

I-38
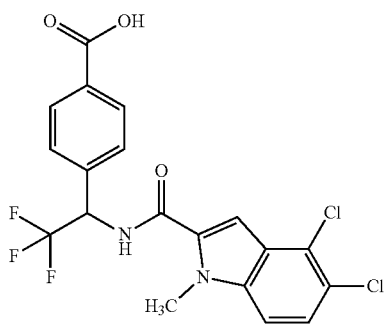
I-45
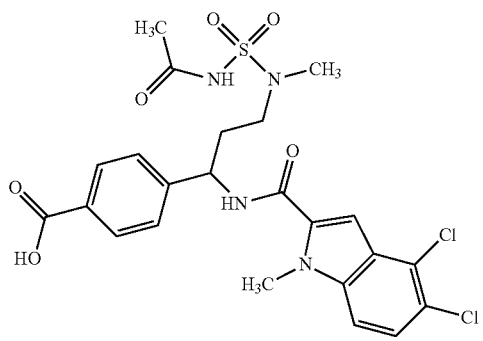 [SMILES: CC(=O)NS(=O)(=O)N(C)CCC(NC(=O)c1cc2c(Cl)c(Cl)ccc2n1C)c1ccc(C(=O)O)cc1]
I-40
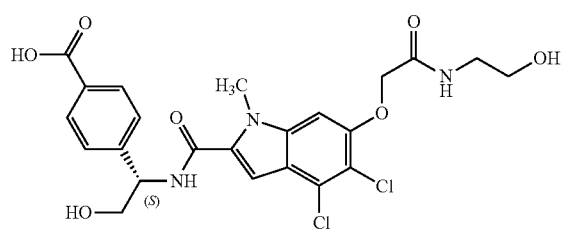
I-46
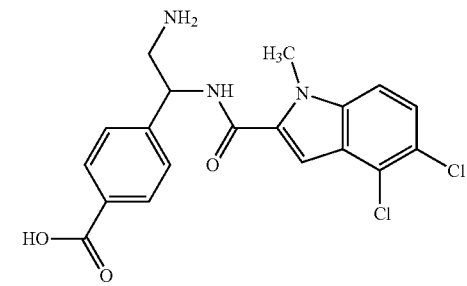 [SMILES: Cn1c(C(=O)NC(CN)c2ccc(C(=O)O)cc2)cc2c(Cl)c(Cl)ccc21]
I-42
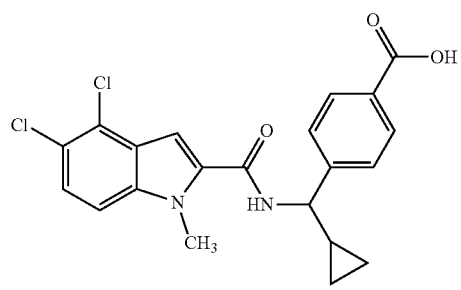
I-47
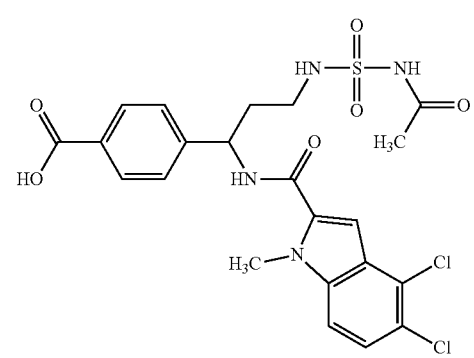 [SMILES: CC(=O)NS(=O)(=O)NCCC(NC(=O)c1cc2c(Cl)c(Cl)ccc2n1C)c1ccc(C(=O)O)cc1]
I-43
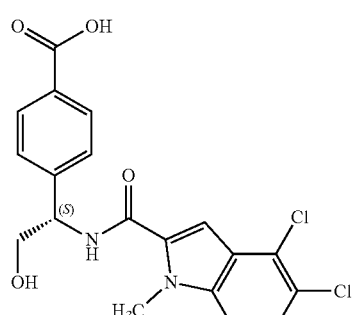
I-48
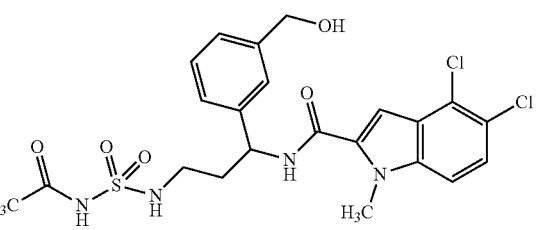
I-44
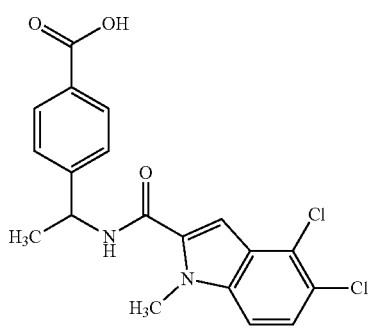
I-49
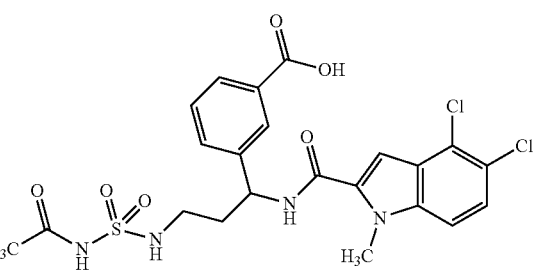

I-50

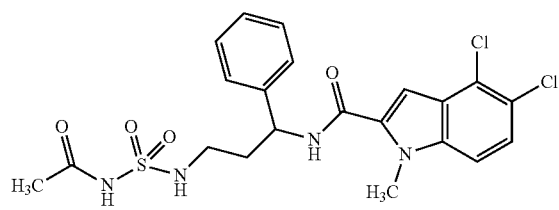

I-51

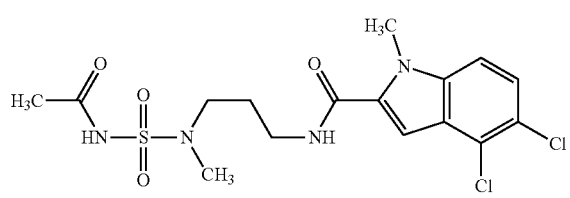 [SMILES: CC(=O)NS(=O)(=O)N(C)CCCNC(=O)c1cc2c(Cl)c(Cl)ccc2n1C]

I-52

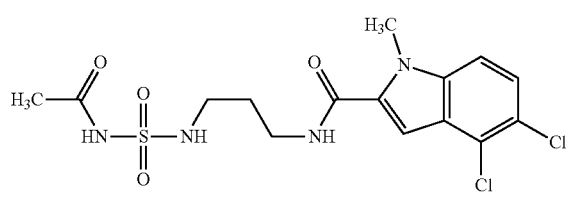 [SMILES: CC(=O)NS(=O)(=O)NCCCNC(=O)c1cc2c(Cl)c(Cl)ccc2n1C]

I-53

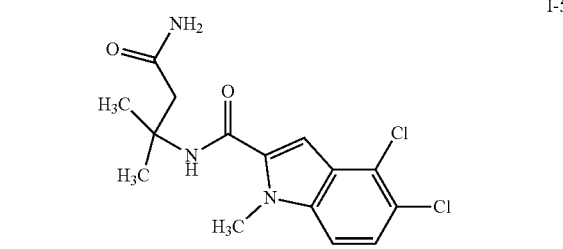

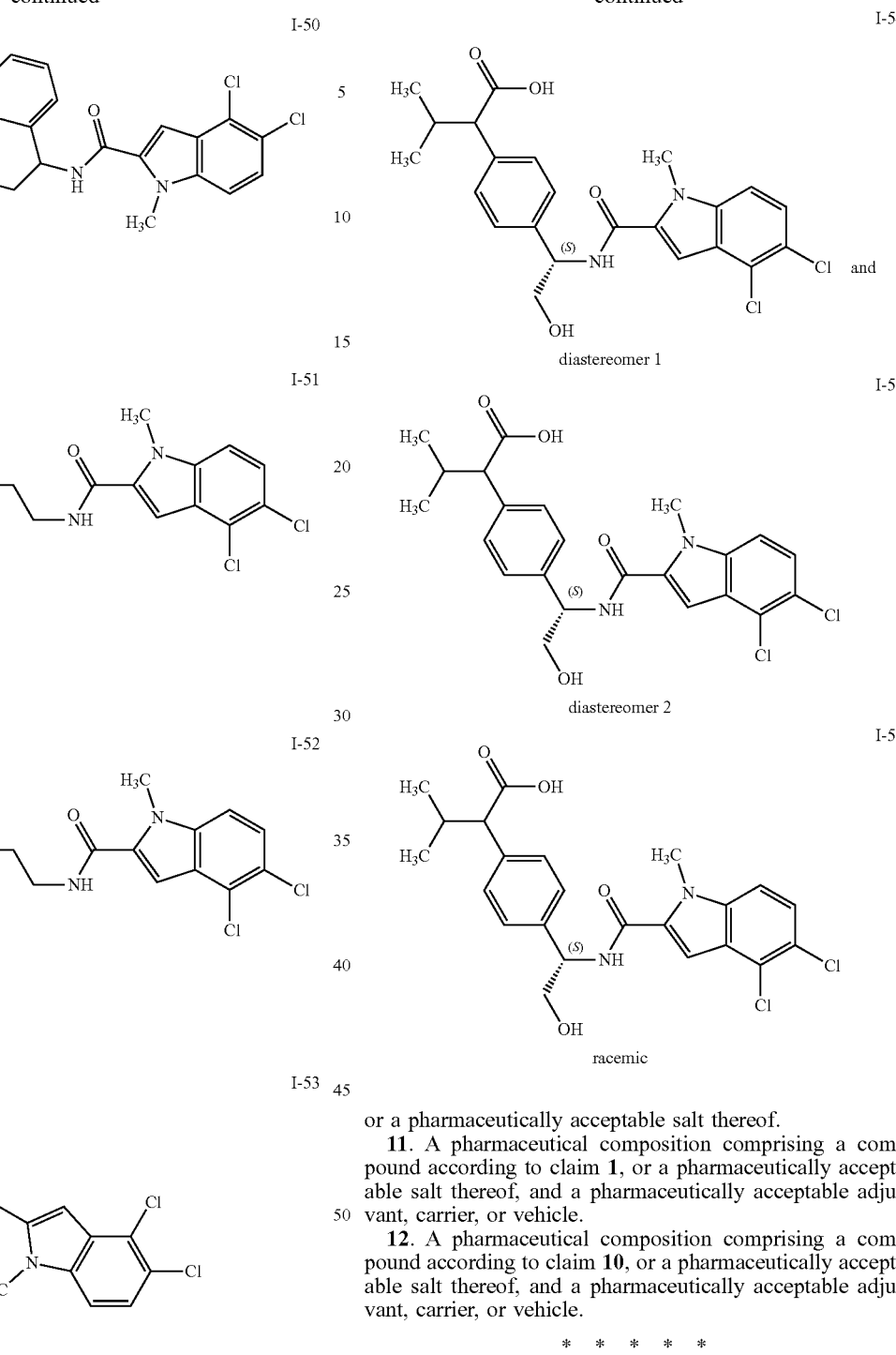

diastereomer 1 diastereomer 2 racemic or a pharmaceutically acceptable salt thereof.

11. A pharmaceutical composition comprising a compound according to claim 1, or a pharmaceutically acceptable salt thereof, and a pharmaceutically acceptable adjuvant, carrier, or vehicle.

12. A pharmaceutical composition comprising a compound according to claim 10, or a pharmaceutically acceptable salt thereof, and a pharmaceutically acceptable adjuvant, carrier, or vehicle.

* * * * *